US008268868B2

(12) United States Patent
Guzzo et al.

(10) Patent No.: US 8,268,868 B2
(45) Date of Patent: Sep. 18, 2012

(54) 5-PYRIDINONE SUBSTITUTED INDAZOLES

(75) Inventors: Peter Robert Guzzo, Niskayuna, NY (US); Matthew David Surman, Albany, NY (US); Alan John Henderson, Albany, NY (US); Mark Hadden, Albany, NY (US); May Xiaowu Jiang, Guilderland, NY (US)

(73) Assignee: Albany Molecular Research, Inc., Albany, NY (US)

( * ) Notice: Subject to any disclaimer, the term of this patent is extended or adjusted under 35 U.S.C. 154(b) by 0 days.

(21) Appl. No.: 12/522,657

(22) PCT Filed: Jan. 9, 2008

(86) PCT No.: PCT/US2008/050601
§ 371 (c)(1),
(2), (4) Date: Aug. 19, 2009

(87) PCT Pub. No.: WO2008/086404
PCT Pub. Date: Jul. 17, 2008

(65) Prior Publication Data
US 2010/0105679 A1 Apr. 29, 2010

Related U.S. Application Data

(60) Provisional application No. 60/884,351, filed on Jan. 10, 2007.

(51) Int. Cl.
*A61K 31/416* (2006.01)
*C07D 401/04* (2006.01)
(52) U.S. Cl. .................................. 514/338; 546/275.7
(58) Field of Classification Search ................ 546/275.7
See application file for complete search history.

(56) References Cited

U.S. PATENT DOCUMENTS

| | | | |
|---|---|---|---|
| 5,182,403 A | 1/1993 | Brickner | |
| 5,225,565 A | 7/1993 | Brickner | |
| 5,232,931 A | 8/1993 | Prucher et al. | |
| 5,393,735 A | 2/1995 | Lange et al. | |
| 5,502,027 A | 3/1996 | Lange et al. | |
| 5,631,209 A | 5/1997 | Lange et al. | |
| 5,650,513 A | 7/1997 | Langhals et al. | |
| 5,763,469 A | 6/1998 | Delucca | |
| 6,107,300 A | 8/2000 | Bakthavatchalam et al. | |
| 6,974,869 B2 | 12/2005 | DeLucca | |
| 2003/0114448 A1 | 6/2003 | Zhang et al. | |
| 2003/0144277 A1 | 7/2003 | DeLucca | |
| 2003/0171380 A1 | 9/2003 | Arvanitis et al. | |
| 2003/0212054 A1 | 11/2003 | Quan et al. | |
| 2005/0049253 A1 | 3/2005 | Tegley | |
| 2005/0054670 A1 | 3/2005 | Tegley et al. | |
| 2005/0137243 A1 | 6/2005 | Souers et al. | |
| 2005/0187279 A1 | 8/2005 | Souers et al. | |
| 2005/0272735 A1 | 12/2005 | Xie et al. | |
| 2005/0277638 A1 | 12/2005 | Souers et al. | |
| 2009/0082359 A1 | 3/2009 | Guzzo et al. | |
| 2010/0105679 A1 | 4/2010 | Guzzo et al. | |

FOREIGN PATENT DOCUMENTS

| | | |
|---|---|---|
| DE | 4018830 | 12/1991 |
| DE | 4338784 | 5/1995 |
| DE | 19651712 | 6/1998 |
| DE | 101 04 279 A1 | 8/2002 |
| EP | 1 741 703 | 1/2007 |
| EP | 1 939 194 | 2/2008 |
| JP | 03-253852 | 11/1991 |
| WO | 97/08150 | 3/1997 |
| WO | 97/12884 | 4/1997 |
| WO | 03/024401 | 3/2003 |
| WO | 03/033476 A1 | 4/2003 |
| WO | 2004/032848 | 4/2004 |
| WO | 2004/092181 A1 | 10/2004 |
| WO | 2004/112719 | 12/2004 |
| WO | 2005/018557 | 3/2005 |
| WO | 2005/042541 A1 | 5/2005 |
| WO | 2005/085200 | 9/2005 |
| WO | 2006/017257 | 2/2006 |
| WO | 2007/029847 | 3/2007 |
| WO | 2008/086404 | 7/2008 |
| WO | 2009/015037 | 1/2009 |

OTHER PUBLICATIONS

Anxiety [online]. retrieved on Sep. 9, 2010 from the internet [URL; http://www.medicinenet.com/anxiety/article.htm}.*
Nonalcoholic fatty liver disease [online], retrieved on Sep. 9, 2010 from the internet [URL; http://www.mayoclinic.com/health/nonal-coholic-fatty-liver-disease/DS00577].*
Vippagunta, et al. Advanced Drug Delivery Reviews 48 (2001) 3-26.*
International Search Report for PCT/US2008/050601 (Jun. 11, 2008).
Written Opinion of the International Search Authority for International Patent Application No. PCT/US2008/050601 (Jun. 11, 2008).
International Preliminary Report on Patentability of the International Preliminary Examining Authority for International Patent Application No. PCT/US2008/050601 (May 22, 2009).
Souers et al., "Synthesis and Evaluation of Urea-Based Indazoles as Melanin-Concentrating Hormone Receptor 1 Antagonists for the Treatment of Obesity," Bioorganic & Medicinal Chemistry Letters, 15:2752-2757 (2005).
Office Action dated Mar. 14, 2011 for U.S. Appl. No. 12/176,144.
International Search Report for PCT/US2008/070535 (Mar. 23, 2009).
Written Opinion of the International Search Authority for International Patent Application No. PCT/US2008/070535.
International Preliminary Report on Patentability of the International Preliminary Examining Authority for International Patent Application No. PCT/US2008/070535 (Feb. 4, 2010).
Communication for European Application No. 08/796 320.3 (Dec. 17, 2010).

* cited by examiner

*Primary Examiner* — Shawquia Young
(74) *Attorney, Agent, or Firm* — LeClairRyan, a Professional Corporation

(57) ABSTRACT

Various 5-substituted 1-substituted indazoles are described, as are pharmaceutical compositions containing these compounds and methods of treatment of diseases using these compounds. Other embodiments are also described.

36 Claims, No Drawings

5-PYRIDINONE SUBSTITUTED INDAZOLES

RELATED APPLICATIONS

This application is a U.S. national stage filing under 35 U.S.C. 371 of PCT International Patent Application Serial No. PCT/US2008/050601, filed Jan. 9, 2008, which claims priority of U.S. Provisional Application No. 60/884,351, filed Jan. 10, 2007, the contents of which are incorporated herein by reference.

FIELD OF THE INVENTION

The invention relates to human melanin-concentrating hormone ($MCH_1$) receptor-selective antagonists 5-pyridinone substituted indazoles that are useful for treating obesity, to pharmaceutical compositions comprising these compounds, and to methods for the treatment of obesity, anxiety, depression, and psychiatric disorders in a mammal.

BACKGROUND

Obesity and the multitude of co-morbidities associated with obesity such as diabetes, dyslipidemia, coronary heart disease, and certain cancers are a major concern for public health. The currently available pharmaceutical therapies for the treatment of obesity have limited efficacy and side effects that limit their use. Thus, there is a significant medical need for better pharmacotherapy for obesity.

Melanin-concentrating hormone (MCH) has been identified as an orexigenic peptide that exerts an effect on food intake and body weight regulation. MCH is a cyclic 19 amino acid neuropeptide expressed in the zona incerta and lateral hypothalamus in response to both energy restriction and leptin deficiency. MCH is known to stimulate feeding when injected into the lateral ventricle of rats and the mRNA for MCH is upregulated in the hypothalamus of genetically obese mice (ob/ob) and in fasted control and ob/ob animals. In addition, animals treated with MCH show increases in glucose, insulin and leptin levels, mimicking human metabolic syndrome (Gomori, A. Chronic infusion of MCH causes obesity in mice Am. J. Physiol. Endocrinol. Metab. 284, E583, 2002). Mice lacking MCH are hypophagic and lean with increased metabolic rate, whereas animals over-expressing MCH gain excess weight on both standard and high fat diets. MCH is thought to have effects on other nervous system functions as well (Rocksz, L. L. Biological Examination of Melanin Concentrating Hormone 1: Multi-tasking from the hypothalamus Drug News Perspect 19(5), 273, 2006). An orphan G-protein coupled receptor (GPCR) was recently identified as a receptor for MCH. Disruption of the binding between MCH and the MCH receptor, i.e. MCH antagonism, may thus be used to counteract the effects of MCH (McBriar, M. D. Recent advances in the discovery of melanin-concentrating hormone receptor antagonists Curr. Opin. Drug Disc. & Dev. 9(4), 496, 2006).

BRIEF DESCRIPTION OF THE INVENTION

There is provided, in accordance with an embodiment of the invention, a compound of formula I.

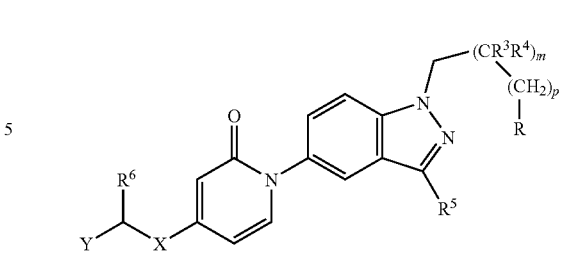

wherein
$R^5$ is H or lower alkyl which is optionally substituted by up to 3 halo atoms;
m and p are each 0 or 1, provided that m+p is at least 1;
$R^3$ and $R^4$ are each independently selected from H, —OH and lower alkyl;
R is —OH, alkoxy, hydroxyalkoxy, alkoxyalkoxy, or —$NR^1R^2$, wherein (i) $R^1$ and $R^2$ are each independently selected from H and optionally substituted alkyl, or (ii) $R^1$ and $R^2$, together with the N atom to which they are attached, form a 4 to 7-membered optionally substituted non-aromatic ring system which optionally contains 1 or 2 heteroatoms in addition to the N atom shown, or (iii) $NR^1R^2$, taken together with $CR^3R^4$ and, if present, the $CH_2$ between $NR^1R^2$ and $CR^3R^4$, forms a 5 to 10-membered optionally substituted non-aromatic ring system which optionally contains 1 or 2 heteroatoms in addition to the N atom shown;
X is selected from —O—, —NH—, —N-alkyl-, and —$CH_2$—;
$R^6$ is selected from H and lower alkyl;
or X and $CHR^6$ are taken together to form —CH=CH—;
Y is selected from $C_{3-10}$ non-aromatic hydrocarbon and

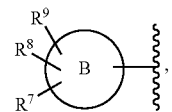

wherein B is an aromatic hydrocarbon or aromatic heterocycle, and $R^7$, $R^8$ and $R^9$ are each independently selected from H, —OH, —O-alkyl, -alkyl, halo, —S(O)-alkyl, —$SO_2$-alkyl, [MDS1]—$CF_3$, —CN and phenyl.

In accordance with some embodiments of the invention, R is selected from the group consisting of pyrrolidin-1-yl, piperidin-1-yl, morpholin-4-yl, 4-methyl-piperazin-1-yl, 2-methylpiperidin-1-yl, 3-fluoropyrrolidin-1-yl, dimethylamino, hydroxyl, diisopropylamino, 3,3-difluoropiperidin-1-yl, (2R,6S)-2,6-dimethylpiperidin-1-yl, (2S,6R)-2,6-dimethylmorphol-4-yl, piperazin-1-yl, 3,5-dimethylmorpholin-4-yl, 4-acetylpiperazin-1-yl, 4,4-difluoropiperidin-1-yl, piperazin-2-one-4-yl, (2R,5R)-2,5-dimethylpyrrolidin-1-yl, isobutylamino, 2,2,6,6-tetramethylpiperidin-1-yl, 2,2-dimethylmorpholin-4-yl, (S)-3-methoxypyrrolidin-1-yl, 2-oxa-5-azabicyclo[2.2.1]heptan-5-yl, 4-fluoropiperidin-1-yl, (S)-3-fluoropyrrolidin-1-yl, 3,3-difluoropyrrolidin-1-yl, 4-hydroxypiperidin-1-yl, (R)-3-hydroxypyrrolidin-1-yl, (R)-2-methoxymethylpyrrolidin-1-yl, (S)-3-hydroxypyrrolidin-1-yl, (R)-2-hydroxymethylpyrrolidin-1-yl, (S)-2-hydroxymethylpyrrolidin-1-yl, and cyclopentylamino. In some embodiments, R is $NR^1R^2$ which, taken together with $CR^3R^4$ and, if present, the $CH_2$ between $NR^1R^2$ and $CR^3R^4$, is a moiety selected from morpholin-2-yl, (R)-pyrrolidin-2-yl, (S)-pyrrolidin-2-yl, 4-(R)-hydroxypyrrolidin-2-yl, 4,5-dihydroimidazol-2-yl, (S)-5,6,7,7a-tetrahydro-1H-pyrrolo[1,2-e]

imidazol-2-yl 1-methyl-4,5-dihydro-1H-imidazol-2-yl, and 4,4-dimethyl-4,5-dihydro-1H-imidazol-2-yl.

In some embodiments of the invention, m+p is 1 In other embodiments, m+p is 2. In some embodiments, $R^3$ and $R^4$ are both H. In some embodiments, $R^3$ and $R^4$ are both methyl. In some embodiments, one of $R^3$ and $R^4$ is H and the other of $R^3$ and $R^4$ is hydroxyl.

In some embodiments of the invention, $R^6$ is H. In other embodiments, $R^6$ is lower alkyl. In some embodiments, $R^6$ is methyl. In some embodiments of the invention, X is O. In some embodiments of the invention, X is NH. In some embodiments of the invention, X is N-alkyl. In some embodiments, X is $CH_2$. In some embodiments, X and $R^6$ are taken together to form —CH=CH—.

In some embodiments of the invention, Y is a $C_{3-10}$ non-aromatic hydrocarbon. In some embodiments, Y is selected from cyclohexane, —$CH_2C(CH_3)_3$, cycloheptane, cyclopropyl, adamant-1-yl, and cyclopentyl. In other embodiments of the invention, Y is

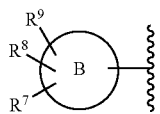

In some embodiments, B is selected from phenyl, pyridinyl and naphthyl. In some embodiments, B is selected from pyridin-2-yl, pyridin-3-yl and naphth-2-yl. In some embodiments, $R^7$, $R^8$ and $R^9$ are selected from H, —OH, —O-alkyl, -alkyl, -halo, —$CF_3$, —CN and phenyl. In some embodiments, B, $R^7$, $R^8$ and $R^9$ taken together are selected from phenyl, 4-trifluoromethylphenyl, 4-chlorophenyl, 3-chlorophenyl, 2-chlorophenyl, 3,4-difluorophenyl, 4-methoxyphenyl, naphthyl, 4-fluorophenyl[MDS2], pyridin-2-yl, 5-chloropyridin-2-yl, 4-cyanophenyl, pyridin-3-yl, biphenyl-4-yl, and 3,5-difluorophenyl.

In some embodiments of the invention, $R^5$ is H. In other embodiments, $R^5$ is lower alkyl which is optionally substituted by up to three halo atoms. In some embodiments, $R^5$ is methyl. In some embodiments, $R^5$ is —$CF_3$ In some embodiments of the invention, m is 0, p is 1, R is pyrrolidin-1-yl, $R^6$ is H, and B is phenyl.

In some embodiments of the invention, the compound is selected from:

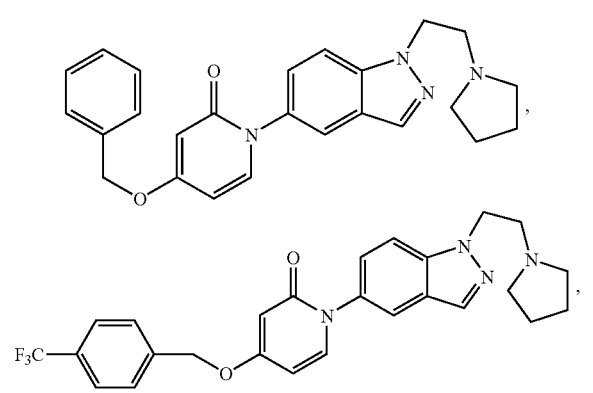

-continued

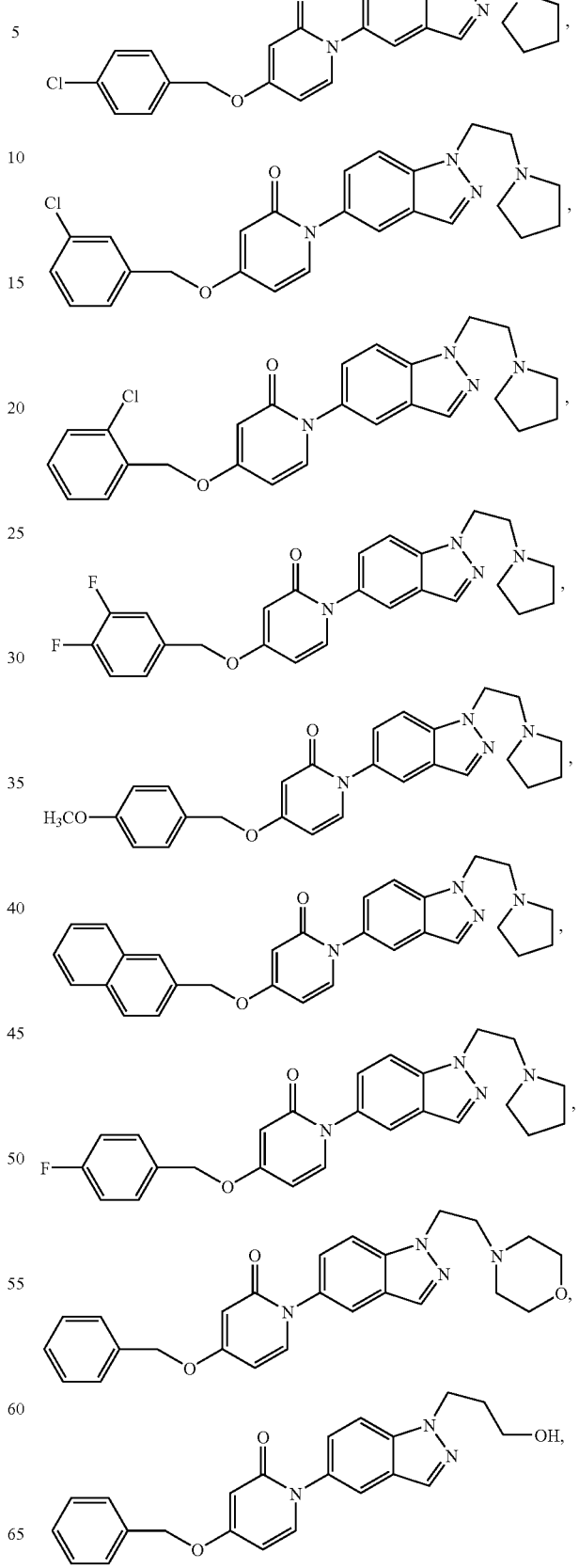

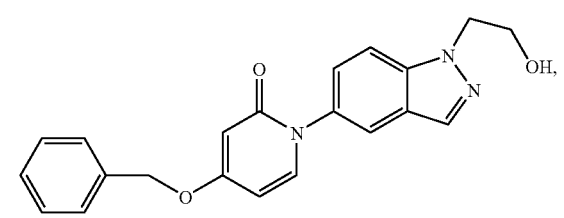
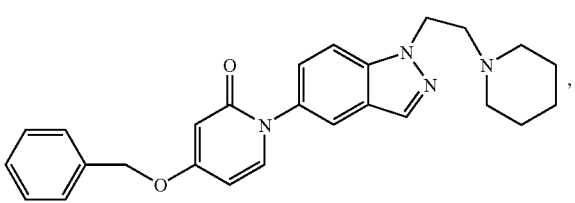
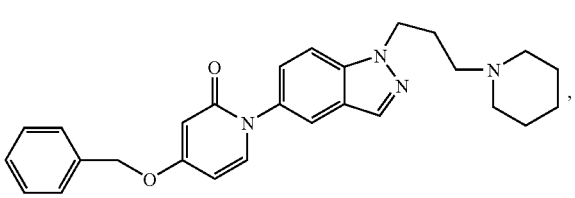
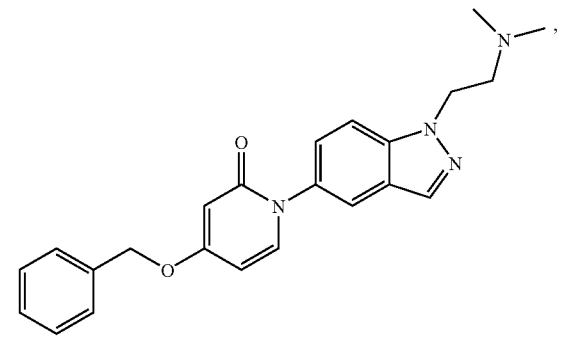
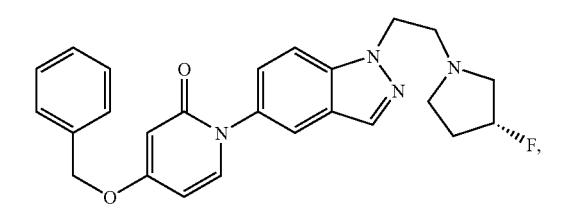
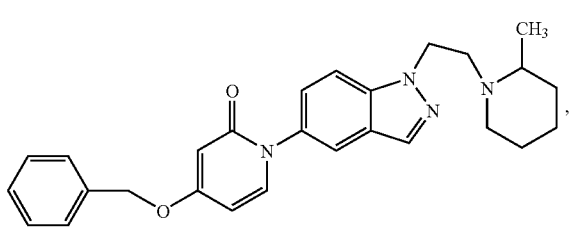
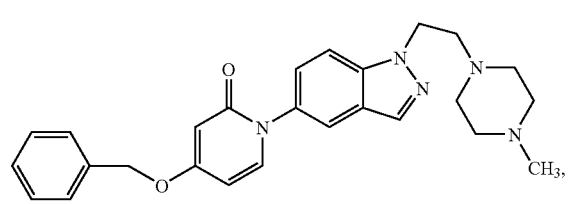
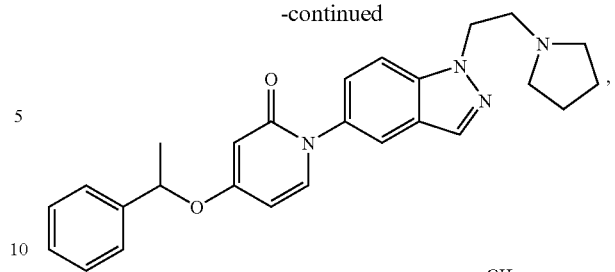
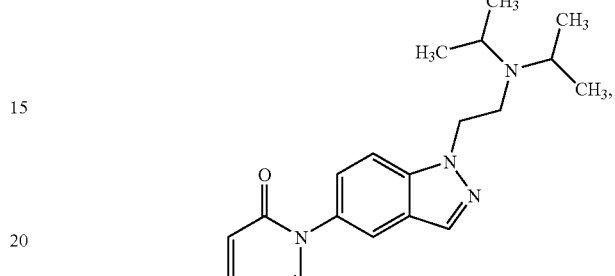
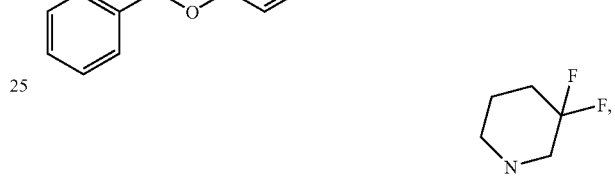
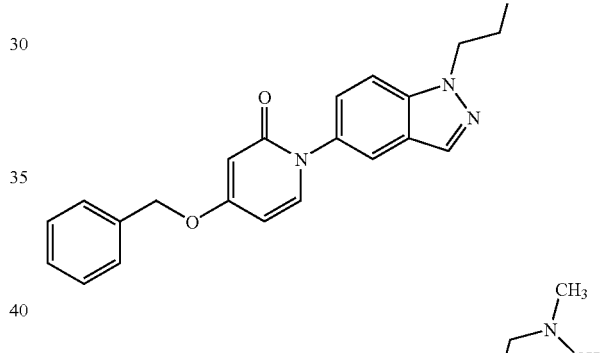
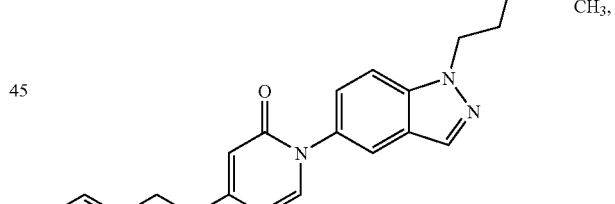
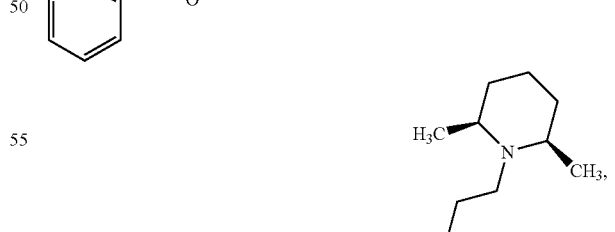
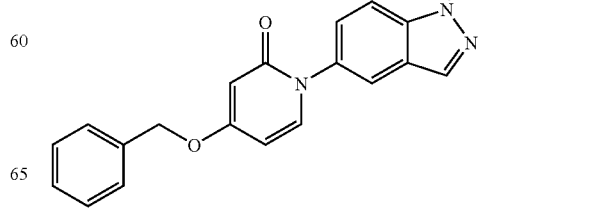

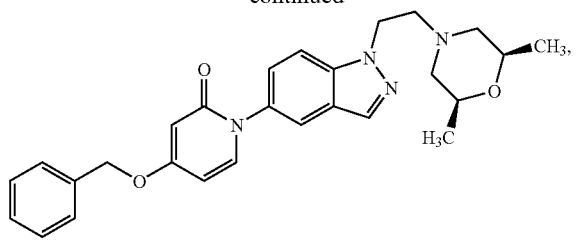
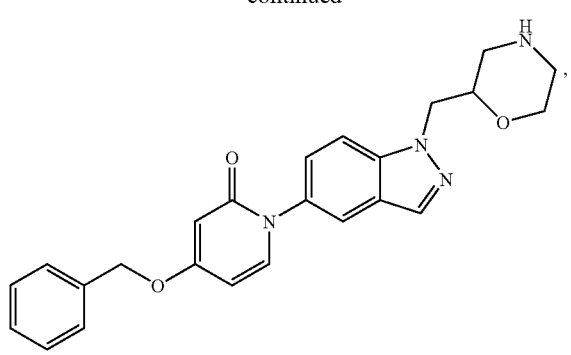

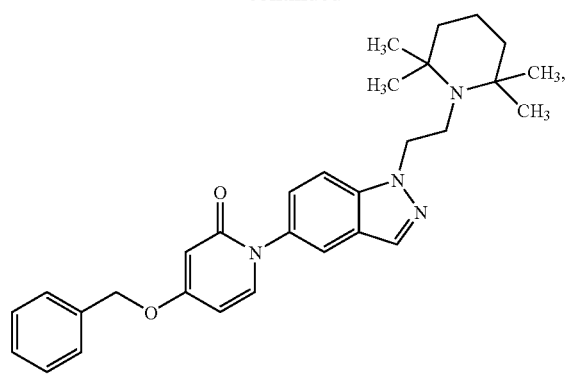
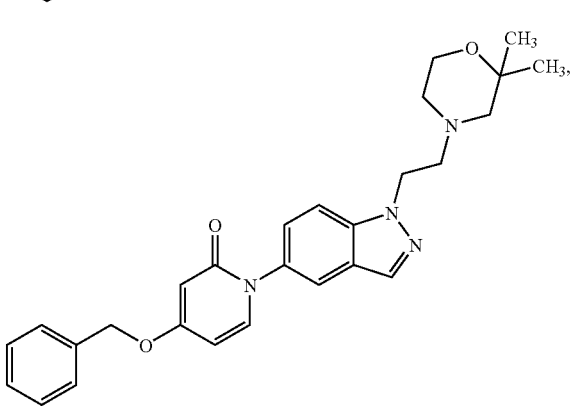
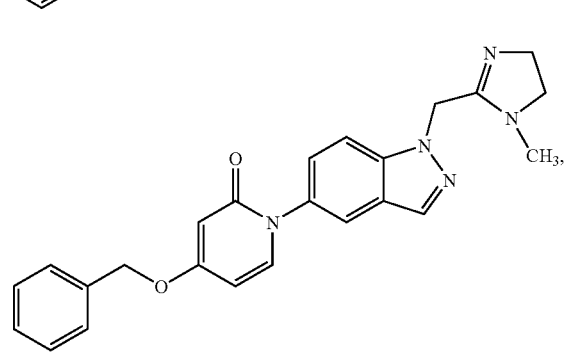
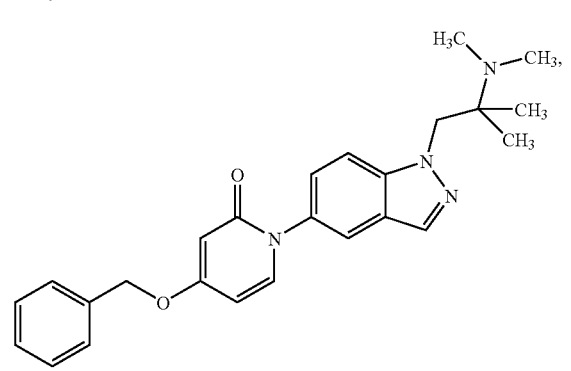
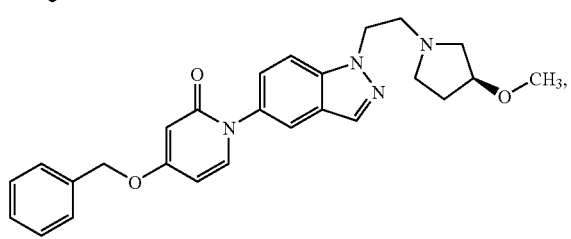
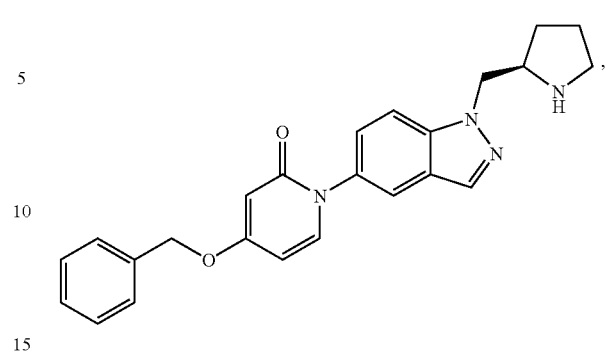
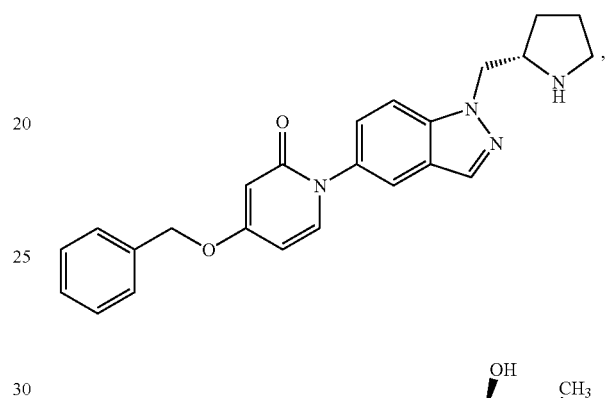
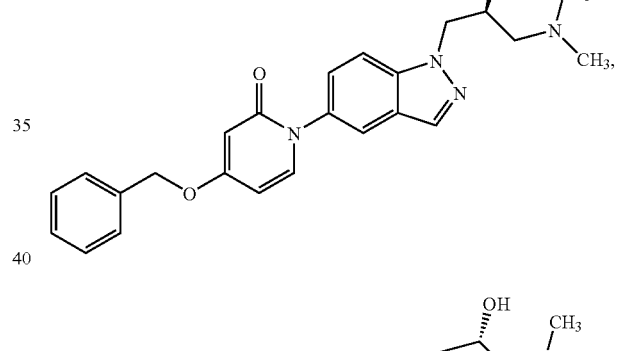
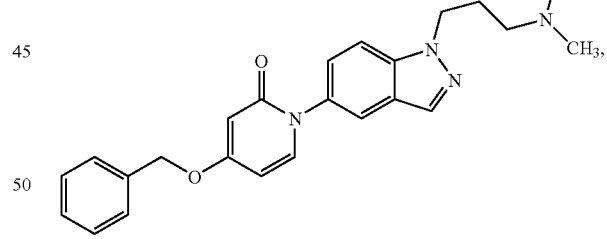
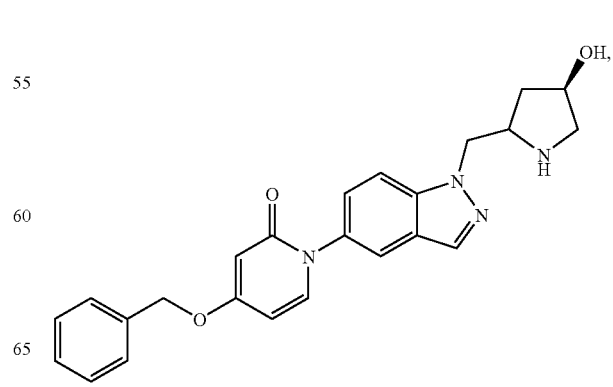

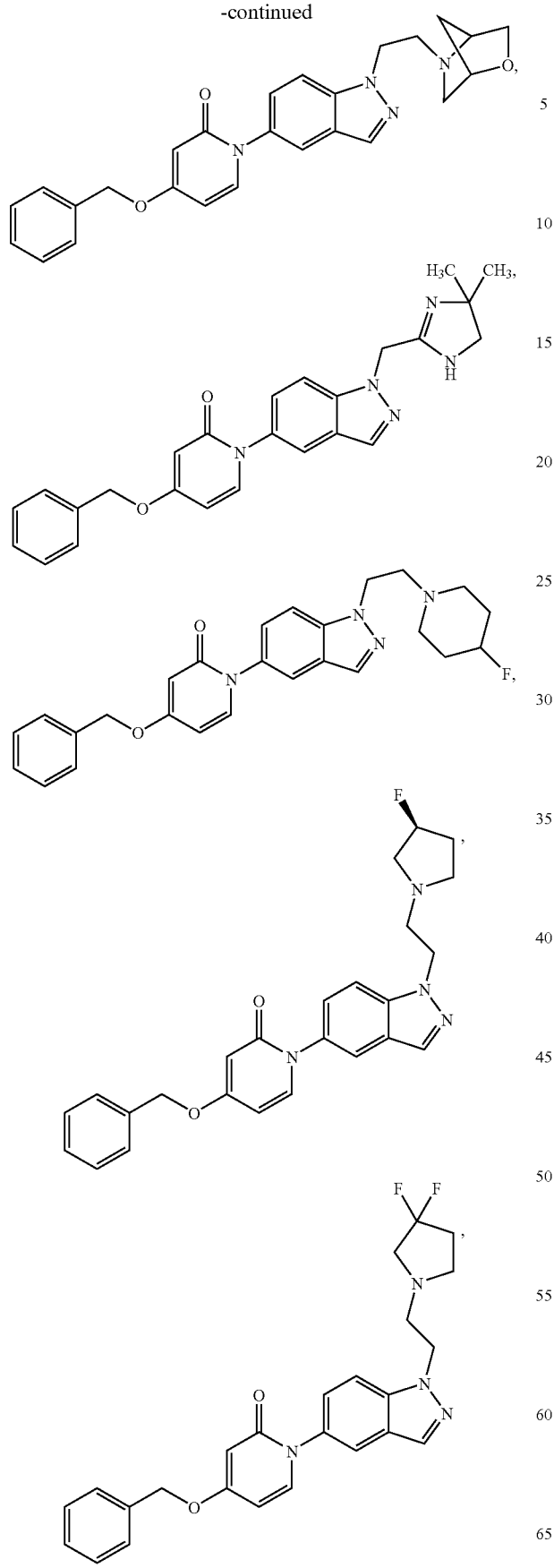
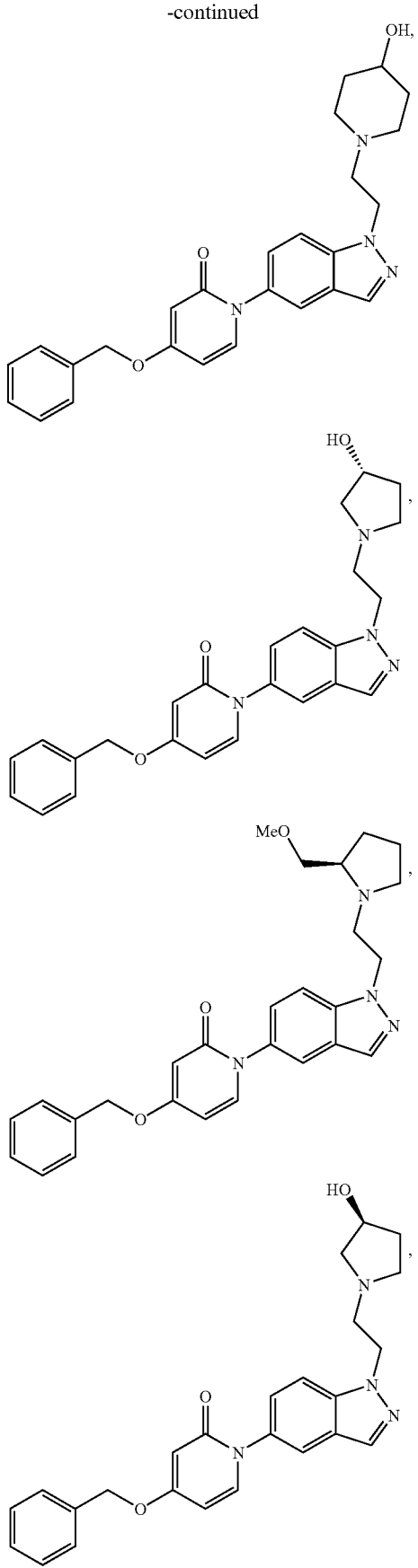

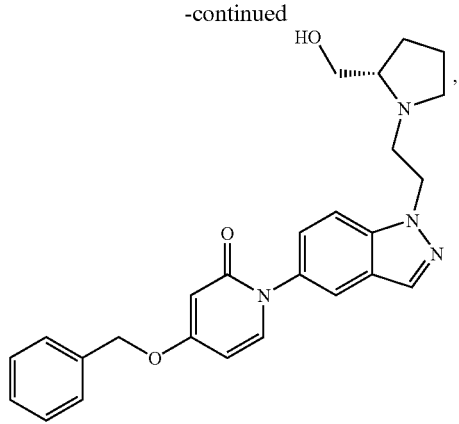
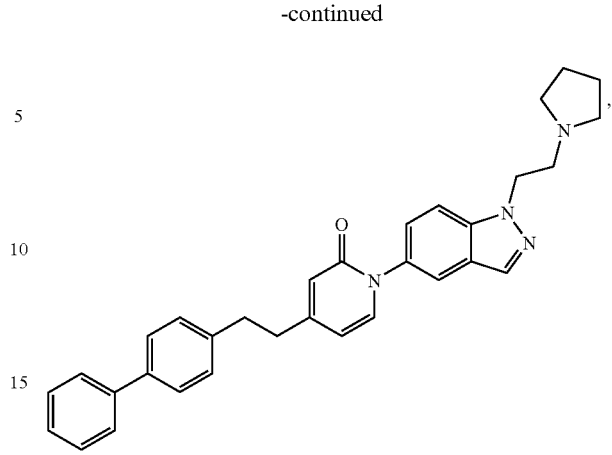

-continued
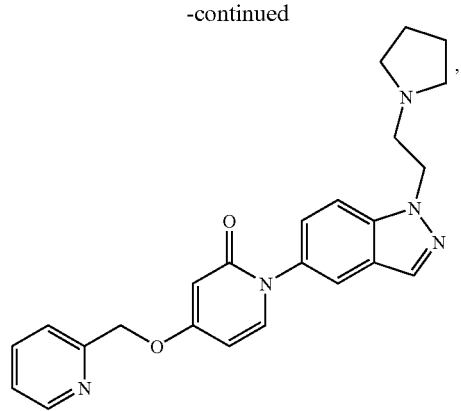
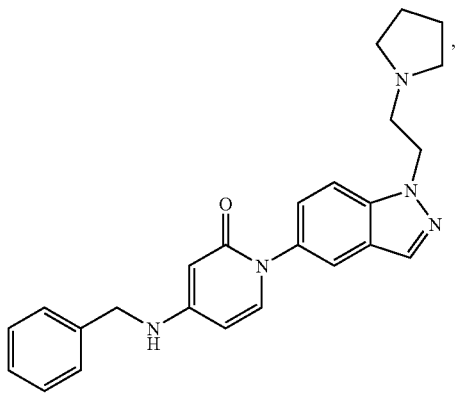
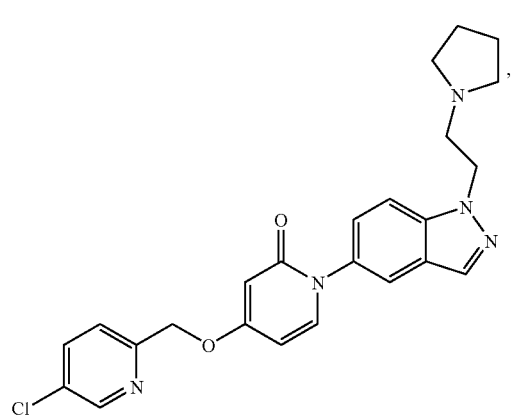
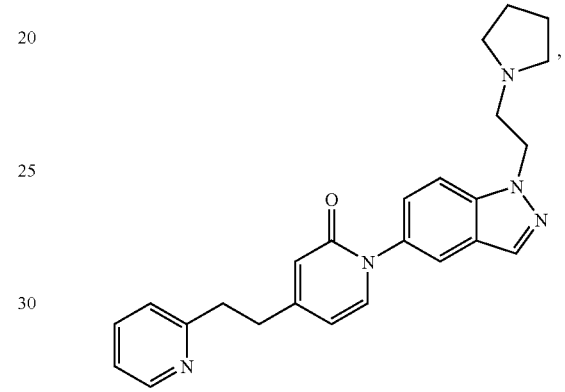
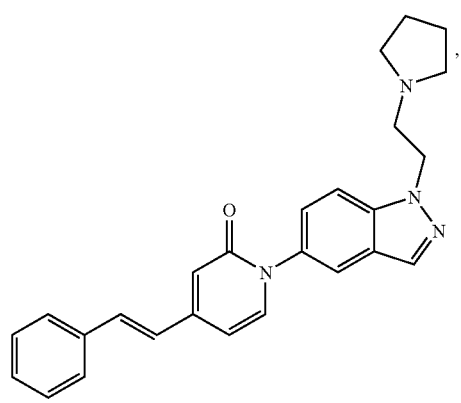
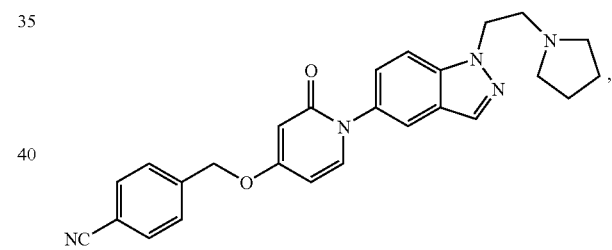
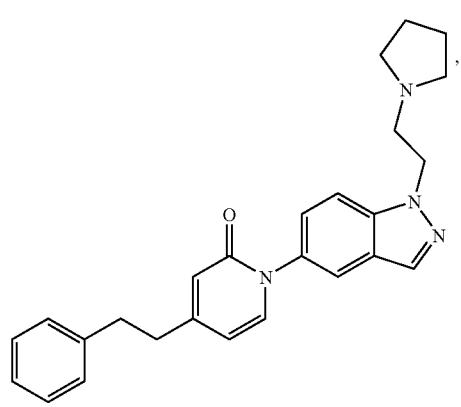
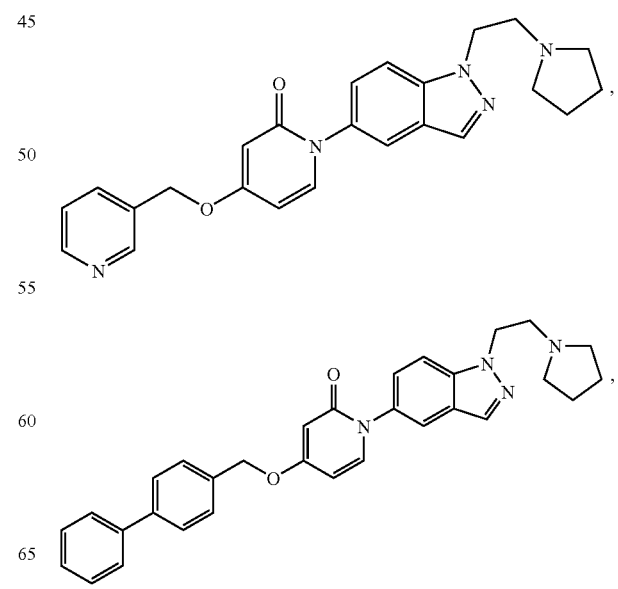

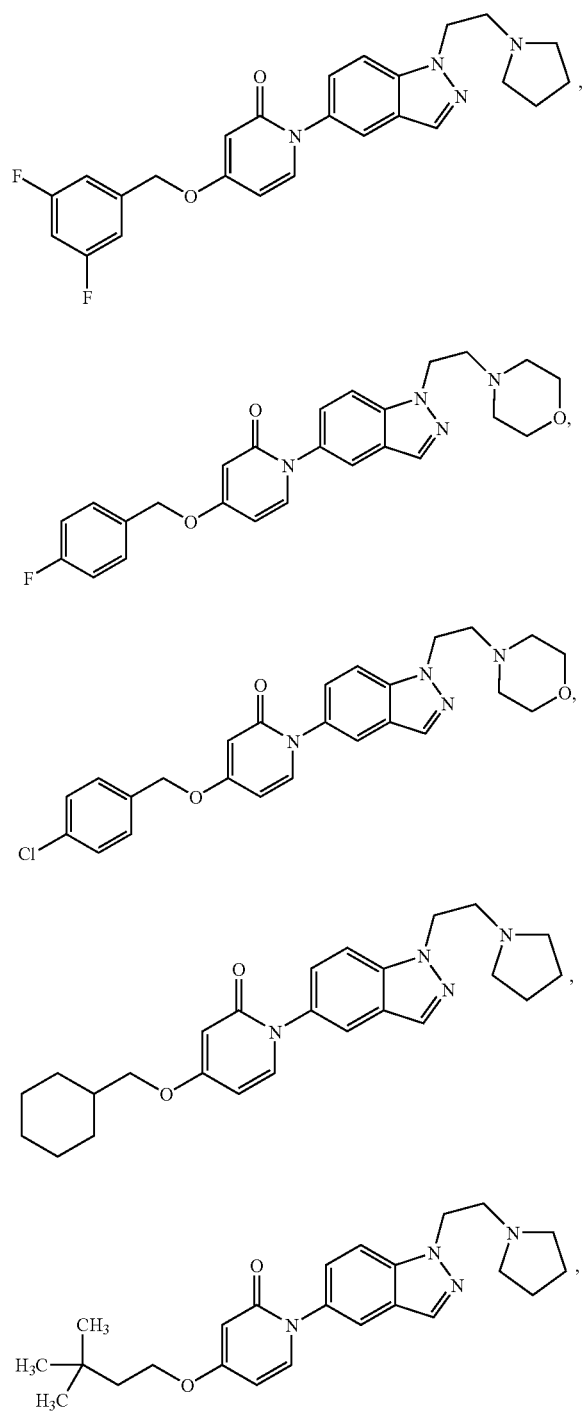

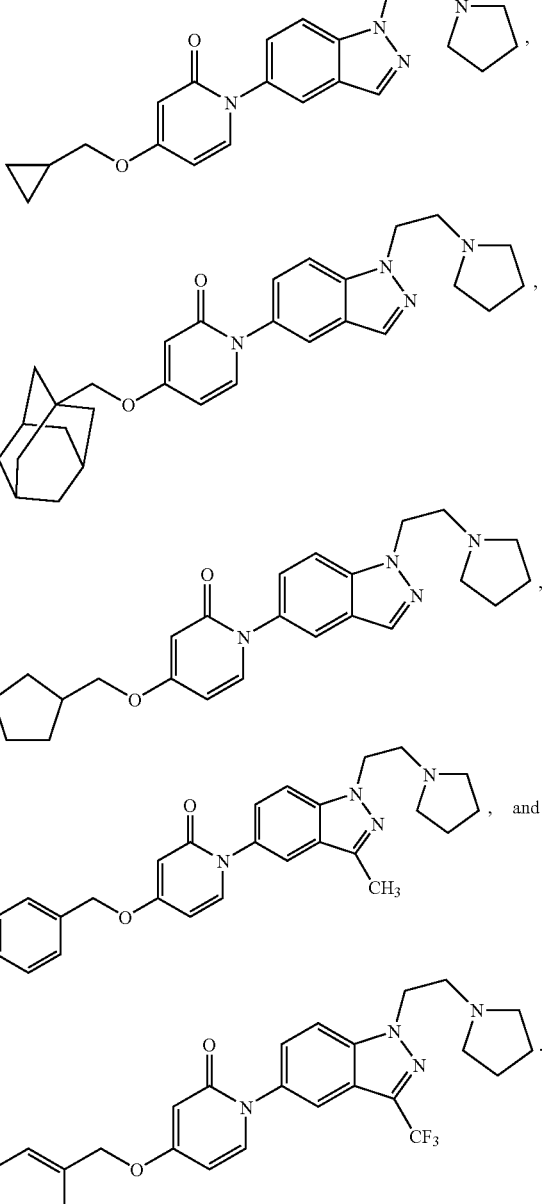

In some embodiments the compound is in a pharmaceutically acceptable salt form. In some embodiments the salt is an HCl salt.

There is also provided, in accordance with embodiments of the invention, a pharmaceutical composition comprising a compound as described herein, and a pharmaceutically acceptable carrier, excipient or diluent therefore.

There is also provided, in accordance with embodiments of the invention, a method of treating obesity, comprising administering to a patient in need of obesity reduction an obesity-reducing effective amount of a compound as described herein.

There is also provided, in accordance with embodiments of the invention, a method of treating anxiety, comprising administering to a patient in need of such treatment a therapeutically effective amount of a compound as described herein.

There is also provided, in accordance with embodiments of the invention, a method of treating depression, comprising administering to a patient in need of such treatment a therapeutically effective amount of a compound as described herein.

There is also provided, in accordance with embodiments of the invention, a method of treating non-alcoholic fatty liver disease, comprising administering to a patient in need of such treatment a therapeutically effective amount of a compound as described herein.

There is also provided, in accordance with embodiments of the invention, a method of treating a disease or condition which is susceptible to treatment with an $MCH_1$ receptor modulator, comprising administering to a patient in need thereof a therapeutically effective amount of a compound as described herein.

DEFINITIONS

Throughout this specification the terms and substituents retain their definitions.

Alkyl is intended to include linear, branched, or cyclic hydrocarbon structures and combinations thereof. When not otherwise restricted, the term refers to alkyl of 20 or fewer carbons. Lower alkyl refers to alkyl groups of 1, 2, 3, 4, 5 and 6 carbon atoms. Examples of lower alkyl groups include methyl, ethyl, propyl, isopropyl, butyl, s- and t-butyl and the like. Cycloalkyl is a subset of alkyl and includes cyclic hydrocarbon groups of 3, 4, 5, 6, 7, and 8 carbon atoms. Examples of cycloalkyl groups include c-propyl, c-butyl, c-pentyl, norbornyl, adamantyl and the like.

$C_1$ to $C_{20}$ Hydrocarbon (e.g. $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$) includes alkyl, cycloalkyl, alkenyl, alkynyl, aryl and combinations thereof. Examples include benzyl, phenethyl, cyclohexylmethyl, camphoryl and naphthylethyl. The term "phenylene" refers to ortho, meta or para residues of the formulae:

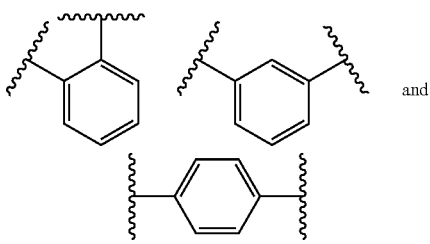

and

Alkoxy or alkoxyl refers to groups of 1, 2, 3, 4, 5, 6, 7 or 8 carbon atoms of a straight, branched, cyclic configuration and combinations thereof attached to the parent structure through an oxygen. Examples include methoxy, ethoxy, propoxy, isopropoxy, cyclopropyloxy, cyclohexyloxy and the like. Lower-alkoxy refers to groups containing one to four carbons. For the purposes of the present patent application alkoxy also includes methylenedioxy and ethylenedioxy in which each oxygen atom is bonded to the atom, chain or ring from which the methylenedioxy or ethylenedioxy group is pendant so as to form a ring. Thus, for example, phenyl substituted by alkoxy may be, for example,

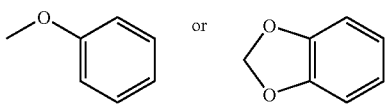

or

Oxaalkyl refers to alkyl residues in which one or more carbons (and their associated hydrogens) have been replaced by oxygen. Examples include methoxypropoxy, 3,6,9-trioxadecyl and the like. The term oxaalkyl is intended as it is understood in the art [see *Naming and Indexing of Chemical Substances for Chemical Abstracts*, published by the American Chemical Society, ¶196, but without the restriction of ¶127(a)], i.e. it refers to compounds in which the oxygen is bonded via a single bond to its adjacent atoms (forming ether bonds). Similarly, thiaalkyl and azaalkyl refer to alkyl residues in which one or more carbons have been replaced by sulfur or nitrogen, respectively. Examples include ethylaminoethyl and methylthiopropyl.

Acyl refers to groups of 1, 2, 3, 4, 5, 6, 7 and 8 carbon atoms of a straight, branched, cyclic configuration, saturated, unsaturated and aromatic and combinations thereof, attached to the parent structure through a carbonyl functionality. One or more carbons in the acyl residue may be replaced by nitrogen, oxygen or sulfur as long as the point of attachment to the parent remains at the carbonyl. Examples include formyl, acetyl, propionyl, isobutyryl, t-butoxycarbonyl, benzoyl, benzyloxycarbonyl and the like. Lower-acyl refers to groups containing one to four carbons.

Aryl and heteroaryl refer to aromatic or heteroaromatic rings, respectively, as substituents. Heteroaryl contains one, two or three heteroatoms selected from O, N, or S. Both refer to monocyclic 5- or 6-membered aromatic or heteroaromatic rings, bicyclic 9- or 10-membered aromatic or heteroaromatic rings and tricyclic 13- or 14-membered aromatic or heteroaromatic rings. Aromatic 6, 7, 8, 9, 10, 11, 12, 13 and 14-membered carbocyclic rings include, e.g., benzene, naphthalene, indane, tetralin, and fluorene and the 5, 6, 7, 8, 9 and 10-membered aromatic heterocyclic rings include, e.g., imidazole, pyridine, indole, thiophene, benzopyranone, thiazole, furan, benzimidazole, quinoline, isoquinoline, quinoxaline, pyrimidine, pyrazine, tetrazole and pyrazole.

Arylalkyl means an alkyl residue attached to an aryl ring. Examples are benzyl, phenethyl and the like.

Substituted alkyl, aryl, cycloalkyl, heterocyclyl etc. refer to alkyl, aryl, cycloalkyl, or heterocyclyl wherein up to three H atoms in each residue are replaced with halogen, haloalkyl, hydroxy, loweralkoxy, carboxy, carboalkoxy (also referred to as alkoxycarbonyl), carboxamido (also referred to as alkylaminocarbonyl), cyano, carbonyl, nitro, amino, alkylamino, dialkylamino, mercapto, alkylthio, sulfoxide, sulfone, acylamino, amidino, phenyl, benzyl, heteroaryl, phenoxy, benzyloxy, or heteroaryloxy.

The term "halogen" means fluorine, chlorine, bromine or iodine.

The term "prodrug" refers to a compound that is made more active in vivo. Commonly the conversion of prodrug to drug occurs by enzymatic processes in the liver or blood of the mammal. Many of the compounds of the invention may be chemically modified without absorption into the systemic circulation, and in those cases, activation in vivo may come about by chemical action (as in the acid-catalyzed cleavage in the stomach) or through the intermediacy of enzymes and microflora in the gastrointestinal GI tract.

In the characterization of some of the substituents, it is recited that certain substituents may combine to form rings. Unless stated otherwise, it is intended that such rings may exhibit various degrees of unsaturation (from fully saturated to fully unsaturated), may include heteroatoms and may be substituted with lower alkyl or alkoxy.

It will be recognized that the compounds of this invention can exist in radiolabeled form, i.e., the compounds may contain one or more atoms containing an atomic mass or mass number different from the atomic mass or mass number usually found in nature. Radioisotopes of hydrogen, carbon, phosphorous, fluorine, iodine and chlorine include $^3$H, $^{14}$C, $^{35}$S, $^{18}$F, $^{32}$P, $^{33}$P, $^{125}$I, and $^{36}$Cl, respectively. Compounds that contain those radioisotopes and/or other radioisotopes of other atoms are within the scope of this invention. Radiolabeled compounds described herein and prodrugs thereof can generally be prepared by methods well known to those skilled in the art. Conveniently, such radiolabeled compounds can be prepared by carrying out the procedures disclosed in the Examples and Schemes by substituting a readily available radiolabeled reagent for a non-radiolabeled reagent.

The terms "methods of treating or preventing" mean amelioration, prevention or relief from the symptoms and/or effects associated with lipid disorders. The term "preventing" as used herein refers to administering a medicament beforehand to forestall or obtund an acute episode or, in the case of a chronic condition to diminish the likelihood or seriousness of the condition. The person of ordinary skill in the medical art (to which the present method claims are directed) recognizes that the term "prevent" is not an absolute term. In the medical art it is understood to refer to the prophylactic administration of a drug to substantially diminish the likelihood or seriousness of a condition, and this is the sense intended in applicants' claims. As used herein, reference to "treatment" of a patient is intended to include prophylaxis Throughout this application, various references are referred to. Each of the patents, patent applications, patent publications, and references mentioned herein is hereby incorporated by reference in its entirety.

The term "mammal" is used in its dictionary sense. The term "mammal" includes, for example, mice, hamsters, rats, cows, sheep, pigs, goats, and horses, monkeys, dogs (e.g., *Canis familiaris*), cats, rabbits, guinea pigs, and primates, including humans.

Compounds described herein may contain one or more asymmetric centers and may thus give rise to enantiomers, diastereomers, and other stereoisomeric forms. Each chiral center may be defined, in terms of absolute stereochemistry, as (R)- or (S)-. The present invention is meant to include all such possible isomers, as well as mixtures thereof, including racemic and optically pure forms. Optically active (R)- and (S)-, (−)- and (+)-, or (D)- and (L)-isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. The configuration of any carbon-carbon double bond appearing herein is selected for convenience only and is not intended to designate a particular configuration; thus a carbon-carbon double bond depicted arbitrarily herein as E may be Z, E, or a mixture of the two in any proportion. Likewise, all tautomeric forms are also intended to be included.

As used herein, and as would be understood by the person of skill in the art, the recitation of "a compound" is intended to include salts, solvates and inclusion complexes of that compound as well as any stereoisomeric form, or a mixture of any such forms of that compound in any ratio Thus, in accordance with some embodiments of the invention, a compound as described herein, including in the contexts of pharmaceutical compositions, methods of treatment, and compounds per se, is provided as the salt form. In accordance with some embodiments of the invention, the salt is a hydrochloride salt.

The term "enantiomeric excess" is well known in the art and is defined for a resolution of ab into a+b as $$ee_a = \left( \frac{conc.\ of\ a - conc.\ of\ b}{conc.\ of\ a + conc.\ of\ b} \right) \times 100$$

The term "enantiomeric excess" is related to the older term "optical purity" in that both are measures of the same phenomenon. The value of ee will be a number from 0 to 100, zero being racemic and 100 being pure, single enantiomer. A compound which in the past might have been called 98% optically pure is now more precisely described as 96% ee; in other words, a 90% ee reflects the presence of 95% of one enantiomer and 5% of the other in the material in question.

Terminology related to "protecting", "deprotecting" and "protected" functionalities occurs throughout this application. Such terminology is well understood by persons of skill in the art and is used in the context of processes which involve sequential treatment with a series of reagents. In that context, a protecting group refers to a group which is used to mask a functionality during a process step in which it would otherwise react, but in which reaction is undesirable. The protecting group prevents reaction at that step, but may be subsequently removed to expose the original functionality. The removal or "deprotection" occurs after the completion of the reaction or reactions in which the functionality would interfere. Thus, when a sequence of reagents is specified, as it is in the processes of the invention, the person of ordinary skill can readily envision those groups that would be suitable as "protecting groups" Suitable groups for that purpose are discussed in standard textbooks in the field of chemistry, such as *Protective Groups in Organic Synthesis* by T. W. Greene [John Wiley & Sons, New York, 1991], which is incorporated herein by reference. Particular attention is drawn to the chapters entitled "Protection for the Hydroxyl Group, Including 1,2- and 1,3-Diols" (pages 10-86).

The following abbreviations and terms have the indicated meanings throughout: Ac=acetyl; Bu=butyl; c-=cyclo; DIEA=N,N-diisopropylethyl amine; HOAc=acetic acid; mesyl=methanesulfonyl, rt=room temperature; sat'd=saturated; s-=secondary; t-=tertiary; TMS=trimethylsilyl; tosyl=p-toluenesulfonyl. The abbreviations HPLC, THF, DCM and DMSO represent high performance liquid chromatography, tetrahydrofuran, dichloromethane and dimethylsulfoxide, respectively. The abbreviations Me, Et, Ph, Tf, Ts, Boc and Ms represent methyl, ethyl, phenyl, trifluoromethanesulfonyl, toluenesulfonyl, tert-butyloxycarbonyl and methanesulfonyl respectively. The term dppf refers to 1,1'-Bis-(diphosphenylphosphino)ferrocene. A comprehensive list of abbreviations utilized by organic chemists (i.e. persons of ordinary skill in the art) appears in the first issue of each volume of the *Journal of Organic Chemistry*. The list, which is typically presented in a table entitled "Standard List of Abbreviations" is incorporated herein by reference.

While it may be possible for the compounds of the invention to be administered as the raw chemical, it is preferable to present them as a pharmaceutical composition. In accordance with an embodiment of the present invention there is provided a pharmaceutical composition comprising a compound of formula I or a pharmaceutically acceptable salt or solvate thereof, together with one or more pharmaceutically carriers thereof and optionally one or more other therapeutic ingredients. The carrier(s) must be "acceptable" in the sense of being compatible with the other ingredients of the formulation and not deleterious to the recipient thereof. Furthermore, notwithstanding the statement in paragraph 36 above regarding the term "compound" including salts thereof as well, so that independent claims reciting "a compound" will be understood as referring to salts thereof as well, if in an independent claim reference is made to a compound or a pharmaceutically acceptable salt thereof, it will be understood that claims which depend from that independent claim which refer to such a compound also include pharmaceutically acceptable salts of the compound, even if explicit reference is not made to the salts in the dependent claim.

The formulations include those suitable for oral, parenteral (including subcutaneous, intradermal, intramuscular, intravenous and intraarticular), rectal and topical (including dermal, buccal, sublingual and intraocular) administration. The most suitable route may depend upon the condition and disorder of the recipient. The formulations may conveniently be presented in unit dosage form and may be prepared by any of the methods well known in the art of pharmacy. Such methods include the step of bringing into association a compound of formula I or a pharmaceutically acceptable salt or solvate thereof ("active ingredient") with the carrier, which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent. The tablets may optionally be coated or scored and may be formulated so as to provide sustained, delayed or controlled release of the active ingredient therein. The pharmaceutical compositions may include a "pharmaceutically acceptable inert carrier", and this expression is intended to include one or more inert excipients, which include starches, polyols, granulating agents, microcrystalline cellulose, diluents, lubricants, binders, disintegrating agents, and the like. If desired, tablet dosages of the disclosed compositions may be coated by standard aqueous or non-aqueous techniques, "Pharmaceutically acceptable carrier" also encompasses controlled release means.

Pharmaceutical compositions may also optionally include other therapeutic ingredients, anti-caking agents, preservatives, sweetening agents, colorants, flavors, desiccants, plasticizers, dyes, and the like. Any such optional ingredient must be compatible with the compound of formula I to insure the stability of the formulation. The composition may contain other additives as needed, including for example lactose, glucose, fructose, galactose, trehalose, sucrose, maltose, raffinose, maltitol, melezitose, stachyose, lactitol, palatinite, starch, xylitol, mannitol, myoinositol, and the like, and hydrates thereof, and amino acids, for example alanine, glycine and betaine, and peptides and proteins, for example albumen.

Examples of excipients for use as the pharmaceutically acceptable carriers and the pharmaceutically acceptable inert carriers and the aforementioned additional ingredients include, but are not limited to binders, fillers, disintegrants, lubricants, anti-microbial agents, and coating agents.

The dose range for adult humans is generally from 0.005 mg to 10 g/day orally. Tablets or other forms of presentation provided in discrete units may conveniently contain an amount of compound of formula I which is effective at such dosage or as a multiple of the same, for instance, units containing 5 mg to 500 mg, usually around 10 mg to 200 mg. The precise amount of compound administered to a patient will be the responsibility of the attendant physician. However, the dose employed will depend on a number of factors, including the age and sex of the patient, the precise disorder being treated, and its severity.

A dosage unit (e.g. an oral dosage unit) can include from, for example, 1 to 30 mg, 1 to 40 mg, 1 to 100 mg, 1 to 300 mg, 1 to 500 mg, 2 to 500 mg, 3 to 100 mg, 5 to 20 mg, 5 to 100 mg (e.g. 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 150 mg, 200 mg, 250 mg, 300 mg, 350 mg, 400 mg, 450 mg, 500 mg) of a compound described herein.

For additional information about pharmaceutical compositions and their formulation, see, for example, Remington. The Science and Practice of Pharmacy, 20$^{th}$ Edition, 2000.

The agents can be administered, e.g., by intravenous injection, intramuscular injection, subcutaneous injection, intraperitoneal injection, topical, sublingual, intraarticular (in the joints), intradermal, buccal, ophthalmic (including intraocular), intranasaly (including using a cannula), or by other routes. The agents can be administered orally, e.g., as a tablet or cachet containing a predetermined amount of the active ingredient, gel, pellet, paste, syrup, bolus, electuary, slurry, capsule, powder, granules, as a solution or a suspension in an aqueous liquid or a non-aqueous liquid, as an oil-in-water liquid emulsion or a water-in-oil liquid emulsion, via a micellar formulation (see, e.g. WO 97/11682) via a liposomal formulation (see, e.g., EP 736299, WO 99/59550 and WO 97/13500), via formulations described in WO 03/094886 or in some other form. The agents can also be administered transdermally (i.e. via reservoir-type or matrix-type patches, microneedles, thermal poration, hypodermic needles, iontophoresis, electroporation, ultrasound or other forms of sonophoresis, jet injection, or a combination of any of the preceding methods (Prausnitz et al. 2004, Nature Reviews Drug Discovery 3:115)). The agents can be administered locally, for example, at the site of injury to an injured blood vessel. The agents can be coated on a stent. The agents can be administered using high-velocity transdermal particle injection techniques using the hydrogel particle formulation described in U.S. 20020061336. Additional particle formulations are described in WO 00/45792, WO 00/53160, and WO 02/19989. An example of a transdermal formulation containing plaster and the absorption promoter dimethylisosorbide can be found in WO 89/04179. WO 96/11705 provides formulations suitable for transdermal administration. The agents can be administered in the form a suppository or by other vaginal or rectal means. The agents can be administered in a transmembrane formulation as described in WO 90/07923. The agents can be administered non-invasively via the dehydrated particles described in U.S. Pat. No. 6,485,706. The agent can be administered in an enteric-coated drug formulation as described in WO 02/49621. The agents can be administered intranasaly using the formulation described in U.S. Pat. No. 5,179,079. Formulations suitable for parenteral injection are described in WO 00/62759. The agents can be administered using the casein formulation described in U.S. 20030206939 and WO 00/06108. The agents can be administered using the particulate formulations described in U.S. 20020034536.

The agents, alone or in combination with other suitable components, can be administered by pulmonary route utilizing several techniques including but not limited to intratracheal instillation (delivery of solution into the lungs by syringe), intratracheal delivery of liposomes, insufflation (administration of powder formulation by syringe or any other similar device into the lungs) and aerosol inhalation. Aerosols (e.g., jet or ultrasonic nebulizers, metered-dose inhalers (MDIs), and dry-Powder inhalers (DPIs)) can also be used in intranasal applications. Aerosol formulations are stable dispersions or suspensions of solid material and liquid droplets in a gaseous medium and can be placed into pressurized acceptable propellants, such as hydrofluoroalkanes (HFAs, i.e. HFA-134a and HFA-227, or a mixture thereof), dichlorodifluoromethane (or other chlorofluorocarbon propellants such as a mixture of Propellants 11, 12, and/or 114), propane, nitrogen, and the like. Pulmonary formulations may include permeation enhancers such as fatty acids, and saccharides, chelating agents, enzyme inhibitors (e.g., protease inhibitors), adjuvants (e.g., glycocholate, surfactin, span 85, and nafamostat), preservatives (e.g., benzalkonium chloride or chlorobutanol), and ethanol (normally up to 5% but possibly up to 20%, by weight). Ethanol is commonly included in aerosol compositions as it can improve the function of the metering valve and in some cases also improve the stability of the dispersion. Pulmonary formulations may also include surfactants which include but are not limited to bile salts and those described in U.S. Pat. No. 6,524,557 and references therein. The surfactants described in U.S. Pat. No. 6,524,557, e.g., a $C_8$-$C_{16}$ fatty acid salt, a bile salt, a phospholipid, or alkyl saccharide are advantageous in that some of them also reportedly enhance absorption of the compound in the formulation. Also suitable in the invention are dry powder formulations comprising a therapeutically effective amount of active compound blended with an appropriate carrier and adapted for use in connection with a dry-Powder inhaler. Absorption enhancers which can be added to dry powder formulations of the present invention include those described in U.S. Pat. No. 6,632,456. WO 02/080884 describes new methods for the surface modification of powders. Aerosol formulations may include U.S. Pat. No. 5,230,884, U.S. Pat. No. 5,292,499, WO 017/8694, WO 01/78696, U.S. 2003019437, U.S. 20030165436, and WO 96/40089 (which includes vegetable oil). Sustained release formulations suitable for inhalation are described in U.S. 20010036481A1, 20030232019A1, and U.S. 20040018243A1 as well as in WO 01/13891, WO 02/067902, WO 03/072080, and WO 03/079885 Pulmonary formulations containing microparticles are described in WO 03/015750, U.S. 20030008013, and WO 00/00176. Pulmonary formulations containing stable glassy state powder are described in U.S. 20020141945 and U.S. Pat. No. 6,309,671. Other aerosol formulations are described in EP 1338272A1 WO 90/09781, U.S. Pat. No. 5,348,730, U.S. Pat. No. 6,436,367, WO 91/04011, and U.S. Pat. No. 6,294,153 and U.S. Pat. No. 6,290,987 describes a liposomal based formulation that can be administered via aerosol or other means. Powder formulations for inhalation are described in U.S. 20030053960 and WO 01/60341 The agents can be administered intranasally as described in U.S. 20010038824.

Solutions of medicament in buffered saline and similar vehicles are commonly employed to generate an aerosol in a nebulizer. Simple nebulizers operate on Bernoulli's principle and employ a stream of air or oxygen to generate the spray particles. More complex nebulizers employ ultrasound to create the spray particles. Both types are well known in the art and are described in standard textbooks of pharmacy such as Sprowls' American Pharmacy and Remington's The Science and Practice of Pharmacy. Other devices for generating aerosols employ compressed gases, usually hydrofluorocarbons and chlorofluorocarbons, which are mixed with the medicament and any necessary excipients in a pressurized container, these devices are likewise described in standard textbooks such as Sprowls and Remington.

The agent can be incorporated into a liposome to improve half-life. The agent can also be conjugated to polyethylene glycol (PEG) chains. Methods for pegylation and additional formulations containing PEG-conjugates (i.e. PEG-based hydrogels, PEG modified liposomes) can be found in Harris and Chess, Nature Reviews Drug Discovery 2:214-221 and the references therein. The agent can be administered via a nanocochleate or cochleate delivery vehicle (BioDelivery Sciences International). The agents can be delivered transmucosally (i.e. across a mucosal surface such as the vagina, eye or nose) using formulations such as that described in U.S. Pat. No. 5,204,108. The agents can be formulated in microcapsules as described in WO 88/01165. The agent can be administered intra-orally using the formulations described in U.S. 20020055496, WO 00/47203, and U.S. Pat. No. 6,495,120. The agent can be delivered using nanoemulsion formulations described in WO 01/91728A2.

Table 1 lists compounds representative of embodiments of the invention.

In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants that are in themselves known, but are not mentioned here.

Processes for obtaining the compounds of the invention are presented below. Other compounds of the invention may be prepared in analogous fashion to those whose synthesis is exemplified herein. The procedures below illustrate such methods. Furthermore, although the syntheses depicted herein may result in the preparation of enantiomers having a particular stereochemistry, included within the scope of the present invention are compounds of formula I in any stereoisomeric form, and preparation of compounds of formula I in stereoisomeric forms other than those depicted herein would be obvious to one of ordinary skill in the chemical arts based on the procedures presented herein.

Synthetic Methods

Scheme 1

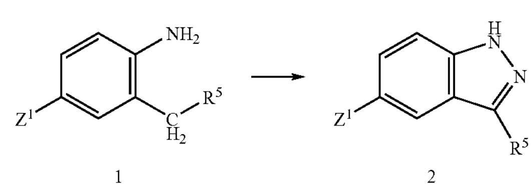

1 2

Compounds of formula 2 (wherein $Z^1$ is chlorine, bromine or iodine; $R^5$ is H or optionally substituted lower alkyl) can be prepared by treating compounds of formula 1 with $NaNO_2$ in acetic acid at room temperature.

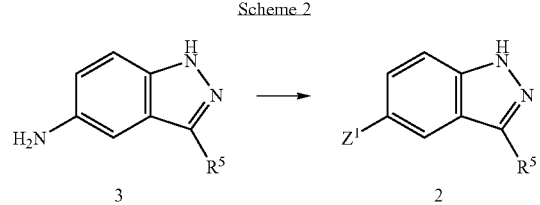

Alternatively, compounds of formula 2 (wherein $Z^1$ is chlorine, bromine or iodine; $R^5$ is H or optionally substituted lower alkyl) can be prepared by treatment of amino indazoles 3 with $NaNO_2$ and copper halide.

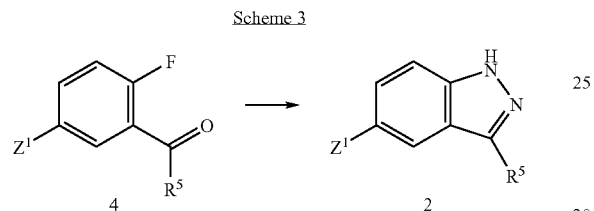

Alternatively, compounds of formula 2 can be prepared by treatment of aldehydes or ketones 4 (wherein $Z^1$ is chlorine, bromine or iodine; $R^5$ is H or optionally substituted lower alkyl) with hydrazine under heated conditions.

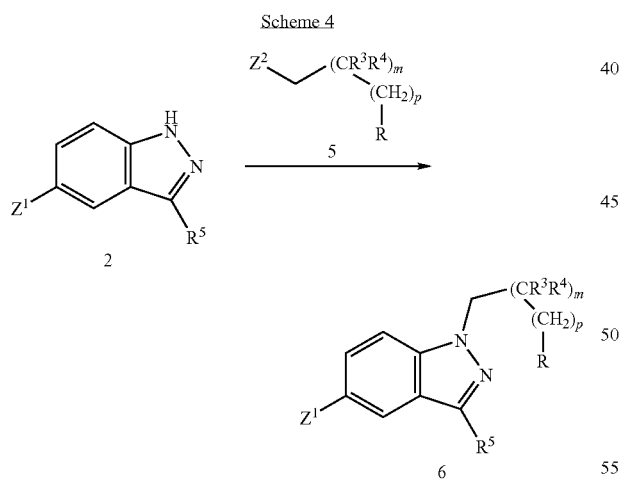

Compounds of formula 2 (wherein $Z^1$ is chlorine, bromine or iodine; $R^5$ is H or optionally substituted lower alkyl) can be treated with base and compounds of formula 5 (wherein $Z^2$=halogen, methanesulfonate, toluenesulfonate or the like; m and p are each or 1, provided that m+p is at least 1; $R^3$ and $R^4$ are each independently selected from H, —OH and lower alkyl; R is as defined above) at ambient temperature or under heated conditions to give compounds of formula 6. Typical bases include but are not limited to cesium carbonate, potassium carbonate and sodium hydride. Typical solvents include but are not limited to N,N-dimethylformamide (DMF), dimethylsulfoxide (DMSO), acetonitrile and tetrahydrofuran (THF).

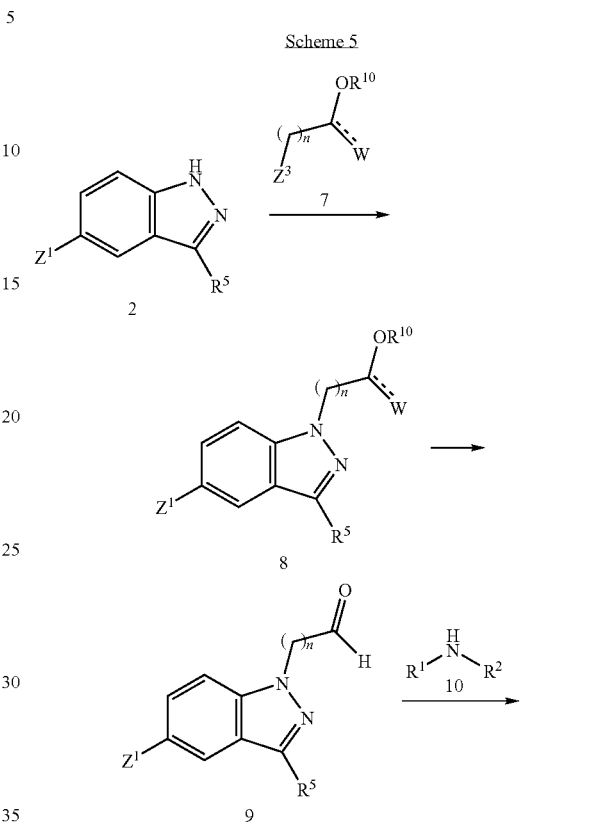

Alternatively, compounds of formula 2 (wherein $Z^1$ is chlorine, bromine or iodine; $R^5$ is H or optionally substituted lower alkyl) can be treated with base and compounds of formula 7 (wherein $Z^3$=halogen, methanesulfonate, toluenesulfonate or the like; W=O, $OR^{11}$ or H; $R^{10}$=an alkyl group, H or a protecting group such as tert-butyldimethylsilyl; $R^{11}$=alkyl; n=1 or 2) at ambient temperature or under heated conditions to give compounds of formula 8. Typical bases include but are not limited to cesium carbonate, potassium carbonate and sodium hydride. Typical solvents include but are not limited to N,N-dimethylformamide, dimethylsulfoxide, acetonitrile and tetrahydrofuran. In the case where W=$OR^{11}$, compounds of formula 8 can be treated under acidic reaction conditions to provide compounds of formula 9. In the case where W=H and $R^{10}$=a protecting group, compounds of formula 8 can be treated under appropriate deprotecting conditions to provide compounds of formula 8 wherein $R^{10}$=H. In the case where W=H and $R^{10}$=H, compounds of formula 8 can be treated with an oxidizing agent such as the Dess-Martin periodane or oxalyl chloride and DMSO to give compounds of formula 9 Treatment of compounds 9 with amines 10 and a reducing agent such as sodium borohydride, sodium cyanoborohydride, sodium triacetoxyborohydride, or picoline-borane complex can provide compounds of formula 11.

Compounds of formula 17 can be prepared by treating compounds of formula 14 (wherein $Z^4$ is chlorine, bromine or iodine) with a base such as sodium hydride and compounds of formula 15 (wherein B is aryl or heteroaryl; $R^7$, $R^8$, $R^9$ are each independently selected from H, —O-alkyl, alkyl, halo, —$CF_3$, —S(O)-alkyl, —S(O)$_2$-alkyl and —CN, $R^6$ is H or lower alkyl, X is O) under heated conditions to give compounds of formula 16. In turn, compounds of formula 16 can be treated with acetic anhydride under heated conditions followed by methanol and water or methanol and sodium hydroxide under ambient to heated conditions to provide compounds of formula 17, wherein X is O.

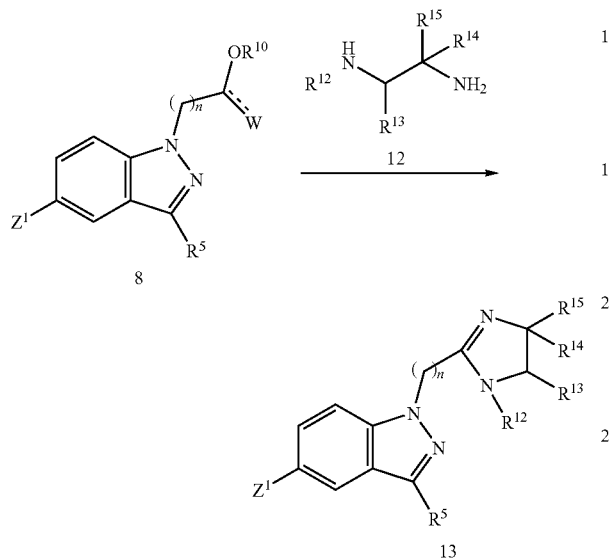

Additionally, in the case where W=O and $R^{10}$=alkyl, compounds of formula 8 can be treated with diamines 12 (wherein $R^{14}$ and $R^{15}$ are each independently H or alkyl, and either (i) $R^{12}$ and $R^{13}$ are each independently H or alkyl, or (ii) $R^{12}$ and $R^{13}$, together with the N atom to which $R^{12}$ is attached, form a 4 to 7-membered optionally substituted non-aromatic ring system) and trimethylaluminum to provide compounds of formula 13.

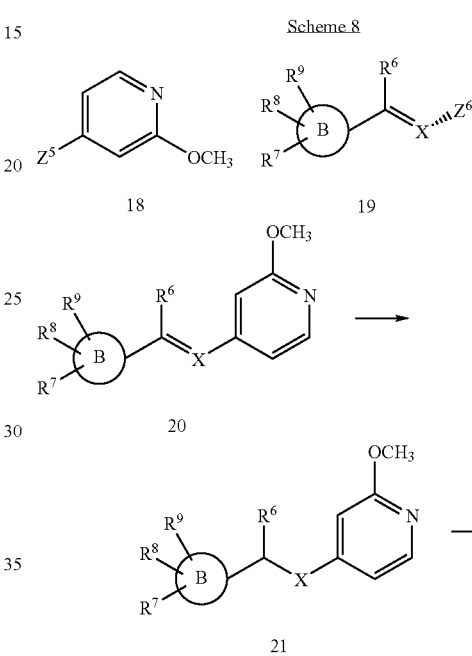

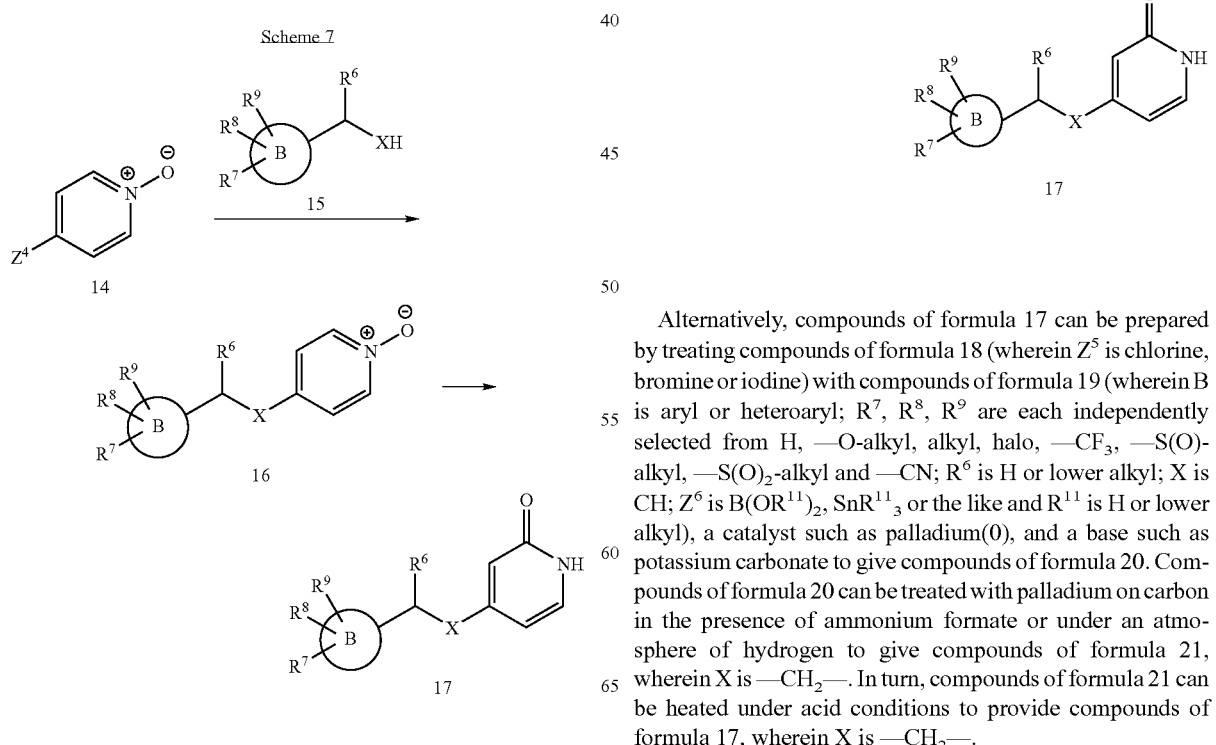

Alternatively, compounds of formula 17 can be prepared by treating compounds of formula 18 (wherein $Z^5$ is chlorine, bromine or iodine) with compounds of formula 19 (wherein B is aryl or heteroaryl; $R^7$, $R^8$, $R^9$ are each independently selected from H, —O-alkyl, alkyl, halo, —$CF_3$, —S(O)-alkyl, —S(O)$_2$-alkyl and —CN; $R^6$ is H or lower alkyl; X is CH; $Z^6$ is B(O$R^{11}$)$_2$, Sn$R^{11}_3$ or the like and $R^{11}$ is H or lower alkyl), a catalyst such as palladium(0), and a base such as potassium carbonate to give compounds of formula 20. Compounds of formula 20 can be treated with palladium on carbon in the presence of ammonium formate or under an atmosphere of hydrogen to give compounds of formula 21, wherein X is —$CH_2$—. In turn, compounds of formula 21 can be heated under acid conditions to provide compounds of formula 17, wherein X is —$CH_2$—.

Scheme 9

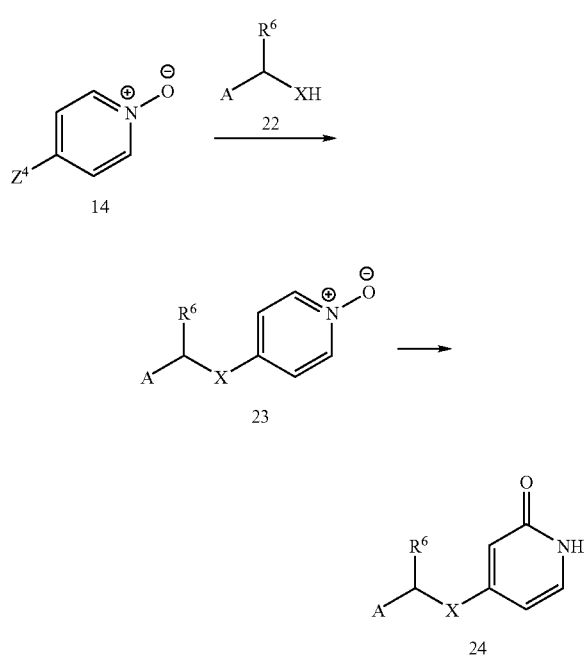

Compounds of formula 24 can be prepared by treating compounds of formula 14 (wherein $Z^4$ is chlorine, bromine or iodine) with a base such as sodium hydride and compounds of formula 22 (wherein A is $C_{3-10}$ non-aromatic hydrocarbon; $R^6$ is H or lower alkyl; X is O) under heated conditions to give compounds of formula 23. In turn, compounds of formula 23 can be treated with acetic anhydride under heated conditions followed by methanol and water or methanol and sodium hydroxide under ambient to heated conditions to provide compounds of formula 24.

Scheme 10

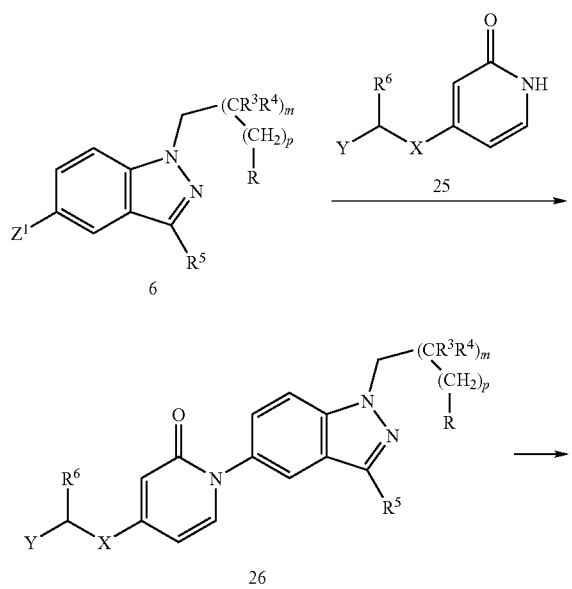

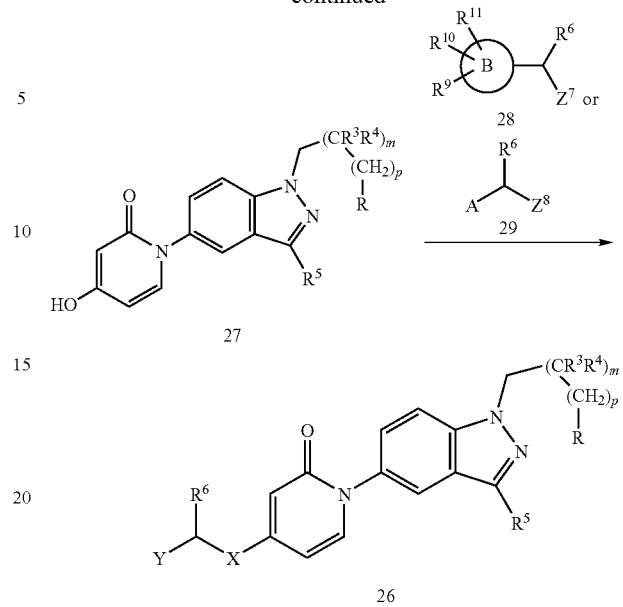

Compounds of formula 6 can be treated under heated conditions with a catalyst such as copper iodide, a ligand such as trans-1,2-diaminocyclohexane or 8-hydroxyquinoline, a base such as potassium carbonate, cesium carbonate or potassium phosphate and compounds of formula 25 (wherein X is —$CH_2$—, O, $R^6$ is H or lower alkyl; Y is as defined above) to give compounds of formula 26.

Additionally, in the case where Y is phenyl, $R^6$ is H and X is O, compounds of formula 26 can be treated with hydrogen and a catalyst such as palladium on carbon to provide compounds of formula 27. Further treatment of compounds of formula 27 with base and compounds of formula 28 (wherein $Z^7$ is $NH_2$, halogen, methanesulfonate, toluenesulfonate or the like; $R^6$ is H or lower alkyl) or compounds of formula 29 (wherein A is $C_{3-10}$ non-aromatic hydrocarbon, $R^6$ is H or lower alkyl; $Z^8$ is halogen, methanesulfonate, toluenesulfonate or the like) at ambient temperature or under heated conditions can provide compounds of formula 26, wherein X is O or N.

Scheme 11

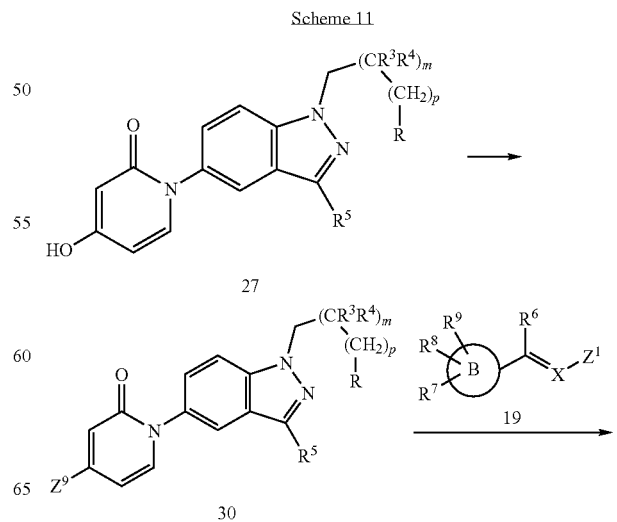

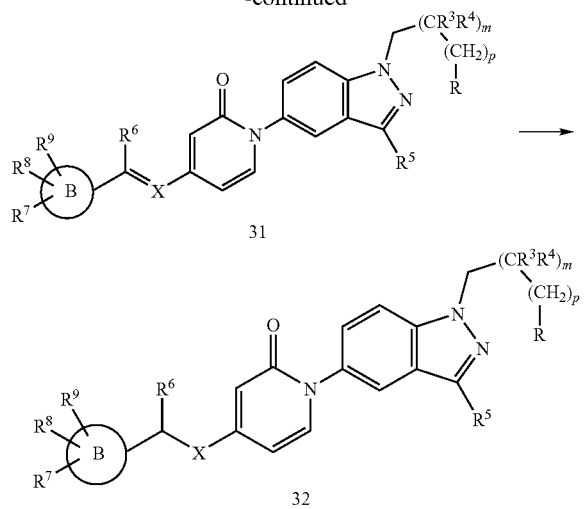

Alternatively, the hydroxyl group on compounds of formula 27 can be converted to an appropriate activating group to give compounds of formula 30. In the case where $Z^9$ is triflate, compounds of formula 27 can be treated with trifluoromethylsulfonic anhydride or N-phenyl trifluoromethanesulfonamide and a base such as pyridine or lithium bis(trimethylsilyl) amide under cooled conditions to give compounds of formula 30. Treatment of compounds of formula 30 with compounds of formula 19 (wherein B is aryl or heteroaryl; $R^7$, $R^8$, $R^9$ are each independently selected from H, —O-alkyl, alkyl, halo, —$CF_3$, —S(O)-alkyl, —$S(O)_2$-alkyl and —CN; $R^6$ is H or lower alkyl; X is CH; $Z^6$ is $B(OR^{11})_2$, $SnR^{11}_3$ or the like and $R^{11}$ is H or lower alkyl), a catalyst such as palladium(0), and a base such as potassium carbonate to give compounds of formula 31. Compounds of formula 31 can be treated with palladium on carbon in the presence of ammonium formate or under an atmosphere of hydrogen to give compounds of formula 32, wherein X is —$CH_2$—.

Scheme 12

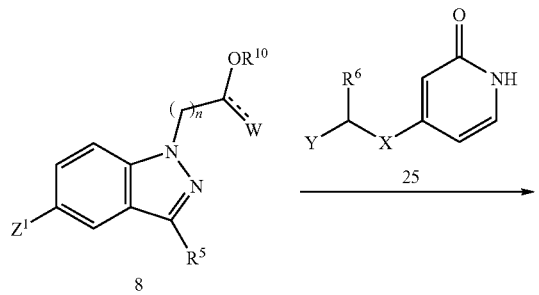

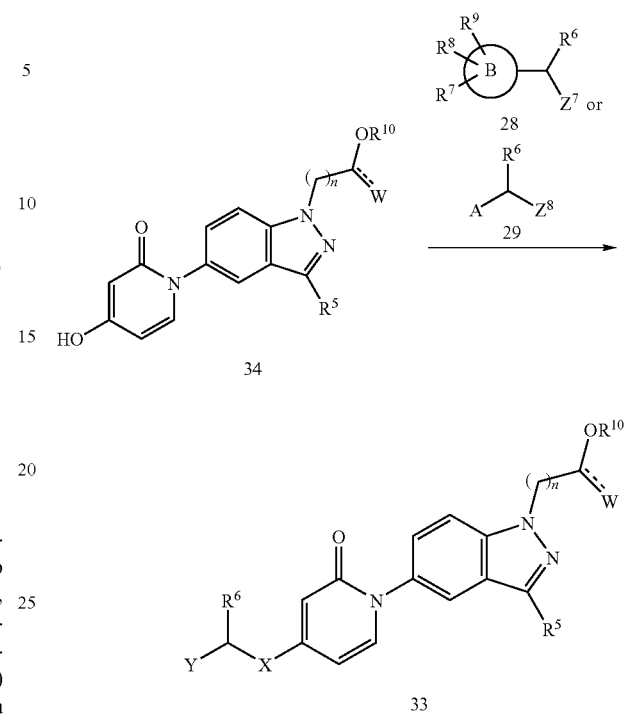

Compounds of formula 8 can be treated under heated conditions with a catalyst such as copper iodide, a ligand such as trans-1,2-diaminocyclohexane or 8-hydroxyquinoline, a base such as potassium carbonate, cesium carbonate or potassium phosphate and compounds of formula 25 (wherein X is —$CH_2$—, O, $R^6$ is H or lower alkyl; Y is as defined above) to give compounds of formula 33.

Additionally, in the case where Y is phenyl, $R^6$ is H and X is O, compounds of formula 19 can be treated with hydrogen and a catalyst such as palladium on carbon to provide compounds of formula 34. Further treatment of compounds of formula 34 with base and compounds of formula 28 (wherein $Z^7$ is $NH_2$, halogen, methanesulfonate, toluenesulfonate or the like; $R^6$ is H or lower alkyl) or compounds of formula 29 (wherein A is $C_{3-10}$ non-aromatic hydrocarbon, $R^6$ is H or lower alkyl; $Z^8$ is halogen, methanesulfonate, toluenesulfonate or the like) at ambient temperature or under heated conditions can provide compounds of formula 33, wherein X is O or NH and Y is as defined above.

Scheme 13

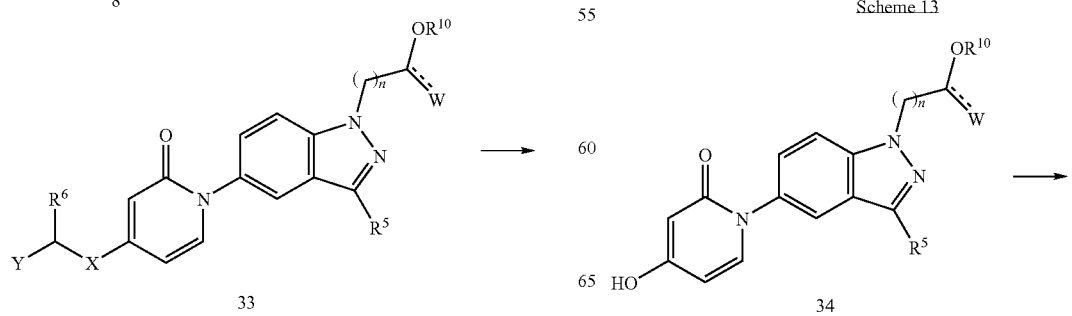

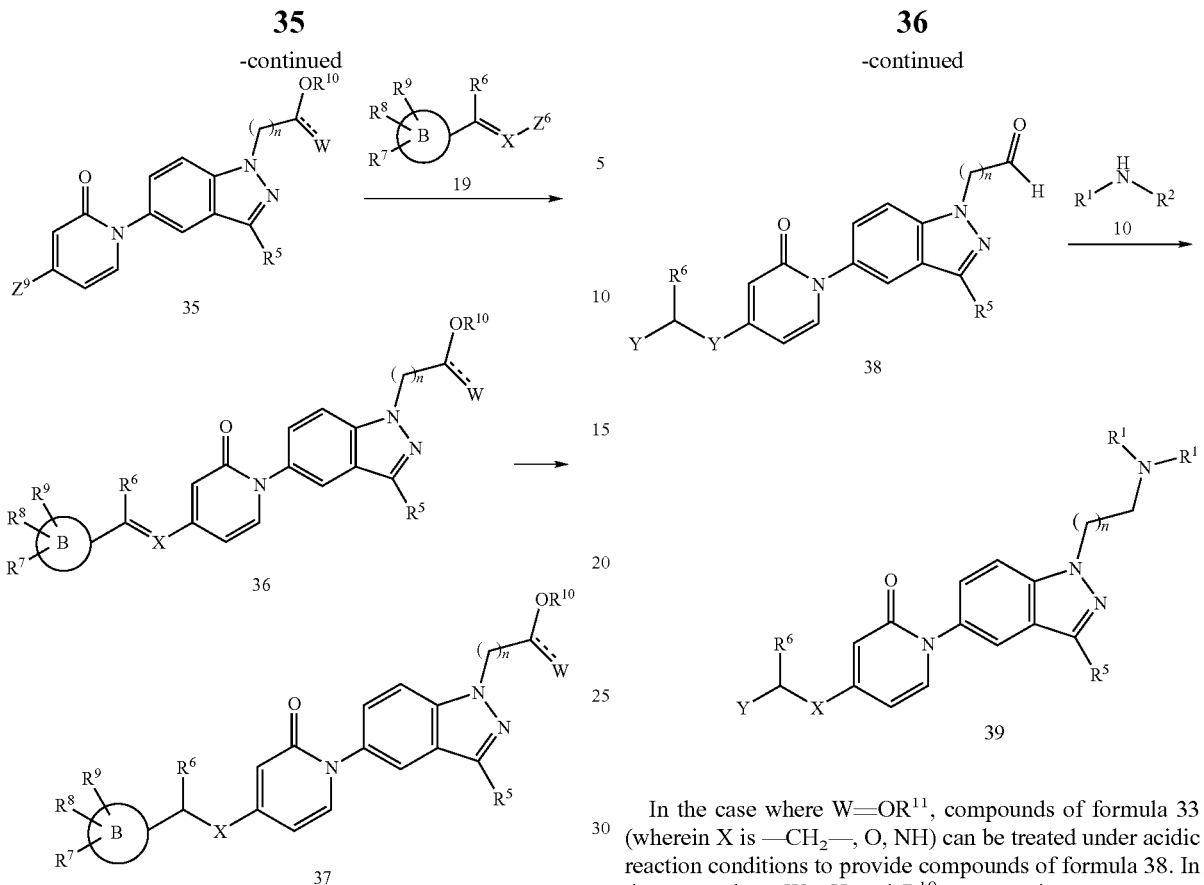

Alternatively, the hydroxyl group on compounds of formula 34 can be converted to an appropriate activating group to give compounds of formula 35. In the case where $Z^9$ is triflate, compounds of formula 34 can be treated with trifluoromethylsulfonic anhydride or N-phenyl trifluoromethanesulfonamide and a base such as pyridine or lithium bis(trimethylsilyl) amide under cooled conditions to give compounds of formula 35. Treatment of compounds of formula 35 with compounds of formula 19 (wherein B is aryl or heteroaryl; $R^7$, $R^8$, $R^9$ are each independently selected from H, —O-alkyl, alkyl, halo, —$CF_3$, —S(O)-alkyl, —S(O)$_2$-alkyl and —CN; $R^6$ is H or lower alkyl; X is CH; $Z^6$ is B(OR$^{11}$)$_2$, SnR$^{11}$$_3$ or the like and $R^{11}$ is H or lower alkyl), a catalyst such as palladium(0), and a base such as potassium carbonate to give compounds of formula 36. Compounds of formula 36 can be treated with palladium on carbon in the presence of ammonium formate or under an atmosphere of hydrogen to give compounds of formula 37, wherein X is —$CH_2$—.

In the case where W=OR$^{11}$, compounds of formula 33 (wherein X is —$CH_2$—, O, NH) can be treated under acidic reaction conditions to provide compounds of formula 38. In the case where W=H and $R^{10}$=a protecting group, compounds of formula 33 can be treated under appropriate deprotecting conditions to provide compounds of formula 33 wherein $R^{10}$=H. In the case where W=H and $R^{10}$=H, compounds of formula 33 can be treated with an oxidizing agent such as the Dess-Martin periodane or oxalyl chloride and DMSO to give compounds of formula 38. Treatment of compounds 38 with amines 10 and a reducing agent such as sodium borohydride, sodium cyanoborohydride, sodium triacetoxyborohydride, or picoline-borane complex can provide compounds of formula 39.

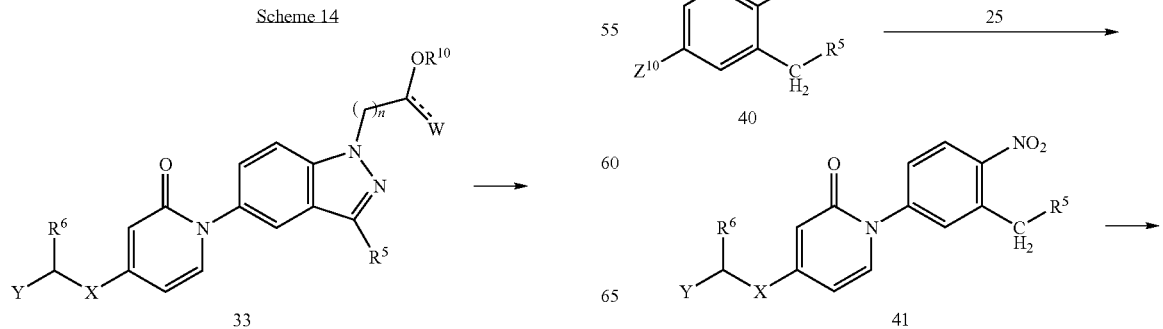

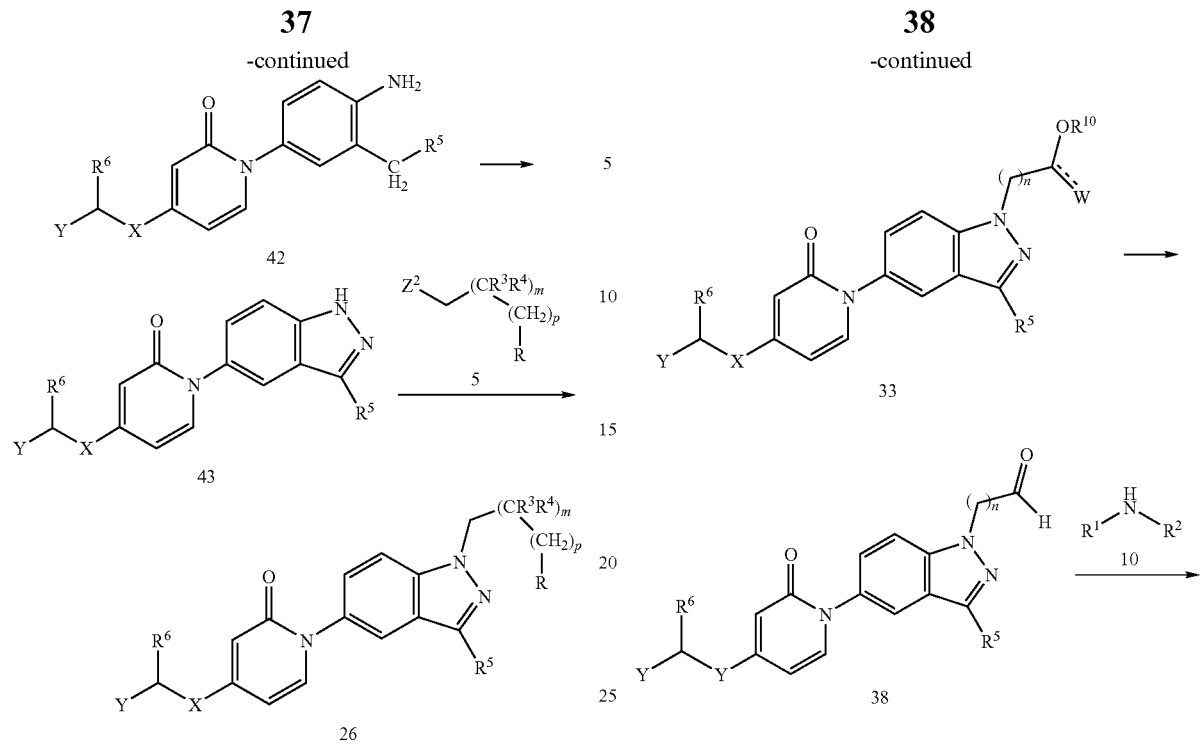

Alternatively, compounds of formula 26 can be made starting from compounds of formula 40. Compounds of formula 40 (wherein $R^5$ is H or optionally substituted lower alkyl, $Z^{10}$ is an activating group such as fluorine, chlorine, bromine, iodine or the like) can be treated under heated conditions in a solvent such as DMF with a base such as sodium carbonate and compounds of formula 25 (wherein X is —CH$_2$—, O; $R^6$ is H or lower alkyl; Y is as defined above) to give compounds of formula 41. In turn, compounds of formula 41 can be treated under reducing conditions such as SnCl$_2$, iron powder and NH$_4$Cl, or palladium on carbon under a hydrogen atmosphere to provide compounds of formula 42. Treatment of compounds of formula 42 with NaNO$_2$ in acetic acid at room temperature can provide compounds of formula 43. Compounds of formula 43 can be treated with base and compounds of formula 5 (wherein $Z^2$=halogen, methanesulfonate, toluenesulfonate or the like; m and p are each 0 or 1, provided that m+p is at least 1; $R^3$ and $R^4$ are each independently selected from H, —OH and lower alkyl; R is as defined above) at ambient temperature or under heated conditions to give compounds of formula 26. Typical bases include but are not limited to cesium carbonate, potassium carbonate and sodium hydride. Typical solvents include but are not limited to N,N-dimethylformamide, dimethylsulfoxide, acetonitrile and tetrahydrofuran.

Scheme 16

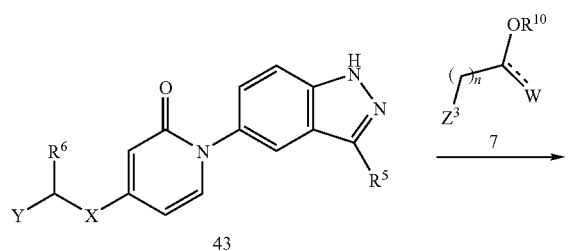

Compounds of formula 43 (wherein $R^5$ is H or optionally substituted lower alkyl; X is —CH$_2$—, O; $R^6$ is H or lower alkyl, Y is as defined above) can be treated with base and compounds of formula 7 (wherein $Z^3$=halogen, methanesulfonate, toluenesulfonate or the like; W=O, OR$^{11}$ or H, $R^{10}$=an alkyl group, H or a protecting group such as tert-butyldimethylsilyl; $R^{11}$=alkyl; n=1 or 2) at ambient temperature or under heated conditions to give compounds of formula 33. Typical bases include but are not limited to cesium carbonate, potassium carbonate and sodium hydride. Typical solvents include but are not limited to N,N-dimethylformamide, dimethylsulfoxide, acetonitrile and tetrahydrofuran. In the case where W=OR$^{11}$, compounds of formula 33 can be treated under acidic reaction conditions to provide compounds of formula 38. In the case where W=H and $R^{10}$=a protecting group, compounds of formula 33 can be treated under appropriate deprotecting conditions to provide compounds of formula 33 wherein $R^{10}$=H. In the case where W=H and $R^{10}$=H, compounds of formula 33 can be treated with an oxidizing agent such as the Dess-Martin periodane or oxalyl chloride and DMSO to give compounds of formula 38. Treatment of compounds 38 with amines 10 and a reducing agent such as sodium borohydride, sodium cyanoborohydride, sodium triacetoxyborohydride, or picoline-borane complex can provide compounds of formula 39.

Scheme 17

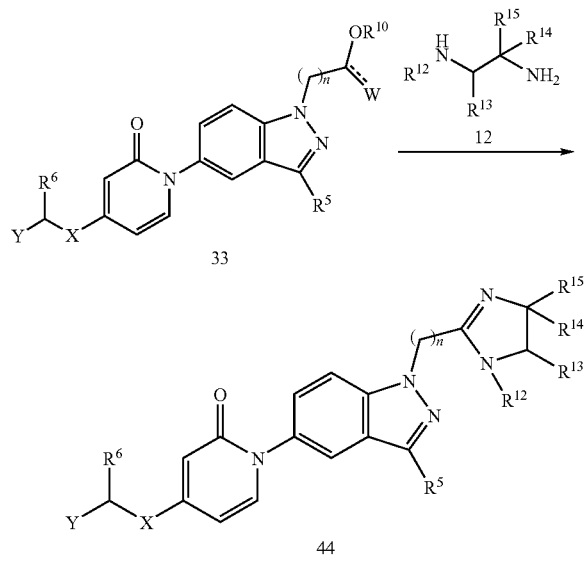

Additionally, in the case where W=O and $R^{10}$=alkyl, compounds of formula 33 can be treated with diamines 12 (wherein $R^{14}$ and $R^{15}$ are each independently H or alkyl, and either (i) $R^{12}$ and $R^{13}$ are each independently H or alkyl, or (ii) $R^{12}$ and $R^{13}$, together with the N atom to which $R^{12}$ is attached, form a 4 to 7-membered optionally substituted non-aromatic ring system) and trimethylaluminum to provide compounds of formula 44.

Scheme 18

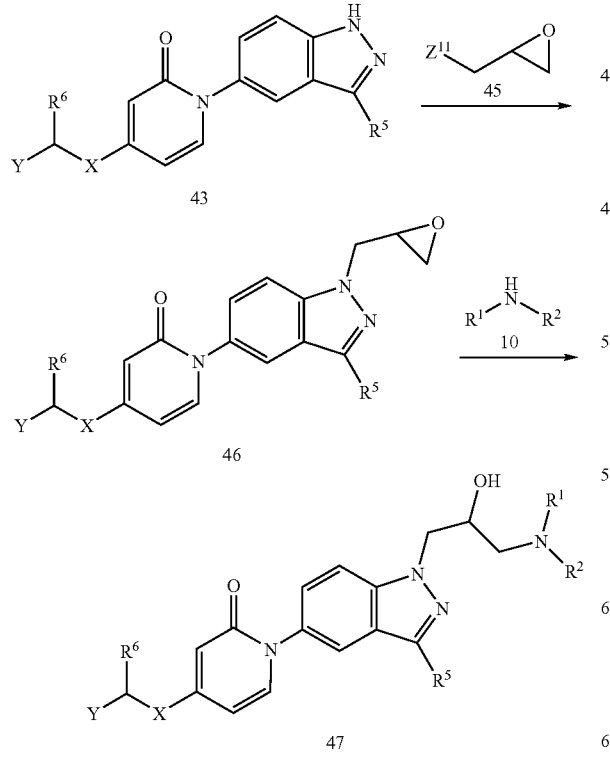

Compounds of formula 43 (wherein $R^5$ is H or optionally substituted lower alkyl; X is —CH$_2$—, O; $R^6$ is H or lower alkyl; Y is as defined above) can be treated with base and compounds of formula 45 (wherein $Z^{11}$=halogen, methanesulfonate, toluenesulfonate, 3-nitrobenzenesulfonate or the like) at ambient temperature or under heated conditions to give compounds of formula 46. Typical bases include but are not limited to cesium carbonate, potassium carbonate and sodium hydride. Typical solvents include but are not limited to N,N-dimethylformamide, dimethylsulfoxide, acetonitrile and tetrahydrofuran. Treatment of compounds 46 with amines 10 and a Lewis acid such as lithium perchlorate in a solvent such as tetrahydrofuran can provide compounds of formula 47.

Scheme 19

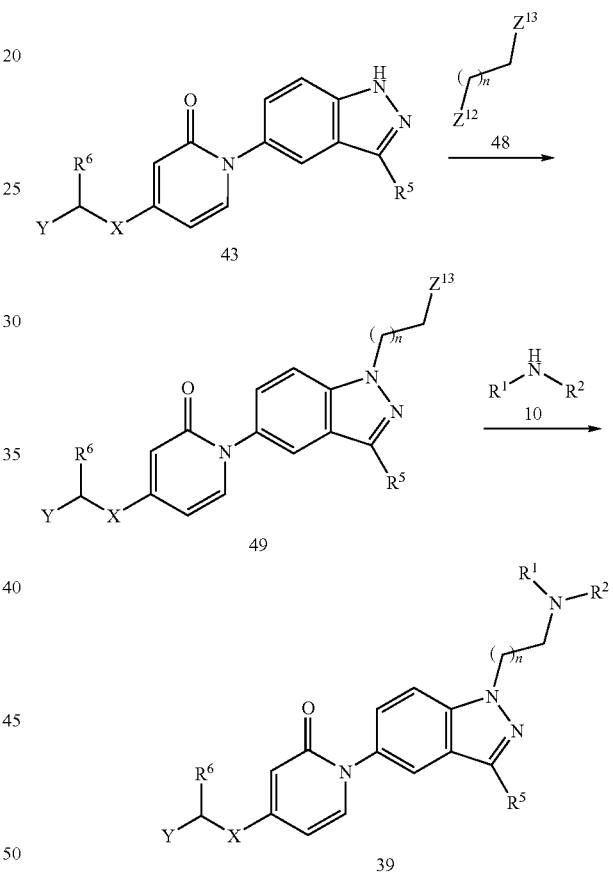

Compounds of formula 43 (wherein $R^5$ is H or optionally substituted lower alkyl; X is —CH$_2$—, O; $R^6$ is H or lower alkyl, Y is as defined above) can be treated with base and compounds of formula 48 (wherein $Z^{12}$ and $Z^{13}$ are each independently halogen, methanesulfonate, toluenesulfonate or the like; n=1 or 2) at ambient temperature or under heated conditions to give compounds of formula 49. Typical bases include but are not limited to cesium carbonate, potassium carbonate and sodium hydride. Typical solvents include but are not limited to N,N-dimethylformamide, dimethylsulfoxide, acetonitrile and tetrahydrofuran. Treatment of compounds 49 with amines 10 and a base such as cesium carbonate, potassium carbonate or sodium hydride at ambient temperature or under heated conditions can provide compounds of formula 39.

EXAMPLES

Unless otherwise noted, reagents and solvents were used as received from commercial suppliers. Proton nuclear magnetic resonance (NMR) spectra were obtained on Bruker spectrometers at 300, 400 or 500 MHz. Spectra are given in ppm (δ) and coupling constants, J, are reported in Hertz. Tetramethylsilane (TMS) was used as an internal standard. Mass spectra were collected using either a Finnigan LCQ Duo LCMS ion trap electrospray ionization (ESI) or a mass Varian 1200L single quadrapole mass spectrometer (ESI). High performance liquid chromatograph (HPLC) analyses were obtained using a Luna C18(2) column (250×4.6 mm, Phenomenex) or a Gemini C18 column (250×4.6 mm, Phenomenex) with UV detection at 254 nm or 223 nm using a standard solvent gradient program (Method A, Method B, Method C, Method D or Method E).

Method A:

| Time (min) | Flow (mL/min) | % A | % B |
|---|---|---|---|
| 0.0 | 1.0 | 90.0 | 10.0 |
| 20.0 | 1.0 | 10.0 | 90.0 |
| 30.0 | 1.0 | 10.0 | 90.0 |
| 31.0 | 1.0 | 90.0 | 10.0 |

A = Water with 0.05% Trifluoroacetic Acid
B = Acetonitrile with 0.05% Trifluoroacetic Acid Method B:

| Time (min) | Flow (mL/min) | % A | % B |
|---|---|---|---|
| 0.0 | 1.0 | 90.0 | 10.0 |
| 20.0 | 1.0 | 10.0 | 90.0 |
| 25.0 | 1.0 | 10.0 | 90.0 |
| 26.0 | 1.0 | 90.0 | 10.0 |

A = Water with 0.05% Trifluoroacetic Acid
B = Acetonitrile with 0.05% Trifluoroacetic Acid Method C:

| Time (min) | Flow (mL/min) | % A | % B |
|---|---|---|---|
| 0.0 | 1.0 | 98.0 | 2.0 |
| 25 | 1.0 | 10.0 | 90.0 |
| 30 | 1.0 | 10.0 | 90.0 |

A = Water with 0.025% Trifluoroacetic Acid
B = Acetonitrile with 0.025% Trifluoroacetic Acid Method D:

| Time (min) | Flow (mL/min) | % A | % B |
|---|---|---|---|
| 0.0 | 1.0 | 98.0 | 2.0 |
| 20 | 1.0 | 10.0 | 90.0 |
| 25 | 1.0 | 10.0 | 90.0 |

A = Water with 0.025% Trifluoroacetic Acid
B = Acetonitrile with 0.025% Trifluoroacetic Acid Method E:

| Time (min) | Flow (mL/min) | % A | % B |
|---|---|---|---|
| 0.0 | 1.0 | 90.0 | 10.0 |
| 20.0 | 1.0 | 30.0 | 70.0 |
| 25.0 | 1.0 | 30.0 | 70.0 |
| 26.0 | 1.0 | 90.0 | 10.0 |

A = Water with 0.05% Trifluoroacetic Acid
B = Acetonitrile with 0.05% Trifluoroacetic Acid

Example 1

Preparation of 4-(Benzyloxy)-1-(1-(2-(pyrrolidin-1-yl)ethyl)-1H-indazol-5-yl)pyridin-2(1H)-one hydrochloride a) 1-(2-(Pyrrolidin-1-yl)ethyl)-1H-indazol-5-amine Beilstein Registry Number 10008406

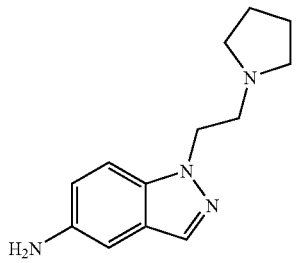

Chemical Formula: $C_{13}H_{18}N_4$
Exact Mass: 230.15
Molecular Weight: 230.31

This compound was prepared in accordance with the procedure of Souers et al., *Bioorg. Med. Chem. Lett.* 2005, 15, 2752-2757.

b) 5-Bromo-1-(2-(pyrrolidin-1-yl)ethyl)-1H-indazole

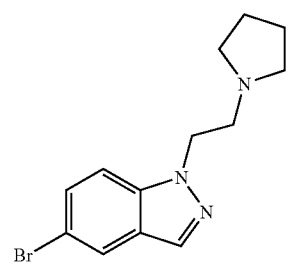

Chemical Formula: $C_{13}H_{16}BrN_3$
Exact Mass: 293.05
Molecular Weight: 294.19

A solution of $NaNO_2$ (0.20 g, 2.8 mmol) in $H_2O$ (5 mL) was cooled in a wet ice bath and treated with a solution of 1-(2-(pyrrolidin-1-yl)ethyl)-1H-indazol-5-amine (0.65 g, 2.8 mmol) in 48% aqueous HBr (2 mL). The resulting mixture was added to a pre-heated solution of CuBr (0.49 g, 3.4 mmol) in 48% aqueous HBr (2 mL) at 100° C. After stirring at 100° C. for 15 min, the dark mixture was allowed to cool. The solids were isolated by filtration, washed with 1N NaOH, and dried under vacuum. Purification by flash column chromatography (silica gel, CH$_2$Cl$_2$/MeOH, 95:5 to 90:10) gave the title compound (0.21 g, 25%) as a brown solid ESI MS m/z 294 [M+H]$^+$.

c) 4-(Benzyloxy)-1-(1-(2-(pyrrolidin-1-yl)ethyl)-1H-indazol-5-yl)pyridin-2(1H)-one

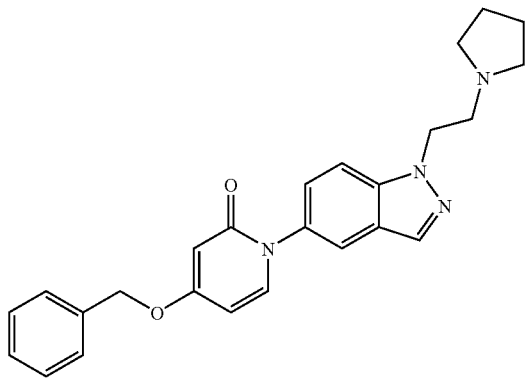

Chemical Formula: C$_{25}$H$_{26}$N$_4$O$_2$
Exact Mass: 414.21
Molecular Weight: 414.5

A suspension of 5-bromo-1-(2-(pyrrolidin-1-yl)ethyl)-1H-indazole (0.21 g, 0.70 mmol) in 1,4-dioxane (10 mL) stirred under nitrogen was treated sequentially with 4-(benzyloxy)pyridin-2(1H)-one (0.14 g, 0.70 mmol), trans-1,2-diaminocyclohexane (0.03 mL, 0.2 mmol), CuI (28 mg, 0.15 mmol) and K$_2$CO$_3$ (0.19 g, 1.4 mmol). After stirring overnight at 110° C., the mixture was allowed to cool to room temperature, diluted with CH$_2$Cl$_2$, washed with brine, dried over Na$_2$SO$_4$, filtered and concentrated to dryness. Purification by flash column chromatography (silica gel, CH$_2$Cl$_2$/MeOH, 95:5 to 90:10) gave the title compound (21 mg, 7%) as an off-white powder: $^1$H NMR (500 MHz, DMSO-d$_6$) δ 8.03 (s, 1H), 7.66 (d, J=1.4 Hz, 1H), 7.53 (d, J=8.8 Hz, 1H), 7.43-7.36 (m, 6H), 7.28 (d, J=7.5 Hz, 1H), 6.09-6.06 (m, 2H), 5.06 (s, 2H), 4.58-4.55 (m, 2H), 3.03 (br m, 2H), 2.61 (br m, 4H), 1.81 (br m, 4H); ESI MS m/z 415 [M+H]$^+$.

d) 4-(Benzyloxy)-1-(1-(2-(pyrrolidin-1-yl)ethyl)-1H-indazol-5-yl)pyridin-2(1H)-one hydrochloride

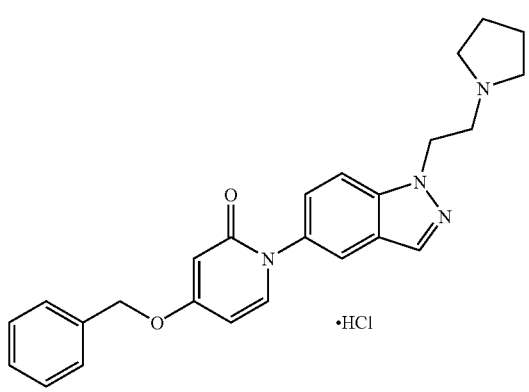

Chemical Formula: C$_{25}$H$_{27}$ClN$_4$O$_2$
Exact Mass: 450.18
Molecular Weight: 450.96

A suspension of 4-(benzyloxy)-1-(1-(2-(pyrrolidin-1-yl)ethyl)-1H-indazol-5-yl)pyridin-2(1H)-one (20 mg, 0.049 mmol) in ethyl acetate (1 mL) was treated with anhydrous HCl in Et$_2$O (0.05 mL, 1.0 M). After stirring for 10 min, the solid was isolated by filtration, washed with Et$_2$O, and dried under vacuum to give the title compound (24 mg, quantitative) as an off-white powder: mp 200-202° C. dec; $^1$H NMR (500 MHz, DMSO-d$_6$) δ 10.42 (s, 1H), 8.23 (s, 1H), 7.86 (d, J=8.8 Hz, 1H), 7.79 (s, 1H), 7.61 (d, J=7.6 Hz, 1H), 7.48-7.36 (m, 6H), 6.12 (dd, J=7.6, 2.6 Hz, 1H), 5.99 (d, J=2.6 Hz, 1H), 5.16 (s, 2H), 4.85 (br m, 2H), 3.70 (br m, 2H), 3.51 (br m, 2H), 3.01 (br m, 2H), 1.97 (br m, 2H), 1.84 (br m, 2H); ESI MS m/z 415 [M+H]$^+$.

Example 2

Preparation of 4-(Benzyloxy)-1-(1-(2-morpholinoethyl)-1H-indazol-5-yl)pyridin-2(1H)-one hydrochloride a) 4-(Benzyloxy)-1-(3-methyl-4-nitrophenyl)pyridin-2(1H)-one

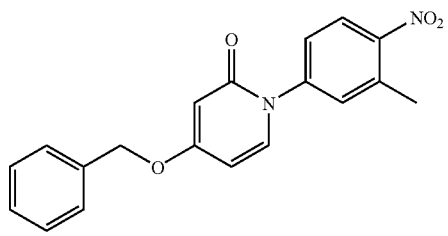

Chemical Formula: C$_{19}$H$_{16}$N$_2$O$_4$
Exact Mass: 336.11
Molecular Weight: 336.34

To a solution of 5-fluoro-2-nitrotoluene (1.00 g, 6.44 mmol) in DMF (6.5 mL) was added 4-benzyloxy-pyridin-2(1H)-one (1.11 g, 5.55 mmol) and Na$_2$CO$_3$ (0.588 g, 5.55 mmol). After stirring at 120° C. for 56 hours, the reaction mixture was cooled, and the solids were collected by filtration and washed with EtOAc (100 ml) and H$_2$O (100 mL). The solids were triturated with hot H$_2$O (50 mL) and then washed with Et$_2$O (50 mL) to yield the title compound (0.94 g, 50%) as a light yellow solid: $^1$H NMR (500 MHz, DMSO-d$_6$) δ 8.08 (d, J=8.5 Hz, 1H), 7.64 (d, J=8.5 Hz, 1H), 7.58 (d, J=2.0 Hz, 1H), 7.50 (dd, J=9.0, 2.5 Hz, 1H), 7.47-7.37 (m, 5H), 6.16 (dd, J=8.0, 3.0 Hz, 1H), 6.01 (d, J=2.5 Hz, 1H), 5.15 (s, 2H), 2.55 (s, 3H); ESI MS m/z 337 [M+H]$^+$.

b) 1-(4-Amino-3-methylphenyl)-4-(benzyloxy)pyridin-2(1H)-one

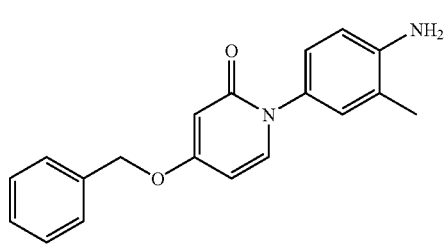

Chemical Formula: C$_{19}$H$_{18}$N$_2$O$_2$
Exact Mass: 306.14
Molecular Weight: 306.36

A solution of 4-(benzyloxy)-1-(3-methyl-4-nitrophenyl)pyridin-2(1H)-one (0.940 mg, 2.79 mmol) in EtOH (19.2 mL) and H$_2$O (4.8 mL) was treated with iron powder (1.35 g, 24.2 mmol) and NH$_4$Cl (64.1 mg). After stirring at reflux for two hours, the reaction mixture was filtered through Celite and the filtrate concentrated to yield the title compound (0.804 g, 94%) as an off-white solid $^1$H NMR (500 MHz, DMSO-d$_6$) δ 7.45-7.34 (m, 6H), 6.85 (s, 1H), 6.81 (d, J=8.5 Hz, 1H), 6.62 (d, J=8.0 Hz, 1H), 6.00 (dd, J=7.5, 5.0 Hz, 1H), 5.90 (d, J=2.0 Hz, 1H), 5.11 (s, 2H), 5.03 (s, 2H), 2.60 (s, 3H).

c) 4-(Benzyloxy)-1-(1H-indazol-5-yl)pyridin-2(1H)-one

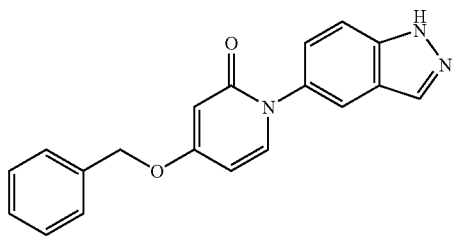

Chemical Formula: $C_{19}H_{15}N_3O_2$
Exact Mass: 317.12
Molecular Weight: 317.34

A solution of 1-(4-amino-3-methylphenyl)-4-(benzyloxy)pyridin-2(1H)-one (0.80 g, 2.6 mmol) in acetic acid (AcOH) (24 mL) was treated with a solution of $NaNO_2$ (0.18 g, 2.6 mmol) in $H_2O$ (0.6 mL). After stirring at ambient temperature for 12 h, the reaction mixture was concentrated. The resulting solid was washed in $CH_2Cl_2$ (25 mL) to yield the title compound (0.362 g, 43%) as a light yellow solid: $^1$H NMR (500 MHz, DMSO-$d_6$) δ 8.13 (s, 1H), 7.72 (s, 1H), 7.61 (d, J=7.5 Hz, 2H), 7.48-7.41 (m, 5H), 7.38-7.35 (m, 1H), 7.28 (dd, J=8.5, 1.5 Hz, 1H), 6.09 (dd, J=7.5, 2.5 Hz, 1H), 5.99 (d, J=2.5 Hz, 1H), 5.14 (s, 2H); ESI MS m/z 318 [M+H]$^+$. Flash column purification of the filtrate (silica gel, $CH_2Cl_2$/MeOH, 100:0 to 95:5) yielded additional title compound (0.396 g, 47%) as a light yellow solid $^1$H NMR (500 MHz, DMSO-$d_6$) δ 13.25 (s, 1H), 8.13 (s, 1H), 7.73 (d, J=1.5 Hz, 1H), 7.60 (t, J=7.5 Hz, 2H), 7.48-7.41 (m, 4H), 7.38-7.35 (m, 1H), 7.28 (dd, J=8.5, 1.5 Hz, 1H), 6.09 (dd, J=7.5, 2.5 Hz, 1H), 5.99 (d, J=3 Hz, 1H), 5.14 (s, 2H); ESI MS m/z 318 [M+H]$^+$.

d) 4-(Benzyloxy)-1-(1-(2-morpholinoethyl)-1H-indazol-5-yl)pyridin-2(1H)-one

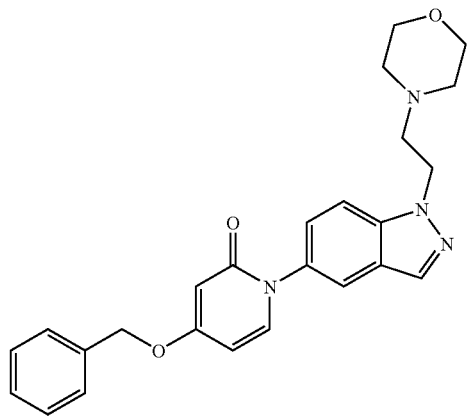

Chemical Formula: $C_{25}H_{26}N_4O_3$
Exact Mass: 430.2
Molecular Weight: 430.5

To a solution of 4-(benzyloxy)-1-(1H-indazol-5-yl)pyridin-2(1H)-one (0.362 g, 1.14 mmol) in DMSO (1.5 mL) was added 4-(2-chloroethyl)morpholine (0.466 g, 2.50 mmol) and $Cs_2CO_3$ (1.85 g, 5.67 mmol). After stirring at ambient temperature for 5.5 h, the reaction mixture was diluted with $H_2O$ (10 mL) and extracted with EtOAc (3×40 mL). The organics were washed with brine (2×25 mL), dried ($Na_2SO_4$), filtered and concentrated. Purification by flash chromatography (silica gel, $CH_2Cl_2$/(80:18:2 $CH_2Cl_2$/MeOH/$NH_4OH$), 100:0 to 0:100) followed by preparative HPLC (Phenomenex Luna C18 (2), 250.0×50.0 mm, 10 micron, $H_2O$ with 0.05% TFA and $CH_3CN$ with 0.05% TFA) yielded the title compound (37.3 mg, 7%) as a white solid: $^1$H NMR (500 MHz, CDCl$_3$) δ 8.02 (d, J=1.0 Hz, 1H), 7.66 (d, J=1.5 Hz, 1H), 7.50 (d, J=9.0 Hz, 1H), 7.43-7.38 (m, 6H), 7.29 (d, J=7.5 Hz, 1H), 6.09-6.06 (m, 2H), 5.06 (s, 2H), 4.53 (t, J=7.0 Hz, 2H), 3.68 (t, J=4.5 Hz, 4H), 2.88 (t, J=6.5 Hz, 2H) 2.52 (t, J=4.5 Hz, 4H); ESI MS m/z 431 [M+H]$^+$; HPLC (Method A) 98.9% (AUC), $t_R$=14.0 min.

e) 4-(Benzyloxy)-1-(1-(2-morpholinoethyl)-1H-indazol-5-yl)pyridin-2(1H)-one hydrochloride

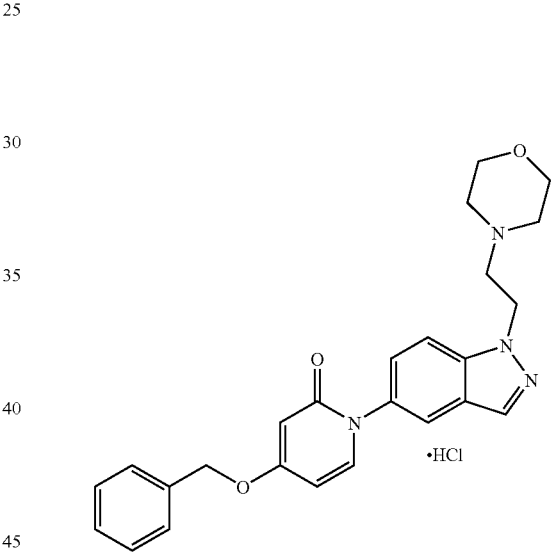

Chemical Formula: $C_{25}H_{27}ClN_4O_3$
Exact Mass: 466.18
Molecular Weight: 466.96

A solution of 4-(benzyloxy)-1-(1-(2-morpholinoethyl)-1H-indazol-5-yl)pyridin-2(1H)-one (37.0 mg, 0.086 mmol) in $CH_2Cl_2$ (0.7 mL) was treated with anhydrous HCl in diethyl ether (86 µL, 0.086 mmol, 1.0 M). After stirring at ambient temperature for 4.5 h, the solids were collected by filtration, dissolved in $CH_3CN$ and $H_2O$, partially concentrated, then lyophilized to yield the title compound (25.6 mg, 64%) as a light yellow solid: $^1$H NMR (500 MHz, DMSO-$d_6$) δ 10.50 (br s, 1H), 8.23 (s, 1H), 7.85 (d, J=8.5 Hz, 1H), 7.79 (s, 1H), 7.60 (d, J=7.5 Hz, 1H), 7.48-7.41 (m, 5H), 7.39-7.36 (m, 1H), 6.12 (dd, J=7.5, 3.0 Hz, 1H), 5.99 (d, J=3.0 Hz, 1H), 5.15 (s, 2H), 4.92 (br s, 2H), 3.99 (d, J=12.0 Hz, 2H), 3.70-3.68 (m, 4H), 3.53 (d, J=12.0 Hz, 2H), 3.19 (br m, 2H); ESI MS m/z 431 [M+H]$^+$; HPLC (Method A) 99.3% (AUC), $t_R$=13.9 min.

Example 3

Preparation of 4-(Benzyloxy)-1-(1-(2-(piperidin-1-yl)ethyl)-1H-indazol-5-yl)pyridin-2(1H)-one hydrochloride a) 4-(Benzyloxy)-1-(1-(2-(piperidin-1-yl)ethyl)-1H-indazol-5-yl)pyridin-2(1H)-one

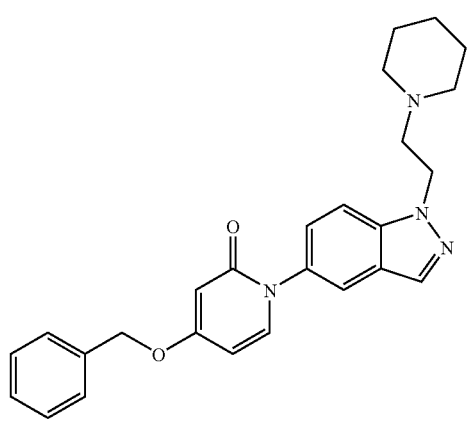

Chemical Formula: $C_{26}H_{28}N_4O_2$
Exact Mass: 428.22
Molecular Weight: 428.53

To a solution of 4-(benzyloxy)-1-(1H-indazol-5-yl)pyridin-2(1H)-one (0.400 g, 1.26 mmol) in DMSO (4.0 mL) was added 4-(2-chloroethyl)piperidine hydrochloride (0.510 g, 2.77 mmol) and $Cs_2CO_3$ (2.46 g, 7.55 mmol). After stirring at ambient temperature for 2.75 h, the reaction mixture was diluted with $H_2O$ (10 mL) and extracted with EtOAc (3×50 mL). The organics were washed with $H_2O$ (2×25 mL) and brine (2×25 mL), dried ($Na_2SO_4$), filtered and concentrated. Purification by flash chromatography (silica gel, EtOAc/$CH_2Cl_2$/(80:18:2 $CH_2Cl_2$/MeOH/$NH_4OH$), 1:1:0 to 1:1:2 to 0:1:1) yielded the title compound (27.2 mg, 5%) as a yellow solid: $^1$H NMR (500 MHz, CDCl$_3$) δ 8.11 (s, 1H), 7.75 (d, J=9.0 Hz, 1H), 7.71 (s, 1H), 7.61 (d, J=7.5 Hz, 1H), 7.48-7.41 (m, 4H), 7.38-7.36 (m, 1H), 7.32-7.31 (m, 1H), 6.10 (dd, J=7.5, 5 Hz, 1H), 5.99 (d, J=2.5 Hz, 1H), 5.15 (s, 2H), 4.53 (t, J=6.5 Hz, 2H), 2.71 (t, J=6.5 Hz, 2H), 2.40 (s, 4H) 1.43-1.42 (m, 4H), 1.35-1.34 (m, 2H); ESI MS m/z 429 [M+H]$^+$; HPLC (Method A) 99.1% (AUC), $t_R$=13.0 min.

b) 4-(Benzyloxy)-1-(1-(2-(piperidin-1-yl)ethyl)-1H-indazol-5-yl)pyridin-2(1H)-one hydrochloride

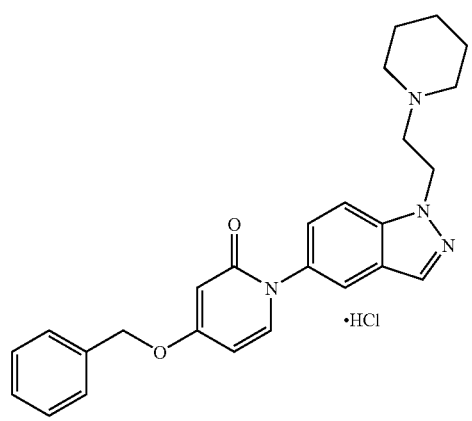

Chemical Formula: $C_{26}H_{29}ClN_4O_2$
Exact Mass: 464.2
Molecular Weight: 464.99

A solution of 4-(benzyloxy)-1-(1-(2-(piperidin-1-yl)ethyl)-1H-indazol-5-yl)pyridin-2(1H)-one (26.7 mg, 0.062 mmol) in $CH_2Cl_2$ (0.3 mL) was treated with anhydrous HCl in diethyl ether (62 µL, 0.062 mmol, 1.0 M). After stirring at ambient temperature for 2.0 h, the solids were collected by filtration, washed with diethyl ether and dried to yield the title compound (22.8 mg, 78%) as a light yellow solid. $^1$H NMR (500 MHz, DMSO-d$_6$) δ 9.85 (br s, 1H), 8.24 (s, 1H), 7.85 (d, J=9.0 Hz, 1H), 7.79 (s, 1H), 7.60 (d, J=7.5 Hz, 1H), 7.48-7.36 (m, 6H), 6.12 (dd, J=7.5, 3.0 Hz, 1H), 5.99 (d, J=3.0 Hz, 1H), 5.15 (s, 2H), 4.89 (t, J=6.5 Hz, 2H), 3.61-3.54 (m, 4H), 3.00-2.94 (m, 2H), 1.84-1.81 (m, 2H), 1.68-1.65 (m, 3H), 1.41-1.36 (m, 1H); ESI MS m/z 429 [M+H]$^+$; HPLC (Method A) 99.5% (AUC), $t_R$=14.2 min.

Example 4

Preparation of 1-(1-(2-(Pyrrolidin-1-yl)ethyl)-1H-indazol-5-yl)-4-(4-(trifluoromethyl) benzyloxy)pyridine-2(1H)-one hydrochloride a) 4-Hydroxy-1-(1-(2-(pyrrolidin-1-yl)ethyl)-1H-indazol-5-yl)pyridin-2(1H)-one

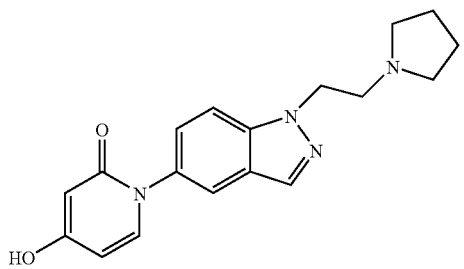

Chemical Formula: $C_{18}H_{20}N_4O_2$
Exact Mass: 324.1586
Molecular Weight: 324.377

To a solution of 4-(benzyloxy)-1-(1-(2-(pyrrolidin-1-yl)ethyl)-1H-indazol-6-yl)pyridin-2(1H)-one (240 mg, 0.58 mmol) in $CH_3OH$ was added Pd/C (200 mg) under an Ar atmosphere. The Ar balloon was replaced with a H₂ balloon and H₂ bubbled through the reaction mixture, which was heated at 55° C. overnight and then allowed to cool. The mixture was filtered through a layer of Celite and the filtrate was concentrated. Purification by flash column chromatography (silica gel, CH₂Cl₂/MeOH, 80:20) gave the title compound as a white solid in 65% yield: ¹H NMR (500 MHz, CD₃OD) δ 8.12 (s, 1H), 7.74 (d, J=2.0 Hz, 1H), 7.71 (d, J=9.0 Hz, 1H), 7.48 (d, J=7.5 Hz, 1H), 7.39 (dd, J=9.0, 2.0 Hz, 1H), 6.12 (d, J=7.5 Hz, 1H), 4.65 (t, J=7.0 Hz, 2H), 3.17 (t, J=7.0 Hz, 2H), 2.72-2.71 (m, 4H), 1.84-1.80 (m, 4H); ESI MS m/z 325 [M+H]⁺.

b) 1-(1-(2-(Pyrrolidin-1-yl)ethyl)-1H-indazol-5-yl)-4-(4-(trifluoromethyl)benzyloxy)pyridine-2(1H)-one hydrochloride

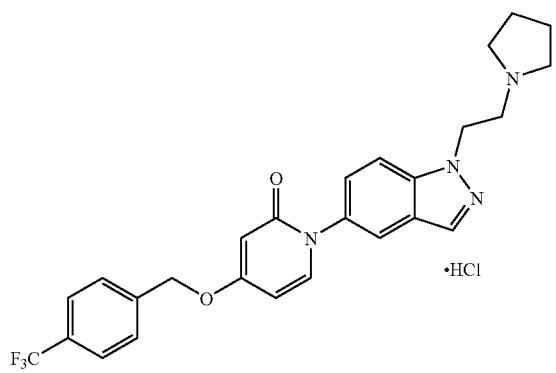

Chemical Formula: C₂₆H₂₆ClF₃N₄O₂
Exact Mass: 518.1696
Molecular Weight: 518.9584

To a solution of 4-hydroxy-1-(1-(2-(pyrrolidin-1-yl)ethyl)-1H-indazol-5-yl)pyridin-2(1H)-one (100 mg, 0.308 mmol) in THF was added NaH (25 mg, 0.62 mmol) followed by 4-(trifluoromethyl)benzyl bromide (88 mg, 0.37 mmol). After heating at 65° C. overnight, the reaction mixture was cooled down, filtered through a thin layer of Celite, washed with CH₂Cl₂, and the filtrate was concentrated. Purification by flash column chromatography (silica gel, CH₂Cl₂/MeOH, 90:10) gave 1-(1-(2-(pyrrolidin-1-yl)ethyl)-1H-indazol-5-yl)-4-(4-(trifluoromethyl)benzyloxy)pyridine-2(1H)-one (20 mg, 13%) as a white solid. According to the procedure of Example 1, the HCl salt was made to give the title compound as a white solid: ¹H NMR (500 MHz, DMSO-d₆) δ 9.65 (s, 1H), 8.12 (m, 1H), 7.80-7.67 (m, 6H), 7.62 (d, J=7.5 Hz, 1H), 7.34 (m, 1H), 6.13 (dd, J=7.5, 2.5 Hz, 1H), 5.98 (d, J=2.5 Hz, 1H), 5.27 (s, 2H), 4.58-4.54 (m, 2H), 2.89 (m, 2H), 2.52-2.42 (m, 4H), 1.73-1.64 (m, 4H); ESI MS m/z 483 [M+H]⁺.

Example 5

Preparation of 4-(4-Chlorobenzyloxy)-1-(1-(2-(pyrrolidin-1-yl)ethyl)-1H-indazol-5-yl) pyridin-2(1H)-one hydrochloride

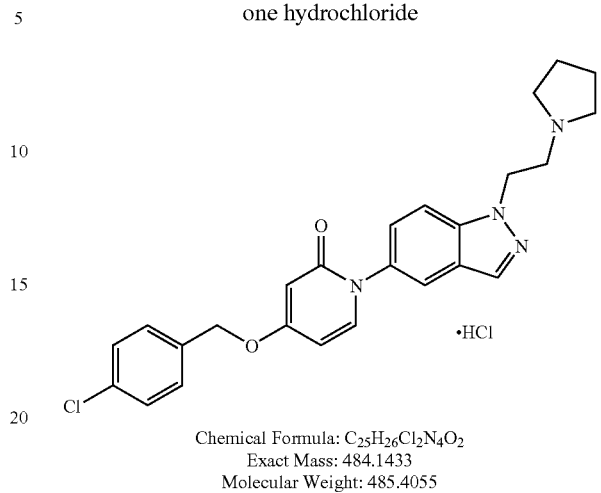

Chemical Formula: C₂₅H₂₆Cl₂N₄O₂
Exact Mass: 484.1433
Molecular Weight: 485.4055

Following the procedure of Example 4, but substituting 4-chlorobenzyl bromide for 4-(trifluoromethyl)benzyl bromide and using 15-crown-5 as an additive, the title compound (230 mg, 79%) was prepared as a white solid: ¹H NMR (500 MHz, DMSO-d₆) δ 9.94 (s, 1H), 8.25 (s, 1H), 7.86 (d, J=8.5 Hz, 1H), 7.80 (d, J=1.5 Hz, 1H), 7.61 (d, J=7.5 Hz, 1H), 7.50 (s, 4H), 7.43 (dd, J=8.5, 1.5 Hz, 1H), 6.13 (dd, J=7.5, 2.5 Hz, 1H), 5.98 (d, J=3.0 Hz, 1H), 5.16 (s, 2H), 4.85 (t, J=6.0 Hz, 2H), 3.74-3.72 (m, 2H), 3.54-3.53 (m, 2H), 3.06 (m, 2H), 2.00-1.99 (m, 2H), 1.85-1.83 (m, 2H); ESI MS m/z 449 [M+H]⁺.

Example 6

Preparation of 4-(3-Chlorobenzyloxy)-1-(1-(2-(pyrrolidin-1-yl)ethyl)-1H-indazol-5-yl) pyridin-2(1H)-one hydrochloride

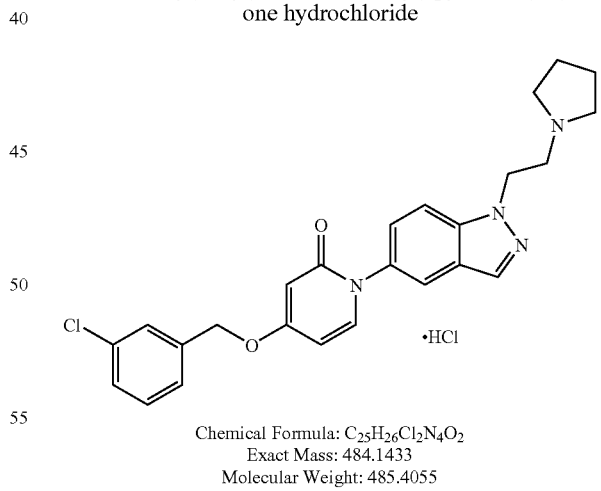

Chemical Formula: C₂₅H₂₆Cl₂N₄O₂
Exact Mass: 484.1433
Molecular Weight: 485.4055

Following the procedure of Example 5, but substituting 3-chlorobenzyl bromide for 4-chlorobenzyl bromide, the title compound (32 mg, 43%) was prepared as a white solid: ¹H NMR (500 MHz, DMSO-d₆) δ 9.80 (s, 1H), 8.25 (s, 1H), 7.85 (d, J=8.0 Hz, 1H), 7.80 (d, J=1.5 Hz, 1H), 7.62 (d, J=8.0 Hz, 1H), 7.56 (s, 1H), 7.48-7.42 (m, 4H), 6.15 (dd, J=7.5, 2.5 Hz, 1H), 5.99 (d, J=2.5 Hz, 1H), 5.18 (s, 2H), 4.84-4.83 (m, 2H), 3.74-3.73 (m, 2H), 3.54-3.53 (m, 2H), 3.07 (m, 2H), 2.00-1.99 (m, 2H), 1.84-1.83 (m, 2H); ESI MS m/z 449 [M+H]⁺.

Example 7

Preparation of 4-(2-Chlorobenzyloxy)-1-(1-(2-(pyrrolidin-1-yl)ethyl)-1H-indazol-5-yl) pyridin-2(1H)-one hydrochloride

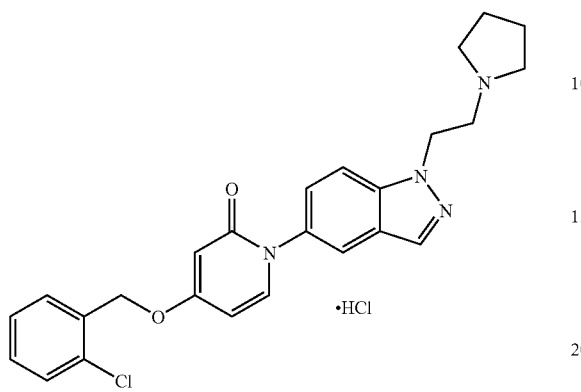

Chemical Formula: C$_{25}$H$_{26}$Cl$_2$N$_4$O$_2$
Exact Mass: 484.1433
Molecular Weight: 485.4055

Following the procedure of Example 5, but substituting 2-chlorobenzyl bromide for 4-chlorobenzyl bromide, the title compound (66 mg, 60%) was prepared as a white solid: $^1$H NMR (500 MHz, DMSO-d$_6$) δ 10.13 (s, 1H), 8.25 (s, 1H), 7.87 (d, J=9.0 Hz, 1H), 7.81 (d, J=2.0 Hz, 1H), 7.64-7.61 (m, 2H), 7.57-7.55 (m, 1H), 7.47-7.42 (m, 3H), 6.13 (dd, J=7.5, 2.5 Hz, 1H), 6.04 (d, J=3.0 Hz, 1H), 5.20 (s, 2H), 4.86 (t, J=6.5 Hz, 2H), 3.75-3.71 (m, 2H), 3.54-3.51 (m, 2H), 3.08-3.01 (m, 2H), 2.03-1.99 (m, 2H), 1.86-1.83 (m, 2H); ESI MS m/z 449 [M+H]$^+$.

Example 8

Preparation of 4-(3,4-Difluorobenzyloxy)-1-(1-(2-(pyrrolidin-1-yl)ethyl)-1H-indazol-5-yl)pyridin-2(1H)-one hydrochloride

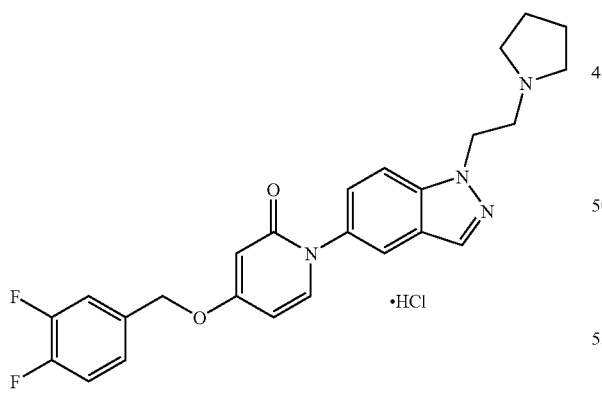

Chemical Formula: C$_{25}$H$_{25}$ClF$_2$N$_4$O$_2$
Exact Mass: 484.1634
Molecular Weight: 486.9414

Following the procedure of Example 5, but substituting 3,4-difluorobenzyl bromide for 4-chlorobenzyl bromide, the title compound (75 mg, 68%) was prepared as a white solid: $^1$H NMR (500 MHz, DMSO-d$_6$) δ 9.96 (s, 1H), 8.25 (s, 1H), 7.86 (d, J=9.0 Hz, 1H), 7.80 (d, J=2.0 Hz, 1H), 7.61 (d, J=7.5 Hz, 1H), 7.60-7.56 (m, 1H), 7.53-7.48 (m, 1H), 7.43 (dd, J=9.0, 2.0 Hz, 1H), 7.36-7.35 (m, 1H), 6.14 (dd, J=7.5, 2.5 Hz, 1H), 5.99 (d, J=2.5 Hz, 1H), 5.15 (s, 2H), 4.86-4.84 (m, 2H), 3.75-3.71 (m, 2H), 3.54-3.53 (m, 2H), 3.08-3.02 (m, 2H), 2.02-1.99 (m, 2H), 1.86-1.83 (m, 2H); ESI MS m/z 451 [M+H]$^+$.

Example 9

Preparation of 4-(4-Methoxybenzyloxy)-1-(1-(2-(pyrrolidin-1-yl)ethyl)-1H-indazol-5-yl) pyridin-2(1H)-one hydrochloride

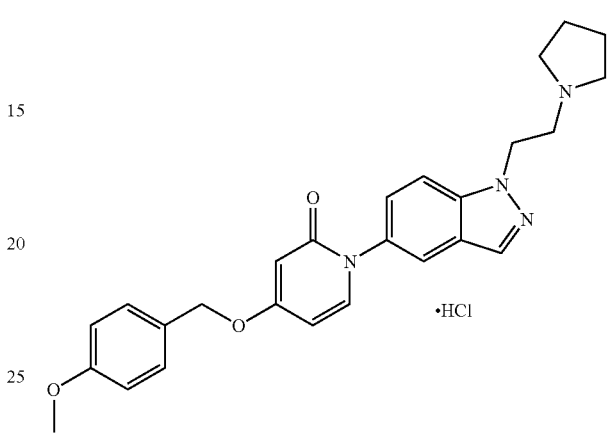

Chemical Formula: C$_{26}$H$_{29}$ClN$_4$O$_3$
Exact Mass: 480.19
Molecular Weight: 480.99

Following the procedure of Example 5, but substituting 4-methoxybenzyl chloride for 4-chlorobenzyl bromide, the title compound (9 mg, 10%) was prepared as a white solid: $^1$H NMR (500 MHz, DMSO-d$_6$) δ 9.86 (s, 1H), 8.25 (s, 1H), 7.85 (d, J=9.0 Hz, 1H), 7.79 (s, 1H), 7.58 (d, J=7.5 Hz, 1H), 7.43-7.39 (m, 3H), 6.99-6.97 (m, 2H), 6.09 (dd, J=7.5, 2.5 Hz, 1H), 5.99 (d, J=2.0 Hz, 1H), 5.06 (s, 2H), 4.84-4.83 (m, 2H), 3.78 (s, 3H), 3.74-3.73 (m, 2H), 3.54 (m, 2H), 3.08-3.06 (m, 2H), 2.00 (m, 2H), 1.83 (m, 2H); ESI MS m/z 445 [M+H]$^+$.

Example 10

Preparation of 4-(Naphthalene-2-ylmethoxy)-1-(1-(2-pyrrolidin-1-yl)ethyl-1H-indazol-yl)pyridin-2(1H)-one hydrochloride

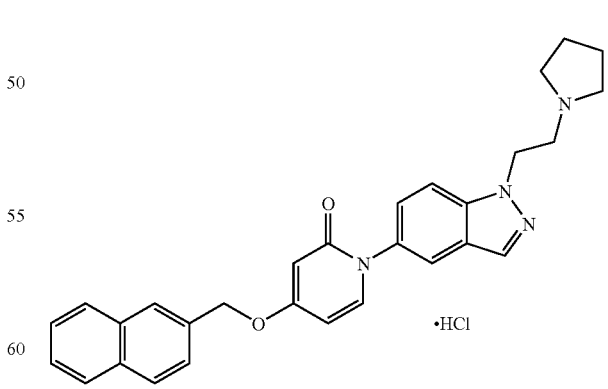

Chemical Formula: C$_{29}$H$_{29}$ClN$_4$O$_2$
Exact Mass: 500.20
Molecular Weight: 501.02

Following the procedure of Example 5, but substituting 2-(bromomethyl) naphthalene for 4-chlorobenzyl bromide, the title compound (21 mg, 16%) was prepared as a white solid: $^1$H NMR (500 MHz, DMSO-$d_6$) δ 10.18 (s, 1H), 8.24 (s, 1H), 8.03 (s, 1H), 8.00-7.95 (m, 3H), 7.86 (d, J=9.0 Hz, 1H), 7.80 (d, J=1.5 Hz, 1H), 7.63-7.54 (m, 4H), 7.43 (dd, J=9.0, 2.0 Hz, 1H), 6.09 (dd, J=7.5, 2.5 Hz, 1H), 6.06 (d, J=2.5 Hz, 1H), 5.34 (s, 2H), 4.87-4.85 (m, 2H), 3.74-3.70 (m, 2H), 3.54-3.52 (m, 2H), 3.06-3.04 (m, 2H), 2.00-1.99 (m, 2H), 1.85-1.83 (m, 2H); ESI MS m/z 465 [M+H]$^+$.

Example 11

Preparation of 4-(Benzyloxy)-1-(1-(3-hydroxypropyl)-1H-indazol-5-yl)pyridin-2(1H)-one hydrochloride

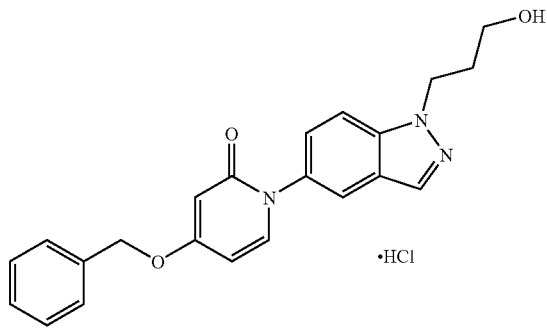

Chemical Formula: $C_{22}H_{22}ClN_3O_3$
Exact Mass: 411.13
Molecular Weight: 411.88

To a solution of 4-(benzyloxy)-1-(1H-indazol-5-yl)pyridine-2(1H)-one (200 mg, 0.63 mmol) in DMSO (5 mL) was added $Cs_2CO_3$ (1.03 g, 3.15 mmol) and (3-bromopropoxy)-tert-butyldimethylsilane (0.15 mL, 0.66 mmol). After stirring overnight at ambient temperature under argon, the reaction mixture was filtered through a layer of Celite and concentrated. Purification by flash column chromatography (silica gel, EtOAc/hexanes, 50:50) gave 4-(benzyloxy)-1-(1-(3-(tert-butyldimethylsilyloxy)propyl)-1H-indazol-5-yl)pyridin-2(1H)-one (90 mg, 29%). To a solution of 4-(benzyloxy)-1-(1-(3-(tert-butyldimethylsilyloxy)propyl)-1H-indazol-5-yl)pyridin-2(1H)-one in THF (3 mL) was added TBAF (0.75 mL, 0.75 mmol, 1.0 M). After the reaction was complete, the mixture was treated with $H_2O$, extracted with $CH_2Cl_2$, and the combined organics were concentrated. Purification by flash column chromatography (silica gel, EtOAc/hexanes, 50:50) gave 4-(benzyloxy)-1-(1-(3-hydroxypropyl)-1H-indazol-5-yl)pyridin-2(1H)-one (50 mg, 88%) as a white solid. In accordance with the procedure of Example 1, the HCl salt was made to give the title compound as a white solid. $^1$H NMR (500 MHz, DMSO-$d_6$) δ 8.12 (s, 1H), 7.73-7.71 (m, 2H), 7.62 (d, J=7.5 Hz, 1H), 7.48-7.36 (m, 5H), 7.33 (dd, J=9.0, 1.5 Hz, 1H), 6.10 (dd, J=7.5, 2.5 Hz, 1H), 5.99 (d, J=2.5 Hz, 1H), 5.15 (s, 2H), 4.50 (t, J=7.0 Hz, 2H), 3.38 (t, J=6.5 Hz, 2H), 2.01-1.96 (m, 2H); ESI MS m/z 376 [M+H]$^+$.

Example 12

Preparation of 4-(Benzyloxy)-1-(1-(2-hydroxyethyl)-1H-indazol-5-yl)pyridin-2(1H)-one hydrochloride

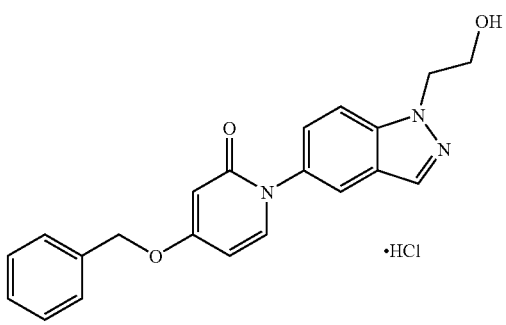

Chemical Formula: $C_{21}H_{20}ClN_3O_3$
Exact Mass: 397.12
Molecular Weight: 397.85

Following the procedure of Example 11, but substituting (2-bromoethoxy)-tert-butyldimethylsilane for (3-bromopropoxy)-tert-butyldimethylsilane, the title compound was prepared as a white solid: $^1$H NMR (500 MHz, DMSO-$d_6$) δ 8.12 (s, 1H), 7.74-7.71 (m, 2H), 7.61 (d, J=7.5 Hz, 1H), 7.48-7.36 (m, 5H), 7.31 (dd, J=9.0, 2.5 Hz, 1H), 6.10 (dd, J=7.5, 2.5 Hz, 1H), 5.99 (d, J=2.5 Hz, 1H), 5.15 (s, 2H), 4.48 (t, J=55 Hz, 2H), 3.81 (t, J=5.5 Hz, 2H); ESI MS m/z 362 [M+H]$^+$.

Example 13

Preparation of 4-(4-Fluorobenzyloxy)-1-(1-(2-(pyrrolidin-1-yl)ethyl)-1H-indazol-5-yl) pyridin-2(1H)-one hydrochloride

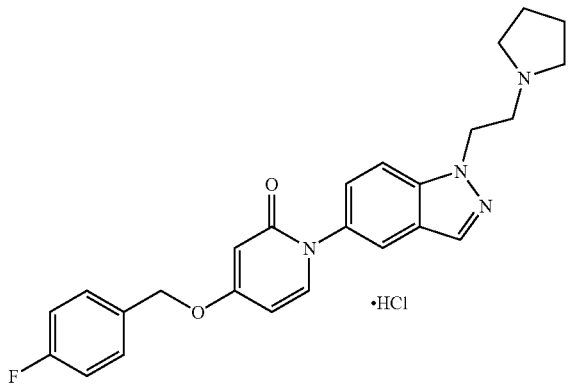

Chemical Formula: $C_{25}H_{26}ClFN_4O_2$
Exact Mass: 468.1728
Molecular Weight: 468.9509

Following the procedure of Example 5, but substituting 4-fluorobenzyl bromide for 4-chlorobenzyl bromide, the title compound (36 mg, 37%) was prepared as a white solid: $^1$H NMR (500 MHz, DMSO-$d_6$) δ 9.79 (s, 1H), 8.25 (s, 1H), 7.85 (d, J=8.5 Hz, 1H), 7.80 (d, J=2.0 Hz, 1H), 7.60 (d, J=7.5 Hz, 1H), 7.55-7.52 (m, 2H), 7.44-7.42 (m, 1H), 7.28-7.25 (m, 2H), 6.12 (dd, J=7.5, 2.5 Hz, 1H), 6.00 (d, J=2.5 Hz, 1H), 5.14

(s, 2H), 4.85-4.84 (m, 2H), 3.74-3.73 (m, 2H), 3.55-3.54 (m, 2H), 3.07 (m, 2H), 2.00-1.99 (m, 2H), 1.84-1.83 (m, 2H); ESI MS m/z 433 [M+H]⁺.

Example 14

Preparation of 4-(Benzyloxy)-1-(1-(3-(piperidin-1-yl)propyl)-1H-indazol-5-yl)pyridin-2(1H)-one hydrochloride

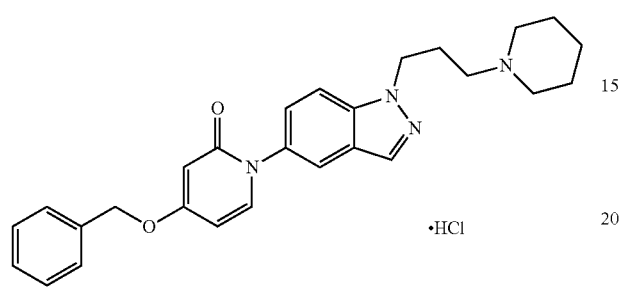

Chemical Formula: C₂₇H₃₁ClN₄O₂
Exact Mass: 478.21
Molecular Weight: 479.01

Following the procedure of Example 2, but substituting 1-(3-chloropropyl)piperidine hydrochloride for 4-(2-chloroethyl)morpholine, the title compound (17.6 mg, 55%) was prepared as a yellow powder. ¹H NMR (500 MHz, DMSO-d₆) δ 9.64 (s, 1H), 8.18 (s, 1H), 7.80 (d, J=8.9 Hz, 1H), 7.76 (s, 1H), 7.60 (d, J=7.6 Hz, 1H), 7.48-7.35 (m, 6H), 6.12 (dd, J=7.6, 2.6 Hz, 1H), 5.99 (d, J=2.6 Hz, 1H), 5.15 (s, 2H), 4.55 (t, J=6.7 Hz, 2H), 3.45-3.35 (m, 2H), 3.08-3.03 (m, 2H), 2.85-2.80 (m, 2H), 2.30-2.26 (m, 2H), 1.78-1.75 (m, 2H), 1.70-1.64 (m, 3H), 1.40-1.30 (m, 1H); ESI MS m/z 443 [M+H]⁺.

Example 15

Preparation of 4-(Benzyloxy)-1-(1-(2-(dimethylamino)ethyl)-1H-indazol-5-yl)pyridin-2(1H)-one hydrochloride

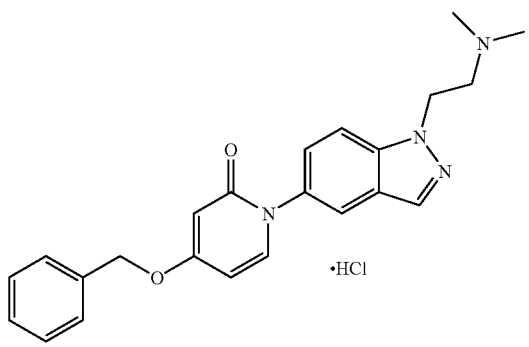

Chemical Formula: C₂₃H₂₅ClN₄O₂·
Exact Mass: 424.17
Molecular Weight: 424.92

Following the procedure of Example 2, but substituting 2-chloro-N,N-dimethylethanamine hydrochloride for 4-(2-chloroethyl)morpholine, the title compound (5.4 mg, 40%) was prepared as a yellow powder: ¹H NMR (500 MHz, DMSO-d₆) δ 9.92 (s, 1H), 8.24 (s, 1H), 7.87 (d, J=9.0 Hz, 1H), 7.79 (d, J=2.0 Hz, 1H), 7.60 (d, J=7.5 Hz, 1H), 7.49-7.41 (m, 5H), 7.39-7.35 (m, 1H), 6.13 (dd, J=7.5, 2.5 Hz, 1H), 5.99 (d, J=3.0 Hz, 1H), 5.16 (s, 2H), 4.88 (t, J=6.5 Hz, 2H), 3.63 (m, 2H), 2.20 (d, J=4.5 Hz, 6H); ESI MS m/z 389 [M+H]⁺.

Example 16

Preparation of (R)-4-(Benzyloxy)-1-(1-(2-(3-fluoropyrrolidin-1-yl)ethyl)-1H-indazol-5-yl)pyridin-2 (1H)-one hydrochloride a) (R)-4-(Benzyloxy)-1-(1-(2-(3-fluoropyrrolidin-1-yl)ethyl)-1H-indazol-5-yl)pyridin-2(1H)-one

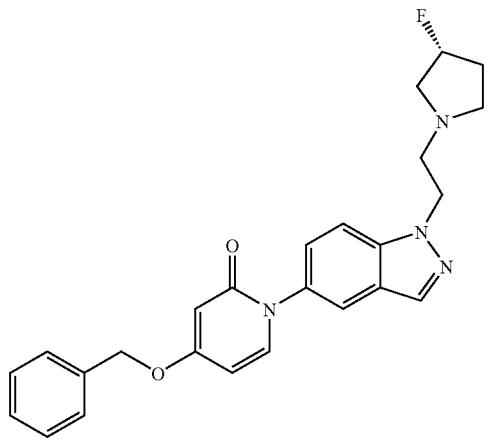

Chemical Formula: C₂₅H₂₅FN₄O₂
Exact Mass: 432.2
Molecular Weight: 432.49

To a solution of 4-(benzyloxy)-1-(1-(2-hydroxyethyl)-1H-indazol-5-yl)pyridin-2(1H)-one (0.264 g, 0.731 mmol) in CH₂Cl₂ (16 mL) was added Dess-Martin periodinane (0.62 g, 1.46 mmol). After stirring at ambient temperature for 4 h, the reaction mixture was diluted with saturated NaHCO₃ with excess sodium thiosulfate (20 mL) and extracted with CH₂Cl₂ (3×20 mL). The organics were washed with brine (2×50 mL), dried (Na₂SO₄), filtered and concentrated. To a portion of the crude (0.121 g) in 1,2-dichloroethane (2.0 mL) was added (R)-3-fluoropyrrolidine hydrochloride (42.3 mg, 0.337 mmol) quickly followed by the addition of sodium triacetoxy borohydride (0.142 g, 0.674 mmol). After stirring at ambient temperature for 1.5 h, the reaction mixture was made basic with 1 N NaOH. The reaction mixture was extracted with CH₂Cl₂ (3×15 mL). The organics were washed with brine (2×20 mL), dried (Na₂SO₄), filtered and concentrated. Purification by flash chromatography (silica gel, hexanes/EtOAc/MeOH, 9:9:2 then CH₂Cl₂/MeOH/NH₄OH, 1:0:0 to 1:0.1:0.01) yielded a mixture of products. The mixture was dissolved in CH₂Cl₂ (20 mL) and extracted with 1 N HCl (5×15 mL). The acidic aqueous phase was made basic with 6 N NaOH and extracted with CH₂Cl₂ (3×20 mL). The organics were dried (Na₂SO₄), filtered and concentrated. Purification by preparative HPLC (Phenomenex Luna C18 (2), 250.0× 50.0 mm, 10 micron, H₂O with 0.05% TFA and CH₃CN with 0.05% TFA) gave the title compound (12.1 mg, 8%) as an off white solid. ¹H NMR (300 MHz, DMSO-d₆) δ 8.12 (s, 1H), 7.78 (d, J=9.0 Hz, 1H), 7.72 (d, J=1.8 Hz, 1H), 7.62 (d, J=7.81H), 7.48-7.30 (m, 6H), 6.10 (dd, J=7.5, 5.1 Hz, 1H), 5.99 (d, J=2.7 Hz, 1H), 5.15 (s, 2H), 5.26-5.03 (m, 1H), 4.56 (t, J=6.6 Hz, 2H), 2.94-2.55 (m, 5H), 2.40-2.27 (m, 1H), 2.11-1.76 (m, 2H); ESI MS m/z 433 [M+H]⁺; HPLC (Method A) 99.8% (AUC), t$_R$=14.6 min.

b) (R)-4-(Benzyloxy)-1-(1-(2-(3-fluoropyrrolidin-1-yl)ethyl)-1H-indazol-5-yl)pyridin-2(1H)-one hydrochloride

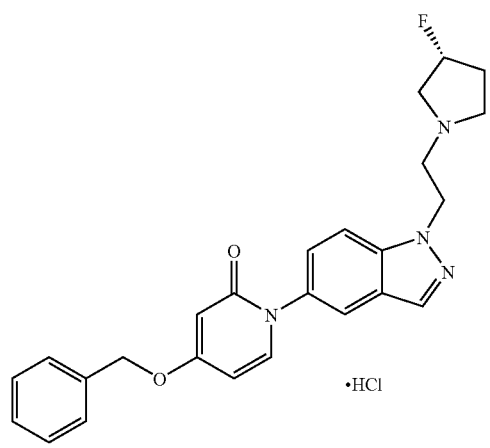

Chemical Formula: C<sub>25</sub>H<sub>26</sub>ClFN<sub>4</sub>O<sub>2</sub>
Exact Mass: 468.17
Molecular Weight: 468.95

A solution of (R)-4-(benzyloxy)-1-(1-(2-(3-fluoropyrrolidin-1-yl)ethyl)-1H-indazol-5-yl)pyridin-2(1H)-one (10.5 mg, 0.024 mmol) in CH$_2$Cl$_2$ (0.3 mL) was treated with anhydrous HCl in diethyl ether (24 μL, 0.024 mmol, 1.0 M). After stirring at ambient temperature for 2.0 h, the reaction mixture was concentrated, dissolved in CH$_3$CN and H$_2$O, partially concentrated, and then lyophilized to yield the title compound (11.9 mg, quantitative) as an off white solid: $^1$H NMR (500 MHz, DMSO-d$_6$) δ 10.58 (br s, 0.5H), 8.24 (s, 1H), 7.84 (d, J=9.0 Hz, 1H), 7.79 (s, 1H), 7.60 (d, J=7.5 Hz, 1H), 7.48-7.36 (m, 6H), 6.12 (dd, J=8.0, 3.0 Hz, 1H), 5.99 (d, J=2.5 Hz, 1H), 5.53-5.39 (m, 1H), 5.15 (s, 2H), 4.87 (s, 2H), 3.88-3.51 (m, 5H), 3.21-3.16 (m, 1H), 2.15-2.08 (m, 1H), 1.30-1.23 (m, 1H); ESI MS m/z 433 [M+H]$^+$, HPLC (Method A)>99.0% (AUC), t$_R$=14.1 min.

Example 17

Preparation of 4-(Benzyloxy)-1-(1-(2-(2-methylpiperidin-1-yl)ethyl)-1H-indazol-5-yl) pyridin-2(1H)-one hydrochloride

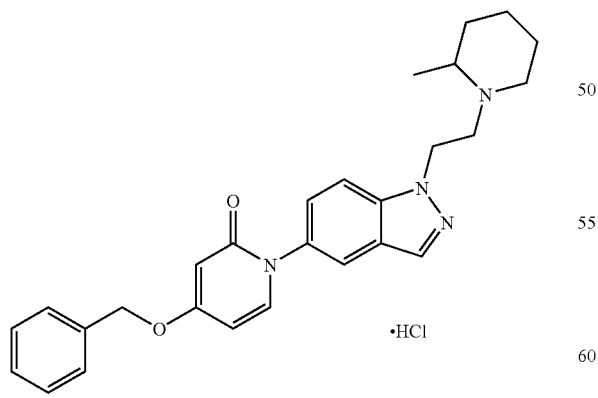

Chemical Formula: C<sub>27</sub>H<sub>31</sub>ClN<sub>4</sub>O<sub>2</sub>·
Exact Mass: 478.21
Molecular Weight: 479.01

Following the procedure of Example 2, but substituting 1-(2-chloroethyl)-2-methylpiperidine hydrochloride for 4-(2-chloroethyl)morpholine, the title compound (11.7 mg, 45%) was prepared as a white powder and as a mixture of conformational isomers: $^1$H NMR (500 MHz, DMSO-d$_6$) δ 10.08 (s, 1H), 8.24 (d, J=3.0 Hz, 1H), 7.89 (t, J=8.8 Hz, 1H), 7.79 (s, 1H), 7.61 (d, J=7.6 Hz, 1H), 7.49-7.41 (m, 5H), 7.39-7.35 (m, 1H), 6.12 (dd, J=7.6, 2.7 Hz, 1H), 5.99 (d, J=2.7 Hz, 1H), 5.16 (s, 2H), 4.94-4.90 (m, 2H), 3.76-3.74 (m, 1H), 3.62-3.52 (m, 2H), 3.23 (m, 1H), 3.06-3.03 (m, 1H), 1.89-1.43 (br m, 6H), 1.31 (d, J=6.3 Hz, 3H); ESI MS m/z 443 [M+H]$^+$.

Example 18

Preparation of 4-(Benzyloxy)-1-(1-(2-(4-methylpiperazin-1-yl)ethyl)-1H-indazol-5-yl)pyridin-2(1H)-one hydrochloride

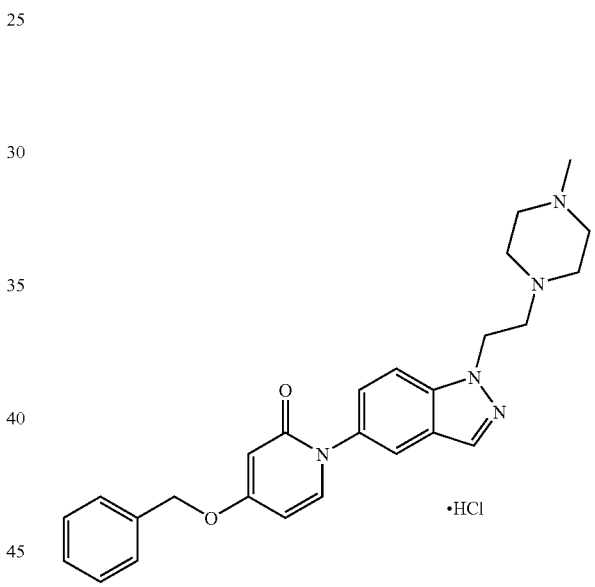

Chemical Formula: C<sub>26</sub>H<sub>30</sub>ClN<sub>5</sub>O<sub>2</sub>·
Exact Mass: 479.21
Molecular Weight: 480

Following the procedure of Example 2, but substituting 1-(2-chloroethyl)-4-methylpiperazine hydrochloride for 4-(2-chloroethyl)morpholine, the title compound (23.6 mg, 75%) was prepared as a yellow powder. $^1$H NMR (500 MHz, DMSO-d$_6$) δ 8.17 (s, 1H), 7.83 (d, J=8.9 Hz, 1H), 7.75 (d, J=1.2 Hz, 1H), 7.61 (d, J=7.5 Hz, 1H), 7.49-7.41 (m, 4H), 7.39-7.35 (m, 2H), 6.12 (dd, J=7.5, 2.5 Hz, 1H), 5.99 (d, J=2.7 Hz, 1H), 5.15 (s, 2H), 4.71 (s, 2H), 3.64 (br m, 6H), 3.40 (br m, 4H), 2.76 (s, 3H); ESI MS m/z 444 [M+H]$^+$.

Example 19

Preparation of 4-(1-Phenylethoxy)-1-(1-(2-(pyrrolidin-1-yl)ethyl-1H-indazol-5-yl)pyridin-2(1H)-one hydrochloride

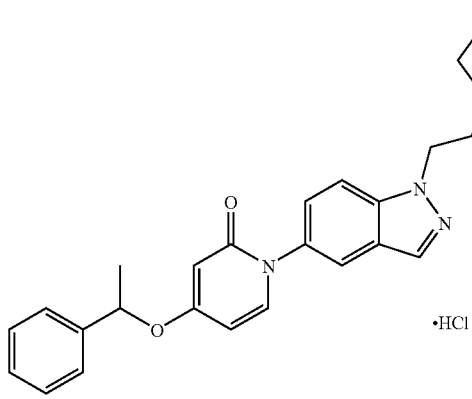

Chemical Formula: C26H29ClN4O2
Exact Mass: 464.20
Molecular Weight: 464.99

To a solution of 4-hydroxy-1-(1-(2-(pyrrolidin-1-yl)ethyl)-1H-indazol-5-yl)pyridin-2(1H)-one (84 mg, 0.26 mmol) in DMF was added Ag$_2$O (120 mg, 0.52 mmol) followed by 1-bromoethylbenzene (71 uL, 0.52 mmol). The reaction mixture was heated to 80° C. for 4 hours, cooled to room temperature and stirred at room temperature for overnight. The reaction mixture was filtered through a thin layer of Celite, washed with CH$_2$Cl$_2$, and the filtrate was concentrated. Purification by flash column chromatography (silica gel, CH$_2$Cl$_2$/MeOH, 90:10) gave 4-(1-phenylethoxy)-1-(1-(2-(pyrrolidin-1-yl)ethyl)-1H-indazol-5-yl)pyridin-2(1H)-one (44 mg, 40%) as an oil. In accordance with the procedure of Example 1, the HCl salt was made to give the title compound as a white foam: $^1$H NMR (500 MHz, DMSO-d$_6$) δ 9.82 (s, 1H), 8.15 (s, 1H), 7.75 (d, J=9.0 Hz, 1H), 7.69 (d, J=2.0 Hz, 1H), 7.49 (d, J=7.5 Hz, 1H), 7.38-7.31 (m, 5H), 7.26-7.24 (m, 1H), 6.04 (dd, J=7.5, 2.5 Hz, 1H), 5.69 (d, J=3.0 Hz, 1H), 5.51 (q, J=6.5 Hz, 1H), 4.77-4.75 (m, 2H), 3.66-3.63 (m, 2H), 3.46-3.45 (m, 2H), 3.00-2.99 (m, 2H), 1.93 (m, 2H), 1.78-1.75 (m, 2H), 1.51 (d, J=6.5 Hz, 3H); ESI MS m/z 429 [M+H]$^+$.

Example 20

Preparation of 4-(Benzyloxy)-1-(1-(2-(diisopropylamino)ethyl)-1H-indazol-5-yl)pyridin-2(1H)-one hydrochloride

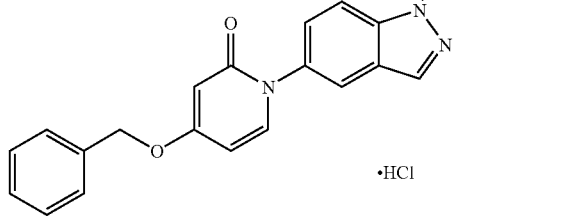

Chemical Formula: C27H33ClN4O2·
Exact Mass: 480.23
Molecular Weight: 481.03

Following the procedure of Example 2, but substituting N-(2-chloroethyl)-N-isopropylpropan-2-amine hydrochloride for 4-(2-chloroethyl)morpholine, the title compound (30.8 mg, 73%) was prepared as a yellow powder: melting point (mp) 214-216° C.; $^1$H NMR (500 MHz, DMSO-d$_6$) δ 9.65 (s, 1H), 8.25 (s, 1H), 7.85 (d, J=8.9 Hz, 1H), 7.78 (d, J=1.7 Hz, 1H), 7.60 (d, J=7.6 Hz, 1H), 7.40-7.49 (m, 5H), 7.35-7.39 (m, 1H), 6.12 (dd, J=7.6, 2.7 Hz, 1H), 5.99 (d, J=2.7 Hz, 1H), 5.16 (s, 2H), 4.90 (t, J=7.3 Hz, 2H), 3.77 (m, 2H), 3.59 (m, 2H), 1.34 (m, 12H); ESI MS m/z 445 [M+H]$^+$.

Example 21

Preparation of 4-(Benzyloxy)-1(1-(2-(3,3-difluoropiperidin-1-yl)ethyl)-1H-indazol-5-yl)pyridin-2(1H)-one hydrochloride

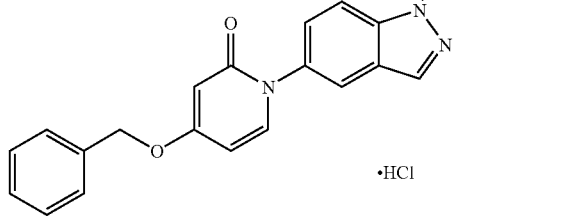

Chemical Formula: C26H27ClF2N4O2·
Exact Mass: 500.18
Molecular Weight: 500.97

Following the procedure of Example 2, but substituting 1-(2-chloroethyl)-3,3-difluoropiperidine for 4-(2-chloroethyl)morpholine, the title compound (23.1 mg, 36%) was prepared as a yellow powder: melting point (mp) 195-196° C.; $^1$H NMR (500 MHz, DMSO-d$_6$) δ 8.22 (s, 1H), 7.85 (d, J=8.9 Hz, 1H), 7.78 (m, 1H), 7.61 (d, J=8.0 Hz, 1H), 7.49-7.35 (m, 6H), 6.13-6.10 (m, 1H), 5.99 (d, J=2.7 Hz, 1H), 5.16 (s, 2H), 4.95-4.85 (m, 2H), 4.15-3.85 (m, 2H), 3.70-3.40 (m, 4H), 2.15-1.75 (m, 4H); ESI MS m/z 465 [M+H]⁺.

Example 22

Preparation of 4-(Benzyloxy)-1(1-(3-(dimethylamino)propyl)-1H-indazol-5-yl)pyridin-2(1H)-one hydrochloride

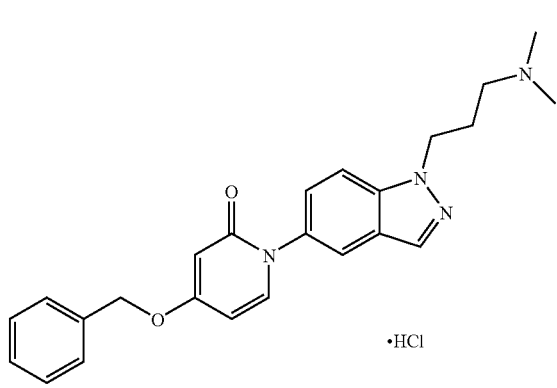

Chemical Formula: C₂₄H₂₇ClN₄O₂·
Exact Mass: 438.18
Molecular Weight: 438.95

Following the procedure of Example 2, but substituting 3-chloro-N,N-dimethylpropan-1-amine hydrochloride for 4-(2-chloroethyl)morpholine, the title compound (34 mg, 73%) was prepared as a yellow powder: melting point (mp) 194-196° C.; ¹H NMR (500 MHz, DMSO-d₆) δ 9.93 (s, 1H), 8.17 (d, J=0.6 Hz, 1H), 7.80 (d, J=8.9 Hz, 1H), 7.76 (d, J=1.7 Hz, 1H), 7.60 (d, J=76 Hz, 1H), 7.49-7.35 (m, 6H), 6.12 (dd, J=7.6, 2.7 Hz, 1H), 5.99 (d, J=2.7 Hz, 1H), 5.15 (s, 2H), 4.55 (t, J=6.7 Hz, 2H), 3.11-3.06 (m, 2H), 2.75 (s, 3H), 2.74 (s, 3H), 2.28-2.21 (m, 2H); ESI MS m/z 403 [M+H]⁺.

Example 23

Preparation of 4-(Benzyloxy)-1-(1-(2-((2R,6S)-2,6-dimethylpiperidin-1-yl)ethyl)-1H-indazol-5-yl)pyridin-2(1H)-one hydrochloride

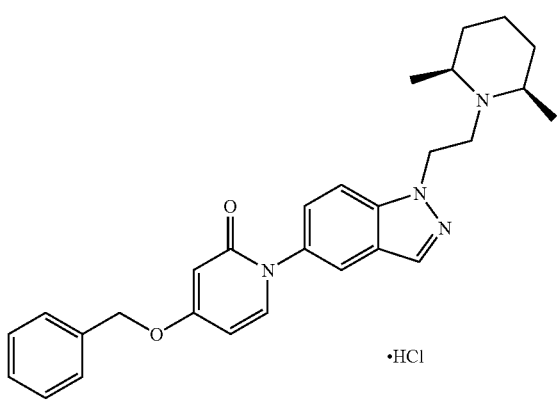

Chemical Formula: C₂₈H₃₃ClN₄O₂
Exact Mass: 492.23
Molecular Weight: 493.04

Following the procedure of Example 2, but substituting (2S,6R)-1-(2-chloroethyl)-2,6-dimethylpiperidine hydrochloride for 4-(2-chloroethyl)morpholine, the title compound (21.6 mg, 53%) was prepared as a yellow powder: melting point (mp) 237-239° C. dec; ¹H NMR (500 MHz, DMSO-d₆) δ 9.95 (s, 1H), 8.27 (s, 1H), 7.91 (d, 9.0 Hz, 1H), 7.78 (d, J=1.8 Hz, 1H), 7.60 (d, J=7.6 Hz, 1H), 7.49-7.36 (m, 6H), 6.12 (dd, J=7.6, 2.7 Hz, 1H), 5.99 (d, J=2.7 Hz, 1H), 5.16 (s, 2H), 4.90 (t, J=6.9 Hz, 2H), 3.71-3.66 (m, 2H), 3.59-3.34 (m, 2H), 1.94-1.85 (m, 2H), 1.75-1.45 (m, 4H), 1.33 (d, J=6.3 Hz, 6H); ESI MS m/z 457 [M+H]⁺.

Example 24

Preparation of 4-(Benzyloxy)-1-(1-(2-((2S,6R)-2,6-dimethylmorpholino)ethyl)-1H-indazol-5-yl)pyridin-2(1H)-one hydrochloride

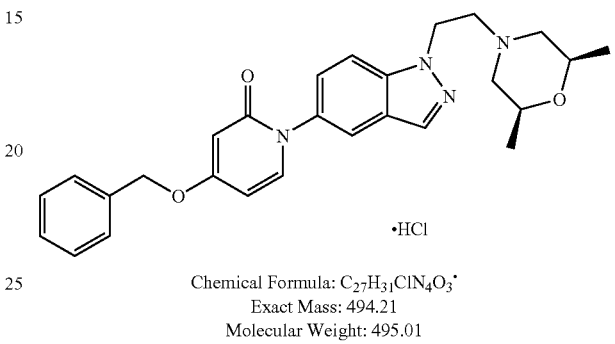

Chemical Formula: C₂₇H₃₁ClN₄O₃·
Exact Mass: 494.21
Molecular Weight: 495.01

Following the procedure of Example 2, but substituting (2R,6S)-4-(2-chloroethyl)-2,6-dimethylmorpholine hydrochloride for 4-(2-chloroethyl)morpholine, the title compound (53.5 mg, 71%) was prepared as a yellow powder: melting point (mp) 172-174° C.; ¹H NMR (500 MHz, DMSO-d₆) δ 11.12 (s, 1H), 8.24 (s, 1H), 7.88 (d, J=8.9 Hz, 1H), 7.79 (s, 1H), 7.61 (d, J=7.6 Hz, 1H), 7.49-7.36 (m, 6H), 6.12 (dd, J=6.6, 1.4 Hz, 1H), 5.99 (d, J=2.3 Hz, 1H), 5.16 (s, 2H), 4.96 (t, J=6.9 Hz, 2H), 4.05-3.89 (m, 2H), 3.60-3.55 (m, 4H), 2.76-2.70 (m, 2H), 1.13 (d, J=6.2 Hz, 6H); ESI MS m/z 459 [M+H]⁺.

Example 25

Preparation of 4-(Benzyloxy)-1-(1-((4,5-dihydro-1H-imidazol-2-yl)methyl-1H-indazol-5-yl)pyridin-2(1H)-one hydrochloride a) Methyl 2-(5-(4-(benzyloxy)-2-oxopyridin-1(2H)-yl)-1H-indazol-1-yl)acetate

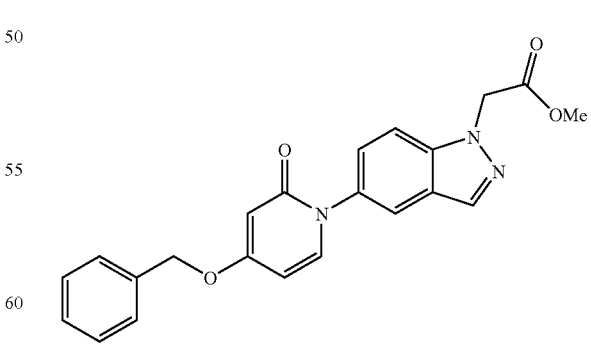

Chemical Formula: C₂₂H₁₉N₃O₄
Exact Mass: 389.14
Molecular Weight: 389.40

Following the procedure of Example 2, but substituting methyl 2-bromoacetate for 4-(2-chloroethyl)morpholine, the title compound (97 mg, 49%) was prepared as a yellow powder: $^1$H NMR (500 MHz, CDCl$_3$) δ 8.08 (s, 1H), 7.70 (s, 1H), 7.45-7.35 (m, 7H), 7.26 (d, J=6.1 Hz, 1H), 6.08-6.03 (m, 2H), 5.19 (s, 2H), 5.06 (s, 2H), 3.76 (s, 3H); ESI MS m/z 390 [M+H]$^+$.

b) 4-(Benzyloxy)-1-(1-((4,5-dihydro-1H-imidazol-2-yl)methyl)-1H-indazol-5-yl)pyridin-2(1H)-one hydrochloride

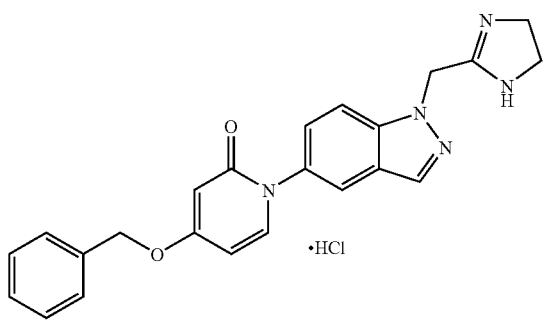

Chemical Formula: C$_{23}$H$_{22}$ClN$_5$O$_2$•
Exact Mass: 435.15
Molecular Weight: 435.91

A solution of methyl 2-(5-(4-(benzyloxy)-2-oxopyridin-1(2H)-yl)-1H-indazol-1-yl)acetate (100 mg, 0.217 mmol) in toluene (0.5 mL) was treated with ethane-1,2-diamine (24 mg, 0.40 mmol) and Al(CH$_3$)$_3$ (0.2 mL, 2 M in toluene, 0.4 mmol) at 0° C. under nitrogen. Then, the reaction mixture was heated to reflux. After stirring at reflux for 16 h, the reaction mixture was diluted with H$_2$O (20 mL) and extracted with CH$_2$Cl$_2$ (2×25 mL). The organics were dried (Na$_2$SO$_4$), filtered and concentrated. Purification by flash column chromatography (silica gel, CH$_2$Cl$_2$/MeOH/NH$_4$OH, 40:1:0.05 to 20:1:0.15) provided the free base. This was dissolved in ethyl acetate (0.3 mL) and treated with 1 equivalent of 1 M HCl in Et$_2$O. The resulting mixture was filtered to provide the title compound (13.5 mg, 14%) as a yellow solid melting point (mp) 164-166° C.; $^1$H NMR (500 MHz, DMSO-d$_6$) δ 10.22 (s, 1H), 8.31 (d, J=0.7 Hz, 1H), 7.84 (d, J=8.9 Hz, 1H), 7.82 (d, J=16 Hz, 1H), 7.59 (d, J=7.6 Hz, 1H), 7.49-7.36 (m, 6H), 6.12 (dd, J=7.6, 2.7 Hz, 1H), 5.99 (d, J=2.7 Hz, 1H), 5.70 (s, 2H), 5.16 (s, 2H), 3.87 (s, 4H); ESI MS m/z 400 [M+H]$^+$.

Example 26

Preparation of (S)-4-(Benzyloxy)-1-(1-((5,6,7,7a-tetrahydro-1H-pyrrolo[1,2-c]imidazol-3-yl)methyl)-1H-indazol-5-yl)pyridin-2(1H)-one hydrochloride

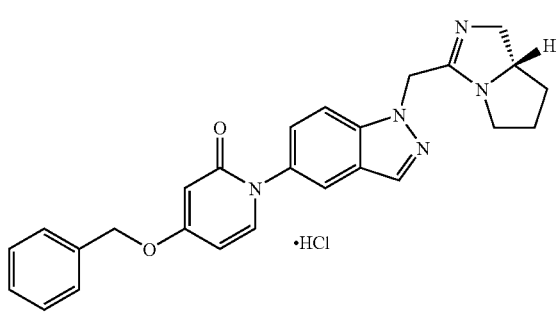

Chemical Formula: C$_{26}$H$_{26}$ClN$_5$O$_2$•
Exact Mass: 475.18
Molecular Weight: 475.97

Following the procedure of Example 25, but substituting (S)-pyrrolidin-2-ylmethanamine for ethane-1,2-diamine, the title compound (9.3 mg, 38%) was prepared as a yellow solid: melting point (mp) 242-244° C. (decompose); $^1$H NMR (500 MHz, DMSO-d$_6$) δ 10.72 (s, 1H), 8.31 (s, 1H), 7.88 (d, J=8.9 Hz, 1H), 7.83 (d, J=1.8 Hz, 1H), 7.61 (d, J=7.6 Hz, 1H), 7.49-7.36 (m, 6H), 6.13 (dd, J=7.6 Hz, 1.3 Hz, 1H), 5.99 (d, J=2.7 Hz, 1H), 5.83 (dd, J=52.1 Hz, 17.3 Hz, 2H), 5.16 (s, 2H), 4.39-4.35 (m, 1H), 4.01 (t, J=11.8 Hz, 1H), 3.80-3.70 (m, 2H), 3.15-3.10 (m, 1H), 2.11-2.05 (m, 2H), 1.99-1.91 (m, 1H), 1.65-1.59 (m, 1H); MS (ESI) m/z 440 [M+H]$^+$.

Example 27

Preparation of 4-(Benzyloxy)-1-(1-(2-(piperazin-1-yl)ethyl)-1H-indazol-5-yl)pyridin-2(1H)-one hydrochloride a) 4-(Benzyloxy)-1-(1-(2-chloroethyl)-1H-indazol-5-yl)pyridin-2(1H)-one

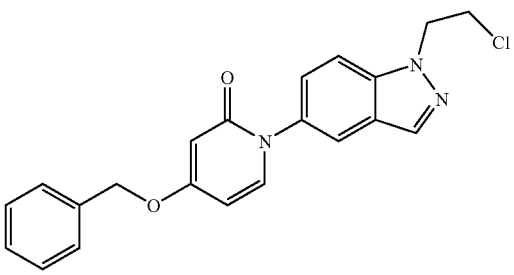

Chemical Formula: C$_{21}$H$_{18}$ClN$_3$O$_2$
Exact Mass: 379.11
Molecular Weight: 379.84

Following the procedure of Example 2, but substituting 1-bromo-2-chloroethane for 4-(2-chloroethyl)morpholine, the title compound (14.43 g, 55%) was prepared as a yellow powder: $^1$H NMR (500 MHz, CDCl$_3$) δ 8.05 (d, J=0.5 Hz, 1H), 7.65 (d, J=1.5 Hz, 1H), 7.50 (d, J=9 Hz, 1H), 7.43-7.33 (m, 6H), 7.26 (d, J=7.5 Hz, 1H), 6.08-6.03 (m, 2H), 5.02 (s, 2H), 4.66 (t, J=6.5 Hz, 2H), 3.94 (t, J=6.5 Hz, 2H); ESI MS m/z 380 [M+H]$^+$.

b) 4-(Benzyloxy)-1-(1-(2-(piperazin-1-yl)ethyl)-1H-indazol-5-yl)pyridin-2(1H)-one hydrochloride

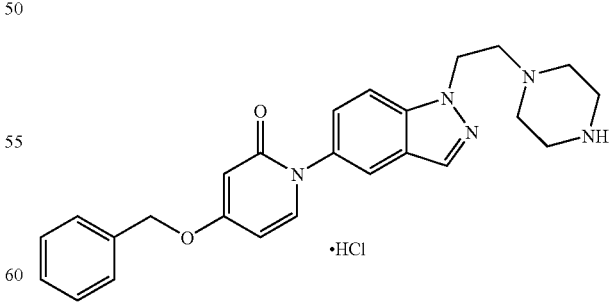

Chemical Formula: C$_{25}$H$_{28}$ClN$_5$O$_2$•
Exact Mass: 465.19
Molecular Weight: 465.98

A solution of 4-(benzyloxy)-1-(1-(2-chloroethyl)-1H-indazol-5-yl)pyridin-2(1H)-one (174 mg, 0.458 mmol) in DMF (2 mL) was treated with piperazine (788 mg, 9.15 mmol), Cs$_2$CO$_3$ (746 mg, 2.29 mmol) and KI (38 mg, 0.23 mmol). After stirring at 50° C. for 16 h, the reaction mixture was diluted with H$_2$O (25 mL) and extracted with EtOAc (3×25 mL). The organics were washed with brine (25 mL), dried (Na$_2$SO$_4$), filtered and concentrated. Purification by flash column chromatography (silica gel, CH$_2$Cl$_2$/MeOH/ NH$_4$OH, 30:1:0.1 to 20:1:0.2) provided the free base. This was dissolved in ethyl acetate (0.5 mL) and treated with 1 equivalent of 1 M HCl in Et$_2$O. The resulting mixture was filtered to provide the title compound (157 mg, 74%) as a yellow solid: melting point (mp) 217-218° C. dec; $^1$H NMR (500 MHz, DMSO-d$_6$) δ 8.80 (s, 1H), 8.17 (s, 1H), 7.81 (d, J=8.8 Hz, 1H), 7.75 (s, 1H), 7.61 (d, J=7.6 Hz, 1H), 7.49-7.41 (m, 4H), 7.40-7.35 (m, 2H), 6.13-6.10 (m, 1H), δ 99 (d, J=2.7 Hz, 1H), 5.15 (s, 2H), 4.79-4.51 (m, 2H), 3.51-3.35 (m, 6H), 3.22-2.98 (m, 4H); ESI MS m/z 430 [M+H]$^+$.

Example 28

Preparation of 4-(Benzyloxy)-1-(1-(2-((5S)-3,5-dimethylmorpholino)ethyl)-1H-indazol-5-yl)pyridin-2(1H)-one hydrochloride

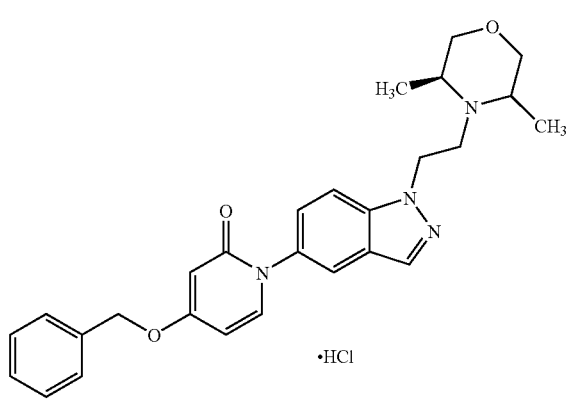

Chemical Formula: C$_{27}$H$_{31}$ClN$_4$O$_3$·
Exact Mass: 494.21
Molecular Weight: 495.01

Following the procedure of Example 2, but substituting (3S)-4-(2-chloroethyl)-3,5-dimethylmorpholine hydrochloride for 4-(2-chloroethyl)morpholine, the title compound (36 mg, 14%) was prepared as a yellow powder: melting point (mp) 224-226° C. dec, $^1$H NMR (500 MHz, DMSO-d$_6$) δ 10.85 (s, 1H), 8.28 (s, 1H), 7.94 (d, J=8.8 Hz, 1H), 7.80 (s, 1H), 7.62 (d, J=7.6 Hz, 1H), 7.45-7.31 (m, 6H), 6.12 (dd, J=7.6, 2.6 Hz, 1H), 6.00 (d, J=2.6 Hz, 1H), 5.16 (s, 2H), 4.95-4.93 (m, 2H), 3.97-3.93 (m, 2H), 3.85-3.75 (m, 2H), 3.61-3.51 (m, 4H), 1.23-1.18 (m, 6H); ESI MS m/z 459 [M+H]$^+$.

Example 29

Preparation of 1-(1-(2-(4-Acetylpiperazin-1-yl) ethyl)-1H-indazol-5-yl)-4-benzyloxy)pyridin-2(1H)-one hydrochloride

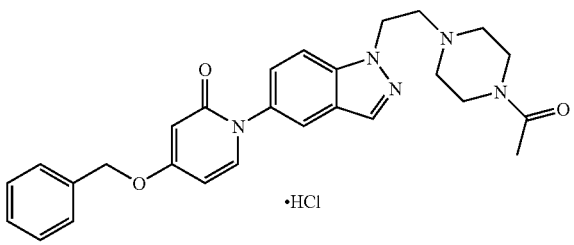

Chemical Formula: C$_{27}$H$_{30}$ClN$_5$O$_3$
Exact Mass: 507.20
Molecular Weight: 508.01

Following the procedure of Example 27 (step b), but substituting 1-(piperazin-1-yl)ethanone for piperazine, the title compound (74 mg, 37%) was prepared as a yellow powder: melting point (mp) 242-244° C.; $^1$H NMR (500 MHz, DMSO-d$_6$) δ 8.13 (s, 1H), 7.76 (d, J=9 Hz, 1H), 7.72 (s, 1H), 7.51 (d, J=7.5 Hz, 1H), 7.47-7.32 (m, 6H), 6.10-6.08 (m, 1H), 5.94 (d, J=2.5 Hz, 1H), 5.15 (s, 2H), 4.80-4.70 (m, 2H), 3.67-3.51 (m, 4H), 3.35-3.27 (m, 4H), 3.05-2.85 (m, 2H), 1.99 (s, 3H); ESI MS m/z 472 [M+H]$^+$.

Example 30

Preparation of 4-(Benzyloxy)-1-(1-(morpholin-2-ylmethyl)-1H-indazol-5-yl)pyridin-2(1H)-one hydrochloride

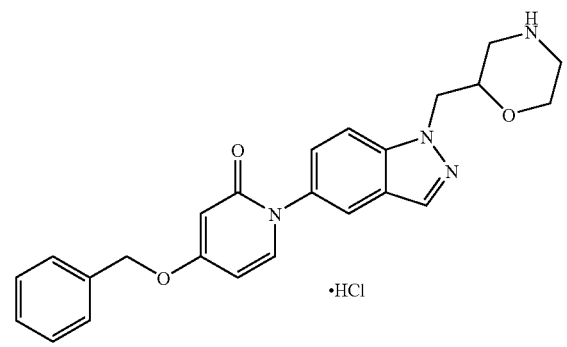

Chemical Formula: C$_{24}$H$_{25}$ClN$_4$O$_3$
Exact Mass: 452.16
Molecular Weight: 452.93

Following the procedure of Example 2, but substituting tert-butyl 2-(bromomethyl)morpholine-4-carboxylate for 4-(2-chloroethyl)morpholine, tert-butyl 2-((5-(4-(benzyloxy)-2-oxopyridin-1(2H)-yl)-1H-indazol-1-yl)methyl)morpholine-4-carboxylate (134 mg, 33%) was prepared as a white powder. A solution of this compound (134 mg, 0.26 mmol) in CH$_2$Cl$_2$ (1 mL) was treated with trifluoroacetic acid (148 mg, 1.3 mmol). After stirring at room temperature for 16 h, the reaction mixture was diluted with CH$_2$Cl$_2$ (50 mL) and washed with 1N NaOH (50 mL). The organics were dried (Na$_2$SO$_4$), filtered and concentrated. Purification by flash column chromatography (silica gel, CH$_2$Cl$_2$/MeOH/ NH$_4$OH, 40:1:0.1 to 20:1.0.2) provided the free base. This was dissolved in ethyl acetate (0.3 mL) and treated with 1 equivalent of 1 M HCl in Et$_2$O and the mixture was filtrated to provide the title compound (68.2 mg, 58%) as a yellow solid:

melting point (mp) 221-223° C. dec; $^1$H NMR (500 MHz, DMSO-d$_6$) δ 9.15 (s, 1H), 8.18 (s, 1H), 7.75-7.70 (m, 2H), 7.62 (d, J=7.6 Hz, 1H), 7.49-7.40 (m, 4H), 7.39-7.35 (m, 2H), 6.11 (dd, J=7.6, 2.7 Hz, 1H), 5.99 (d, J=2.7 Hz, 1H), 5.15 (s, 2H), 4.64-4.60 (m, 2H), 4.20-4.15 (m, 1H), 3.93-3.88 (dd, J=12.6, 3.3 Hz, 1H), 3.68-3.60 (m, 1H), 3.36-3.32 (m, 1H), 3.15 (d, J=12.6 Hz, 1H), 2.96-2.84 (m, 2H); ESI MS m/z 417 [M+H]$^+$.

Example 31

Preparation of 4-(Benzyloxy)-1-(1-(2-(4,4-difluoropiperidin-1-yl)ethyl-1H-indazol-yl)pyridin-2(1H)-one hydrochloride

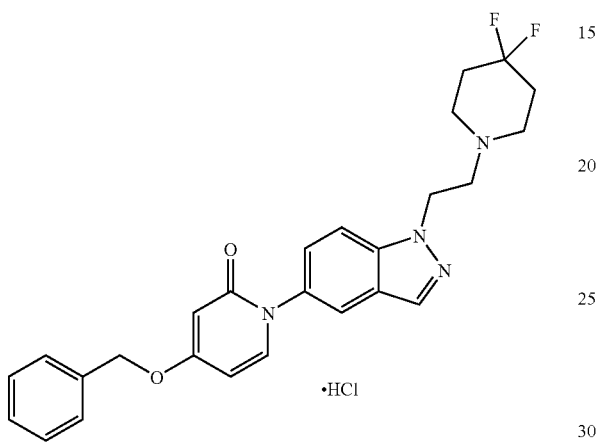

Chemical Formula: C$_{26}$H$_{27}$ClF$_2$N$_4$O$_2$•
Exact Mass: 500.18
Molecular Weight: 500.97

Following the procedure of Example 2, but substituting 1-(2-chloroethyl)-4,4-difluoropiperidine hydrochloride for 4-(2-chloroethyl)morpholine, the title compound (20.9 mg, 46%) was prepared as a yellow powder: melting point (mp) 219-220° C. dec; $^1$H NMR (500 MHz, DMSO-d$_6$) δ 8.23 (s, 1H), 7.86 (d, J=8.9 Hz, 1H), 7.79 (s, 1H), 7.60 (d, J=7.6 Hz, 1H), 7.49-7.41 (m, 5H), 7.40-7.36 (m, 1H), 6.12 (dd, J=7.6, 2.7 Hz, 1H), 5.99 (d, J=2.7 Hz, 1H), 5.16 (s, 2H), 4.95-4.85 (m, 2H), 3.75-3.65 (m, 4H), 3.29-3.21 (m, 2H), 2.42-2.28 (m, 4H); ESI MS m/z 465 [M+H]$^+$.

Example 32

Preparation of 4-(2-(5-(4-(Benzyloxy)-2-oxopyridin-1(2H)-yl)-1H-indazol-1-yl)ethyl)piperazin-2-one hydrochloride

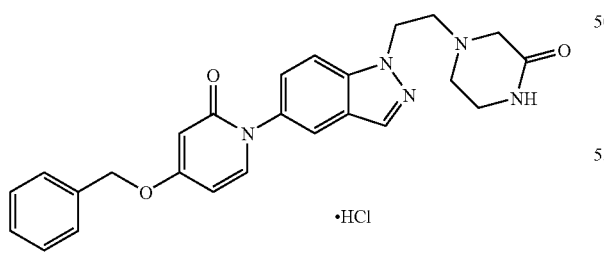

Chemical Formula: C$_{25}$H$_{26}$ClN$_5$O$_3$
Exact Mass: 479.17
Molecular Weight: 479.96

Following the procedure of Example 27 (step b), but substituting piperazin-2-one for piperazine, the title compound (35.7 mg, 10%) was prepared as a yellow powder: melting point (mp) 224-226° C.; $^1$H NMR (500 MHz, DMSO-d$_6$) δ 8.23 (s, 1H), 7.86 (d, J=8.9 Hz, 1H), 7.78 (s, 1H), 7.61 (d, J=7.6 Hz, 1H), 7.49-7.35 (m, 6H), 6.12 (dd, J=7.6, 27 Hz, 1H), 5.99 (d, J=2.7 Hz, 1H), 5.16 (s, 2H), 4.95-4.85 (m, 2H), 3.90-3.55 (m, 4H), 3.41-3.31 (m, 4H), 1.99 (s, 1H); ESI MS m/z 444 [M+H]$^+$.

Example 33

Preparation of 4-(Benzyloxy)-1(1-(2-(2R,5R)-2,5-dimethylpyrrolidin-1-yl)ethyl-1H-indazol-5-yl)pyridin-2(1H)-one hydrochloride

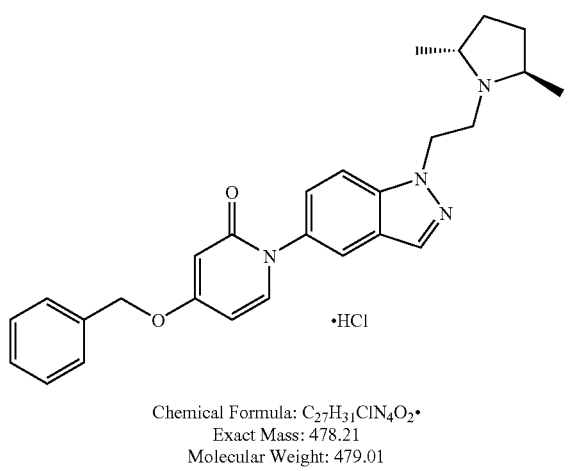

Chemical Formula: C$_{27}$H$_{31}$ClN$_4$O$_2$•
Exact Mass: 478.21
Molecular Weight: 479.01

Following the procedure of Example 2, but substituting (2R,5R)-1-(2-chloroethyl)-2,5-dimethylpyrrolidine hydrochloride for 4-(2-chloroethyl)morpholine, the title compound (24.7 mg, 67%) was prepared as a yellow powder: melting point (mp) 236-238° C.; $^1$H NMR (500 MHz, DMSO-d$_6$) δ 10.31 (s, 1H), 8.26 (s, 1H), 7.88 (d, J=8.9 Hz, 1H), 7.79 (d, J=1.8 Hz, 1H), 7.61 (d, J=7.6 Hz, 1H), 7.49-7.41 (m, 5H), 7.40-7.35 (m, 1H), 6.12 (dd, J=7.6, 2.7 Hz, 1H), 5.99 (d, J=2.7 Hz, 1H), 5.16 (s, 2H), 4.92-4.86 (m, 2H), 3.99-3.95 (m, 1H), 3.71-3.65 (m, 2H), 3.47-3.43 (m, 1H), 2.30-2.24 (m, 1H), 2.16-2.12 (m, 1H), 1.75-1.71 (m, 1H), 1.63-1.58 (m, 1H), 1.40 (d, J=6.5 Hz, 3H), 1.13 (d, J=6.6 Hz, 3H); ESI MS m/z 443 [M+H]$^+$; Optical Rotation [α]$^{23}_D$-18.2° (c 1.00, Methanol).

Example 34

Preparation of 4-(Benzyloxy)-1-(1-(2-isobutylamino)ethyl)-1H-indazol-5-yl)pyridin-2(1H)-one hydrochloride

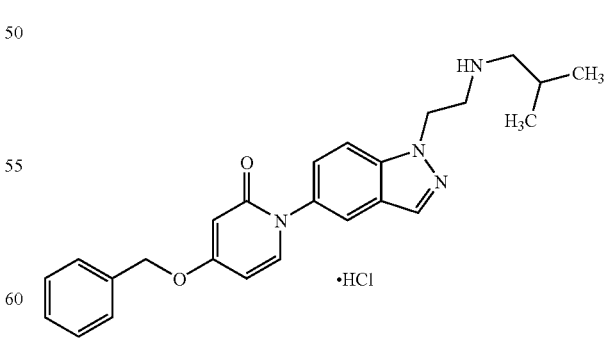

Chemical Formula: C$_{25}$H$_{29}$ClN$_4$O$_2$•
Exact Mass: 452.2
Molecular Weight: 452.98

Following the procedure of Example 27 (step b), but substituting 2-methylpropan-1-amine for piperazine, the title compound (59 mg, 50%) was prepared as a yellow powder: melting point (mp) 224-226° C.; $^1$H NMR (500 MHz, DMSO-d$_6$) δ 8.90 (s, 1H), 8.23 (s, 1H), 7.84 (d, J=8.9 Hz, 1H), 7.78 (d, J=1.8 Hz, 1H), 7.60 (d, J=7.6 Hz, 1H), 7.49-7.40 (m, 5H), 7.39-7.35 (m, 1H), 6.12 (dd, J=7.6, 2.7 Hz, 1H), 5.99 (d, J=2.9 Hz, 1H), 5.16 (s, 2H), 4.84 (t, J=6.7 Hz, 2H), 3.45-3.40 (m, 2H), 2.85-2.80 (m, 2H), 2.01-1.94 (m, 1H), 0.95 (d, J=6.7 Hz, 6H); ESI MS m/z 417 [M+H]$^+$.

Example 35

Preparation of 4-(Benzyloxy)-1(1-(2-(2,2,6,6-tetramethylpiperidin-1-yl) ethyl)-1H-indazol-5-yl)pyridin-2(1H)-one hydrochloride

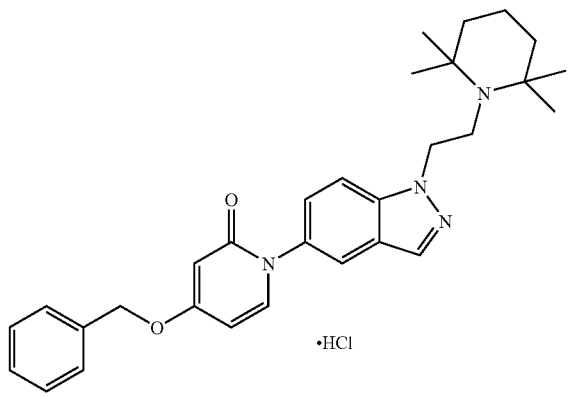

Chemical Formula: C$_{30}$H$_{37}$ClN$_4$O$_2$•
Exact Mass: 520.26
Molecular Weight: 521.09

Following the procedure of Example 2, but substituting 1-(2-chloroethyl)-2,2,6,6-tetramethylpiperidine hydrochloride for 4-(2-chloroethyl)morpholine, the title compound (57.8 mg, 78%) was prepared as a yellow powder: melting point (mp) 232-234° C. (decompose); $^1$H NMR (500 MHz, DMSO-d$_6$) δ 8.85 (s, 1H), 8.26 (s, 1H), 7.81 (d, J=9.0 Hz, 1H), 7.78 (s, J=1.8 Hz, 1H), 7.60 (d, J=7.6 Hz, 1H), 7.49-7.41 (m, 5H), 7.40-7.35 (m, 1H), 6.12 (dd, J=7.6, 2.7 Hz, 1H), δ 99 (d, J=2.7 Hz, 1H), 5.16 (s, 2H), 4.87 (t, J=8.0 Hz, 2H), 3.62-3.55 (m, 2H), 2.05-1.95 (m, 2H), 1.91-1.83 (m, 1H), 1.78-1.71 (m, 2H), 1.63-1.61 (m, 1H), 1.61-1.56 (m, 6H), 1.37-1.31 (m, 6H); ESI MS m/z 485 [M+H]$^+$.

Example 36

Preparation of 4-(Benzyloxy)-1-(1-(2-(2,2-dimethylmorpholino)ethyl)-1H-indazol-5-yl)pyridin-2(1H)-one hydrochloride

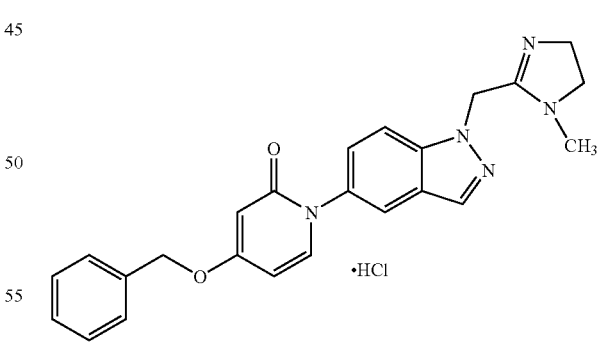

Chemical Formula: C$_{27}$H$_{31}$ClN$_4$O$_3$•
Exact Mass: 494.21
Molecular Weight: 495.01

Following the procedure of Example 27 (step b), but substituting 2,2-dimethylmorpholine for piperazine, the title compound (20 mg, 18%) was prepared as a yellow powder: melting point (mp) 226-228° C. dec; $^1$H NMR (500 MHz, DMSO-d$_6$) δ 10.19 (s, 1H), 8.24 (s, 1H), 7.89 (d, J=8.9 Hz, 1H), 7.79 (d, J=1.4 Hz, 1H), 7.61 (d, J=7.6 Hz, 1H), 7.49-7.41 (m, 5H), 7.40-7.35 (m, 1H), 6.12 (dd, J===7.6, 27 Hz, 1H), 5.99 (d, J=2.7 Hz, 1H), 5.16 (s, 2H), 4.98 (m, 2H), 3.89-3.70 (m, 2H), 3.65-3.52 (m, 3H), 3.45-3.35 (m, 1H), 3.10-2.85 (m, 2H), 1.41 (s, 3H), 1.21 (s, 3H); ESI MS m/z 459 [M+H]$^+$.

Example 37

Preparation of 4-(Benzyloxy)-1-(1-((1-methyl-4,5-dihydro-1H-imidazol-2-yl)methyl)-1H-indazol-5-yl)pyridin-2(1H)-one hydrochloride Chemical Formula: C$_{24}$H$_{24}$ClN$_5$O$_2$
Exact Mass: 449.16
Molecular Weight: 449.93

Following the procedure of Example 25 (step b), but substituting N-methylethane-1,2-diamine for ethane-1,2-diamine, the title compound (23 mg, 75%) was prepared as a yellow powder melting point (mp) 230-232° C.; $^1$H NMR (500 MHz, DMSO-d$_6$) δ 9.75 (s, 1H), 8.31 (d, J=0.8 Hz, 1H), 7.86 (d, J=8.9 Hz, 1H), 7.83 (d, 1.5 Hz, 1H), 7.59 (d, J=7.6 Hz, 1H), 7.49-7.41 (m, 5H), 7.40-7.35 (m, 1H), 6.13 (dd, J=7.6, 2.9 Hz, 1H), 5.99 (d, J=2.8 Hz, 1H), 5.82 (s, 2H), 5.16 (s, 2H), 3.95 (t, J=9.9 Hz, 2H), 3.80-3.75 (m, 2H), 3.15 (s, 3H); ESI MS m/z 414 [M+H]+.

Example 38

Preparation of 4-(Benzyloxy)-1-(1-(2-(dimethylamino)-2-methylpropyl)-1H-indazol-5-yl)pyridin-2(1H)-one hydrochloride

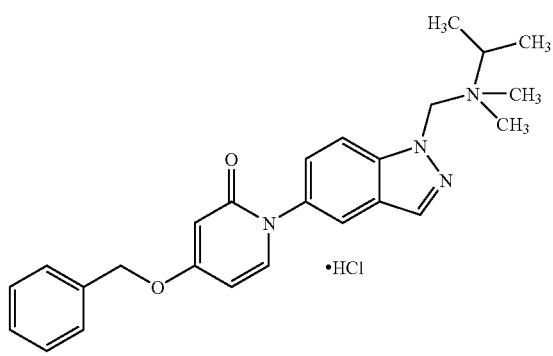

Chemical Formula: C25H29ClN4O2•
Exact Mass: 452.2
Molecular Weight: 452.98

Following the procedure of Example 2, but substituting 1-chloro-N,N,2-trimethylpropan-2-amine hydrochloride for 4-(2-chloroethyl)morpholine, the title compound (2 mg, 55%) was prepared as a white powder: $^1$H NMR (500 MHz, DMSO-$d_6$) δ 9.38 (s, 1H), 8.26 (s, 1H), 8.00 (d, J=9.0 Hz, 1H), 7.82 (s, J=15 Hz, 1H), 7.62 (d, J=7.5 Hz, 1H), 7.49-7.35 (m, 6H), 6.12 (dd, J=7.5, 2.5 Hz, 1H), 5.99 (d, J=3.0 Hz, 1H), 5.16 (s, 2H), 3.91 (d, J=4.5 Hz, 2H), 2.71 (d, J=5.0 Hz, 6H), 1.85 (s, 6H); ESI MS m/z 417 [M+H]+.

Example 39

Preparation of(S)-4-(Benzyloxy)-1-(1-(2-(3-methoxypyrrolidin-1-yl)ethyl)-1H-indazol-yl)pyridin-2(1H)-one hydrochloride

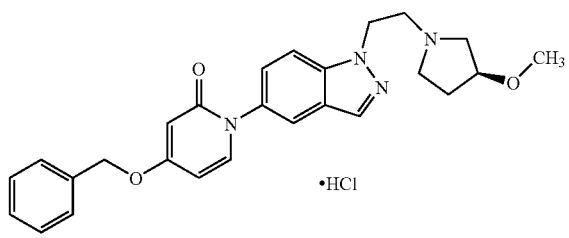

Chemical Formula: C26H29ClN4O3•
Exact Mass: 480.19
Molecular Weight: 480.99

Following the procedure of Example 27 (step b), but substituting (S)-3-methoxypyrrolidine for piperazine, the title compound (20.4 mg, 99%) was prepared as a yellow solid: melting point (mp) 232-234° C.; $^1$H NMR (500 MHz, DMSO-$d_6$) δ 8.24 (d, J=4.5 Hz, 1H), 7.88-7.81 (m, 1H), 7.79 (d, J=1.3 Hz, 1H), 7.60 (d, J=7.6 Hz, 1H), 7.48-7.35 (m, 6H), 6.13-6.10 (m, 1H), 5.99 (d, J=2.7 Hz, 1H), 5.16 (s, 2H), 4.89-4.84 (m, 2H), 4.15-4.10 (m, 0.6H), 4.08-4.02 (m, 0.4H), 3.71-3.68 (m, 3H), 3.59-3.51 (m, 1H), 3.23 (s, 3H), 3.20-3.05 (m, 2H), 2.31-2.21 (m, 0.6H), 2.19-2.10 (m, 0.4H), 1.99-1.89 (m, 1H); ESI MS m/z 445 [M+H]+; Optical Rotation $[α]^{23}_D$ −9.1° (c 1.00, Methanol).

Example 40

Preparation of (R)-4-(Benzyloxy)-1(1-(pyrrolidin-2-ylmethyl)-1H-indazol-5-yl)pyridin-2(1H)-one hydrochloride a) (R)-tert-Butyl 2-(bromomethyl)pyrrolidine-1-carboxylate

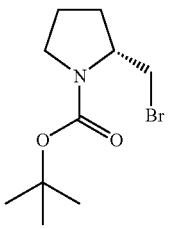

Chemical Formula: C10H18BrNO2
Exact Mass: 263.05
Molecular Weight: 264.16

To a solution of (R)-pyrrolidin-2-ylmethanol (0.7 g, 6.93 mmol) in CH2Cl2 (5 mL) was added (Boc)2O (1.66 g, 7.62 mmol) and triethylamine (1.40 g, 13.86 mmol) at 0° C. After stirring at 0° C. for about 10 minutes, the reaction mixture was allowed to stir at room temperature for 16 h. The mixture was quenched with aqueous acetic acid, then diluted with CH2Cl2 (20 mL), extracted with H2O (2×20 mL). The organics were dried over Na2SO4, filtered and concentrated to give (R)-tert-butyl (hydroxymethyl)pyrrolidine-1-carboxylate (1.26 g, 91%) as a solid. A solution of (R)-tert-butyl 2-(hydroxymethyl)pyrrolidine-1-carboxylate (1.26 g, 6.26 mmol) in CH2Cl2 (25 mL) was treated with CBr4 (3.13 g, 9.45 mmol) and PPh3 (2.48 g, 9.45 mmol) at 0° C. under N2 atmosphere. The reaction mixture was allowed to stir at room temperature for 16 h. Silica gel was added to the mixture, and then the mixture was concentrated to dryness. Purification by flash column chromatography (silica gel, Hexane/EtOAc, 100:0 to 3:1) gave the title compound (0.99 g, 60%) as a solid: $^1$H NMR (500 MHz, DMSO-$d_6$) δ 4.08-3.98 (m, 1H), 3.69-3.50 (m, 1H), 3.48-3.21 (m, 3H), 2.10-1.75 (m, 4H), 1.47 (s, 9H); ESI MS m/z 164 [M+H]+.

b) (R)-4-(Benzyloxy)-1-(1-(pyrrolidin-2-ylmethyl)-1H-indazol-5-yl)pyridin-2(1H)-one hydrochloride

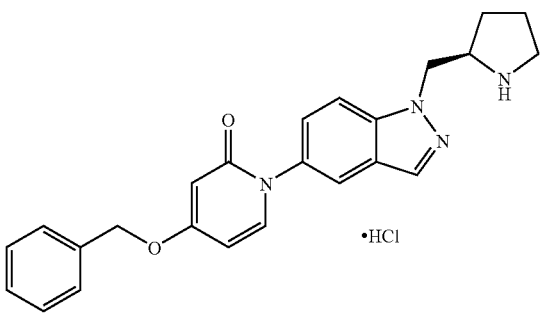

Chemical Formula: C24H25ClN4O2
Exact Mass: 436.17
Molecular Weight: 436.93

Following the procedure of Example 2, but substituting (R)-tert-butyl 2-(bromomethyl)pyrrolidine-1-carboxylate for 4-(2-chloroethyl)morpholine, (R)-tert-butyl 2-((5-(4-(benzyloxy)-2-oxopyridin-1(2H)-yl)-1H-indazol-1-yl)methyl)pyrrolidine-1-carboxylate (22 mg, 8%) was prepared as a yellow powder. A solution of this compound (22 mg, 0.044 mmol) in CH2Cl2 (2 mL) was treated with trifluoroacetic acid (25 mg, 0.22 mmol). After stirring at room temperature for 16 h, the reaction mixture was diluted with EtOAc (10 mL) and washed with 1N NaOH (10 mL). The organics were dried (Na$_2$SO$_4$), filtered and concentrated. Purification by flash column chromatography (silica gel, CH$_2$Cl$_2$/MeOH/NH$_4$OH, 40:1:0.1 to 20:1:0.2) provided the free base. This was dissolved in ethyl acetate (0.4 mL) and treated with 1 equivalent of 1 M HCl in Et$_2$O and the mixture was filtered to provide the title compound (14.8 mg, 77%) as a yellow solid: $^1$H NMR (500 MHz, DMSO-d$_6$) δ 9.25 (s, 1H), 9.01 (s, 1H), 8.25 (s, 1H), 7.86 (d, J=8.9 Hz, 1H), 7.79 (d, J=17 Hz, 1H), 7.60 (d, J=7.6 Hz, 1H), 7.49-7.35 (m, 6H), 6.12 (dd, J=7.6, 2.6 Hz, 1H), 5.99 (d, J=2.7 Hz, 1H), 5.16 (s, 2H), 4.85-4.71 (m, 2H), 4.02-3.92 (m, 1H), 3.32-3.22 (m, 1H), 3.20-3.11 (m, 1H), 2.14-2.05 (m, 1H), 2.02-1.92 (m, 1H), 1.91-1.85 (m, 1H), 1.78-1.68 (m, 1H); ESI MS m/z 401 [M+H]$^+$.

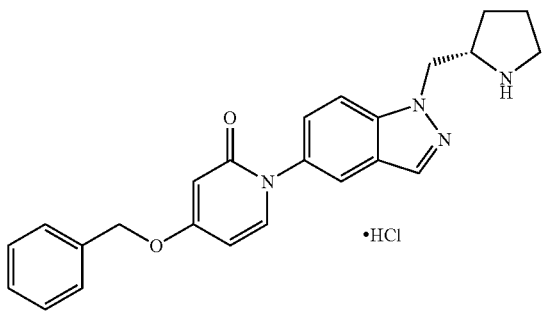

Chemical Formula: C$_{24}$H$_{25}$ClN$_4$O$_2$
Exact Mass: 436.17
Molecular Weight: 436.93

Example 41

Preparation of (S)-4-(Benzyloxy)-1-(1-pyrrolidin-2-ylmethyl)-1H-indazol-5-yl)pyridin-2(1H)-one hydrochloride Following the procedure of Example 40, but substituting (S)-pyrrolidin-2-ylmethanol for (R)-pyrrolidin-2-ylmethanol, the title compound (17.8 mg, 8%) was prepared as a yellow powder: $^1$H NMR (500 MHz, DMSO-d$_6$) δ 9.15 (s, 1H), 9.01 (s, 1H), 8.26 (s, 1H), 7.86 (d, J=9.0 Hz, 1H), 7.79 (d, J=1.5 Hz, 1H), 7.60 (d, J=8.0 Hz, 1H), 7.49-7.35 (m, 6H), 6.12 (dd, J=7.5, 2.5 Hz, 1H), 5.99 (d, J=2.5 Hz, 1H), 5.16 (s, 2H), 4.85-4.71 (m, 2H), 4.02-3.95 (m, 1H), 3.32-3.22 (m, 1H), 3.20-3.11 (m, 1H), 2.14-2.05 (m, 1H), 2.02-1.92 (m, 1H), 1.91-1.85 (m, 1H), 1.78-1.68 (m, 1H); ESI MS m/z 401 [M+H]$^+$.

Example 42

Preparation of (S)-4-(Benzyloxy)-1-(1-(3-(dimethylamino)-2-hydroxypropyl)-1H-indazol-5-yl)pyridin-2(1H)-one hydrochloride

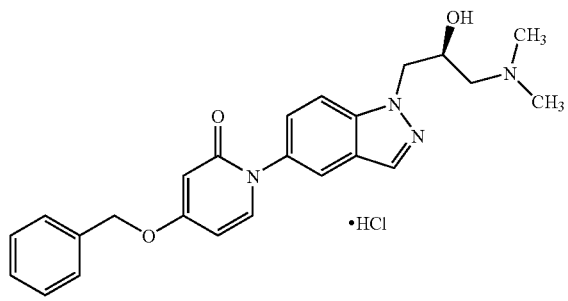

Chemical Formula: C$_{24}$H$_{27}$ClN$_4$O$_3$
Exact Mass: 454.18
Molecular Weight: 454.95

Following the procedure of Example 2, but substituting (R)-oxiran-2-ylmethyl 3-nitrobenzenesulfonate for 4-(2-chloroethyl)morpholine, (S)-4-(benzyloxy)-1-(1-(oxiran-2-ylmethyl)-1H-indazol-5-yl)pyridin-2(1H)-one (70 mg, 83%) was prepared as a yellow powder. A solution of this compound (66 mg, 0.18 mmol) in THF (2 mL) was treated with LiClO$_4$ (281 mg, 2.65 mmol) and dimethylamine (1 M in THF, 1.77 mmol) under a nitrogen atmosphere. After stirring at 60° C. for 24 h, the reaction mixture was diluted with CH$_2$Cl$_2$ (50 mL) and washed with H$_2$O (25 mL). The organics were dried (Na$_2$SO$_4$), filtered and concentrated. Purification by flash column chromatography (silica gel, CH$_2$Cl$_2$/MeOH/NH$_4$OH, 30:1:0.1 to 20:1:0.1) provided the free base. This was dissolved in ethyl acetate (0.4 mL) and treated with 1 equivalent of 1 M HCl in Et$_2$O and the mixture was filtered to provide the title compound (57.7 mg, 72%) as a yellow solid $^1$H NMR (500 MHz, DMSO-d$_6$) δ 9.49 (s, 1H), 8.18 (s, 1H), 7.78 (d, J=9.0 Hz, 1H), 7.74 (d, J=2.0 Hz, 1H), 7.59 (d, J=7.5 Hz, 1H), 7.49-7.27 (m, 6H), 6.12 (dd, J=8.0 Hz, 3.0 Hz, 1H), 5.99 (d, J=3.0 Hz, 1H), 5.96 (s, 1H), 5.16 (s, 2H), 4.56-4.46 (m, 2H), 4.41-4.33 (s, 1H), 3.23-317 (m, 1H), 3.12-3.04 (m, 1H), 2.76 (s, 6H); ESI MS m/z 419 [M+H]$^+$; Optical Rotation [α]$^{23}_D$-12.0° (c 1.00, Methanol).

Example 43

Preparation of (R)-4-(Benzyloxy)-1-(1-(3-(dimethylamino)-2-hydroxypropyl)-1H-indazol-5-yl)pyridin-2(1H)-one hydrochloride

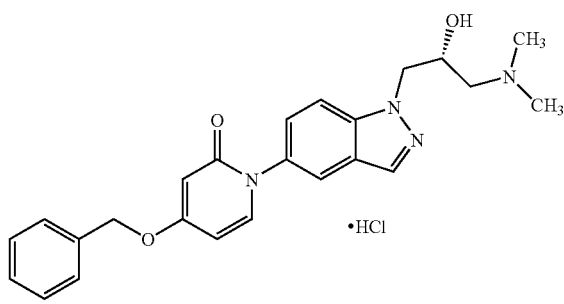

Chemical Formula: C$_{24}$H$_{27}$ClN$_4$O$_3$
Exact Mass: 454.18
Molecular Weight: 454.95

Following the procedure of Example 42, but substituting (S)-oxiran-2-ylmethyl 3-nitrobenzenesulfonate for (R)-oxiran-2-ylmethyl 3-nitrobenzenesulfonate, the title compound (71 mg, 35%) was prepared as a yellow solid: $^1$H NMR (500 MHz, DMSO-d$_6$) δ 9.46 (s, 1H), 8.17 (s, 1H), 7.78 (d, J=8.5 Hz, 1H), 7.74 (d, J=1.5 Hz, 1H), 7.60 (d, J=7.5 Hz, 1H), 7.49-7.34 (m, 6H), 6.13-6.10 (m, 1H), 5.99 (d, J=3.0 Hz, 1H), 5.85 (s, 1H), 5.15 (s, 2H), 4.56-4.46 (m, 2H), 4.41-4.33 (s, 1H), 3.20-3.05 (m, 1H), 3.05-2.95 (m, 1H), 2.71 (s, 6H); ESI MS m/z 419 [M+H]$^+$; Optical Rotation [α]$^{24}_D$+13.0° (c 1.00, Methanol).

Example 44

Preparation of (R)-4-(Benzyloxy)-1-(1-((4-hydroxy-pyrrolidin-2-yl)methyl)-1H-indazol-5-yl)pyridin-2(1H)-one hydrochloride

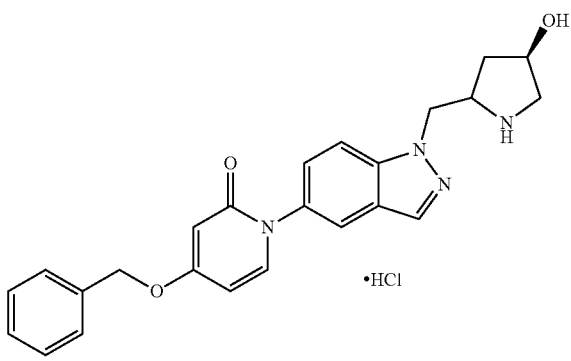

Chemical Formula: $C_{24}H_{25}ClN_4O_3$
Exact Mass: 452.16
Molecular Weight: 452.93

Following the procedure of Example 40 (step b), but substituting (R)-tert-butyl 2-(bromomethyl)-4-hydroxypyrrolidine-1-carboxylate for (R)-tert-butyl 2-(bromomethyl)pyrrolidine-1-carboxylate, the title compound (71.3 mg, 52%) was prepared as a yellow solid melting point (mp) 210-212° C.; $^1$H NMR (500 MHz, DMSO-d$_6$) δ 9.38 (s, 1H), 8.91 (s, 1H), 8.27 (s, 1H), 7.84 (d, J=8.9 Hz, 1H), 7.80 (d, J=1.4 Hz, 1H), 7.61 (d, J=7.6 Hz, 1H), 7.49-7.34 (m, 6H), 6.12 (dd, J=7.6, 2.7 Hz, 1H), 5.99 (d, J=2.7 Hz, 1H), 5.39 (s, 1H), 5.16 (s, 2H), 4.86 (dd, J=14.8, 4.7 Hz, 1H), 4.78-4.71 (m, 1H), 4.43 (s, 1H), 4.18 (s, 1H), 3.45-3.38 (m, 1H), 3.08-3.01 (m, 1H), 2.08-2.02 (m, 1H), 1.89-1.81 (m, 1H); ESI MS m/z 417 [M+H]$^+$.

Example 45

Preparation of (S,S)-1-(1-(2-(2-Oxa-5-azabicyclo[2.2.1]heptan-5-yl)ethyl)-1H-indazol-5-yl)-4-(benzyloxy)pyridin-2(1H)-one hydrochloride

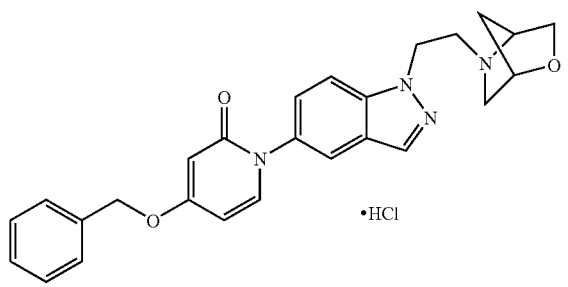

Chemical Formula: $C_{26}H_{27}ClN_4O_3$
Exact Mass: 478.18
Molecular Weight: 478.97

Following the procedure of Example 27 (step b), but substituting 2-oxa-5-azabicyclo[2.2.1]heptane for piperazine, 1-(1-(2-(2-Oxa-5-azabicyclo[2.2.1]heptan-5-yl)ethyl)-1H-indazol-5-yl)-4-(benzyloxy)pyridin-2(1H)-one was prepared as a yellow powder: $^1$H NMR (500 MHz, DMSO-d$_6$) δ 8.02 (s, 1H), 7.66 (d, J=1.6 Hz, 1H), 7.51 (d, J=8.9 Hz, 1H), 7.44-7.35 (m, 6H), 7.29 (d, J=7.4 Hz, 1H), 6.10-6.05 (m, 2H), 5.06 (s, 2H), 4.48 (t, J=6.9 Hz, 2H), 4.36 (s, 1H), 3.95 (d, J=7.8 Hz, 1H), 3.59 (dd, J=7.6, 1.7 Hz, 1H), 3.40 (s, 1H), 3.15-3.05 (m, 1H), 2.88 (dd, J=9.9, 1.6 Hz, 1H) 2.53 (d, J=9.8 Hz, 1H), 1.80-1.74 (m, 2H), 1.72-1.67 (m, 1H); ESI MS m/z 443 [M+H]$^+$ This was converted to the HCl salt to give the title compound (17.4 mg, 18%) as a yellow powder: ESI MS m/z 443 [M+H]$^+$.

Example 46

Preparation of 4-(Benzyloxy)-1-(1-((4,4-dimethyl-4,5-dihydro-1H-imidazol-2-yl)methyl)-1H-indazol-5-yl)pyridin-2(1H)-one hydrochloride

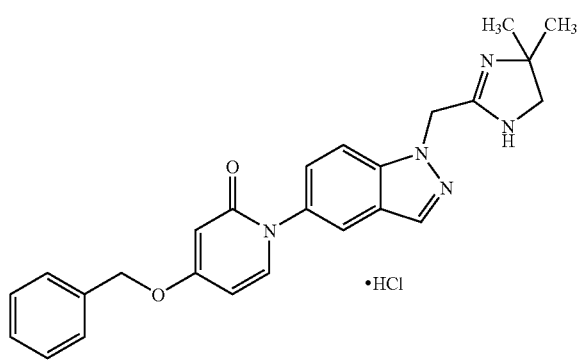

Chemical Formula: $C_{25}H_{26}ClN_5O_2$
Exact Mass: 463.18
Molecular Weight: 463.96

Following the procedure of Example 25, but substituting 2-methylpropane-1,2-diamine for ethane-1,2-diamine, the title compound (37.1 mg, 31%) was prepared as a yellow powder: melting point (mp) 170-172° C. dec; $^1$H NMR (500 MHz, DMSO-d$_6$) δ 10.39 (s, 1H), 10.21 (s, 1H), 8.32 (s, 1H), 7.85-7.83 (m, 2H), 7.59 (d, J=7.5 Hz, 1H), 7.49-7.36 (m, 6H), 6.13 (dd, J=8.0, 3.0 Hz, 1H), 5.99 (d, J=3.0 Hz, 1H), 5.69 (s, 2H), 5.16 (s, 2H), 3.65 (s, 2H), 1.33 (s, 6H); ESI MS m/z 428 [M+H]$^+$.

Example 47

Preparation of 4-(Benzyloxy)-1-(1-(2-(4-fluoropiperidin-1-yl)ethyl-1H-indazol-5-yl)pyridin-2(1H)-one hydrochloride

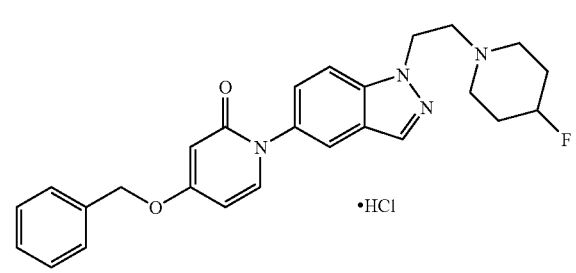

Chemical Formula: $C_{26}H_{28}ClFN_4O_2$
Exact Mass: 482.19
Molecular Weight: 482.98

Following the procedure of Example 27 (step b), but substituting 4-fluoropiperidine hydrochloride for piperazine, 4-(Benzyloxy)-1-(1-(2-(4-fluoropiperidin-1-yl)ethyl)-1H-indazol-5-yl)pyridin-2(1H)-one was prepared as a yellow powder: $^1$H NMR (500 MHz, DMSO-d$_6$) δ 8.02 (s, 1H), 7.66 (d, J=1.0 Hz, 1H), 7.48 (d, J=11.0 Hz, 1H), 7.44-7.35 (m, 6H), 7.29 (d, J=7.0 Hz, 1H), 6.10-6.05 (m, 2H), 5.06 (s, 2H), 4.73-4.59 (m, 1H), 4.52 (t, J=7.0 Hz, 2H), 2.88 (t, J=7.0 Hz, 2H), 2.69-2.60 (m, 2H), 2.49-2.42 (m, 2H), 1.94-1.81 (m, 4H); ESI MS m/z 447 [M+H]$^+$. This was converted to the HCl salt to give the title compound (136.6 mg, 48%) as a yellow powder: melting point (mp) 245-246° C.; ESI MS m/z 447 [M+H]+.

Example 48

Preparation of (S)-4-(Benzyloxy)-1-(1-(2-(3-fluoropyrrolidin-1-yl)ethyl-1H-indazol-5-yl)pyridin-2(1H)-one hydrochloride a) (S)-1-(2-Chloroethyl)-3-fluoropyrrolidine

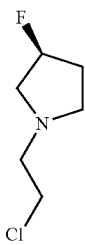

Chemical Formula: $C_6H_{11}ClFN$
Exact Mass: 151.06
Molecular Weight: 151.61

To a solution of 3-fluoropyrrolidine hydrochloride (0.59 g, 4.7 mmol) in 1,2-dichloroethane (8.2 mL) and AcOH (0.54 mL) was added chloroacetaldehyde (0.74 mL, 4.7 mmol, 50% in H$_2$O solution) and Na(AcO)$_3$BH (3.7 g, 17 mmol). The reaction mixture was stirred at ambient temperature for 1 h, and then the reaction mixture was diluted with 1 N NaOH and extracted with CH$_2$Cl$_2$ (3×50 mL). The organics were washed with brine (2×25 mL), dried (Na$_2$SO$_4$) and concentrated to yield the title compound (0.242 g, 33%) as a red-orange oil: $^1$H NMR (500 MHz, DMSO-d$_6$) δ 5.24-5.11 (m, 1H), 4.25-4.23 (m, 1H), 3.60 (t, J=7.0 Hz, 2H), 2.95-2.82 (m, 4H), 2.60-2.56 (m, 1H), 2.20-2.04 (m, 2H); ESI MS m/z 152 [M+H]+.

b) (S)-4-(Benzyloxy)-1-(1-(2-(3-fluoropyrrolidin-1-yl)ethyl)-1H-indazol-5-yl)pyridin-2(1H)-one

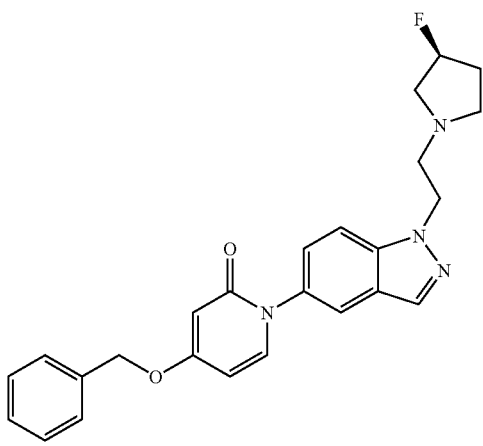

Chemical Formula: $C_{25}H_{25}FN_4O_2$
Exact Mass: 432.2
Molecular Weight: 432.49

To a solution of 4-(benzyloxy)-1-(1H-indazol-5-yl)pyridin-2(1H)-one (0.51 g, 1.6 mmol) in DMSO (5.0 mL) was added (S)-1-(2-chloroethyl)-3-fluoropyrrolidine (0.24 g, 1.6 mmol) and Cs$_2$CO$_3$ (3.1 g, 9.5 mmol). The reaction mixture was stirred at ambient temperature for 18 h, and then the reaction mixture was diluted with H$_2$O (10 mL) and extracted with EtOAc (4×20 mL). The organic extracts were washed with brine (3×20 mL) and dried (Na$_2$SO$_4$). Purification by flash chromatography (silica gel, CH$_2$Cl$_2$/80:18:2 CH$_2$Cl$_2$/MeOH/NH$_4$OH, 100.0 to 0:100), followed by additional flash column chromatography (silica gel, CH$_2$Cl$_2$/10% MeOH in CH$_2$Cl$_2$, 100:0 to 10:90), followed by treatment with activated charcoal, followed by final purification by preparative HPLC (Phenomenex Luna C18 (2), 250.0×21.2 mm, 10 micron, H$_2$O with 0.05% TFA and CH$_3$CN with 0.05% TFA) gave the title compound (58.3 mg, 8%) as a white powder: $^1$H NMR (500 MHz, CDCl$_3$) δ 8.04 (s, 1H), 7.67 (d, J=1.5 Hz, 1H), 7.55 (d, J=9 Hz, 1H), 7.45-7.37 (m, 6H), 7.31-7.30 (m, 1H), 6.12-6.10 (m, 2H), 5.16 (dt, J=55.5, 4.5 Hz, 1H), 5.07 (s, 2H), 4.58 (t, J=7.0 Hz, 2H), 3.01 (br m, 2H), 2.97-2.93 (m, 2H) 2.92-2.90 (m, 1H), 2.56 (br s, 1H), 2.17-2.03 (m, 2H); ESI MS m/z 433 [M+H]+; HPLC (Method A)>99% (AUC), $t_R$=13.9 min.

c) (S)-4-(Benzyloxy)-1-(1-(2-(3-fluoropyrrolidin-1-yl)ethyl)-1H-indazol-5-yl)pyridin-2(1H)-one hydrochloride

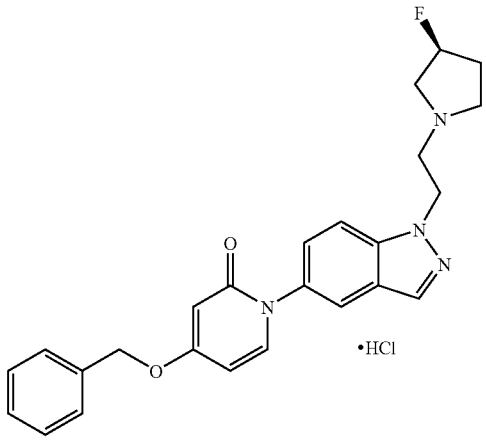

Chemical Formula: $C_{25}H_{26}ClFN_4O_2$
Exact Mass: 468.17
Molecular Weight: 468.95

A solution of (S)-4-(benzyloxy)-1-(1-(2-(3-fluoropyrrolidin-1-yl)ethyl)-1H-indazol-5-yl)pyridin-2(1H)-one (56 mg, 0.12 mmol) in CH$_2$Cl$_2$ (1.5 mL) was treated with anhydrous HCl in diethyl ether (0.12 mL, 0.12 mmol, 1.0 M). The reaction mixture was stirred at ambient temperature for 2 h, and then the solids were collected by filtration and dried to yield the title compound (51.4 mg, 85%) as a white powder: mp 197-200° C.; $^1$H NMR (500 MHz, DMSO-d$_6$) δ 10.62-10.50 (m, 1H), 8.25 (s, 1H), 7.85 (d, J=8.0 Hz, 1H), 7.80 (s, 1H), 7.61 (d, J=7.5 Hz, 1H), 7.48-7.42 (m, 5H), 7.39-7.36 (m, 1H), 6.13 (dd, J=7.5, 3.0 Hz, 1H), 5.99 (d, J=2.5 Hz, 1H), 5.54-5.39 (m, 1H), 5.16 (s, 2H), 4.87-4.82 (m, 2H), 3.81-3.53 (m, 4H), 3.55-3.20 (m, 2H, overlapping with H$_2$O peak), 2.14-2.01 (s, 2H); ESI MS m/z 433 [M+H]+; HPLC (Method A)>99% (AUC), $t_R$=14.4 min; optical rotation $[\alpha]^{22.5}_D$-8.4° (c 0.095, Methanol).

Example 49

Preparation of 4-(Benzyloxy)-1-(1-(2-(3,3-difluoropyrrolidin-1-yl)ethyl)-1H-indazol-yl)pyridin-2(1H)-one hydrochloride a) 1-(2-Chloroethyl)-3,3-difluoropyrrolidine

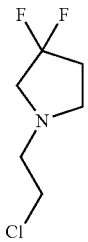

Chemical Formula: C$_6$H$_{10}$ClF$_2$N
Exact Mass: 169.05
Molecular Weight: 169.6

Following the procedure of Example 48 (step a), but substituting 3,3-difluoropyrrolidine hydrochloride for 3-fluoropyrrolidine hydrochloride, the title compound (0.155 g, 22%) was prepared as an orange-red oil. $^1$H NMR (500 MHz, DMSO-d$_6$) δ 3.57 (t, J=7. Hz, 2H), 2.99 (t, J=13.5 Hz, 1H), 2.86-2.81 (m, 4H), 2.32-2.24 (m, 3H).

b) 4-(Benzyloxy)-1-(1-(2-(3,3-difluoropyrrolidin-1-yl)ethyl)-1H-indazol-5-yl)pyridin-2(1H)-one

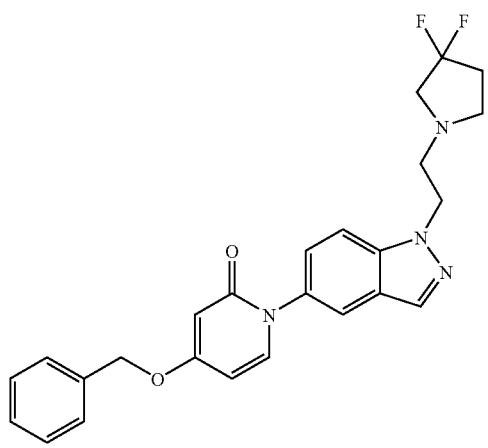

Chemical Formula: C$_{25}$H$_{24}$F$_2$N$_4$O$_2$
Exact Mass: 450.19
Molecular Weight: 450.48

Following the procedure of Example 48 (step b), but substituting 1-(2-chloroethyl)-3,3-difluoropyrrolidine for (S)-1-(2-chloroethyl)-3-fluoropyrrolidine, the title compound (76.7 mg, 18%) was prepared as a yellow foam: $^1$H NMR (500 MHz, CDCl$_3$) δ 8.03 (s, 1H), 7.67 (d, J=2.0 Hz, 1H), 7.50 (d, J=9 Hz, 1H), 7.43-7.38 (m, 6H), 7.29 (d, J=7.5 Hz, 1H), 6.10-6.07 (m, 2H), 5.06 (s, 2H), 4.52 (t, J=7 Hz, 2H), 3.03 (t, J=7.0 Hz, 2H), 2.94 (t, J=13.0 Hz, 2H) 2.78 (t, J=7.0 Hz, 2H), 2.27-2.21 (m, 2H); ESI MS m/z 451 [M+H]$^+$.

c) 4-(Benzyloxy)-1-(1-(2-(3,3-difluoropyrrolidin-1-yl)ethyl)-1H-indazol-5-yl)pyridin-2(1H)-one hydrochloride

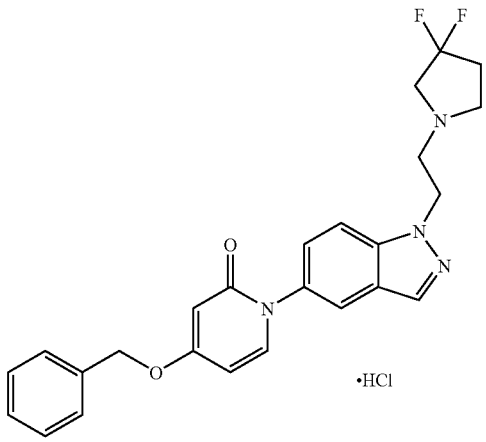

Chemical Formula: C$_{25}$H$_{25}$ClF$_2$N$_4$O$_2$
Exact Mass: 486.16
Molecular Weight: 486.94

Following the procedure of Example 48 (step c), but substituting 4-(benzyloxy)-1-(1-(2-(3,3-difluoropyrrolidin-1-yl)ethyl)-1H-indazol-5-yl)pyridin-2(1H)-one for (S)-4-(benzyloxy)-1-(1-(2-(3-fluoropyrrolidin-1-yl)ethyl)-1H-indazol-5-yl)pyridin-2(1H)-one, the title compound (70.1 mg, 84%) was prepared as an off-white powder: mp 212-216° C.; $^1$H NMR (500 MHz, DMSO-d$_6$) δ 8.22 (s, 1H), 7.84 (d, 9.0 Hz, 1H), 7.77 (s, 1H), 7.61 (d, J=7.5 Hz, 1H), 7.48-7.36 (m, 6H), 6.12 (dd, J=7.5, 3.0 Hz, 1H), 5.99 (d, J=2.5 Hz, 1H), 5.16 (s, 2H), 4.76 (br s, 2H), 3.71 (br s, 8H, overlapping with H$_2$O peak); ESI MS m/z 451 [M+H]$^+$; HPLC (Method A) 98.1% (AUC), t$_R$=15.1 min.

Example 50

Preparation of 4-(Benzyloxy)-1(1-(2-(4-hydroxypiperidin-1yl)ethyl-1H-indazol-5-yl)pyridin-2(1H)-one hydrochloride a) 1-(2-Chloroethyl)piperidin-4-ol

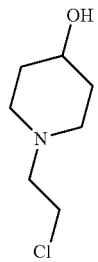

Chemical Formula: C$_7$H$_{14}$ClNO
Exact Mass: 163.08
Molecular Weight: 163.65

Following the procedure of Example 48 (step a), but substituting piperidin-4-ol hydrochloride for 3-fluoropyrrolidine hydrochloride, the title compound (0.826 g, 50%) was prepared as a light yellow oil. $^1$H NMR (500 MHz, CDCl$_3$) δ 4.52 (br s, 1H), 3.90 (s, 1H), 7.71 (s, 1H), 3.45-3.40 (s, 1H), 2.73-2.70 (m, 2H), 2.59 (t, J=7.0 Hz, 2H), 2.10 (t, J=10.0 Hz, 2H), 1.70-1.66 (m, 2H), 1.39-1.32 (m, 2H).

b) 4-(Benzyloxy)-1-(1-(2-(4-hydroxypiperidin-1yl)ethyl)-1H-indazol-5-yl)pyridin-2(1H)-one

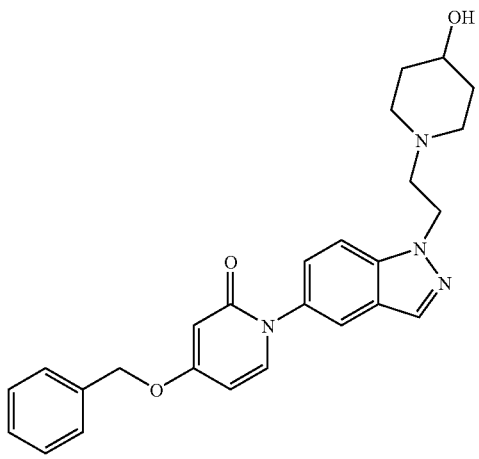

Chemical Formula: C<sub>26</sub>H<sub>28</sub>N<sub>4</sub>O<sub>3</sub>
Exact Mass: 444.22
Molecular Weight: 444.53

Following the procedure of Example 48 (step b), but substituting 1-(2-chloroethyl)piperidin-4-ol for (S)-1-(2-chloroethyl)-3-fluoropyrrolidine, the title compound (116 mg, 20%) was prepared as a yellow film: $^1$H NMR (500 MHz, DMSO-d$_6$) δ 8.11 (s, 1H), 7.75 (d, J=9.0 Hz, 1H), 7.71 (d, J=1.5 Hz, 1H), 7.62 (d, J=7.5 Hz, 1H), 7.48-7.47 (m, 2H), 7.44-7.42 (m, 2H), 7.39-7.36 (m, 1H), 7.32 (dd, J=9.0, 2.0 Hz, 1H), 6.10 (dd, J=7.5, 2.5 Hz, 1H), 5.99 (d, J=30 Hz, 1H), 5.15 (s, 2H), 4.53 (t, J=6.5 Hz, 2H), 4.49 (d, J=4.5 Hz, 1H), 3.43-3.39 (m, 1H) 2.77-2.72 (m, 4H), 2.10 (t, J=9.5 Hz, 2H), 1.66-1.64 (m, 2H), 1.34-1.27 (m, 2H); ESI MS m/z 445 [M+H]$^+$; HPLC (Method A) 96.1% (AUC), t$_R$=14.2 min.

c) 4-(Benzyloxy)-1-(1-(2-(4-hydroxypiperidin-1yl)ethyl)-1H-indazol-5-yl)pyridin-2(1H)-one hydrochloride

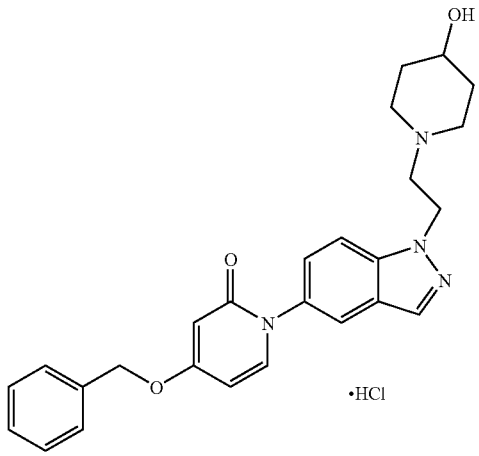

Chemical Formula: C<sub>26</sub>H<sub>29</sub>ClN<sub>4</sub>O<sub>3</sub>
Exact Mass: 480.19
Molecular Weight: 480.99

Following the procedure of Example 48 (step c), but substituting 4-(benzyloxy)-1-(1-(2-(4-hydroxypiperidin-1-yl)ethyl)-1H-indazol-5-yl)pyridin-2(1H)-one for (S)-4-(benzyloxy)-1-(1-(2-(3-fluoropyrrolidin-1-yl)ethyl)-1H-indazol-5-yl)pyridin-2(1H)-one, the title compound (104 mg, 93%) was prepared as a yellow powder: mp: 180-186° C. decompose; $^1$H NMR (500 MHz, DMSO-d$_6$) δ 9.56 (br s, 1H), 8.24 (s, 1H), 7.86 (t, J=9.5 Hz, 1H), 7.79 (s, 1H), 7.60 (d, J=7.5 Hz, 1H), 7.48-7.42 (m, 5H), 7.39-7.36 (m, 1H), 6.13 (dd, J=7.5, 2.5 Hz, 1H), 5.99 (d, J=2.5 Hz, 1H), 5.16 (s, 2H), 5.08-4.99 (m, 1H), 4.91-4.88 (m, 2H), 3.96-3.93 (m, 1H), 3.72-3.57 (m, 4H), 3.46-3.78 (m, 1H), 3.19-3.15 (m, 1H), 2.09-1.99 (m, 1H), 1.89-1.84 (m, 1H), 1.77-1.70 (m, 1H), 1.59-1.57 (m, 1H); ESI MS m/z 445 [M+H]$^+$; HPLC (Method A) 95.8% (AUC), t$_R$=14.2 min.

Example 51

Preparation of (R)-4-(benzyloxy)-1-(1-(2-(3-hydroxypyrrolidin-1-yl)ethyl-1H-indazol-5-yl)pyridin-2(1H)-one hydrochloride a) (R)-1-(2-Chloroethyl)pyrrolidine-3-ol

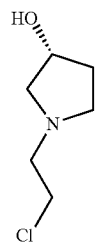

Chemical Formula: C<sub>6</sub>H<sub>12</sub>ClNO
Exact Mass: 149.06
Molecular Weight: 149.62

To a solution of (R)-3-hydroxypyrrolidine (0.47 g, 5.5 mmol) in MeOH (14.4 mL) and AcOH (1.44 mL) was added chloroacetaldehyde (0.86 mL, 5.5 mmol, 50% in H$_2$O solution) and picolineborane complex (0.58 g, 5.5 mmol). The reaction mixture was stirred at ambient temperature for 0.5 h. Then additional picoline borane complex (0.29 g, 2.7 mmol) was added. The reaction mixture was stirred for an additional 0.5 h. Then the reaction mixture was diluted with HCl (30 mL, 10% in H$_2$O) and stirred for 0.5 h at ambient temperature. The mixture was slowly basified with solid NaHCO$_3$ (7.85 g) and extracted with EtOAc (3×20 mL). The organics extracts were dried (Na$_2$SO$_4$) and concentrated to yield the title compound (0.19 g, 23%) as a light yellow oil. $^1$H NMR (300 MHz, CD$_3$OD) δ 4.36-4.32 (m, 1H), 3.63 (t, J=6.6 Hz, 2H), 2.91-2.76 (m, 4H), 2.66-2.52 (m, 3H), 2.16-2.09 (m, 1H), 1.74-1.70 (m, 1H).

b) (R)-4-(Benzyloxy)-1-(1-(2-(3-hydroxypyrrolidin-1-yl)ethyl)-1H-indazol-5-yl)pyridin-2(1H)-one

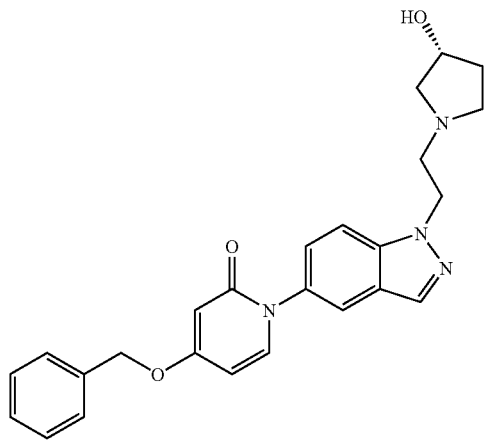

Chemical Formula: C$_{25}$H$_{26}$N$_4$O$_3$
Exact Mass: 430.20
Molecular Weight: 430.50

Following the procedure of Example 48 (step b), but substituting (R)-1-(2-chloroethyl)pyrrolidine-3-ol for (S)-1-(2-chloroethyl)-3-fluoropyrrolidine, the title compound (29.6 mg, 11%) was prepared as an off-white powder: $^1$H NMR (500 MHz, DMSO-d$_6$) δ 8.11 (d, J=1 Hz, 1H), 7.75 (d, J=9.0 Hz, 1H), 7.71 (d, J=15 Hz, 1H), 7.62 (d, J=7.5 Hz, 1H), 7.48-7.42 (m, 4H), 7.39-7.37 (m, 1H), 7.32 (dd, J=9.0, 2.0 Hz, 1H), 6.10 (dd, J=7.5, 3.0 Hz, 1H), 5.99 (d, J=3.0 Hz, 1H), 5.15 (s, 2H), 4.64 (d, J=4.5 Hz, 1H), 4.52 (t, J=65 Hz, 2H), 4.15-4.11 (m, 1H), 2.88 (t, J=7.0 Hz, 2H), 2.77-2.74 (m, 1H), 2.61-2.57 (m, 1H), 2.32 (dd, J=9.5, 3.5 Hz, 1H), 2.07 (s, 1H), 1.92-1.86 (m, 1H), 1.51-1.47 (m, 1H); ESI MS m/z 431 [M+H]$^+$.

c) (R)-4-(Benzyloxy)-1-(1-(2-(3-hydroxypyrrolidin-1-yl)ethyl)-1H-indazol-5-yl)pyridin-2(1H)-one hydrochloride

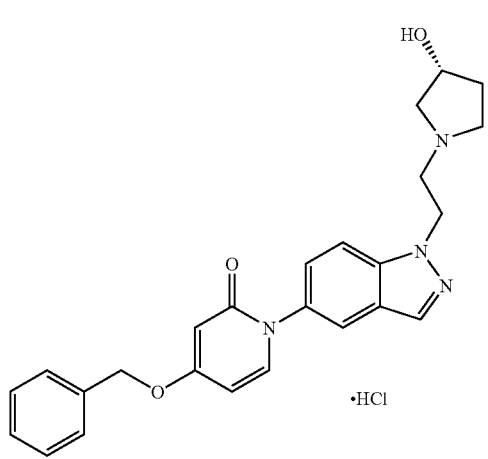

Chemical Formula: C$_{25}$H$_{27}$ClN$_4$O$_3$
Exact Mass: 466.18
Molecular Weight: 466.96

Following the procedure of Example 48 (step c), but substituting (R)-4-(benzyloxy)-1-(1-(2-(3-hydroxypyrrolidin-1-yl)ethyl)-1H-indazol-5-yl)pyridin-2(1H)-one for (S)-4-(benzyloxy)-1-(1-(2-(3-fluoropyrrolidin-1-yl)ethyl)-1H-indazol-5-yl)pyridin-2(1H)-one, the title compound (29.8 mg, 93%) was prepared as a yellow powder: mp 198-200° C.; $^1$H NMR (500 MHz, DMSO-d$_6$) δ 10.28 (br s, 1H), 8.20 (s, 1H), 7.82 (d, J=8.0 Hz, 1H), 7.77 (s, 1H), 7.61 (d, J=7.5 Hz, 1H), 7.48-7.36 (m, 6H), 6.12 (dd, J=7.5, 2.5 Hz, 1H), 5.99 (d, J=2.5 Hz, 1H), 5.15 (s, 2H), 4.75 (br s, 2H), 4.32 (br s, 1H), 3.57 (br s, 2H), 3.15-2.99 (m, 2H), 2.11-2.00 (m, 2H) 1.71 (br s, 2H), ESI MS m/z 431 [M+H]$^+$; HPLC 94.5% (AUC), t$_R$=13.2 min; optical rotation [α]$^{22.0}_D$ +5.4° (c 1.05, Methanol).

Example 52

Preparation of (R)-4-(Benzyloxy)-1-(1-(2-(2-methoxypyrrolidin-1yl)ethyl-1H-indazol-5-yl)pyridin-2(1H)-one hydrochloride a. (R)-1-(2-Chloroethyl)-2-methyoxypyrrolidine

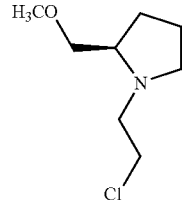

Chemical Formula: C$_8$H$_{16}$ClNO
Exact Mass: 177.09
Molecular Weight: 177.67

Following the procedure of Example 51 (step a), but substituting (R)-2-(methoxymethyl)pyrrolidine for (R)-3-hydroxypyrrolidine, the title compound (0.29 g, 68%) was prepared as a light yellow oil. $^1$H NMR (300 MHz, CDCl$_3$) δ 3.58 (t, J=6.9 Hz, 2H), 3.40-3.29 (m, 5H), 3.20-3.14 (m, 2H) 2.75-2.66 (m, 2H), 2.32-2.27 (m, 1H), 1.89-1.57 (m, 4H); ESI MS m/z 178 [M+H]$^+$.

b) (R)-4-(Benzyloxy)-1-(1-(2-(2-methoxypyrrolidin-1-yl)ethyl)-1H-indazol-5-yl)pyridin-2(1H)-one

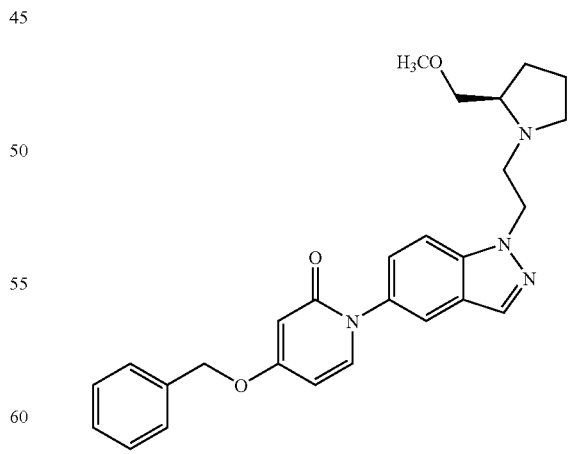

Chemical Formula: C$_{27}$H$_{30}$N$_4$O$_3$
Exact Mass: 458.23
Molecular Weight: 458.55

Following the procedure of Example 48 (step b), but substituting (R)-1-(2-chloroethyl)-2-methyoxypyrrolidine for (S)-1-(2-chloroethyl)-3-fluoropyrrolidine, the title compound (0.13 mg, 37%) was prepared as a yellow solid ¹H NMR (500 MHz, CDCl₃) δ 8.01 (d, J=1 Hz, 1H), 7.65 (d, J=1.5 Hz, 1H), 7.52 (d, J=9 Hz, 1H), 7.47-7.37 (m, 6H), 7.29 (d, J=7.5 Hz, 1H), 6.09-6.07 (m, 2H), 5.06 (s, 2H), 4.54 (t, J=7.5 Hz, 2H), 3.45-3.32 (m, 1H), 3.31 (s, 3H), 3.29-3.25 (m, 2H) 3.19-3.15 (m, 1H), 2.90-2.85 (m, 1H), 2.72-2.68 (m, 1H), 2.38-2.33 (m, 1H), 1.92-1.84 (m, 1H), 1.78-1.72 (m, 2H), 1.60-1.54 (m, 1H); ESI MS m/z 459 [M+H]⁺, HPLC (Method A) 97.7% (AUC), $t_R$=14.2 min.

c) (R)-4-(Benzyloxy)-1-(1-(2-(2-methoxypyrrolidin-1-yl)ethyl)-1H-indazol-5-yl)pyridin-2(1H)-one hydrochloride

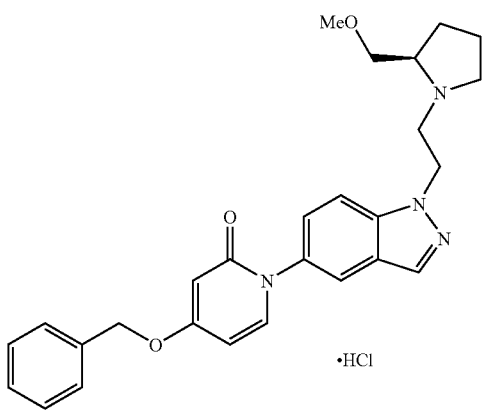

Chemical Formula: C₂₇H₃₁ClN₄O₃
Exact Mass: 494.21
Molecular Weight: 495.01

Following the procedure of Example 48 (step c), but substituting (R)-4-(benzyloxy)-1-(1-(2-(2-methoxypyrrolidin-1-yl)ethyl)-1H-indazol-5-yl)pyridin-2(1H)-one for (S)-4-(benzyloxy)-1-(1-(2-(3-fluoropyrrolidin-1-yl)ethyl)-1H-indazol-5-yl)pyridin-2(1H)-one, the title compound (109 mg, 80%) was prepared as a yellow powder: mp 198-202° C.; ¹H NMR (500 MHz, DMSO-d₆) δ 9.86 (br s, 1H), 8.25 (s, 1H), 7.84 (d, J=9.0 Hz, 1H), 7.79 (d, J=1.5 Hz, 1H), 7.61 (d, J=7.5 Hz, 1H), 7.48-7.42 (m, 5H), 7.39-7.36 (m, 1H), 6.13 (dd, J=7.5, 2.5 Hz, 1H), 5.99 (d, J=2.5 Hz, 1H), 5.16 (s, 2H), 4.89-4.81 (m, 2H), 3.94-3.92 (m, 1H), 3.79 (m, 1H), 3.69-3.62 (m, 3H), 3.57-3.54 (m, 1H), 3.32 (s, 3H, overlapping with H₂O peak), 3.15-3.11 (m, 1H), 2.14-2.12 (m, 1H), 2.11-1.99 (m, 1H), 1.89-1.83 (m, 1H), 1.71-1.67 (m, 1H); ESI MS m/z 459 [M+H]⁺; HPLC (Method A) 96.9% (AUC), $t_R$=14.2 min; optical rotation $[α]^{23.0}_D$+13.9° (c 115, Methanol).

Example 53

Preparation of (S)-4-(Benzyloxy)-1-(1-(2-(3-hydroxypyrrolidin-1-yl)ethyl)-1H-indazol-pyridin-2(1H)-one hydrochloride a) (S)-4-(Benzyloxy)-1-(1-(2-(3-hydroxypyrrolidin-1-yl)ethyl)-1H-indazol-5-yl)pyridin-2(1H)-one

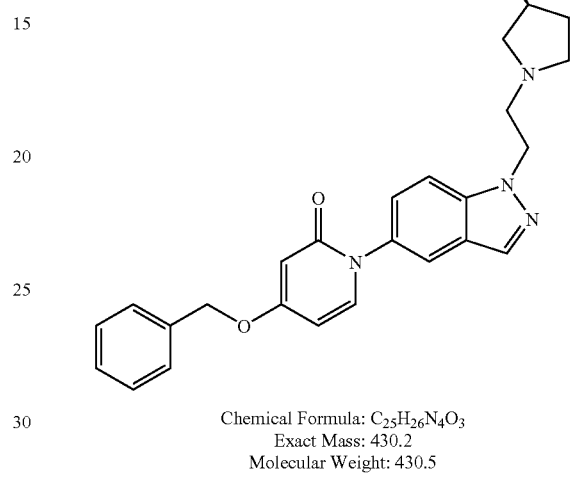

Chemical Formula: C₂₅H₂₆N₄O₃
Exact Mass: 430.2
Molecular Weight: 430.5

To a solution of 4-(benzyloxy)-1-(1-(2-hydroxyethyl)-1H-indazol-5-yl)pyridin-2(1H)-one (0.800 g, 2.21 mmol) in CH₂Cl₂ (48.0 mL) was added Dess-Martin periodinane (1.87 g, 4.43 mmol). After stirring at ambient temperature for 5 h, the reaction mixture was diluted with a solution of saturated sodium bicarbonate and excess Na₂S₂O₃ then extracted with CH₂Cl₂ (3×50 mL). The organics were dried (Na₂SO₄), filtered and concentrated. The material was used without further purification.

To a solution of this intermediate (0.20 g, 0.56 mmol) in 1,2-dichloroethane (3.3 mL) was added (S)-3-pyrrolidinol (46 mL, 0.56 mmol) and NaB(AcO)₃H (0.24 g, 1.1 mmol). After stirring at ambient temperature for 6 h, the reaction mixture was diluted with 1 N NaOH and extracted with CH₂Cl₂ (3×15 mL). The organics were washed with 1 N HCl (4×15 mL), and then the aqueous layer was basified and extracted with CH₂Cl₂ (4×20 mL), dried (Na₂SO₄) and concentrated. Purification by preparative HPLC (Phenomenex Luna C18 (2), 250.0×21.2 mm, 10 micron, H₂O with 0.05% TFA and CH₃CN with 0.05% TFA) yielded the title compound (12.7 mg, 5%) as a white solid: ¹H NMR (500 MHz, DMSO-d₆) δ 8.12 (s, 1H), 7.75 (d, J=9.5 Hz, 1H), 7.72 (d, J=2.0 Hz, 1H), 7.62 (d, J=7.5 Hz, 1H), 7.48-7.42 (m, 4H), 7.39-7.36 (m, 1H), 7.32 (dd, J=9.0, 2.0 Hz, 1H), 6.10 (dd, J=7.5, 2.5 Hz, 1H), 5.99 (d, J=2.5 Hz, 1H), 5.15 (s, 2H), 4.64 (d, J=4.5 Hz, 1H), 4.52 (t, J=6.5 Hz, 2H), 4.13-4.12 (m, 1H), 2.88 (t, J=6.5 Hz, 2H), 2.76 (dd, J=9.5, 6.5 Hz, 2H) 2.61-2.53 (m, 1H), 2.32 (dd, J=9.5, 4.0 Hz, 1H), 1.92-1.88 (m, 1H), 1.50-1.48 (m, 1H); ESI MS m/z 431 [M+H]⁺. HPLC (Method A) >99.0% (AUC), $t_R$=14.0 min.

b) (S)-4-(Benzyloxy)-1-(1-(2-(3-hydroxypyrrolidin-1-yl)ethyl)-1H-indazol-5-yl)pyridin-2(1H)-one hydrochloride

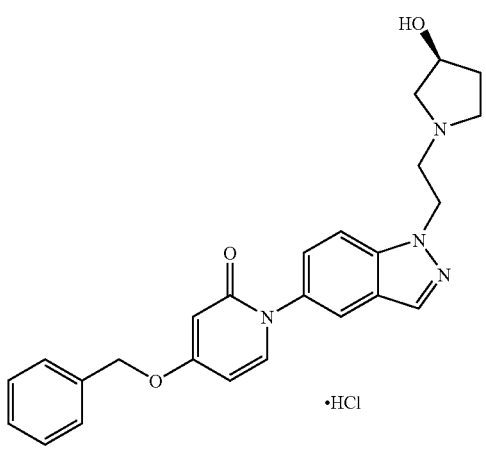

Chemical Formula: C$_{25}$H$_{27}$ClN$_4$O$_3$
Exact Mass: 466.18
Molecular Weight: 466.96

Following the procedure of Example 48 (step c), but substituting (S)-4-(benzyloxy)-1-(1-(2-(3-hydroxypyrrolidin-1-yl)ethyl)-1H-indazol-5-yl)pyridin-2(1H)-one for (S)-4-(benzyloxy)-1-(1-(2-(3-fluoropyrrolidin-1-yl)ethyl)-1H-indazol-5-yl)pyridin-2(1H)-one, the title compound (10.5 mg, 86%) was prepared as a white powder: mp 276-280° C. decompose; ESI MS m/z 431 [M+H]$^+$; HPLC (Method A) >99.0% (AUC), t$_R$=14.1 min.

Example 54

Preparation of (S)-4-(Benzyloxy)-1-(1-(2-(2-hydroxymethylpyrrolidin-1-yl)ethyl)-1H-indazol-5-yl)pyridin-2(1H)-one hydrochloride a) (S)-4-(Benzyloxy)-1-(1-(2-(2-hydroxymethylpyrrolidin-1-yl)ethyl)-1H-indazol-5-yl)pyridin-2(1H)-one

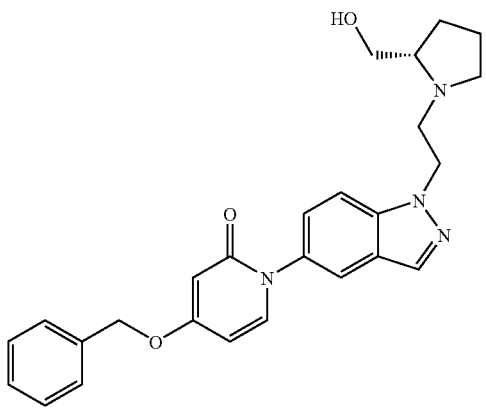

Chemical Formula: C$_{26}$H$_{28}$N$_4$O$_3$
Exact Mass: 444.22
Molecular Weight: 444.53

Following the procedure of Example 53 (step a), but substituting (S)-1-(2-chloroethyl)-2-hydroxymethylpyrrolidine for (S)-3-pyrrolidinol, the title compound (23 mg, 9%) was prepared as a white solid: $^1$H NMR (500 MHz, DMSO-d$_6$) δ 8.12 (s, 1H), 7.74 (d, J=9.0 Hz, 1H), 7.72 (d, J=2.0 Hz, 1H), 7.62 (d, J=7.5 Hz, 1H), 7.48-7.42 (m, 4H), 7.39-7.36 (m, 1H), 7.33 (dd, J=9.0, 1.5 Hz, 1H), 6.10 (dd, J=8.0, 3.0 Hz, 1H), 5.99 (d, J=3.0 Hz, 1H), 5.15 (s, 2H), 4.55-4.51 (m, 2H), 4.29 (m, 1H), 3.33-3.24 (m, 3H), 3.12-3.10 (m, 1H), 3.05-3.03 (m, 1H), 2.77-2.75 (m, 1H), 2.27-2.22 (m, 1H), 1.78-1.72 (m, 1H), 1.63-1.55 (m, 2H), 1.46-1.45 (m, 1H); ESI MS m/z 445 [M+H]$^+$; HPLC (Method A)>99% (AUC), t$_R$=14.6 min.

b) (S)-4-(Benzyloxy)-1-(1-(2-(2-hydroxymethylpyrrolidin-1-yl)ethyl)-1H-indazol-5-yl)pyridin-2(1H)-one hydrochloride

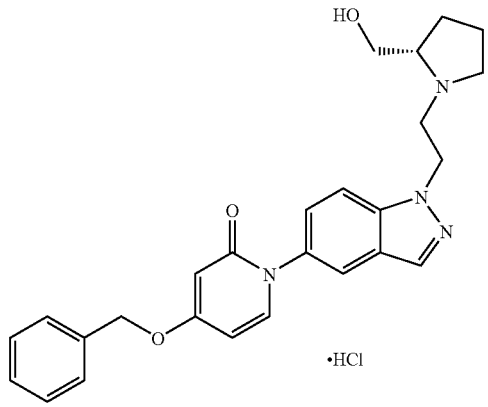

Chemical Formula: C$_{26}$H$_{29}$ClN$_4$O$_3$
Exact Mass: 480.19
Molecular Weight: 480.99

Following the procedure of Example 48 (step c), but substituting (S)-4-(benzyloxy)-1-(1-(2-(2-hydroxymethylpyrrolidin-1-yl)ethyl)-1H-indazol-5-yl)pyridin-2(1H)-one for (S)-4-(benzyloxy)-1-(1-(2-(3-fluoropyrrolidin-1-yl)ethyl)-1H-indazol-5-yl)pyridin-2(1H)-one, the title compound (19 mg, 83%) was prepared as a yellow powder: mp 198-206° C.; $^1$H NMR (500 MHz, DMSO-d$_6$) δ 9.62 (br s, 1H), 8.24 (s, 1H), 7.84 (d, J=8.5 Hz, 1H), 7.79 (d, J=1.5 Hz, 1H), 7.61 (d, J=7.5 Hz, 1H), 7.48-7.42 (m, 5H), 7.39-7.36 (m, 1H), 6.13 (dd, J=7.5, 2.5 Hz, 1H), 5.99 (d, J=2.5 Hz, 1H), 5.54-5.53 (m, 1H), 5.16 (s, 2H), 4.91-4.82 (m, 2H), 3.94-3.92 (m, 1H), 3.78-3.77 (m, 1H), 3.68-3.62 (m, 3H), 3.57-3.55 (m, 1H), 3.22-3.15 (m, 1H), 2.11-1.98 (m, 2H), 1.87-1.71 (2H); ESI MS m/z 445 [M+H]$^+$; HPLC (Method A) >99.0% (AUC), t$_R$=14.2 min.

Example 55

Preparation of (R)-4-(Benzyloxy)-1-(1-(2-(2-hydroxymethylpyrrolidin-1-yl)ethyl-1H-indazol-5-yl)pyridin-2(1H)-one hydrochloride a) (R)-4-(Benzyloxy)-1-(1-(2-(2-(hydroxymethyl)pyrrolidin-1-yl)ethyl)-1H-indazol-5-yl)pyridin-2(1H)-one

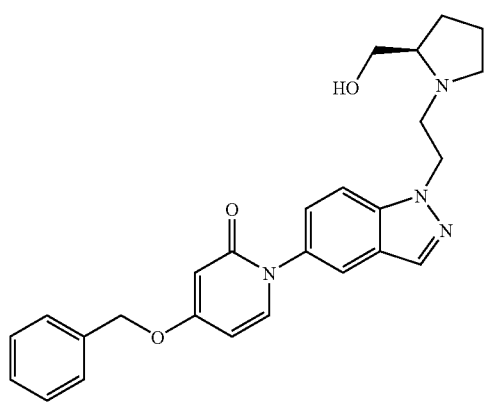

Chemical Formula: $C_{26}H_{28}N_4O_3$
Exact Mass: 444.22
Molecular Weight: 444.53

To a solution of 4-(benzyloxy)-1-(1-(2-chloroethyl)-1H-indazol-5-yl)pyridin-2(1H)-one (0.15 g, 0.40 mmol) in DMF (2.1 mL) was added $Cs_2CO_3$ (0.64 g, 2.0 mmol) and (R)-2-hydroxymethylpyrrolidine (0.78 mL, 7.9 mmol). The reaction mixture was heated at 90° C. for 3 h. The reaction mixture was cooled and diluted with $H_2O$ (25 mL) and was extracted with EtOAc (3×20 mL) The organic extracts were washed with brine (2×20 mL), dried ($Na_2SO_4$), filtered and concentrated. Purification by flash chromatography (silica gel, Hexanes/EtOAc/9:1 MeOH/$NH_4OH$, 1:1:0 to 9:9:2) followed by preparative HPLC (Phenomenex Luna C18 (2), 250.0×21.2 mm, 10 micron, $H_2O$ with 0.05% TFA and $CH_3CN$ with 0.05% TFA) gave the title compound (30 mg, 17%) as a clear film. $^1$H NMR (500 MHz, $CDCl_3$) δ 8.05 (s, 1H), 7.67 (s, 1H), 7.49-7.46 (m, 1H), 7.42-7.36 (m, 6H), 7.30-7.26 (m, 1H), 6.09-6.08 (m, 2H), 5.06 (s, 2H), 4.50-4.49 (m, 2H), 3.47-3.45 (m, 1H), 3.39-3.37 (m, 1H), 3.28-3.19 (m, 2H), 2.88-2.86 (m, 1H) 2.69 (br s, 1H), 2.60-2.45 (br s, 1H), 2.39-2.38 (m, 1H), 1.86-1.70 (m, 4H); ESI MS m/z 445 [M+H]$^+$.

b) (R)-4-(Benzyloxy)-1-(1-(2-(2-(hydroxymethyl)pyrrolidin-1-yl)ethyl)-1H-indazol-5-yl)pyridin-2(1H)-one hydrochloride

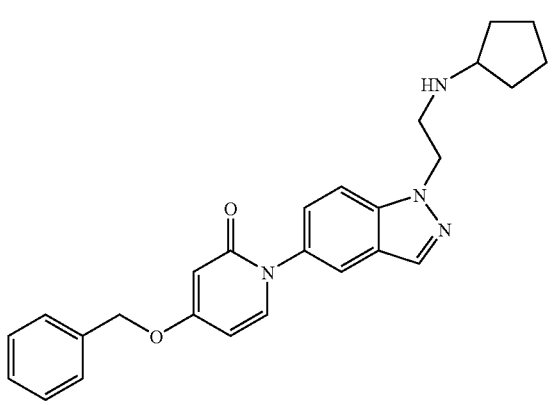

Chemical Formula: $C_{26}H_{29}ClN_4O_3$
Exact Mass: 480.19
Molecular Weight: 480.99

Following the procedure of Example 48 (step c), but substituting (R)-4-(benzyloxy)-1-(1-(2-(2-hydroxymethylpyrrolidin-1-yl)ethyl)-1H-indazol-5-yl)pyridin-2(1H)-one for (S)-4-(benzyloxy)-1-(1-(2-(3-fluoropyrrolidin-1-yl)ethyl)-1H-indazol-5-yl)pyridin-2(1H)-one, the title compound (28 mg, 91%) was prepared as a brown yellow powder. $^1$H NMR (500 MHz, DMSO-$d_6$) δ 9.70 (br s, 1H), 8.24 (s, 1H), 7.84 (d, J=9.0 Hz, 1H), 7.79 (d, J=2.0 Hz, 1H), 7.61 (d, J=7.5 Hz, 1H), 7.48-7.42 (m, 5H), 7.39-7.36 (m, 1H), 6.12 (dd, J=8.0, 3.0 Hz, 1H), 5.99 (d, J=2.5 Hz, 1H), 5.52 (br s, 1H), 5.15 (s, 2H), 4.92-4.83 (m, 2H), 3.94-3.92 (m, 1H), 3.80-3.78 (m, 1H), 3.69-3.64 (m, 3H), 3.57-3.52 (m, 1H), 3.16-3.11 (m, 1H), 2.10-1.97 (m, 2H), 1.87-1.71 (m, 2H); ESI MS m/z 445 [M+H]$^+$; HPLC (Method A)>99% (AUC), $t_R$=13.9 min; optical rotation $[α]^{22.5}_D$+12.0° (c 1.00, Methanol).

Example 56

Preparation of 4-(Benzyloxy)-1-(1-(2-cyclopentylamino)ethyl)-1H-indazol-5-yl)pyridin-2(1H)-one hydrochloride a) 4-(Benzyloxy)-1-(1-(2-(cyclopentylamino)ethyl)-1H-indazol-5-yl)pyridin-2(1H)-one Chemical Formula: $C_{26}H_{28}N_4O_2$
Exact Mass: 428.22
Molecular Weight: 428.53

Following the procedure of Example 55 (step a), but substituting cyclopentyl amine for (R)-2-hydroxymethylpyrrolidine, the title compound (88 mg, 52%) was prepared as a clear film: $^1$H NMR (500 MHz, $CDCl_3$) δ 8.04 (s, 1H), 7.67 (d, J=1.5 Hz, 1H), 7.53 (d, J=8.5 Hz, 1H), 7.46-7.36 (m, 6H), 7.29 (d, J=7.5 Hz, 1H), 6.09-6.06 (m, 2H), 5.06 (s, 2H), 4.51 (t, J=6.0 Hz, 2H), 3.15 (t, J=6.5 Hz, 2H), 3.12-3.07 (m, 1H), 1.85-1.78 (m, 2H) 1.67-1.62 (m, 2H), 1.55-1.48 (m, 3H), 1.31-1.27 (m, 2H); ESI MS m/z 429 [M+H]$^+$.

b) 4-(Benzyloxy)-1-(1-(2-(cyclopentylamino)ethyl)-1H-indazol-5-yl)pyridin-2(1H)-one hydrochloride

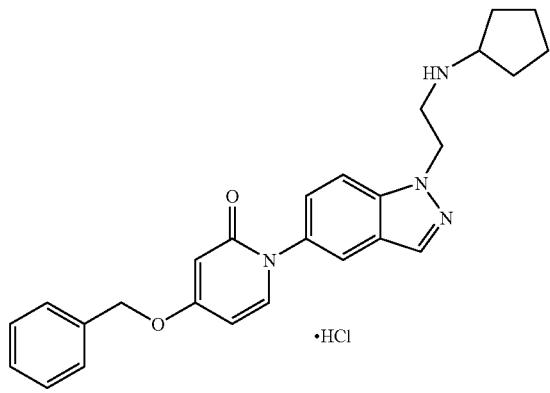

Chemical Formula: $C_{26}H_{28}N_4O_2$
Exact Mass: 428.22
Molecular Weight: 428.53

Following the procedure of Example 48 (step c), but substituting 4-(benzyloxy)-1-(1-(2-(cyclopentylamino)ethyl)-1H-indazol-5-yl)pyridin-2(1H)-one for (S)-4-(benzyloxy)-1-(1-(2-(3-fluoropyrrolidin-1-yl)ethyl)-1H-indazol-5-yl)pyridin-2(1H)-one, the title compound (71 mg, 76%) was prepared as an off-white powder: mp 221-222° C.; $^1$H NMR (500 MHz, DMSO-d$_6$) δ 8.95 (br s, 2H), 8.23 (s, 1H), 7.82 (d, J=8.5 Hz, 1H), 7.79 (d, J=2.0 Hz, 1H), 7.60 (d, J=8.0 Hz, 1H), 7.48-7.40 (m, 5H), 7.39-7.36 (m, 1H), 6.12 (dd, J=7.5, 3.0 Hz, 1H), 5.99 (d, J=2.5 Hz, 1H), 5.16 (s, 2H), 4.77 (t, J=6.0 Hz, 2H), 3.55 (br s, 1H), 3.45 (br s, 2H), 1.97-1.93 (m, 2H), 1.71-1.67 (m, 2H), 1.64-158 (m, 2H), 1.56-1.51 (m, 2H); ESI MS m/z 429 [M+H]$^+$; HPLC (Method A) 98.6% (AUC), $t_R$=14.2 min.

Example 57

Preparation of 4-(4-Fluorophenethyl)-1-(1-(2-(pyrrolidin-1-yl)ethyl)-1H-indazol-5-yl)pyridin-2(1H)-one hydrochloride a) 1-(2-(Pyrrolidin-1-yl)ethyl)-1H-indazol-5-yl)pyridin-2(1H)-one-4-trifluoromethanesulfonate

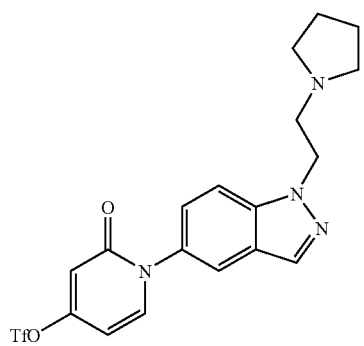

Chemical Formula: $C_{19}H_{19}F_3N_4O_4S$
Exact Mass: 456.11
Molecular Weight: 456.44

4-Hydroxy-1-(1-(2-(pyrrolidin-1-yl)ethyl)-1H-indazol-5-yl)pyridin-2(1H)-one (900 mg, 2.7 mmol) was suspended in THF (20 mL) under a nitrogen atmosphere and LiN(SiMe$_3$)$_2$ (1M in THF) (4.2 mL, 4.2 mmol) added. After stirring for 1 minute, PhNTf$_2$ (1.48 g, 4.16 mmol) was added in one portion and the mixture was stirred for 2 h. The mixture was concentrated, diluted with methylene chloride (50 mL) and washed successively with saturated NH$_4$Cl and saturated Na$_2$CO$_3$, dried over sodium sulfate and concentrated. The residue was purified by column chromatography (40 g ISCO column eluting with methylene chloride and a methanol/ammonia mixture (10:1); gradient 100% methylene chloride to 80% methylene chloride over 30 min at 40 mL/min) to provide the title compound (780 mg, 60%) as a white solid; $^1$H NMR (500 MHz, CDCl$_3$) δ 8.05 (s, 1H), 7.68 (d, J=1.8 Hz, 1H), 7.57 (d, J=8.9 Hz, 1H), 7.53 (d, J=7.4 Hz, 1H), 7.37-7.35 (dd, J=8.9, 2.0 Hz, 1H), 6.60 (d, J=2.7 Hz, 1H), 6.30-6.28 (dd, J=8.7, 2.5 Hz, 1H), 4.57 (t, J=7.2 Hz, 2H), 3.01 (t, J=7.2 Hz, 2H), 2.60-2.57 (m, 4H), 1.80-1.76 (m, 4H) ESI MS m/z 457 [M+H]$^+$.

b) (E)-4-(4-Fluorostyryl)-1-(1-(2-(pyrrolidin-1-yl)ethyl)-1H-indazol-5-yl)pyridin-2(1H)-one

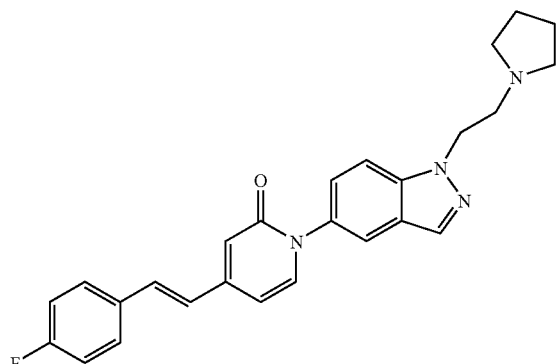

Chemical Formula: $C_{26}H_{25}FN_4O$
Exact Mass: 428.20
Molecular Weight: 428.50

1-(2-(Pyrrolidin-1-yl)ethyl)-1H-indazol-5-yl)pyridin-2(1H)-one-4-trifluoromethanesulfonate (100 mg, 0.22 mmol), (4-fluoro)phenylvinylboronic acid (90.9 mg, 0.55 mmol), K$_2$CO$_3$ (75 mg, 0.55 mmol) and PdCl$_2$dppf (18 mg, 0.022 mmol) were stirred in DMSO (2 mL) under vacuum for 30 min. The flask was flushed with nitrogen and the mixture was heated at 80° C. for 30 min. Upon cooling, the mixture was diluted with methylene chloride and washed with 5% lithium chloride solution (5×), dried, concentrated and the residue was purified by column chromatography (12 g ISCO column eluting with methylene chloride and a methanol/ammonia mixture (10:1); gradient 100% methylene chloride to 80% methylene chloride over 30 min at 25 mL/min) to provide the title compound (70.4 mg, 16%): $^1$H NMR (500 MHz, CD$_3$OD) δ 8.04 (s, 1H), 7.70 (d, J=1.8 Hz, 1H), 7.57-7.48 (m, 3H), 7.46-7.40 (dd, J=8.9, 1.9 Hz, 1H), 7.38 (d, J=7.71 Hz, 1H), 7.1 (d, J=16.3 Hz, 1H), 7.09 (t, J=8.6 Hz, 2H), 6.85 (d, J=16.3 Hz, 1H), 6.65 (d, J=1.6 Hz, 1H), 6.52-6.46 (dd, J=7.2, 1.9 Hz, 1H), 4.56 (t, J=7.3 Hz, 2H), 3.01 (t, J=7.3 Hz, 2H), 2.63-2.53 (m, 4H), 1.86-1.75 (m, 4H).

c) 4-(4-Fluorophenethyl)-1-(1-(2-(pyrrolidin-1-yl)ethyl)-1H-indazol-5-yl)pyridin-2(1H)-one hydrochloride

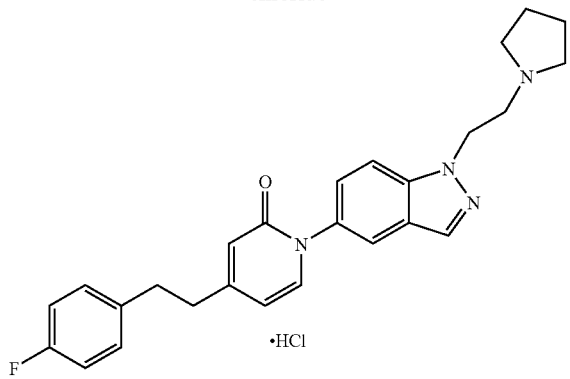

Chemical Formula: $C_{26}H_{27}FN_4O$
Exact Mass: 430.22
Molecular Weight: 430.52

(E)-4-(4-Fluorostyryl)-1-(1-(2-(pyrrolidin-1-yl)ethyl)-1H-indazol-5-yl)pyridin-2(1H)-one (70 mg, 0.16 mmol), and ammonium formate (20.7 mg, 0.328 mmol) were stirred in methanol (4 ml) for 5 min. Palladium on carbon (100 mg) was added, and the mixture was heated to reflux for 1.5 h. The reaction mixture was cooled to room temperature, filtered through celite, rinsed with ethanol, and then concentrated. The residue was dissolved in methanol (2 mL) and treated with 1 equivalent of 2 M HCl in $Et_2O$ and the mixture was concentrated to provide the title compound (39.4 mg, 9.1%) as a yellow solid: mp 55-60° C.; $^1$H NMR (500 MHz, $CD_3OD$) δ 8.23 (s, 1H), 7.84-7.75 (m, 2H), 7.60-7.54 (dd, J=6.7, 0.6 Hz, 1H), 7.47-7.41 (dd, J=8.9, 2.0 Hz, 1H), 7.28-7.20 (m, 2H), 7.04-6.96 (m, 2H), 6.47-6.40 (m, 2H), 4.87 (t, J=5.7 Hz, 2H), 3.86 (t, J=5.7 Hz, 2H), 3.74-3.63 (br m, 2H), 3.21-3.10 (br m, 2H), 3.01-2.92 (m, 2H), 2.92-2.83 (m, 2H), 2.23-2.09 (m, 2H), 2.08-1.95 (m, 2H); ESI MS m/z 431 [M+H]$^+$; HPLC (Method D) 92.5% (AUC), $t_R$=12.9 min.

Example 58

Preparation of 4-(4-Fluorophenethyl)-1-(1-(2-pyrrolidin-1-yl)ethyl)-1H-indazol-5-yl)pyridin-2(1H)-one hydrochloride a) (E)-4-(2-(Biphenyl-4-yl)vinyl)-1-(1-(2-(pyrrolidin-1-yl)ethyl)-1H-indazol-5-yl)pyridin-2(1H)-one

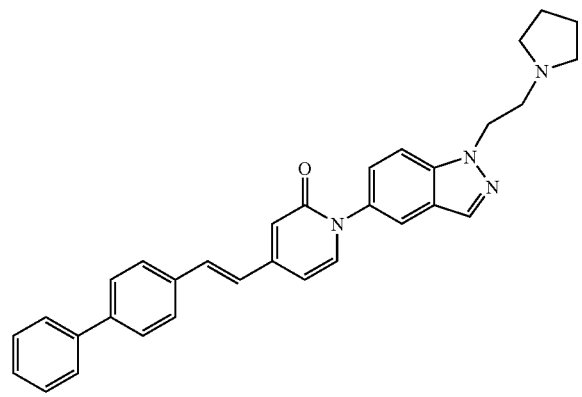

Chemical Formula: $C_{32}H_{30}N_4O$
Exact Mass: 486.24
Molecular Weight: 486.61

1-(2-(Pyrrolidin-1-yl)ethyl)-1H-indazol-5-yl)pyridin-2(1H)-one-4-trifluoromethanesulfonate (100 mg, 0.22 mmol), (4-phenyl)phenylvinylboronic acid (120 mg, 0.55 mmol), $K_2CO_3$ (75 mg, 0.55 mmol) and $PdCl_2dppf$ (18 mg, 0.022 mmol) were stirred in DMSO (2 mL) under vacuum for 30 min. The flask was flushed with nitrogen and the mixture was heated at 80° C. for 30 min. Upon cooling, the mixture was diluted with methylene chloride and washed with 5% lithium chloride solution (5×), dried, concentrated and the residue was purified by column chromatography (12 g ISCO column eluting with methylene chloride and a methanol/ammonia mixture (10:1); gradient 100% methylene chloride to 80% methylene chloride over 30 min at 25 mL/min) to provide the title compound (51.4 mg, 11%): $^1$H NMR (500 MHz, $CD_3OD$) δ 8.04 (s, 1H), 7.71 (d, J=1.5 Hz, 1H), 7.68-7.59 (m, 6H), 7.54 (d, J=2.9 Hz, 1H), 7.50-7.41 (m, 3H), 7.4-7.34 (m, 2H), 7.26 (d, J=16.3 Hz, 1H), 6.98 (d, J=16.3 Hz, 1H), 6.69 (d, J=1.65 Hz, 1H), 6.56-6.51 (dd, J=7.3, 1.9 Hz, 1H), 4.56 (t, J=7.3 Hz, 2H), 3.01 (t, J=7.3 Hz, 2H), 2.65-2.53 (m, 4H), 1.84-1.75 (m, 4H).

b) 4-(4-Fluorophenethyl)-1-(1-(2-(pyrrolidin-1-yl)ethyl)-1H-indazol-5-yl)pyridin-2(1H)-one hydrochloride

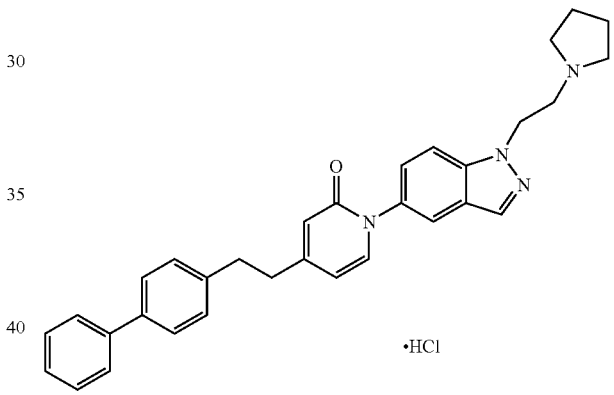

Chemical Formula: $C_{32}H_{32}N_4O$
Exact Mass: 488.26
Molecular Weight: 488.62

(E)-4-(4-Fluorostyryl)-1-(1-(2-(pyrrolidin-1-yl)ethyl)-1H-indazol-5-yl)pyridin-2(1H)-one (51 mg, 0.11 mmol) and ammonium formate (13.3 mg, 0.211 mmol) were stirred in methanol (4 ml) for 5 min. Palladium on carbon (100 mg) was added, and the mixture was heated to reflux for 1.5 h. The reaction mixture was cooled to room temperature, filtered through celite, rinsed with ethanol, and then concentrated. The residue was dissolved in methanol (2 mL) and treated with 1 equivalent of 2 M HCl in $Et_2O$, and the mixture was concentrated to provide the title compound (42.3 mg, 8.5%) as a yellow solid. mp 200-210° C.; $^1$H NMR (500 MHz, $CD_3OD$) δ 8.23 (s, 1H), 7.83 (s, 1H), 7.78 (d, J=8.8 Hz, 1H), 7.61-7.51 (m, 6H), 7.48-7.44 (dd, J=9.0, 2.0 Hz, 1H), 7.41 (t, J=7.6 Hz, 2H), 7.35-7.27 (m, 3H), 6.49-6.47 (m, 1H), 4.86 (t, J=57 Hz, 2H), 3.85 (t, J=57 Hz, 2H), 3.74-3.62 (br m, 2H), 3.20-3.11 (br m, 2H), 3.07-3.00 (m, 2H), 2.97-2.91 (br m, 2H), 2.19-2.11 (m, 2H), 2.05-1.96 (br m, 2H); ESI MS m/z 489 [M+H]$^+$; HPLC (Method D)>92.7% (AUC), $t_R$=14.8 min.

Example 59

Preparation of (S)-1-(1-(2-(3-Hydroxypyrrolidin-1-yl)ethyl)-1H-indazol-5-yl)-4-phenethylpyridin-2(1H)-one hydrochloride a) 5-Bromo-1-(2,2-dimethoxyethyl)-1H-indazole

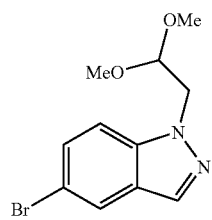

Chemical Formula: C₁₁H₁₃BrN₂O₂
Exact Mass: 284.02
Molecular Weight: 285.14

To a solution of 5-bromo-1H-indazole (10.0 g, 51.2 mmol) in DMSO (120 mL) was added 2-bromoacetaldehyde dimethyl acetal (12.1 mL, 103 mmol) and Cs₂CO₃ (66.8 g, 205 mmol). The reaction mixture was stirred at 40° C. for 18 h; then the reaction mixture was diluted with H₂O (100 mL) and EtOAc (175 mL). The aqueous layer was extracted with EtOAc (4×175 mL). The combined organics were washed with brine (2×100 mL), dried (Na₂SO₄), filtered, and concentrated. Purification by flash chromatography (ISCO 330 g column, 95:5 hexanes/EtOAc to hexanes/EtOAc 50:50, 60 min, 40 mL/min) gave the title compound (8.52 g, 46%) as a light orange solid: ¹H NMR (300 MHz, CDCl₃) 7.94 (s, 1H), 7.85 (d, J=1.2, 1H), 7.48-7.42 (dd, J=8.9, 1.7 Hz, 1H), 7.37 (d, J=8.9 Hz, 1H), 4.71 (t, J=5.4 Hz, 1H), 4.44 (d, J=5.5 Hz, 2H), 3.33 (s, 6H).

b) 4-(Benzyloxy)-1-(1-(2,2-dimethoxyethyl)-1H-indazol-5-yl)pyridin-2(1H)-one

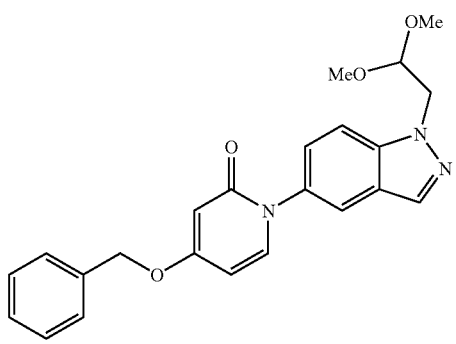

Chemical Formula: C₂₃H₂₃N₃O₄
Exact Mass: 405.17
Molecular Weight: 405.45

A suspension of 5-bromo-1-(2,2-dimethoxyethyl)-1H-indazole (4.0, 14 mmol), 4-(benzyloxy)pyridin-2(1H)-one (3.1 g, 16 mmol), K₂CO₃ (2.1 g, 16 mmol), 8-hydroxyquinoline (310 mg, 2.1 mmol) and CuI (3.1 g, 16 mmol) in DMSO (20 mL) was evacuated for 30 minutes under high vacuum then backfilled with nitrogen. The mixture was stirred under nitrogen at 130° C. for 20 h and then allowed to cool. The mixture was diluted with 20% MeOH/NH₄OH (10:1) in CH₂Cl₂ (200 mL), stirred for 15 min, and then loaded onto a silica plug. The material was eluted through the plug with 20% MeOH/NH₄OH (10:1) in CH₂Cl₂ (400 ml) and then concentrated. The residue was dissolved in CH₂Cl₂, washed with LiCl (4×100 mL) and brine (1×100 mL), dried over Na₂SO₄, filtered and concentrated to dryness. Purification by flash column chromatography (120 g ISCO column eluting with methylene chloride and a methanol/ammonia mixture (10:1); gradient 100% methylene chloride to 80% methylene chloride over 60 min at 40 mL/min) gave the title compound (4.96 g, 85%) as a light orange solid ¹H NMR (300 MHz, CDCl₃) δ 8.04 (s, 1H), 7.66 (d, J=1.6 Hz, 1H), 7.56 (d, J===8.9 Hz, 1H), 7.45-7.33 (m, 6H), 7.27 (d, J===2.9 Hz, 1H), 6.12-6.04 (m, 2H), 5.05 (s, 2H), 4.76 (t, J=5.3 Hz, 1H), 4.59 (d, J=5.3 Hz, 2H), 3.37 (s, 6H).

c) 1-(1-(2,2-Dimethoxyethyl)-1H-indazol-5-yl)-4-hydroxypyridin-2(1H)-one

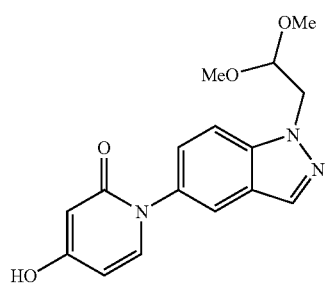

Chemical Formula: C₁₆H₁₇N₃O₄
Exact Mass: 315.12
Molecular Weight: 315.32

A solution of 4-(benzyloxy)-1-(1-(2,2-Dimethoxyethyl)-1H-indazol-5-yl)pyridin-2(1H)-one (4.96 g, 12.2 mmol) and ammonium formate (1.53 g, 24.4 mmol) in CH₃OH was stirred for 10 min. Pd/C (5.5 g) was added under a nitrogen atmosphere. The reaction mixture was heated at 80° C. for 2 h and then allowed to cool. The mixture was filtered through a layer of Celite, and the filtrate was concentrated. The residue was triturated with MeOH, concentrated to dryness, triturated with EtOAc, sonicated for 20 min and then concentrated to give the title compound (3.62 g, 95%) as a yellow/white solid: ¹H NMR (500 MHz, CDCl₃) 8.06 (s, 1H), 7.68 (s, 1H), 7.58 (d, J=8.9 Hz, 1H), 7.39 (d, J=8.9 Hz, 1H), 7.27 (d, 1H, overlapping with solvent peak), 6.12 (s, 1H), 6.05 (d, J=7.3 Hz, 1H), 4.78 (t, J=5.2 Hz, 2H), 4.50 (d, J=5.2 Hz, 2H), 3.38 (s, 6H).

d) 1-(1-(2,2-Dimethoxyethyl)-1H-indazol-5-yl)-2-oxo-1,2-dihydropyridin-4-yl trifluoromethanesulfonate

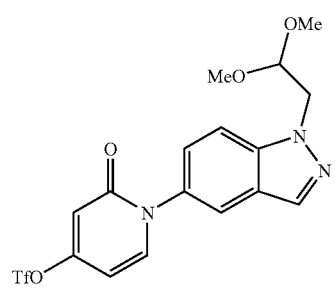

Chemical Formula: C₁₇H₁₆F₃N₃O₆S
Exact Mass: 447.07
Molecular Weight: 447.39

1-(1-(2,2-Dimethoxyethyl)-1H-indazol-5-yl)-4-hydroxypyridin-2(1H)-one (3.62 g, 11.4 mmol) was suspended in THF (80 mL) under a nitrogen atmosphere, and LiN(SiMe$_3$)$_2$ (1M in THF) (14.9 mL, 14.9 mmol) was added. After stirring for 10 minutes, PhNTf$_2$ (5.31 g, 14.9 mmol) was added in one portion, and the mixture was stirred for 1.5 h. The mixture was diluted with methylene chloride (500 mL) and washed successively with saturated NH$_4$Cl and saturated Na$_2$CO$_3$, dried over sodium sulfate and concentrated. The residue was purified by column chromatography (120 g ISCO column eluting with methylene chloride and a methanol/ammonia mixture (10:1); gradient 100% methylene chloride to 80% methylene chloride over 60 min at 40 mL/min) to provide the title compound (4.33 g, 85%) as a white solid: $^1$H NMR (500 MHz, CDCl$_3$) 8.07 (s, 1H), 7.69 (d, J=1.9 Hz, 1H), 7.61 (d, J=9.0 Hz, 1H), 7.53 (d, J=7.6 Hz, 1H), 7.37-7.34 (dd, J=8.9, 1.8 Hz, 1H), 6.61 (d, J=2.7 Hz, 1H), 6.31-6.28 (dd, J=7.6, 2.7 Hz, 1H), 4.77 (t, J=5.3 Hz, 1H), 4.51 (d, J=5.3 Hz, 2H), 3.38 (s, 6H).

e) (E)-1-(1-(2,2-Dimethoxyethyl)-1H-indazol-5-yl)-4-styrylpyridin-2(1H)-one

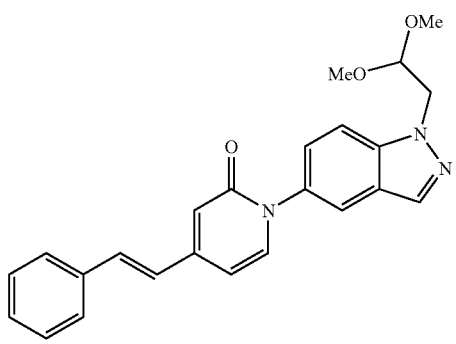

Chemical Formula: C$_{24}$H$_{23}$N$_3$O$_3$
Exact Mass: 401.17
Molecular Weight: 401.46

1-(1-(2,2-Dimethoxyethyl)-1H-indazol-5-yl)-2-oxo-1,2-dihydropyridin-4-yl trifluoromethanesulfonate (2.66 mg, 5.95 mmol), phenylvinylboronic acid (2.23 g, 14.8 mmol), K$_2$CO$_3$ (2.05 g, 14.8 mmol) and PdCl$_2$dppf (500 mg, 0.595 mmol) were stirred in DMSO (15 mL) under vacuum for 30 min. The flask was flushed with nitrogen and the mixture was heated at 80° C. for 1 h. Upon cooling, the mixture was diluted with methylene chloride, washed with 5% lithium chloride solution (5×), dried, concentrated, and the residue was purified by column chromatography (120 g ISCO column eluting with methylene chloride and a methanol/ammonia mixture (10:1); gradient 100% methylene chloride to 10% methanol/ammonia mixture (10:1) over 60 min at 40 mL/min) to provide the title compound (2.08 g, 87%): $^1$H NMR (500 MHz, CD$_3$OD) 8.06 (s, 1H), 7.72 (d, J=17 Hz, 1H), 7.60-7.54 (m, 3H), 7.45-7.34 (m, 5H), 7.23 (d, J=16.6 Hz, 1H), 6.95 (d, J=16.6 Hz, 1H), 6.68 (d, J=1.5 Hz, 1H), 6.54-6.51 (dd, J=7.3, 1.8 Hz, 1H), 4.78 (t, J=5.3 Hz, 1H), 4.51 (t, J=5.3 Hz, 2H), 3.38 (s, 6H).

f) 1-(1-(2,2-Dimethoxyethyl)-1H-indazol-5-yl)-4-phenethylpyridin-2(1H)-one

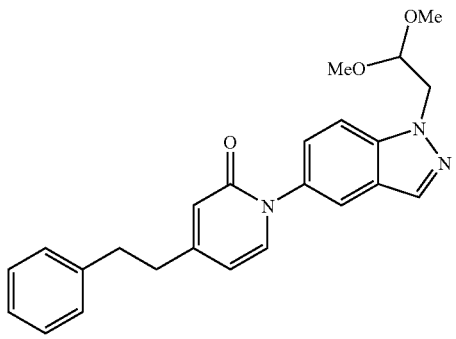

Chemical Formula: C$_{24}$H$_{25}$N$_3$O$_3$
Exact Mass: 403.19
Molecular Weight: 403.47

(E)-1-(1-(2,2-dimethoxyethyl)-1H-indazol-5-yl)-4-styrylpyridin-2(1H)-one (2.08 g, 5.19 mmol) was stirred in CH$_3$OH (100 mL) for 2 h under nitrogen atmosphere. Palladium on carbon (3.1 g) was added under nitrogen atmosphere, and the mixture was stirred for 20 min. The nitrogen line was then replaced with a H$_2$ balloon and the reaction mixture was stirred under an H$_2$ atmosphere at room temperature for 2 h and then flushed with nitrogen (10 min). The mixture was filtered through a layer of Celite, and the filtrate was concentrated. The residue was triturated with MeOH and concentrated to gave the title compound (1.77 g, 84%) as a orange solid $^1$H NMR (300 MHz, CDCl$_3$) 8.04 (s, 1H), 7.68 (d, J=15 Hz, 1H), 7.57 (d, J=9.0 Hz, 1H), 7.44-7.36 (dd, J=8.9, 1.9 Hz, 1H), 7.36-7.28 (m, 2H, overlapping with solvent peak), 7.26-7.18 (m, 3H), 6.51 (s, 1H), 6.16-6.06 (dd, J=7.0, 1.8 Hz, 1H), 4.76 (t, J=5.3 Hz, 2H), 4.48 (t, J=5.3 Hz, 2H), 3.36 (s, 6H) 3.01-2.90 (m, 2H), 2.90-2.76 (m, 2H).

g) 1-(1-(2-Hydroxy-2-methoxyethyl)-1H-indazol-5-yl)-4-phenethylpyridin-2(1H)-one

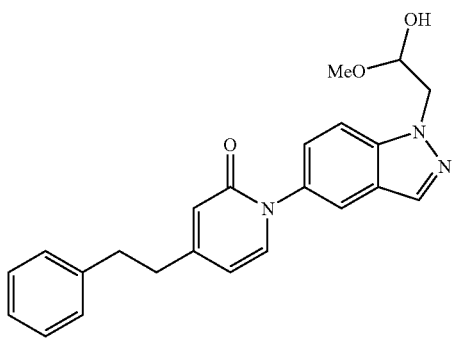

Chemical Formula: C$_{23}$H$_{23}$N$_3$O$_3$
Exact Mass: 389.17
Molecular Weight: 389.45

A solution of 1-(1-(2,2-dimethoxyethyl)-1H-indazol-5-yl)-4-phenethylpyridin-2(1H)-one (1.77 g, 4.39 mmol) in THF (20 mL) was treated with aqueous HCl (20 mL, 2.0 M). The solution was heated at 60° for 18 h, allowed to cool and then treated with H$_2$O (50 mL). The mixture was extracted with EtOAc (3×100 mL), dried with Na$_2$SO$_4$, filtered and concentrated to give the title compound (1.72 g, 98%) as an orange solid: ESI MS m/z 390 [M+H]$^+$.

h) (S)-1-(1-(2-(3-Hydroxypyrrolidin-1-yl)ethyl)-1H-indazol-5-yl)-4-phenethylpyridin-2(1H)-one hydrochloride

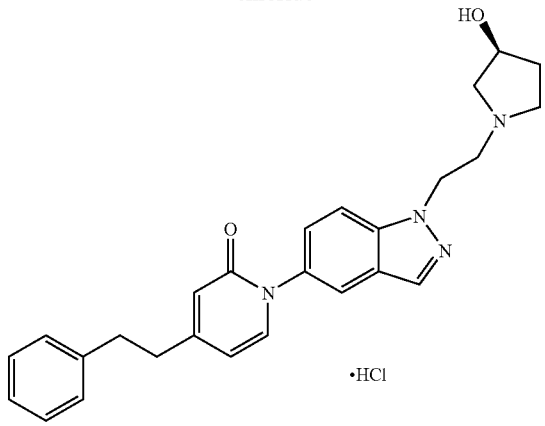

Chemical Formula: C₂₆H₂₈N₄O₂
Exact Mass: 428.22
Molecular Weight: 428.53

To a solution of 1-(1-(2-hydroxy-2-methoxyethyl)-1H-indazol-5-yl)-4-phenethylpyridin-2(1H)-one (200 mg, 0.51 mmol) in MeOH (20.0 mL) and AcOH (2.0 mL) was added S-3-pyrrolidinol (134 mg, 1.54 mmol) and picoline-borane complex (55 mg, 0.51 mmol). After stirring at ambient temperature under nitrogen atmosphere for 2.5 h, the solution was concentrated, treated with 1N HCl (10.0 mL) and stirred vigorously for 30 minutes. The mixture was treated with NaOH (10 mL, 1M) and loaded onto an SCX-2 column. The material was eluted with 7N NH₃ in MeOH and then purified by preparatory HPLC. The residue was then loaded to onto an SCX-2 column, eluted with 7N NH₃ in MeOH and concentrated. The residue was treated with 2N HCl in ether to make the mono-HCl salt. This material was further purified by triturating with hot 2-propanol to yield the title compound (41.0 mg, 17%): mp 175-185° C.; ¹H NMR (500 MHz, CDCl₃) δ 8.23 (s, 1H), 7.82 (d, J=1.7 Hz, 1H), 7.77 (d, J=8.9 Hz, 1H), 7.56 (d, J=7.5 Hz, 1H), 7.49-7.42 (dd, J=8.9, 2.0 Hz, 1H), 7.31-7.21 (m, 4H), 7.21-7.15 (m, 1H), 6.47-6.40 (m, 2H), 4.87 (t, J=5.8, 2H), 4.45 (s, 1H), 4.00-3.78 (br m, 3H), 3.76-3.41 (br m, 2H), 3.24-3.11 (br s, 1H), 3.03-2.95 (m, 2H), 2.95-2.87 (m, 2H), 2.45-1.90 (br m, 2H); ESI MS m/z 429 [M+H]⁺; HPLC (Method D) 98.8% (AUC), t_R=12.8 min.

Example 60

Preparation of (R)-1-(1-(2-(2-(Hydroxymethyl)pyrrolidin-1-yl)ethyl)-1H-indazol-5-yl)-4-phenethylpyridin-2(1H)-one hydrochloride

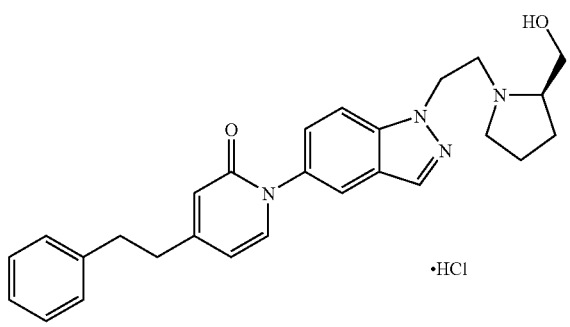

Chemical Formula: C₂₇H₃₀N₄O₂
Exact Mass: 442.24
Molecular Weight: 442.55

Following the procedure of Example 59, but substituting (R)-(−)-2pyrrolidine methanol (200 mg, 0.513 mmol) for (S)-3-pryrrolidinol, the title compound (65.7 mg, 28%) was prepared as an off-white powder: mp 145-155° C.; ¹H NMR (500 MHz, CD₃OD) δ 8.18 (s, 1H), 7.77 (d, J=17 Hz, 1H), 7.72 (d, J=8.9 Hz, 1H), 7.52 (d, J=7.5 Hz, 1H), 7.41-7.39 (dd, J=8.9, 19 Hz, 1H), 7.25-7.19 (m, 4H), 7.14 (t, J=7.2 Hz, 1H), 6.40-6.39 (m, 2H), 4.90-4.85 (m, 2H), 4.09-4.03 (m, 1H), 3.87-3.84 (m, 2H), 3.76-3.64 (m, 4H), 2.95-2.92 (m, 2H), 2.87-2.84 (m, 2H), 2.23-2.07 (m, 2H), 2.03-1.84 (m, 2H); ESI MS m/z 443 [M+H]⁺; HPLC (Method D) 98.3% (AUC), t_R=13.1 min.

Example 61

Preparation of 4-Phenethyl-1-(1-(2-(piperazin-1-yl)ethyl)-1H-indazol-5-yl)pyridin-2(1H)-one dihydrochloride a) tert-Butyl 4-(2-(5-(2-oxo-4-phenethylpyridin-1(2H)-yl)-1H-indazol-1-yl)ethyl)piperazine-1-carboxylate

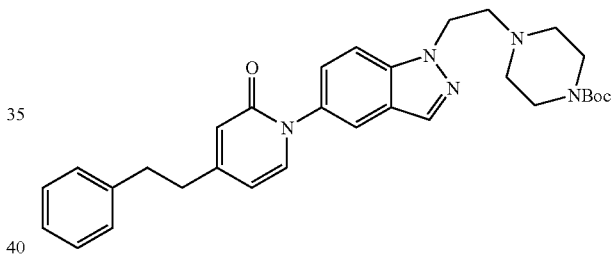

Chemical Formula: C₃₁H₃₇N₅O₃
Exact Mass: 527.29
Molecular Weight: 527.66

Following the procedure of Example 59, but substituting tert-butyl piperazine-1-carboxylate (300 mg, 0.771 mmol) for (S)-3-pyrrolidinol, the title compound was prepared with a modified work-up, as follows. After stirring at room temperature for 2.5 h, the reaction mixture was treated with 1N HCl (10 mL), stirred for 5 min, and then treated with 1N NaOH (10 mL). The aqueous mixture was extracted with EtOAc (3×50 mL). The organics were washed with brine (50 mL), dried over Na₂SO₄, filtered and concentrated. Purification by flash chromatography (40 g ISCO column, 100% CH₂Cl₂ to 92.5% CH₂Cl₂/7.5% MeOH/NH₄OH (10:1) over 35 min at 25 mL/min) gave the title compound (247 mg, 70%) as a yellow solid: ¹H NMR (500 MHz, CDCl₃) δ 8.02 (s, 1H), 7.68 (d, J=1.7 Hz, 1H), 7.50 (d, J=8.9 Hz, 1H), 7.41-7.39 (dd, J=8.9, 1.9 Hz, 1H), 7.33-7.29 (m, 3H), 7.24-7.21 (m, 3H), 6.51 (s, 1H), 6.12-6.10 (dd, J=7.0, 1.7 Hz, 1H), 4.53 (t, J=6.9, 2H), 3.39 (m, 4H), 2.97-2.94 (m, 2H), 2.90-2.87 (m, 2H), 2.83-2.80 (m, 2H), 2.45 (s, 4H), 1.45 (m, 9H).

b) 4-Phenethyl-1-(1-(2-(piperazin-1-yl)ethyl)-1H-indazol-5-yl)pyridin-2(1H)-one dihydrochloride

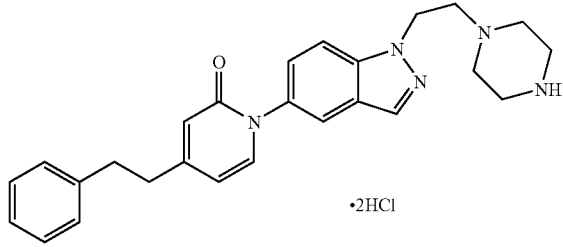

Chemical Formula: C$_{26}$H$_{29}$N$_5$O
Exact Mass: 427.24
Molecular Weight: 427.54

A solution of tert-butyl 4-(2-(5-(2-oxo-4-phenethylpyridin-1(2H)-yl)-1H-indazol-1-yl)ethyl)piperazine-1-carboxylate (247 mg, 0.468 mmol) in MeOH (2 mL) was treated with 2N HCl in ether (7 mL) under a nitrogen atmosphere. The solution was stirred at room temperature for 2 h and then treated with CH$_2$Cl$_2$ (20 mL) to precipitate product. The liquid was decanted off, and the solids were triturated with ether (3×100 mL) and concentrated to yield the title compound (161.7 mg, 69%) as yellow solid: mp 280-290° C.; $^1$H NMR (500 MHz, CD$_3$OD) δ 8.23 (s, 1H), 7.83 (s, 2H), 7.62 (d, J=6.95 Hz, 1H), 7.46 (d, J=1.4 Hz, 1H), 7.30-7.17 (m, 5H), 6.51 (dd, J=7.0, 1.1 Hz, 1H), 6.48 (s, 1H), 4.95 (t, J=5.85, 2H), 3.57 (m, 2H), 3.61-3.56 (m, 8H), 3.01-2.98 (m, 2H), 2.94-2.91 (m, 2H); ESI MS m/z 428 [M+H]$^+$. HPLC (Method D) 95.4% (AUC), t$_R$=12.9 min.

Example 62

Preparation of 1-(1-(2-Morpholinoethyl)-1H-indazol-5-yl)-4-phenethylpyridin-2(1H)-one hydrochloride a) 1-(2,2-Dimethoxyethyl)-5-iodo-1H-indazole

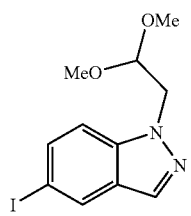

Chemical Formula: C$_{11}$H$_{13}$IN$_2$O$_2$
Exact Mass: 332
Molecular Weight: 332.14

To a solution of 5-iodio-1H-indazole (8.28 g, 33.9 mmol) in DMSO (104 mL) was added 2-bromoacetaldehyde dimethyl acetal (7.9 mL, 68 mmol) and Cs$_2$CO$_3$ (44.1 g, 136 mmol). The reaction mixture was stirred at 40° C. for 18 h; then the reaction mixture was diluted with H$_2$O (100 mL) and EtOAc (175 mL). The partitioned material was extracted with EtOAc (4×175 mL). The organics were washed with brine (2×100 mL), dried (Na$_2$SO$_4$), filtered, and concentrated. Purification by flash chromatography (silica gel, hexanes with 0.1% Et$_3$N/EtOAc with 0.1% Et$_3$N, 100:0 to 90:10) gave the title compound (4.49 g, 46%) as a light orange powder. $^1$H NMR (500 MHz, CDCl$_3$) δ 8.07 (d, J=1.0 Hz, 1H), 7.92 (d, J=0.5 Hz, 1H), 7.60 (dd, J=9.0, 1.5 Hz, 1H), 7.28 (d, J=9.0 Hz, 1H), 4.71 (t, J=5.5 Hz, 1H), 4.44 (d, J=5.5 Hz, 2H), 3.33 (s, 6H).

b) 2-(5-Iodo-1H-indazol-1-yl)-1-methoxyethanol

Chemical Formula: C$_{10}$H$_{11}$IN$_2$O$_2$
Exact Mass: 317.99
Molecular Weight: 318.11

To a solution of 1-(2,2-dimethoxyethyl)-5-iodo-1H-indazole (920 mg, 2.77 mmol) in THF (20 mL) at 40° C. was added 2M HCl (20 mL). The solution was heated at 70° C. for 18 h. The reaction mixture was cooled and diluted with H$_2$O (60 mL). The aqueous mixture was extracted with EtOAc (3×50 mL), dried over Na$_2$SO$_4$ and concentrated to yield the title compound (737 mg, 88%) as a light brown solid: ESI MS m/z 318 [M+H]$^+$.

b) 4-(2-(5-iodo-1H-indazol-1-yl)ethyl)morpholine

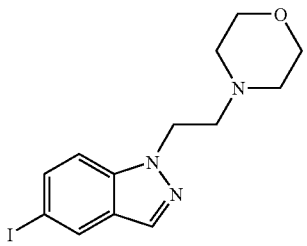

Chemical Formula: C$_{13}$H$_{16}$IN$_3$O
Exact Mass: 357.03
Molecular Weight: 357.19

To a solution of 2-(5-iodo-1H-indazol-1-yl)-1-methoxyethanol (360 mg, 1.13 mmol) in CH$_2$Cl$_2$ (10.0 mL), MeOH (10.0 mL) and AcOH (4.0 mL) was added morpholine (295 mg, 3.39 mmol) and picoline-borane complex (120 mg, 1.13 mmol). The solution was stirred at ambient temperature for 1.5 h. The reaction mixture was concentrated, diluted with 1 N HCl (10.0 mL) and stirred at ambient temperature for 30 minutes. The mixture was made basic with 1N NaOH (10.0 mL) and extracted with EtOAc (3×50 mL). The organics were dried (Na$_2$SO$_4$), filtered, and concentrated. Purification by flash chromatography (12 g ISCO column, eluting with methylene chloride and a methanol/ammonia mixture (10:1); gradient 100% methylene chloride to 90% methylene chloride over 30 min at 20 mL/min) gave the title compound (164 mg, 41%) as an off-white powder. $^1$H NMR (300 MHz, CDCl$_3$) 8.08 (d, J=1.0 1H), 7.90 (s, 1H), 7.7.62-7.56 (dd, J=8.8, 1.6 Hz, 1H), 7.23 (d, J=8.8 Hz, 1H), 4.47 (t, J=6.9 Hz, 2H), 3.64 (t, J=4.7 Hz, 4H), 2.85 (t, J=6.9 Hz, 2H), 2.48 (d, J=4.7 Hz, 4H).

c) (E)-2-Methoxy-4-styrylpyridine

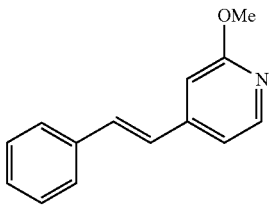

Chemical Formula: C$_{14}$H$_{13}$NO
Exact Mass: 211.10
Molecular Weight: 211.26

4-Bromo-2-methoxypyridine (1.85 g, 9.84 mmol), (E)-phenylvinylboronic acid (4.3 g, 30 mmol), K$_2$CO$_3$ (4.0 g, 30 mmol) and [1,1'-Bis-(diphosphenylphosphino)ferrocene]dichloropalladium(II) (PdCl$_2$dppf) (400 mg, 0.5 mmol) were stirred in DMSO (15 mL) under vacuum for 30 min. The flask was flushed with nitrogen and the mixture was heated at 90° C. for 30 min. Upon cooling, the mixture was diluted with methylene chloride and washed with 5% lithium chloride solution (5×), dried, concentrated, and the residue was purified by column chromatography (silica gel, hexanes/ethyl acetate, 97:3 to 75:25) to provide the title compound (1.93 g, 93%) as an orange oil: $^1$H NMR (300 MHz, CDCl$_3$) δ 8.12 (d, J=5.2 Hz, 1H), 7.51 (m, 2H), 7.40-7.22 (m, 4H), 7.02-6.94 (m, 2H), 6.78 (s, 1H), 3.95 (s, 3H).

d) 2-Methoxy-4-phenethylpyridine

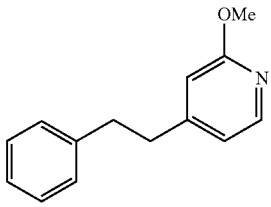

Chemical Formula: C$_{14}$H$_{15}$NO
Exact Mass: 213.12
Molecular Weight: 213.28

(E)-2-Methoxy-4-styrylpyridine (22.15 g, 104.8 mmol) was dissolved in MeOH (400 mL) and degassed with a nitrogen stream for 10 minutes. Palladium on charcoal (10%, wet, 5 g) was added and the reaction mixture was stirred under an atmosphere of hydrogen for 24 h. The reaction mixture was degassed again, and the catalyst was removed by filtration. Concentration of the filtrate provided the title compound (22 g, 98%) as a green oil: $^1$H NMR (500 MHz, CDCl$_3$) δ 8.04 (d, J=5.3 Hz, 1H), 7.29-7.24 (m, 2H), 7.21-7.15 (m, 3H), δ 69-6.67 (m, 1H), 6.54 (s, 1H), 3.91 (s, 3H), 2.91-2.89 (m, 2H), 2.87-2.84 (m, 2H).

e) 4-Phenethylpyridin-2(1H)-one

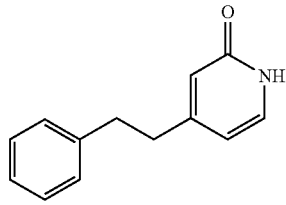

Chemical Formula: C$_{13}$H$_{13}$NO
Exact Mass: 199.10
Molecular Weight: 199.25

2-Methoxy-4-phenethylpyridine (22.0 g, 102 mmol) was stirred in concentrated hydrochloric acid (200 mL) at 120° C. for 18 h and then concentrated. The residue was dissolved in MeOH (100 mL) and made basic with 6 N NaOH and re-concentrated until most of the solvent had been removed. The solids were filtered off, washed with water and dried under vacuum to provide the title compound (21.3 g, 95%) as a beige solid $^1$H NMR (500 MHz, DMSO-d$_6$) δ 11.31 (br s, 1H), 7.28-7.21 (m, 5H), 7.17 (t, J=7.1 Hz, 1H), 6.10-6.08 (m, 2H), 2.85-2.82 (m, 2H), 2.70-2.67 (m, 2H).

f) 1-(1-(2-Morpholinoethyl)-1H-indazol-5-yl)-4-phenethylpyridin-2(1H)-one hydrochloride

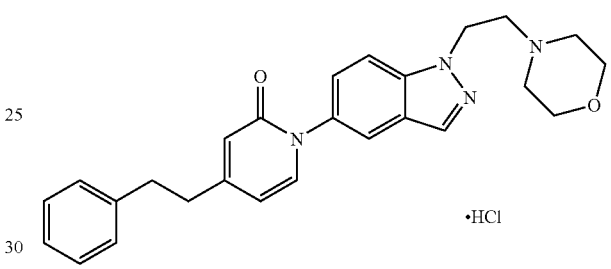

Chemical Formula: C$_{26}$H$_{28}$N$_4$O$_2$
Exact Mass: 428.22
Molecular Weight: 428.53

A suspension of 4-(2-(5-iodo-1H-indazol-1-yl)ethyl)morpholine (160 mg, 0.45 mmol), 4-phenethylpyridin-2(1H)-one (100 mg, 0.49 mmol), K$_2$CO$_3$ (68 mg, 0.49 mmol), 8-hydroxyquinoline (10 mg, 0.067 mmol) and CuI (100 g, 0.52 mmol) in DMSO (2 mL) was evacuated for 30 minutes under high vacuum then backfilled with nitrogen. The mixture was stirred under nitrogen at 130° C. for 20 h and then allowed to cool. The mixture was diluted with 20% MeOH/NH$_4$OH (10:1) in CH$_2$Cl$_2$ (80 mL), stirred for 10 min, and then loaded onto a silica plug. The material was eluted through the plug with 20% MeOH/NH$_4$OH (10:1) in CH$_2$Cl$_2$ (200 ml) and then concentrated. The residue was dissolved in CH$_2$Cl$_2$, washed with LiCl (4×100 mL) and brine (1×100 mL), dried over Na$_2$SO$_4$, filtered, and concentrated to dryness. Purification by preparatory HPLC, followed by conversion to the HCl salt in methanol with 2N HCl in ether provided the title compound (59.3 mg, 30%) as a light yellow solid: mp 240-250° C.; $^1$H NMR (500 MHz, CD$_3$OD) δ 8.23 (s, 1H), 7.82 (d, J=1.4 Hz, 1H), 7.78 (d, J=8.9 Hz, 1H), 7.56 (d, J=7.6 Hz, 1H), 7.47-7.44 (dd, J=8.9, 1.9 Hz, 1H), 7.30-7.23 (m, 4H), 7.20-7.17 (t, J=7.2 Hz, 1H), 6.45 (m, 2H), 4.94 (m, 2H), 4.07 (br m, 2H), 3.84-3.78 (m, 4H) 3.63 (m, 2H), 3.34-3.26, (m, 2H, overlapping with solvent peak), 3.00-2.97 (m, 2H), 2.92-2.89 (m, 2H); ESI MS m/z 429 [M+H]$^+$; HPLC (Method D)>99% (AUC), t$_R$=13.1 min.

Example 63

Preparation of 4-(Pyridin-2-ylmethoxy)-1-(1-(2-pyrrolidin-1-yl)ethyl)-1H-indazol-5-yl)pyridin-2(1H)-one dihydrochloride a) 4-(Pyridin-2-ylmethoxy)pyridine 1-oxide

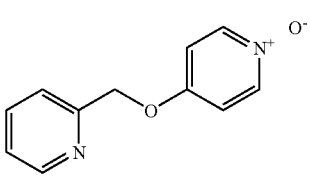

Chemical Formula: C$_{11}$H$_{10}$N$_2$O$_2$
Exact Mass: 202.07
Molecular Weight: 202.21

2-Pyridylbenzylalcohol (1.67 g, 15.3 mmol) was dissolved in 1,4-dioxane (25 mL) and NaH (0.92 g, 23 mmol) was added. After stirring for 30 minutes, 4-chloropyridine-N-oxide (2.27 g, 17.5 mmol) was added and the reaction mixture was heated for 1 h at 120° C. Upon cooling, the mixture was purified by column chromatography (40 g ISCO column eluting with methylene chloride and a methanol/ammonia mixture (10:1), gradient 100% methylene chloride to 90% methylene chloride over 30 min at 40 mL/min) to provide the title compound (600 mg, 38%) as a brown solid: $^1$H NMR (500 MHz, CDCl$_3$) δ 8.62-8.61 (m, 1H), 8.13-8.10 (m, 2H), 7.74-7.73 (dt, J=7.8, 1.4 Hz, 1H), 7.44 (d, J=7.8 Hz, 1H), 7.30-7.29 (d, J=4.8 Hz, 1H), 6.92-6.89 (m, 2H), 5.23 (s, 2H).

b) 4-(Pyridin-2-ylmethoxy)pyridin-2(1H)-one

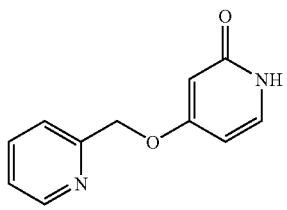

Chemical Formula: C$_{11}$H$_{10}$N$_2$O$_2$
Exact Mass: 202.07
Molecular Weight: 202.21

4-(Pyridin-2-ylmethoxy)pyridine 1-oxide (9.0 g, 45 mmol) was heated at 140° C. in acetic anhydride (100 mL) for 2 h. The solution was concentrated and then heated at 80° C. for 1 h in a mixture of MeOH (50 mL) and H$_2$O (50 mL). The resultant black solution was concentrated and the residue was dissolved in hot i-PrOH (40 ml). Et$_2$O (250 mL) was added and the mixture was placed in the freezer for 16 h. The solid was filtered off to provide the title compound (19 g, 21%) as a brown solid: $^1$H NMR (300 MHz, DMSO-d$_6$) δ 11.13 (br s, 1H), 8.58 (d, J=4.7 Hz, 1H), 7.88-7.81 (dt, J=7.9, 1.6 Hz, 1H), 7.49 (d, J=7.9 Hz, 1H), 7.38-7.34 (m, 1H), 7.26 (d, J=7.3 Hz, 1H), 5.96-5.95 (dd, J=7.3, 2.5 Hz, 1H), 5.76 (d, J=3.4 Hz, 1H), 5.12 (s, 2H).

c) 4-(Pyridin-2-ylmethoxy)-1-(1-(2-(pyrrolidin-1-yl)ethyl)-1H-indazol-5-yl)pyridin-2(1H)-one dihydrochloride

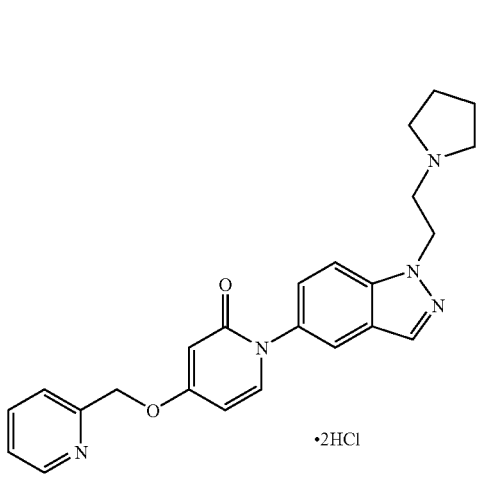

Chemical Formula: C$_{24}$H$_{27}$Cl$_2$N$_5$O$_2$
Exact Mass: 487.15
Molecular Weight: 488.41

A stirred solution of 5-bromo-1-(2-(pyrrolidin-1-yl)ethyl)-1H-indazole (145 mg, 0.493 mmol) and 4-(pyridin-2-ylmethoxy)pyridin-2(1H)-one (100 mg, 0.5 mmol) in DMSO (4 mL) under nitrogen was treated sequentially with 8-hydroxyquinoline (11 mg, 0.075 mmol), CuI (109 mg, 0.575 mmol) and K$_2$CO$_3$ (79 mg, 0.58 mmol). The mixture was placed under vacuum for 30 minutes and then flushed with nitrogen. After stirring at 130° C. for 16 h, the mixture was allowed to cool to room temperature, diluted with CH$_2$Cl$_2$, washed with brine, dried over Na$_2$SO$_4$ and concentrated. Purification by column chromatography (12 g ISCO column eluting with methylene chloride and a methanol/ammonia mixture (10:1), gradient 100% methylene chloride to 80% methylene chloride over 30 min at 25 mL/min) provided the free-base. This material was dissolved in methylene chloride (2 mL) and treated with 2 equivalents of 2 N HCl in Et$_2$O and the mixture was concentrated to provide the title compound (61 mg, 25%) as a white solid: mp 120-131° C. deliquesced; $^1$H NMR (500 MHz, CD$_3$OD) δ 8.78-8.77 (d, J=4.9 Hz, 1H), 8.37 (t, J=7.9 Hz, 1H), 8.23 (s, 1H), 7.96 (d, J=7.9 Hz, 1H), 7.82-7.79 (m, 3H), 7.66-7.64 (dd, J=7.4, 1.4 Hz, 1H), 7.47-7.44 (d, J=9.2 Hz, 1H), 6.41-6.39 (dd, J=7.5, 2.6 Hz, 1H), 6.17 (d, J=2.8 Hz, 1H), 5.46 (s, 2H), 4.87 (t, J=6.0 Hz, 2H), 3.86 (t, J=6.0 Hz, 2H), 3.70-3.69 (m, 2H), 3.18-3.13 (m, 2H), 2.18-2.15 (m, 2H), 2.03-2.00 (m, 2H); ESI MS m/z 416 [M+H]$^+$; HPLC (Method D)>99% (AUC), t$_R$=9.1 min.

Example 64

Preparation of 4-((5-Chloropyridin-2-yl)methoxy)-1-(1-(2-pyrrolidin-1-yl)ethyl)-1H-indazol-5-yl)pyridin-2(1H)-one hydrochloride a) 4-((5-Chloropyridin-2-yl)methoxy)pyridine 1-oxide

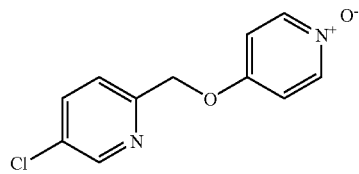

Chemical Formula: $C_{11}H_9ClN_2O_2$
Exact Mass: 236.04
Molecular Weight: 236.65

5-Chloro-2-pyridylbenzylalcohol (4.9 g, 34 mmol) and 4-chloropyridine-N-oxide (2.94 g, 22.7 mmol) were reacted according to Example 63 (step a) to provide the title compound (2.2 g, 40%) as a tan solid. $^1$H NMR (300 MHz, CDCl$_3$) δ 8.58 (d, J=2.2 Hz, 1H), 8.13 (d, J=7.7 Hz, 2H), 7.76-7.72 (dd, J=8.4, 2.5 Hz, 1H), 7.43 (d, J=8.4 Hz, 1H), 6.90 (d, J=7.7 Hz, 2H), 5.20 (s, 2H).

b) 4-((5-Chloropyridin-2-yl)methoxy)pyridin-2(1H)-one

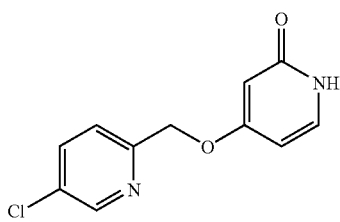

Chemical Formula: $C_{11}H_9ClN_2O_2$
Exact Mass: 236.04
Molecular Weight: 236.65

4-((5-Chloropyridin-2-yl)methoxy)pyridine 1-oxide (2.2 g, 9.2 mmol) was reacted according to Example 63 (step b) to provide the title compound (1.52 g, 69%) as a tan solid: $^1$H NMR (500 MHz, CD$_3$OD) δ 8.56 (d, J=2.3 Hz, 1H), 7.91-7.89 (dd, J=8.4, 2.5 Hz, 1H), 7.56 (d, J=8.4 Hz, 1H), 7.34 (d, J=8.3 Hz, 1H), 6.21-6.19 (dd, J=7.2, 2.5 Hz, 1H), 5.97 (d, J=2.4 Hz, 1H), 5.18 (s, 2H).

c) 4-((5-Chloropyridin-2-yl)methoxy)-1-(1-(2-(pyrrolidin-1-yl)ethyl)-1H-indazol-5-yl)pyridin-2(1H)-one hydrochloride

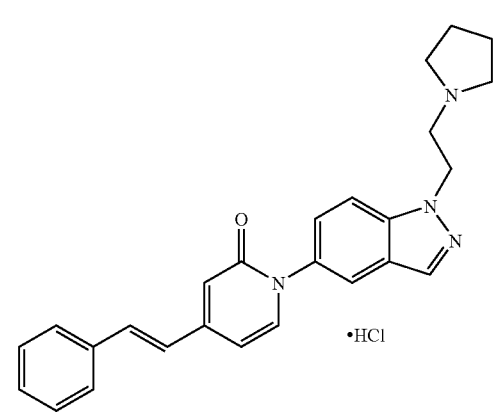

Chemical Formula: $C_{24}H_{25}Cl_2N_5O_2$
Exact Mass: 485.14
Molecular Weight: 486.39

5-Bromo-1-(2-(pyrrolidin-1-yl)ethyl)-1H-indazole (200 mg, 0.68 mmol) and 4-((5-chloropyridin-2-yl)methoxy)pyridin-2(1H)-one (160 mg, 0.68 mmol) were reacted according to the procedure in Example 63 (step c) to provide the title compound (119 mg, 36%) as a brown solid: mp 95-101° C. deliquesced; $^1$H NMR (500 MHz, CD$_3$OD) δ 8.63 (s, 1H), 8.23 (s, 1H), 8.00-7.98 (dd, J=8.3, 2.1 Hz, 1H), 7.82 (d, J=19 Hz, 1H), 7.79 (d, J=8.9 Hz, 1H), 7.66-7.64 (2 overlapping d, J=8.5, 7.6 Hz, 2H), 7.47-7.44 (dd, J=8.9, 1.8 Hz, 1H), 6.41-6.39 (dd, J=7.5, 2.8 Hz, 1H), 6.16 (d, J=2.6 Hz, 1H), 5.30 (s, 2H), 4.87 (t, J=5.9 Hz, 2H), 3.86 (t, J=5.9 Hz, 2H), 3.72 (m, 2H), 3.19-3.13 (m, 2H), 2.18-2.15 (m, 2H), 2.03-1.99 (m, 2H); ESI MS m/z 450 [M+H]$^+$; HPLC (Method D) 97.4% (AUC), $t_R$=11.9 min.

Example 65

Preparation of (E)-1-(1-(2-Pyrrolidin-1-yl)ethyl)-1H-indazol-5-yl)-4-styrylpyridin-2(1H)-one hydrochloride Chemical Formula: $C_{26}H_{27}ClN_4O$
Exact Mass: 446.19
Molecular Weight: 446.97

2-Oxo-1-(1-(2-(pyrrolidin-1-yl)ethyl)-1H-indazol-5-yl)-1,2-dihydropyridin-4-yl trifluoromethanesulfonate (550 mg, 1.2 mmol) and (E)-phenylvinylboronic acid (535 mg, 3.6 mmol) were reacted according to the procedure in Example 58 to provide the title compound (108 mg, 20%) as a yellow solid: ¹H NMR (500 MHz, CD₃OD) δ 8.25 (s, 1H), 7.89 (d, J=1.4 Hz, 1H), 7.82 (d, J=8.9 Hz, 1H), 7.69 (d, J=7.1 Hz, 1H), 7.66 (d, J=7.4 Hz, 2H), 7.53-7.50 (dd, J=8.9, 1.7 Hz, 1H), 7.42 (t, J=7.1 Hz, 2H), 7.49 (d, J=15.4 Hz, 1H), 7.37-7.33 (m, 1H), 7.17 (d, J=15.4 Hz, 1H), 6.96-6.94 (m, 1H), 6.75 (s, 1H), 4.89 (t, J=6.0 Hz, 2H), 3.87 (t, J=6.0 Hz, 2H), 3.74-3.67 (m, 2H), 3.21-3.12 (m, 2H), 2.22-2.11 (m, 2H), 2.06-1.95 (m, 2H); ESI MS m/z 411 [M+H]⁺; HPLC (Method D)>99% (AUC), $t_R$=13.9 min.

Example 66

Preparation of 4-Phenethyl-1-(1-(2-(pyrrolidin-1-yl)ethyl)-1H-indazol-5-yl)pyridin-2(1H)-one hydrochloride

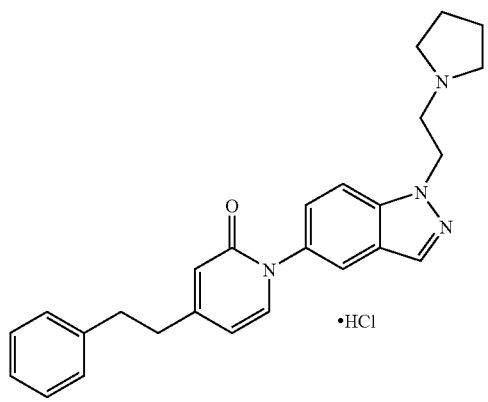

Chemical Formula: C₂₆H₂₉ClN₄O
Exact Mass: 448.20
Molecular Weight: 448.99

(E)-1-(1-(2-(Pyrrolidin-1-yl)ethyl)-1H-indazol-5-yl)-4-styrylpyridin-2(1H)-one (110 mg, 0.26 mmol), ammonium formate (37 mg, 0.59 mmol) and palladium on charcoal (5% wet, 300 mg) were combined in MeOH (10 mL) and refluxed under nitrogen for 30 min. Upon cooling the solids were filtered off, and the filtrate was purified by preparative HPLC to provide the free-base. Conversion to the hydrochloride as in Example 64 provided the title compound (37 mg, 31%) as a white solid mp 169-173° C.; ¹H NMR (500 MHz, CD₃OD) δ 8.24 (s, 1H), 7.85 (d, J=1.9 Hz, 1H), 7.80 (d, J=8.9 Hz, 1H), 7.65 (d, J=6.9 Hz, 1H), 7.48-7.46 (dd, J=8.9, 19 Hz, 1H), 7.30-7.24 (m, 4H), 7.19 (m, 1H), 6.56-6.54 (dd, J=6.9, 19 Hz, 1H), 6.52 (s, 1H), 4.88 (t, J=5.7 Hz, 2H), 3.87-3.85 (m, 2H), 3.73-3.68 (m, 2H), 3.19-3.15 (m, 2H), 3.02-2.98 (m, 2H), 2.95-2.92 (m, 2H), 2.18-2.15 (m, 2H), 2.03-2.00 (m, 2H); ESI MS m/z 413 [M+H]⁺; HPLC (Method D)>99% (AUC), $t_R$=13.8 min.

Example 67

Preparation of 4-(Benzylamino)-1-(1-(2-(pyrrolidin-1-yl)ethyl)-1H-indazol-5-yl)pyridin-2(1H)-one dihydrochloride

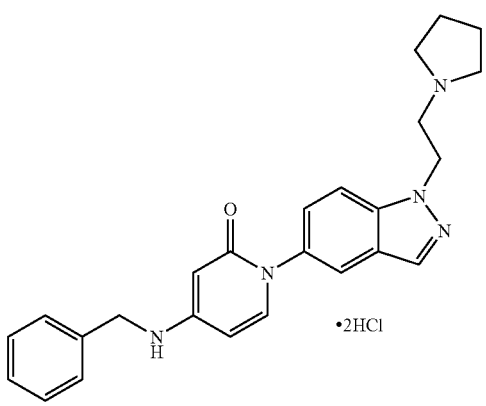

Chemical Formula: C₂₅H₂₉Cl₂N₅O
Exact Mass: 485.17
Molecular Weight: 486.44

4-Hydroxy-1-(1-(2-(pyrrolidin-1-yl)ethyl)-1H-indazol-5-yl)pyridin-2(1H)-one (120 mg, 0.37 mmol) and benzylamine (0.3 mL) were irradiated in a microwave tube for min at 300 W. Purification by column chromatography (12 g ISCO column eluting with ethyl acetate and a methanol/ammonia mixture (10:1); gradient 100% ethyl acetate to 80% ethyl acetate over 30 min at 25 mL/min) provided the free-base. This was converted to the dihydrochloride as in Example 64 to provide the title compound (43 mg, 22%) as a yellow solid: mp 180-185° C.; ¹H NMR (500 MHz, CD₃OD) δ 8.25 (s, 1H), 7.90 (d, J=1.8 Hz, 1H), 7.87 (d, J=8.9 Hz, 1H), 7.75 (s, 1H), 7.51-7.49 (dd, J=8.9, 1.9 Hz, 1H), 7.40-7.39 (m, 4H), 7.33-7.30 (dd, J=8.5, 4.3 Hz, 1H), 6.63 (d, J=76 Hz, 1H), 4.90 (t, J=5.9 Hz, 2H), 4.54 (s, 2H), 3.86 (t, J=5.9 Hz, 2H), 3.77-3.68 (m, 2H), 3.18-3.13 (m, 2H), 2.17-2.13 (m, 2H), 2.03-2.00 (m, 2H); ESI MS m/z 414 [M+H]⁺; HPLC (Method C)>99% (AUC), $t_R$=12.9 min.

Example 68

Preparation of 4-(2-(Pyridin-2-yl)ethyl)-1-(1-(2-(pyrrolidin-1-yl)ethyl)-1H-indazol-5-yl)pyridin-2(1H)-one dihydrochloride a) (E)-2-Methoxy-4-(2-(pyridin-2-yl)vinyl)pyridine

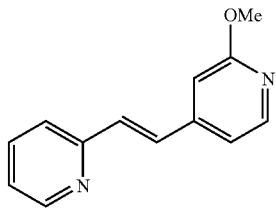

Chemical Formula: C₁₃H₁₂N₂O
Exact Mass: 212.09
Molecular Weight: 212.25

4-Chloro-2-methoxypyridine (182 mg, 1.27 mmol) and (E)-2-(2-(tributylstannyl)vinyl)pyridine (R. A. Hacck, et al. Tet. Lett 1988, 29, 2783-2786) (500 mg, 1.27 mmol) were stirred in dry toluene (4 mL) and degassed with a nitrogen stream as the temperature was increased to 100° C. Palladium tetrakistriphenylphosphine (146 mg, 0.127 mmol) was added and the reaction mixture was maintained at 100° C. under a nitrogen atmosphere for 16 h. Upon cooling, the mixture was purified by column chromatography (12 g ISCO column eluting with methylene chloride and a methanol/ammonia mixture (10:1); gradient 100% methylene chloride to 80% methylene chloride over 30 min at 25 mL/min) to provide the title compound (225 mg, 83%) as a green oil: $^1$H NMR (500 MHz, CD$_3$OD) δ 8.63 (d, J=4.7 Hz, 1H), 8.15 (d, J=5.4 Hz, 1H), 7.71-7.67 (dt, J=7.5, 1.6 Hz, 1H), 7.53 (d, J=16.4 Hz, 1H), 7.40 (d, J=7.9 Hz, 1H), 7.28 (d, J=16.4 Hz, 1H), 7.22-7.18 (dd, J=7.2, 4.7 Hz, 1H), 7.06 (d, J=5.4 Hz, 1H), 6.85 (s, 1H), 3.96 (s, 3H).

b) 2-Methoxy-4-(2-(pyridin-2-yl)ethyl)pyridine

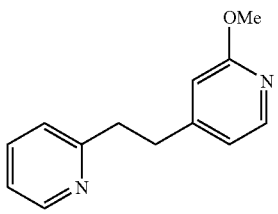

Chemical Formula: C$_{13}$H$_{14}$N$_2$O
Exact Mass: 214.11
Molecular Weight: 214.26

(E)-2-Methoxy-4-(2-(pyridin-2-yl)vinyl)pyridine (290 mg, 0.13 mmol) was dissolved in MeOH (15 mL) and degassed with a nitrogen stream for 10 minutes. Palladium on charcoal (10%, wet, 5 g) was added and the reaction mixture stirred under an atmosphere of hydrogen for 24 h. The reaction mixture was degassed again and the catalyst removed by filtration. Concentration of the filtrate provided the title compound (200 mg, 90%) as a green oil: $^1$H NMR (500 MHz, CD$_3$OD) δ 8.56 (d, J=5.1 Hz, 1H), 8.03 (d, J=5.1 Hz, 1H), 7.59-7.55 (dt, J=7.9, 19 Hz, 1H), 7.14-7.10 (dd, J=7.2, 5.1 Hz, 1H), 7.08 (d, J=7.6 Hz, 1H), 6.71 (d, J=5.4 Hz, 1H), 6.56 (s, 1H), 3.90 (s, 3H), 3.10-3.06 (m, 2H), 3.04-3.00 (m, 2H).

c) 4-(2-(Pyridin-2-yl)ethyl)pyridin-2(1H)-one

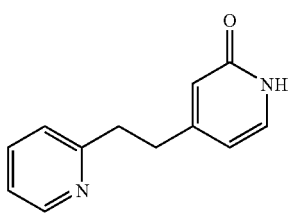

Chemical Formula: C$_{12}$H$_{12}$N$_2$O
Exact Mass: 200.09
Molecular Weight: 200.24

2-Methoxy-4-(2-(pyridin-2-yl)ethyl)pyridine (200 mg, 0.93 mmol) was stirred in concentrated hydrochloric acid (5 mL) at 120° C. for 18 h and then concentrated. The residue was dissolved in MeOH (5 mL) and passed down an Isolute SCX-2 column (10 g). Elution with 7 N NH$_3$ in MeOH and concentration of the eluent provided the title compound (180 mg, 96%) as a white solid: $^1$H NMR (500 MHz, CD$_3$OD) δ 8.45 (d, J=4.7 Hz, 1H), 7.75-7.71 (dd, J=7.8, 1.8 Hz, 1H), 7.32 (d, J=6.9 Hz, 1H), 7.28 (d, J=7.8 Hz, 1H), 7.27-7.23 (dd, J=7.8, 5.1 Hz, 1H), 6.34-6.29 (m, 2H), 3.08 (t, J=7.3 Hz, 2H), 2.92 (t, J=7.9 Hz, 2H).

d) 4-(2-(Pyridin-2-yl)ethyl)-1-(1-(2-(pyrrolidin-1-yl)ethyl)-1H-indazol-5-yl)pyridin-2(1H)-one dihydrochloride

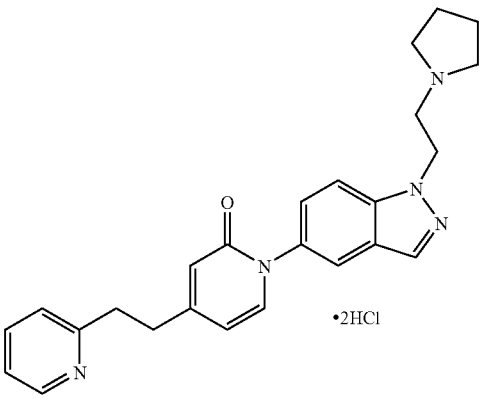

Chemical Formula: C$_{25}$H$_{29}$Cl$_2$N$_5$O
Exact Mass: 485.17
Molecular Weight: 486.44

5-Bromo-1-(2-(pyrrolidin-1-yl)ethyl)-1H-indazole (240 mg, 0.81 mmol) and 4-(2-(pyridin-2-yl)ethyl)pyridin-2(1H)-one (180 mg, 0.90 mmol) were reacted according to the procedure in Example 64, and the crude product was purified by preparative HPLC. The obtained residue was triturated with i-PrOH/Et$_2$O and then converted to the dihydrochloride salt to provide the title compound (45 mg, 11%) as a yellow solid: mp 82-85° C. deliquesced; $^1$H NMR (500 MHz, CD$_3$OD) δ 8.80-8.79 (d, J=5.9 Hz, 1H), 8.62-8.58 (t, J=7.0 Hz, 1H), 8.24 (s, 1H), 8.09 (d, J=8.1 Hz, 1H), 7.98 (t, J=7.1 Hz, 1H), 7.83-7.82 (m, 2H), 7.67 (d, J=6.8 Hz, 1H), 7.47-7.45 (dd, J=8.9, 1.8 Hz, 1H), 6.52-6.52 (m, 2H), 4.89 (t, J=5.6 Hz, 2H), 3.86 (t, J=5.6 Hz, 2H), 3.72-3.68 (m, 2H), 3.48-3.45 (m, 2H), 3.18-3.11 (m, 4H), 2.17-2.13 (m, 2H), 2.04-1.99 (m, 2H); ESI MS m/z 414 [M+H]$^+$; HPLC (Method D) 97.5% (AUC), t$_R$=8.4 min.

Example 69

Preparation of 4-(4-Cyanobenzyloxy)-1-(1-(2-pyrrolidin-1-yl)ethyl-1H-indazol-5-yl)pyridin-2(1H)-one hydrochloride

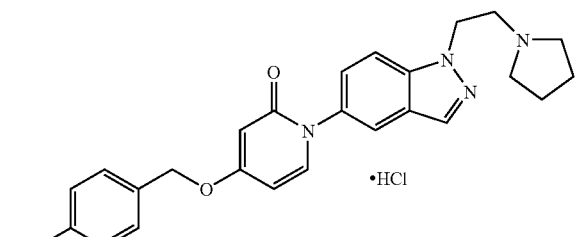

Chemical Formula: C$_{26}$H$_{25}$N$_5$O$_2$
Exact Mass: 439.20
Molecular Weight: 439.51

Following the procedure of Example 5, but substituting 4-cyanobenzyl bromide for 4-chlorobenzyl bromide, the title compound (43 mg, 30%) was obtained as a white solid mp 204-206° C., $^1$H NMR (500 MHz, DMSO-d$_6$) δ 9.83 (s, 1H), 8.25 (s, 1H), 7.92 (d, J=8.5 Hz, 2H), 7.85 (d, J=9.0 Hz, 1H), 7.80 (s, 1H), 7.67 (d, J=8.0 Hz, 2H), 7.63 (d, J=7.5 Hz, 1H), 7.43 (d, J=9.0 Hz, 1H), 6.16 (dd, J=8.0, 2.5 Hz, 1H), 5.98 (d, J=2.5 Hz, 1H), 5.28 (s, 2H), 4.84 (t, J=6.5 Hz, 2H), 3.73-3.74 (m, 2H), 3.53-3.54 (m, 2H), 3.05-3.07 (m, 2H), 1.99-2.00 (m, 2H), 1.83-1.85 (m, 2H); ESI MS m/z 440 [M+H]$^+$; HPLC (Method B) 98.0% (AUC), t$_R$=12.6 min.

Example 70

Preparation of 4-(Pyridin-3-ylmethoxy)-1-(1-(2-(pyrrolidin-1-yl)ethyl-1H-indazol-5-yl)pyridin-2(1H)-one hydrochloride

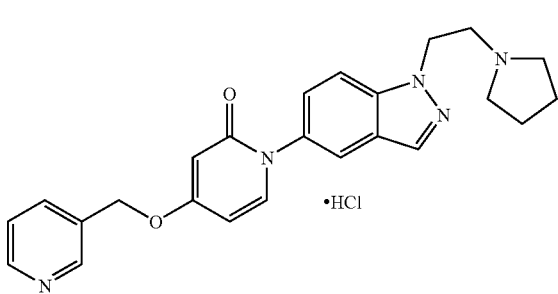

Chemical Formula: C$_{24}$H$_{26}$ClN$_5$O$_2$·
Exact Mass: 451.1775
Molecular Weight: 451.9485

Following the procedure of Example 5, but substituting 3-bromomethyl pyridine hydrobromide for 4-chlorobenzyl bromide, the title compound (100 mg, 73%) was obtained as an off-white solid. mp 214-216° C.; $^1$H NMR (500 MHz, DMSO-d$_6$) δ 10.24 (s, 1H), 8.81 (s, 1H), 8.70 (d, J=4.5 Hz, 1H), 8.25 (s, 1H), 8.13 (d, J=7.5 Hz, 1H), 7.88 (d, J=9.0 Hz, 1H), 7.80 (d, J=2.0 Hz, 1H), 7.65-7.68 (m, 1H), 7.64 (d, J=7.5 Hz, 1H), 7.43 (dd, J=9.0, 2.0 Hz, 1H), 6.15 (dd, J=7.5, 2.5 Hz, 1H), 6.05 (d, J=2.5 Hz, 1H), 5.27 (s, 2H), 4.87 (t, J=6.5 Hz, 2H), 3.71-3.74 (m, 2H), 3.51-3.54 (m, 2H), 3.02-3.06 (m, 2H), 2.00-2.03 (m, 2H), 1.83-1.85 (m, 2H); ESI MS m/z 416 [M+H]$^+$; HPLC (Method B) 98.7% (AUC), t$_R$=7.5 min.

Example 71

Preparation of 4-(Biphenyl-4-ylmethoxy)-1-(1-(2-pyrrolidin-1-yl)ethyl-1H-indazol-5-yl)pyridin-2(1H)-one hydrochloride

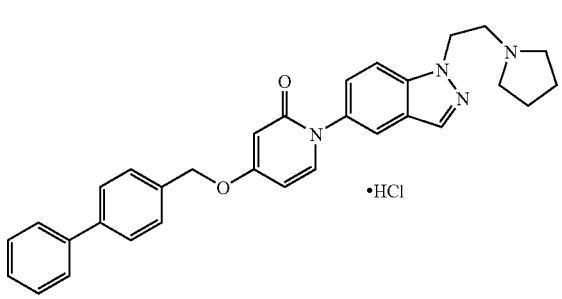

Chemical Formula: C$_{31}$H$_{30}$N$_4$O$_2$
Exact Mass: 490.24
Molecular Weight: 490.60

Following the procedure of Example 5, but substituting 4-(bromomethyl)biphenyl for 4-chlorobenzyl bromide, the title compound (83 mg, 55%) was obtained as an off-white solid. mp 227-230° C.; $^1$H NMR (500 MHz, DMSO-d$_6$) δ 10.23 (s, 1H), 8.25 (s, 1H), 7.87 (d, J=9.0 Hz, 1H), 7.80 (d, J=2.0 Hz, 1H), 7.69-7.74 (m, 4H), 7.62 (d, J=7.5 Hz, 1H), 7.56-7.57 (m, 2H), 7.47-7.50 (m, 2H), 7.43 (dd, 9.0, 2.0 Hz, 1H), 7.37-7.40 (m, 1H), 6.15 (dd, J=7.5, 2.5 Hz, 1H), 6.02 (d, J=2.5 Hz, 1H), 5.21 (s, 2H), 4.87 (t, J=6.5 Hz, 2H), 3.70-3.74 (m, 2H), 3.51-3.54 (m, 2H), 3.02-3.06 (m, 2H), 1.99-2.01 (m, 2H), 1.82-1.86 (m, 2H); ESI MS m/z 491 [M+H]$^+$HPLC (Method B)>99% (AUC), t$_R$=16.9 min.

Example 72

Preparation of 4-(3,5-Difluorobenzyloxy)-1-(1-(2-(pyrrolidin-1-yl)ethyl-1H-indazol-5-yl)pyridin-2 (1H)-one hydrochloride

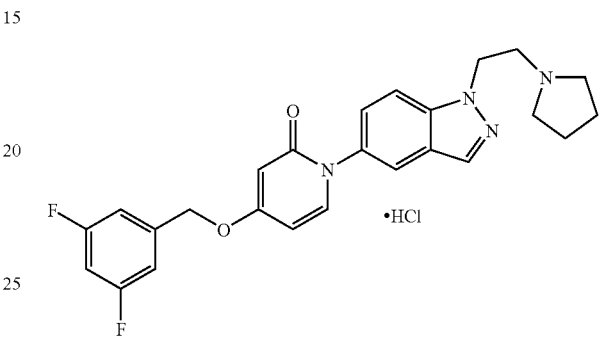

Chemical Formula: C$_{25}$H$_{25}$ClF$_2$N$_4$O$_2$·
Exact Mass: 486.1634
Molecular Weight: 486.9414

Following the procedure of Example 5, but substituting 3,5-difluorobenzyl bromide for 4-chlorobenzyl bromide, the title compound (71 mg, 51%) was obtained as an off-white solid. mp 138-140° C.; $^1$H NMR (500 MHz, DMSO-d$_6$) δ 9.99 (s, 1H), 8.25 (s, 1H), 7.86 (d, J=9.0 Hz, 1H), 7.80 (d, J=2.0 Hz, 1H), 7.63 (d, J=7.5 Hz, 1H), 7.43 (dd, J=9.0, 2.0 Hz, 1H), 7.22-7.28 (m, 3H), 6.17 (dd, J=7.5, 2.5 Hz, 1H), 5.98 (d, 2.5 Hz, 1H), 5.20 (s, 2H), 4.85 (t, J=6.0 Hz, 2H), 3.71-3.75 (m, 2H), 3.53-3.54 (m, 2H), 3.02-3.08 (m, 2H), 1.99-2.02 (m, 2H), 1.83-1.88 (m, 2H); ESI MS m/z 451 [M+H]$^+$; HPLC (Method B) 97.4% (AUC), t$_R$=15.1 min.

Example 73

Preparation of 4-(4-Fluorobenzyloxy)-1-(1-(2-morpholinoethyl)-1H-indazol-5-yl)pyridin-2(1H)-one hydrochloride

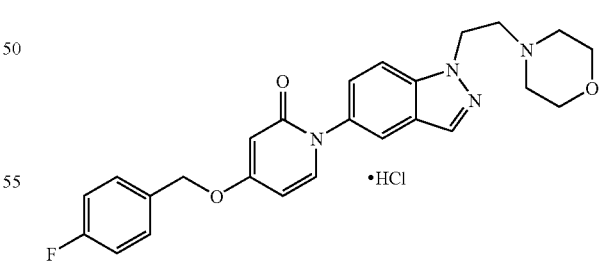

Chemical Formula: C$_{25}$H$_{25}$FN$_4$O$_3$
Exact Mass: 448.19
Molecular Weight: 448.49

Following the procedure of Example 4, but substituting 4-(benzyloxy)-1-(1-(2-morpholinoethyl)-1H-indazol-5-yl)pyridin-2(1H)-one for 4-(benzyloxy)-1-(1-(2-(pyrrolidin-1-yl)ethyl)-1H-indazol-5-yl)pyridin-2(1H)-one in step a and substituting 4-fluorobenzyl bromide for 4-chlorobenzyl bromide and using 15-crown-5 as an additive in step b, the title compound (28 mg, 30%) was obtained as a white solid: mp 196-200° C.; $^1$H NMR (500 MHz, DMSO-d$_6$) δ 10.61 (s, 1H), 8.24 (s, 1H), 7.86 (d, J=9.0 Hz, 1H), 7.79 (s, 1H), 7.61 (d, J=7.5 Hz, 1H), 7.52-7.55 (m, 2H), 7.43 (d, J=9.0 Hz, 1H), 7.24-7.29 (m, 2H), 6.12 (dd, J=7.5, 2.5 Hz, 1H), 6.00 (d, J=2.5 Hz, 1H), 5.14 (s, 2H), 4.93 (m, 2H), 3.98-4.00 (m, 2H), 3.64-3.74 (m, 4H), 3.52-3.54 (m, 2H), 3.18-3.19 (m, 2H); ESI MS m/z 449 [M+H]; HPLC (Method B) 99% (AUC), t$_R$=13.4 min.

Example 74

Preparation of 4-(4-Chlorobenzyloxy)-1-(1-(2-morpholinoethyl)-1H-indazol-5-yl)pyridin-2(1H)-one hydrochloride

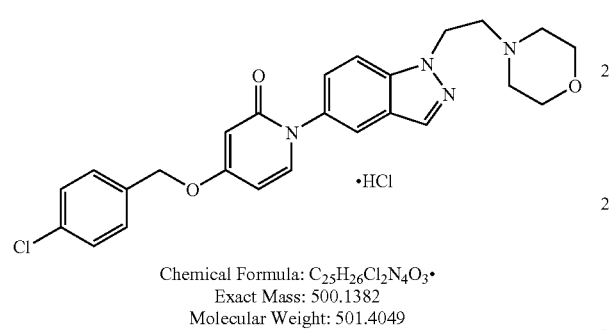

Chemical Formula: C$_{25}$H$_{26}$Cl$_2$N$_4$O$_3$•
Exact Mass: 500.1382
Molecular Weight: 501.4049

Following the procedure of Example 73, but substituting 4-chlororobenzyl bromide for 4-fluorobenzyl bromide, the title compound (45 mg, 25%) was obtained as a white solid: mp 148-150° C.; $^1$H NMR (500 MHz, DMSO-d$_6$) δ 10.77 (s, 1H), 8.24 (s, 1H), 7.87 (d, J=8.5 Hz, 1H), 7.79 (d, J=1.0 Hz, 1H), 7.61 (d, J=7.5 Hz, 1H), 7.49-7.50 (m, 4H), 7.43 (d, J=9.0 Hz, 1H), 6.12 (dd, J=7.5, 2.5 Hz, 1H), 5.98 (d, J=2.5 Hz, 1H), 5.16 (s, 2H), 4.94 (m, 2H), 3.98-4.00 (m, 2H), 3.67-3.76 (m, 4H), 3.51-3.54 (m, 2H), 3.17-3.19 (m, 2H); ESI MS m/z 465 [M+H]$^+$; HPLC (Method B) 97.8% (AUC), t$_R$=14.9 min.

Example 75

Preparation of 4-(Cyclohexylmethoxy)-1-(1-(2-pyrrolidin-1-yl)ethyl-1H-indazol-5-yl)pyridin-2(1H)-one hydrochloride

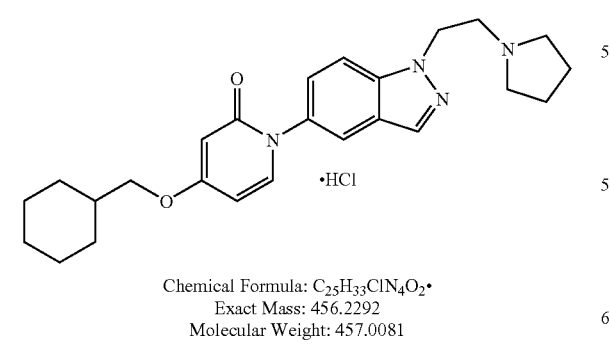

Chemical Formula: C$_{25}$H$_{33}$ClN$_4$O$_2$•
Exact Mass: 456.2292
Molecular Weight: 457.0081

To a solution of 4-hydroxy-1-(1-(2-(pyrrolidin-1-yl)ethyl)-1H-indazol-5-yl)pyridin-2(1H)-one (76 mg, 0.23 mmol) in DMF (2 mL) was added Ag$_2$O (35 mg, 0.28 mmol) and cyclohexylmethyl bromide (39 uL, 0.28 mmol). The reaction mixture was heated to 100° C. and stirred at 100° C. until the starting material was consumed. Then the reaction mixture was cooled, filtered through a layer of Celite, and concentrated to dryness. Purification by flash column chromatography (silica gel, 5% CH$_3$OH in CH$_2$Cl$_2$) gave the title compound (34 mg, 35%) as a white solid. mp 246-247° C. (dec.); $^1$H NMR (500 MHz, DMSO-d$_6$) δ 10.21 (s, 1H), 8.25 (s, 1H), 7.86 (d, J=9.0 Hz, 1H), 7.78 (d, J=1.5 Hz, 1H), 7.57 (d, J=7.5 Hz, 1H), 7.42 (dd, J=9.0, 2.0 Hz, 1H), 6.05 (dd, J=8.0, 3.0 Hz, 1H), 5.86 (d, J=2.5 Hz, 1H), 4.86 (t, J=6.5 Hz, 2H), 3.83 (d, J=6.0 Hz, 2H), 3.72 (q, J=6.0 Hz, 2H), 3.52-3.54 (m, 2H), 3.02-3.06 (m, 2H), 1.99-2.00 (m, 2H), 1.65-1.86 (m, 8H), 1.16-1.30 (m, 3H), 1.00-1.08 (m, 2H); ESI MS m/z 421 [M+H]$^+$; HPLC (Method B)>99% (AUC), t$_R$=17.3 min.

Example 76

Preparation of 4-(3,3-Dimethylbutoxy-1-(1-(2-pyrrolidin-1-yl)ethyl)-1H-indazol-5-yl)pyridin-2(1H)-one hydrochloride

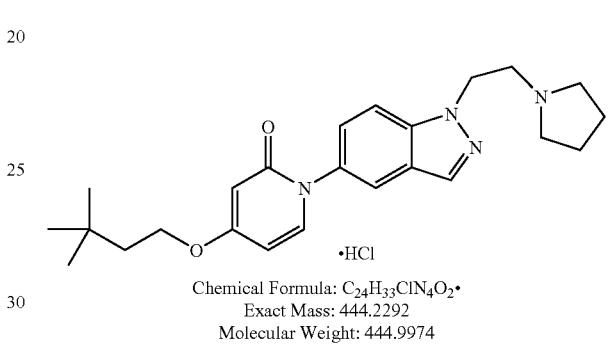

Chemical Formula: C$_{24}$H$_{33}$ClN$_4$O$_2$•
Exact Mass: 444.2292
Molecular Weight: 444.9974

Following the procedure of Example 75, but substituting 1-bromo-3,3-dimethylbutane for cyclohexylmethyl bromide, the title compound (55 mg, 41%) was obtained as an off-white solid: mp 182-184° C.; $^1$H NMR (500 MHz, DMSO-d$_6$) δ 9.94 (s, 1H), 8.25 (s, 1H), 7.85 (d, J=9.0 Hz, 1H), 7.79 (d, J=2.0 Hz, 1H), 7.57 (d, J=7.5 Hz, 1H), 7.43 (dd, J=9.0, 1.5 Hz, 1H), 6.03 (dd, J=7.5, 2.5 Hz, 1H), 5.93 (d, J=2.5 Hz, 1H), 4.86 (t, J=5.5 Hz, 2H), 4.07 (t, J=7.0 Hz, 2H), 3.73-3.74 (m, 2H), 3.53-3.54 (m, 2H), 3.05-3.07 (m, 2H), 1.96-2.01 (m, 2H), 1.83-1.86 (m, 2H), 1.67 (t, J=7.0 Hz, 2H), 0.9 (s, 9H); ESI MS m/z 409 [M+H]$^+$, HPLC (Method B) 98.8% (AUC), t$_R$=15.5 min.

Example 77

Preparation of 4-(Cycloheptylmethoxy)-1-(1-(2-pyrrolidin-1-yl)ethyl)-1H-indazol-5-yl)pyridin-2(1H)-one hydrochloride

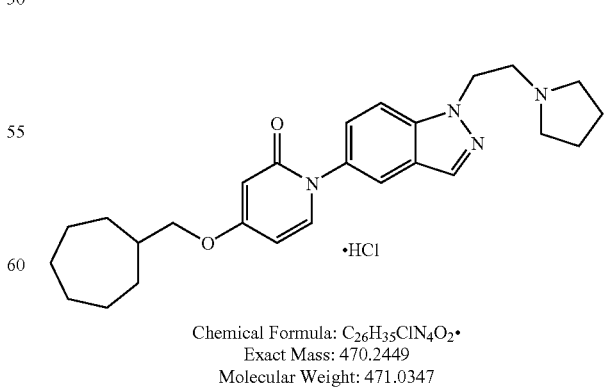

Chemical Formula: C$_{26}$H$_{35}$ClN$_4$O$_2$•
Exact Mass: 470.2449
Molecular Weight: 471.0347

Following the procedure of Example 75, but substituting cycloheptylmethyl bromide for cyclohexylmethyl bromide, the title compound (55 mg, 41%) was obtained as yellow foam: mp 158-160° C.; $^1$H NMR (500 MHz, DMSO-$d_6$) δ 9.85 (s, 1H), 8.25 (s, 1H), 7.85 (d, J=9.0 Hz, 1H), 7.79 (d, J=15 Hz, 1H), 7.56 (d, J=8.0 Hz, 1H), 7.43 (dd, J=9.0, 2.0 Hz, 1H), 6.05 (dd, J=7.5, 2.5 Hz, 1H), 5.87 (d, J=3.0 Hz, 1H), 4.84 (t, J=6.5 Hz, 2H), 3.81 (d, J=7.0 Hz, 2H), 3.73 (q, J=6.0 Hz, 2H), 3.52-3.55 (m, 2H), 3.03-3.08 (m, 2H), 1.77-2.02 (m, 7H), 1.42-1.70 (m, 8H), 1.24-1.31 (m, 2H); ESI MS m/z 435 [M+H]$^+$; HPLC (Method D) 97.7% (AUC), $t_R$=15.6 min.

Example 78

Preparation of 4-(Cyclopropylmethoxy)-1-(1-(2-(pyrrolidin-1-yl)ethyl)-1H-indazol-5-yl)pyridin-2(1H)-one hydrochloride

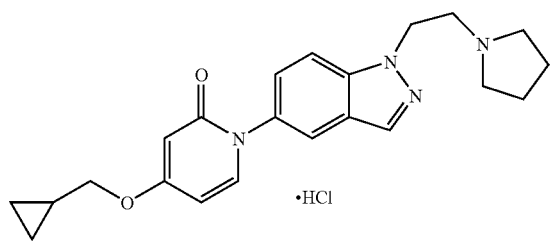

Chemical Formula: $C_{22}H_{27}ClN_4O_2$•
Exact Mass: 414.1823
Molecular Weight: 414.9284

Following the procedure of Example 75, but substituting cyclopropylmethyl bromide for cyclohexylmethyl bromide, the title compound (17 mg, 15%) was obtained as a white powder. mp 226-228° C.; $^1$H NMR (500 MHz, DMSO-$d_6$) δ 9.58 (s, 1H), 8.19 (s, 1H), 7.78 (d, J=9.0 Hz, 1H), 7.72 (s, 1H), 7.50 (d, J=7.5 Hz, 1H), 7.36 (d, J=8.5 Hz, 1H), 6.01 (dd, J=8.0, 3.0 Hz, 1H), 5.77 (d, J=2.5 Hz, 1H), 4.77 (t, J=6.5 Hz, 2H), 3.80 (d, J=7.0 Hz, 2H), 3.66-3.68 (m, 2H), 3.48-3.56 (m, 2H), 3.00-3.07 (m, 2H), 1.77-1.94 (m, 4H), 1.17 (m, 1H), 0.53-0.56 (m, 2H), 0.28-0.29 (m, 2H); ESI MS m/z 379 [M+H]$^+$; HPLC (Method E)>99% (AUC), $t_R$=12.7 min.

Example 79

Preparation of 4-(1-Adamantylmethoxy)-1-(1-(2-(pyrrolidin-1-yl)ethyl)-1H-indazol-5-yl)pyridin-2(1H)-one hydrochloride

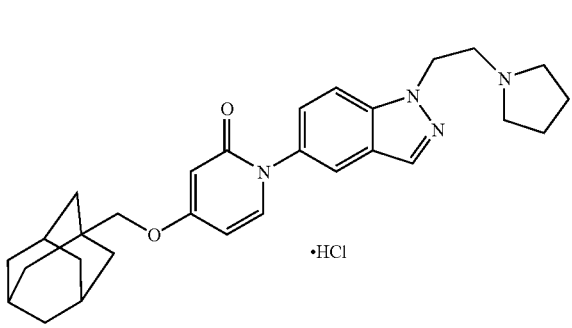

Chemical Formula: $C_{29}H_{37}ClN_4O_2$•
Exact Mass: 508.2605
Molecular Weight: 509.0827

To a solution of adamantanemethanol (1.2 g, 7.4 mmol) in DMF (8 mL) was added NaH (0.3 g, 7.4 mmol) in a single portion. After gas evolution subsided, 4-chloropyridine N-oxide (0.8 g, 6.17 mmol) was added. The reaction mixture was stirred at room temperature under Ar until the reaction was complete. The mixture was quenched with water and extracted with $CH_2Cl_2$. The organic layer was washed with $H_2O$ and 5% LiCl, dried over $Na_2SO_4$, filtered and concentrated to dryness. Purification by flash column chromatography (silica gel, 10% $CH_3OH$ in $CH_2Cl_2$) gave 4-(adamantylmethoxy)pyridine N-oxide (1.55 g, 97%) as a yellow solid. This material was suspended in $Ac_2O$ (5 mL), heated to 140° C. and stirred at 140° C. for 4 h. After cooling, the mixture was diluted with $CH_3OH$ and $H_2O$ (10 mL, 1:1 mixture) and stirred at room temperature for 1 h. The mixture was concentrated, and the residue was purified by flash column chromatography (silica gel, 10% $CH_3OH$ in $CH_2Cl_2$) to give 4-(adamantylmethoxy)pyridin-2(1H)-one (1.08 g, 70%) as a brown solid. Following the procedure of Example 62 (step f), but substituting 5-bromo-1-(2-(pyrrolidin-1-yl)ethyl)-1H-indazole for 4-(2-(5-iodo-1H-indazol-1-yl)ethyl)morpholine, 4-(adamantylmethoxy)pyridin-2(1H)-one for 4-phenethylpyridin-2(1H)-one, and 1,2-trans-cyclohexyldiamine for 8-hydroxyquinoline, the title compound (142 mg, 79%) was obtained as a yellow powder: mp 252-254° C.; $^1$H NMR (500 MHz, CD$_3$OD) δ 8.24 (s, 1H), 7.82 (d, J=2.0 Hz, 1H), 7.78 (d, J=9.0 Hz, 1H), 7.58 (d, J=7.5 Hz, 1H), 7.46 (dd, J=9.0, 2.0 Hz, 1H), 6.29 (dd, J=7.5, 3.0 Hz, 1H), 6.04 (d, J=2.5 Hz, 1H), 4.87 (t, J=6.5 Hz, 2H), 3.86 (t, J=5.5 Hz, 2H), 3.69-3.72 (m, 2H), 3.63 (s, 2H), 3.16-3.20 (m, 2H), 2.16-2.19 (m, 2H), 2.00-2.03 (m, 3H), 1.71-1.84 (m, 12H), 1.24-1.31 (m, 2H); ESI MS m/z 473 [M+H]$^+$; HPLC (Method D) 98.9% (AUC), $t_R$=15.4 min.

Example 80

Preparation of 4-(Cyclopentylmethoxy)-1-(1-(2-(pyrrolidin-1-yl)ethyl)-1H-indazol-5-yl)pyridin-2(1H)-one hydrochloride

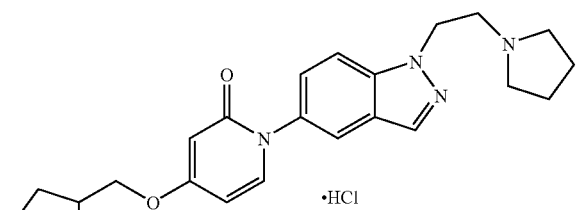

Chemical Formula: $C_{24}H_{31}ClN_4O_2$•
Exact Mass: 442.2136
Molecular Weight: 442.9815

Following the procedure of Example 79, but substituting cyclopentanemethanol for adamantanemethanol, the title compound (180 mg. 71%) was obtained as yellow powder. mp 228-231° C. (dec.); $^1$H NMR (500 MHz, CD$_3$OD) δ 8.24 (s, 1H), 7.83 (d, J=2.0 Hz, 1H), 7.78 (d, J=9.0 Hz, 1H), 7.60 (d, J=7.5 Hz, 1H), 7.46 (dd, J=9.0, 2.0 Hz, 1H), 6.30 (dd, J=7.5, 2.5 Hz, 1H), 6.07 (d, J=3.0 Hz, 1H), 4.88 (t, J=6.0 Hz, 2H), 3.98 (d, J=7.0 Hz, 2H), 3.86 (t, J=6.0 Hz, 2H), 3.69-3.73 (m, 2H), 3.15-3.17 (m, 2H), 2.39-2.42 (m, 1H), 2.16-2.19 (m, 2H), 2.00-2.03 (m, 2H), 1.86-1.90 (m, 2H), 1.67-1.72 (m, 4H), 1.38-1.42 (m, 2H); ESI MS m/z 407 [M+H]$^+$. HPLC (Method D)>99% (AUC), $t_R$=13.1 min.

Example 81

Preparation of 4-(Benzyloxy)-1-(3-methyl-1-(2-pyrrolidin-1-yl)ethyl)-1H-indazol-5-yl)pyridin-2(1H)-one hydrochloride a) 5-Bromo-3-methyl-1H-indazole Beilstein Registry Number 10424854

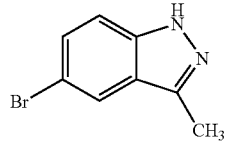

Chemical Formula: C$_8$H$_7$BrN$_2$
Exact Mass: 209.98
Molecular Weight: 211.06

A solution of 4-bromo-2-ethylaniline (5.00 mL, 35.3 mmol) in glacial acetic acid (300 mL) was treated with a solution of NaNO$_2$ (2.43 g, 35.2 mmol) in water (10 mL). After stirring for 4.5 hours, the mixture was concentrated to dryness. Purification by flash column chromatography (silica gel, CH$_2$Cl$_2$/MeOH, 100:0 to 97:3) provided the title compound (4.24 g, 57%) as a dark red semi-solid: $^1$H NMR (500 MHz, CDCl$_3$) δ 7.82 (d, J=1.5 Hz, 1H), 7.45 (dd, J=9.0, 1.5 Hz, 1H), 7.31 (d, J=9.0, 1H), 2.56 (s, 3H); ESI MS m/z 211 [M+H]$^+$.

c) 5-Bromo-3-methyl-1-(2-(pyrrolidin-1-yl)ethyl)-1H-indazole

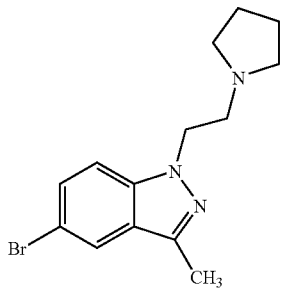

Chemical Formula: C$_{14}$H$_{18}$BrN$_3$
Exact Mass: 307.07
Molecular Weight: 308.22

A solution of 5-bromo-3-methyl-1H-indazole (4.23 g, 20.0 mmol) in DMSO (150 mL) was treated with Cs$_2$CO$_3$ (19.55 g, 60.00 mmol) and 1-(2-chloroethyl)pyrrolidine hydrochloride (5.27 g, 31.0 mmol). After stirring for 16 hours at room temperature, the mixture was diluted with water (300 mL) and extracted with EtOAc (3×200 mL). The combined organics were washed with water (200 mL) and brine (200 mL), dried over Na$_2$SO$_4$, filtered and concentrated to dryness. Purification by flash column chromatography (silica gel, MeOH/EtOAc/hexanes, 1.4:5) gave the title compound (0.67 g, 11%) as an orange oil. $^1$H NMR (500 MHz, CDCl$_3$) δ 7.77 (d, J=1.5 Hz, 1H), 7.42 (dd, J=9.0, 1.5 Hz, 1H), 7.26 (d, J=9.0, 1H, overlapping with solvent peak), 4.43 (t, J=7.5 Hz, 2H), 2.96 (t, J=7.5 Hz, 2H), 2.58-2.55 (m, 4H), 2.53 (s, 3H), 1.79-1.74 (m, 4H).

c) 4-(Benzyloxy)-1-(3-methyl)-1-(2-(pyrrolidin-1-yl)ethyl-1H-indazol-5-yl)pyridin-2(1H)-one hydrochloride

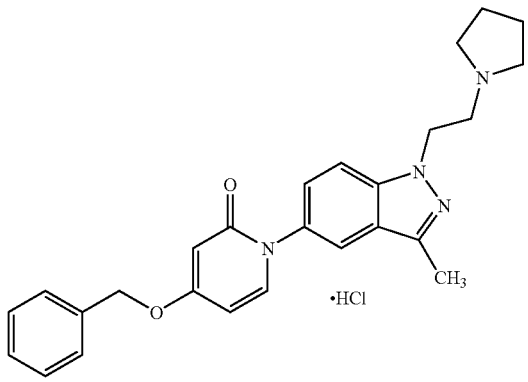

Chemical Formula: C$_{26}$H$_{28}$N$_4$O$_2$
Exact Mass: 428.22
Molecular Weight: 428.53

Following the procedure of Example 1 (steps c and d), but substituting 5-bromo-3-methyl-1-(2-(pyrrolidin-1-yl)ethyl)-1H-indazole for 5-bromo-1-(2-(pyrrolidin-1-yl)ethyl)-1H-indazole, the title compound (93 mg, 14%) was prepared as an off-white powder: mp 163-167° C.; $^1$H NMR (500 MHz, DMSO-d$_6$) δ 10.16 (br s, 1H), 7.78-7.77 (m, 2H), 7.60 (d, J=7.6 Hz, 1H), 7.48-7.38 (m, 6H), 6.12 (dd, J=7.6, 2.7 Hz, 1H), 5.99 (d, J=2.7 Hz, 1H), 5.16 (s, 2H), 4.76 (t, J=6.4 Hz, 2H), 3.70-3.67 (m, 2H), 3.53-3.49 (m, 2H), 3.06-3.03 (m, 2H), 2.52 (s, 3H, overlapping with solvent peak), 2.01-1.98 (m, 2H), 1.85-1.83 (m, 2H); ESI MS m/z 429 [M+H]$^+$; HPLC (Method A) 98.7% (AUC), t$_R$=14.5 min.

Example 82

Preparation of 4-(Benzyloxy)-1-(1-(2-(pyrrolidin-1-yl)ethyl)-3-(trifluoromethyl)-1H-indazol-5-yl)pyridin-2(1H)-one hydrochloride a) 1-(5-Bromo-2-fluorophenyl)-2,2,2-trifluoroethanol

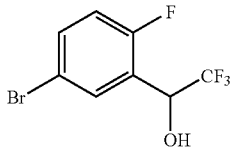

Chemical Formula: C$_8$H$_5$BrF$_4$O
Exact Mass: 271.95
Molecular Weight: 273.02

A solution of 5-bromo-2-fluorobenzaldehyde (5.05 g, 24.9 mmol) in THF (200 mL) was cooled in a wet ice bath and treated dropwise with TMS-CF$_3$ over five minutes. After stirring for 10 minutes, a solution of tetrabutylammonium fluoride (TBAF) in THF (1.0 mL, 1.0M) was added dropwise over 5 minutes. After stirring for 10 minutes, the ice bath was removed and the reaction mixture was stirred at room temperature for 16 hours. The reaction mixture was treated with 1N HCl (50 mL) and allowed to stir for 2 hours. The mixture was diluted with 1N HCl (50 mL) and extracted with EtOAc (200 mL). The organic layer was washed with saturated aqueous NaHCO$_3$ (2×50 mL) and brine (50 mL), dried over Na$_2$SO$_4$, filtered and concentrated. Purification by flash column chromatography (silica gel, hexanes/EtOAc, 100:0 to 95:5) provided the title compound (3.28 g, 48%) as a colorless liquid. $^1$H NMR (500 MHz, CDCl$_3$) δ 7.76 (dd, J=6.0, 2.0 Hz, 1H), 7.50 (ddd, J=8.5, 4.5, 2.5 Hz, 1H), 7.00 (overlapping dd, J=9.0, 9.0 Hz, 1H), 5.39 (overlapping dq, J=6.0, 6.0 Hz, 1H), 2.86 (d, J=5.5 Hz, 1H).

b)
1-(5-Bromo-2-fluorophenyl)-2,2,2-trifluoroethanone

Beilstein Registry Number 9622366

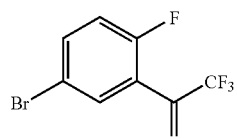

Chemical Formula: C$_8$H$_3$BrF$_4$O
Exact Mass: 269.93
Molecular Weight: 271.01

A solution of 1-(5-bromo-2-fluorophenyl)-2,2,2-trifluoroethanol (2.26 g, 8.29 mmol) in CH$_2$Cl$_2$ (80 mL) was treated sequentially with Dess-Martin periodinane (5.83 g, 13.75 mmol) and TFA (1.1 mL, 15 mmol). After stirring at room temperature for 3 hours, the mixture was treated with silica gel and concentrated. The adsorbed material was loaded onto a silica gel column and purified (CH$_2$Cl$_2$) to give the title compound (1.99 g, 88%) as a colorless liquid: $^1$H NMR (500 MHz, CDCl$_3$) δ 7.99 (dd, J=6.0, 2.5 Hz, 1H), 7.78 (ddd, J=9.0, 4.5, 2.5 Hz, 1H), 7.15 (dd, J=10.0, 9.0 Hz, 1H).

c) 5-Bromo-3-(trifluoromethyl)-1H-indazole

Beilstein Registry Number 914313

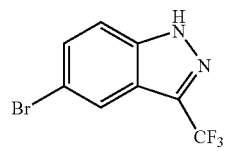

Chemical Formula: C$_8$H$_4$BrF$_3$N$_2$
Exact Mass: 263.95
Molecular Weight: 265.03

A solution of 1-(5-bromo-2-fluorophenyl)-2,2,2-trifluoroethanone (1.49 g, 5.50 mmol) in 1-butanol (25 mL) was treated with hydrazine hydrate (5.0 mL, 100 mmol) and heated to reflux. After stirring at reflux for 6 hours, the mixture was allowed to cool, diluted with H$_2$O (100 mL) and extracted with EtOAc (4×100 mL). The combined organics were washed with brine (100 mL), dried over Na$_2$SO$_4$, filtered and concentrated. Purification by flash column chromatography (silica gel, CH$_2$Cl$_2$) provided the title compound (0.64 g, 44%) as an off-white powder: $^1$H NMR (500 MHz, CDCl$_3$) δ 8.04 (s, 1H), 7.59 (dd, J=9.0, 1.5 Hz, 1H), 7.46 (d, J=9.0, 1H).

d) 5-Bromo-1-(2-(pyrrolidin-1-yl)ethyl)-3-(trifluoromethyl)-1H-indazole

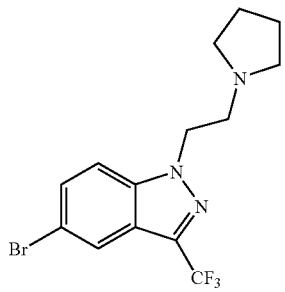

Chemical Formula: C$_{14}$H$_{15}$BrF$_3$N$_3$
Exact Mass: 361.04
Molecular Weight: 362.19

A solution of 5-bromo-3-(trifluoromethyl)-1H-indazole (282 mg, 1.07 mmol) in DMSO (15 mL) was treated with Cs$_2$CO$_3$ (1.45 g, 4.45 mmol) and 1-(2-chloroethyl)pyrrolidine hydrochloride (376 mg, 2.21 mmol). After stirring for 16 hours at room temperature, the mixture was diluted with water (50 mL) and extracted with EtOAc (3×50 mL). The combined organics were washed with brine (50 mL), dried over Na$_2$SO$_4$, filtered and concentrated to dryness. Purification by flash column chromatography (silica gel, MeOH/EtOAc/hexanes, 0:1:1 to 1.49:50) gave the title compound (250 mg, 65%) as a light yellow oil: $^1$H NMR (500 MHz, CDCl$_3$) δ 7.98 (s, 1H), 7.54 (dd, J=8.9, 1.7 Hz, 1H), 7.40 (d, J=8.9, 1H), 4.54 (t, J=7.1 Hz, 2H), 3.01 (t, J=7.1 Hz, 2H), 2.56-2.54 (m, 4H), 1.79-1.75 (m, 4H); ESI MS m/z 362 [M+H]$^+$.

e) 4-(Benzyloxy)-1-(1-(2-(pyrrolidin-1-yl)ethyl)-3-(trifluoromethyl)-1H-indazol-5-yl)pyridin-2(1H)-one hydrochloride

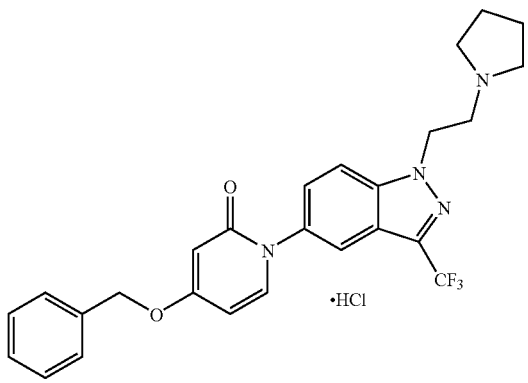

Chemical Formula: C$_{26}$H$_{25}$F$_3$N$_4$O$_2$
Exact Mass: 482.19
Molecular Weight: 482.50

Following the procedure of Example 1 (steps c and d), but substituting 5-bromo-1-(2-(pyrrolidin-1-yl)ethyl)-3-(trifluo romethyl)-1H-indazole for 5-bromo-1-(2-(pyrrolidin-1-yl) ethyl)-1H-indazole, the title compound (14 mg, 4%) was prepared as an off-white powder: $^1$H NMR (500 MHz, DMSO-$d_6$) δ 10.10 (s, 1H), 8.07 (d, J=9.0 Hz, 1H), 7.85 (s, 1H), 7.66-7.62 (m, 2H), 7.48-7.38 (m, 5H), 6.15 (dd, J=7.5, 2.5 Hz, 1H), 6.00 (d, J=2.0 Hz, 1H), 5.17 (s, 2H), 4.99 (t, J=6.5 Hz, 2H), 3.81-3.77 (m, 2H), 3.55-3.54 (m, 2H), 3.12-3.09 (m, 2H), 2.02-1.99 (m, 2H), 1.86-1.84 (m, 2H); ESI MS m/z 483 [M+H]$^+$; HPLC (Method A) 98.4% (AUC), $t_R$=15.9 min.

Binding Assay for Human Melanin-Concentrating Hormone (MCH$_1$) Receptor

Evaluation of the affinity of compounds for the human MCH$_1$ receptor was accomplished in transfected Chinese Hamster Ovary (CHO) cells determined in a radioligand binding assay, as described in MacDonald et al., "Molecular characterization of the melanin-concentrating hormone/receptor complex: identification of critical residues involved in binding and activation", Mol. Pharmacol., 58:217 (2000). Cell membrane homogenates (5 μg protein) were incubated for 60 min at 22° C. with 0.1 nM [$^{125}$I][Phe$^{13}$,Tyr$^{19}$]-MCH in the absence or presence of the test compound in a buffer containing 25 mM Hepes/Tris (pH 7.4), 5 mM MgCl$_2$, 1 mM CaCl$_2$ and 0.5% BSA. Nonspecific binding was determined in the presence of 0.1 μM MCH. Following incubation, the samples were filtered rapidly under vacuum through glass fiber filters (GF/B, Packard) and rinsed several times with an ice-cold buffer containing 25 mM Hepes/Tris (pH 7.4), 500 mM NaCl, 5 mM MgCl$_2$, 1 mM CaCl$_2$ and 0.1% BSA using a 96-sample cell harvester (Unifilter, Packard). The filters were dried, then counted for radioactivity in a scintillation counter (Topcount, Packard) using a scintillation cocktail (Microscint 0, Packard).

The results are expressed as a percent inhibition of the control radioligand specific binding. The IC$_{50}$ value (concentration causing a half-maximal inhibition of control specific binding) and Hill coefficient (n$_H$) were determined by nonlinear regression analysis of the competition curve using Hill equation curve fitting. The inhibition constant (K$_i$) was calculated from the Cheng Prusoff equation: (K$_i$=IC$_{50}$/(1+(L/K$_D$)), where L=concentration of radioligand in the assay, and K$_D$=affinity of the radioligand for the receptor).

By methods described above, the compounds listed in Table 1 were synthesized and tested for biological activity. All of the compounds in Table 1 exhibited K$_i$ of less than or equal to 2.0 μM in the MCH$_1$ binding assay.

TABLE 1

| Ex. No. | Structure | Mass Spec | $^1$H NMR Data |
|---|---|---|---|
| 1 | 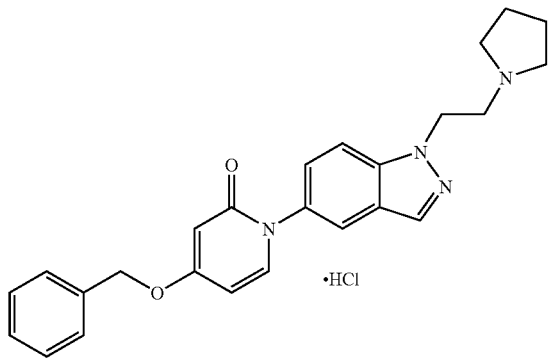 | 415 | $^1$H NMR (500 MHz, DMSO-$d_6$) δ 10.42 (s, 1H), 8.23 (s, 1H), 7 86 (d, J = 8.8 Hz, 1H), 7.79 (s, 1H), 7.61 (d, J = 7.6 Hz, 1H), 7.48-7.36 (m, 6H), 6.12 (dd, J = 2.6, 7.6 Hz, 1H), 5.99 (d, J = 2.6 Hz, 1H), 5 16 (s, 2H), 4.85 (br m, 2H), 3.70 (br m, 2H), 3.51 (br m, 2H), 3.01 (br m, 2H), 1.97 (br m, 2H), 1.84 (br m, 2H) |
| 2 | 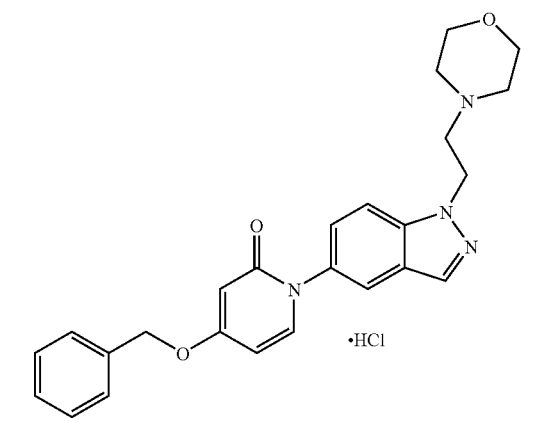 | 431 | $^1$H NMR (500 MHz, DMSO-$d_6$) δ 10.50 (br s, 1H), 8.23 (s, 1H), 7.85 (d, J = 8.5 Hz, 1H), 7.79 (s, 1H), 7.60 (d, J = 7.5 Hz, 1H), 7.48-7.41 (m, 5H), 7.39-7.36 (m, 1H), 6.12 (dd, J = 7.5, 3.0 Hz, 1H), 5.99 (d, J = 3.0 Hz, 1H), 5.15 (s, 2H), 4.92 (br s, 2H), 3.99 (d, J = 12.0 Hz, 2H), 3.70-3.68 (m, 4H), 3.53 (d, J = 12.0 Hz, 2H), 3.19 (br m, 2H) |

TABLE 1-continued

| Ex. No. | Structure | Mass Spec | $^1$H NMR Data |
|---|---|---|---|
| 3 | 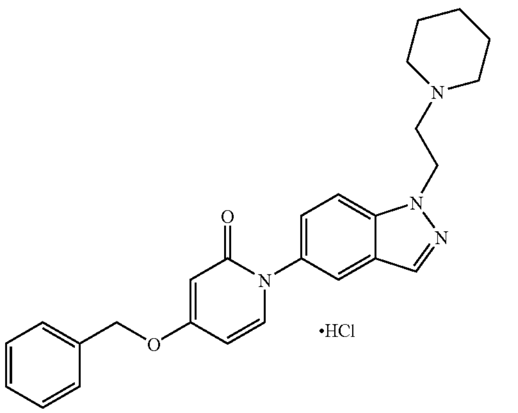 | 429 | $^1$H NMR (500 MHz, DMSO-d$_6$) δ 9.85 (br s, 1H), 8.24 (s, 1H), 7.85 (d, J = 9.0 Hz, 1H), 7.79 (s, 1H), 7.60 (d, J = 7.5 Hz, 1H), 7.48-7.36 (m, 6H), 6.12 (dd, J = 7.5, 3.0 Hz, 1H), 5.99 (d, J = 3.0 Hz, 1H), 5.15 (s, 2H), 4.89 (t, J = 6.5 Hz, 2H), 3.61-3.54 (m, 4H), 3.00-2.94 (m, 2H), 1.84-1.81 (m, 2H), 1.68-1.65 (m, 3H), 1.41-1.36 (m, 1H) |
| 4 | 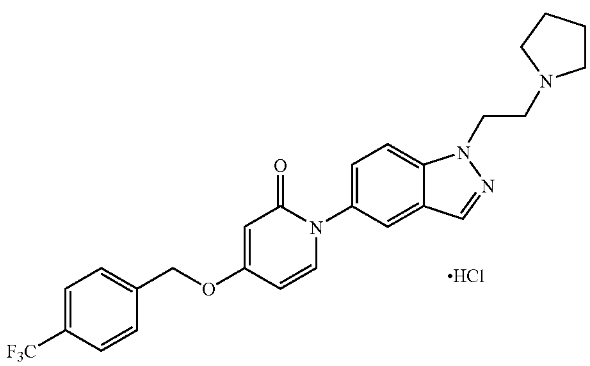 | 483 | $^1$H NMR (500 MHz, DMSO-d$_6$) δ 9.65 (s, 1H), 8.12 (m, 1H), 7.80-7.67 (m, 6H), 7.62 (d, J = 7.5 Hz, 1H), 7.34 (m, 1H), 6.13 (dd, J = 7.5, 2.5 Hz, 1H), 5.98 (d, J = 2.5 Hz, 1H), 5.27 (s, 2H), 4.58-4.54 (m, 2H), 2.89 (m, 2H), 2.52-2.42 (m, 4H), 1.73-1.64 (m, 4H) |
| 5 | 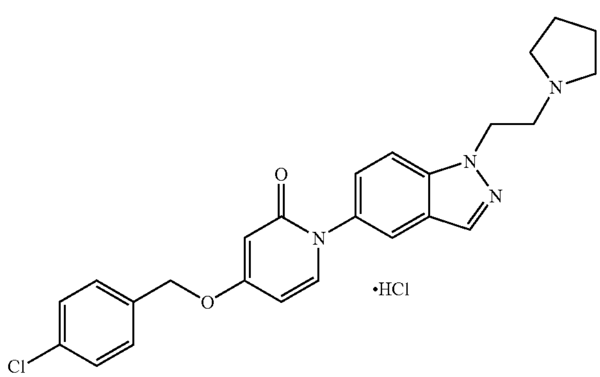 | 449 | $^1$H NMR (500 MHz, DMSO-d$_6$) δ 9.94 (s, 1H), 8.25 (s, 1H), 7.86 (d, J = 8.5 Hz, 1H), 7.80 (d, J = 1.5 Hz, 1H), 7.61 (d, J = 7.5 Hz, 1H), 7.50 (s, 4H), 7.43 (dd, J = 8.5, 1.5 Hz, 1H), 6.13 (dd, J = 7.5, 2.5 Hz, 1H), 5.98 (d, J = 3.0 Hz, 1H), 5.16 (s, 2H), 4.85 (t, J = 6.0 Hz, 2H), 3.74-3.72 (m, 2H), 3.54-3.53 (m, 2H), 3.06 (m, 2H), 2.00-1.99 (m, 2H), 1.85-1.83 (m, 2H) |
| 6 | 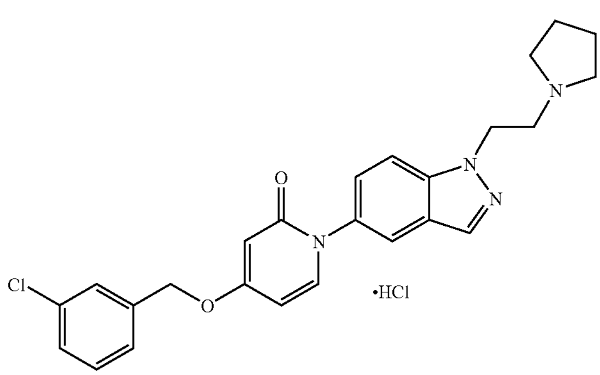 | 449 | $^1$H NMR (500 MHz, DMSO-d$_6$) δ 9.80 (s, 1H), 8.25 (s, 1H), 7.85 (d, J = 8.0 Hz, 1H), 7.80 (d, J = 1.5 Hz, 1H), 7.62 (d, J = 8.0 Hz, 1H), 7.56 (s, 1H), 7.48-7.42 (m, 4H), 6.15 (dd, J = 7.5, 2.5 Hz, 1H), 5.99 (d, J = 2.5 Hz, 1H), 5.18 (s, 2H), 4.84-4.83 (m, 2H), 3.74-3.73 (m, 2H), 3.54-3.53 (m, 2H), 3.07 (m, 2H), 2.00-1.99 (m, 2H), 1.84-1.83 (m, 2H) |

TABLE 1-continued

| Ex. No. | Structure | Mass Spec | $^1$H NMR Data |
|---|---|---|---|
| 7 | 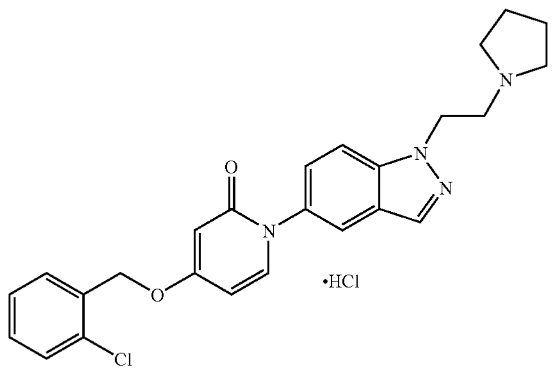 | 449 | $^1$H NMR (500 MHz, DMSO-d$_6$) δ 10.13 (s, 1H), 8.25 (s, 1H), 7.87 (d, J = 9.0 Hz, 1H), 7.81 (d, J = 2.0 Hz, 1H), 7.64-7.61 (m, 2H), 7.57-7.55 (m, 1H), 7.47-7.42 (m, 3H), 6.13 (dd, J = 7.5, 2.5 Hz, 1H), 6.04 (d, J = 3.0 Hz, 1H), 5.20 (s, 2H), 4.86 (t, J = 6.5 Hz, 2H), 3.75-3.71 (m, 2H), 3.54-3.51 (m, 2H), 3.08-3.01 (m, 2H), 2.03-1.99 (m, 2H), 1.86-1.83 (m, 2H) |
| 8 | 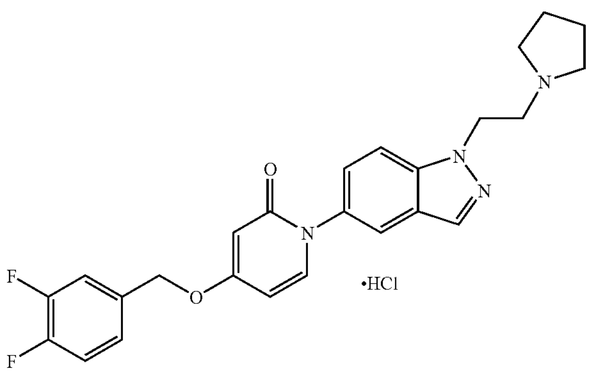 | 451 | $^1$H NMR (500 MHz, DMSO-d$_6$) δ 9.96 (s, 1H), 8.25 (s, 1H), 7.86 (d, J = 9.0 Hz, 1H), 7 80 (d, J = 2.0 Hz, 1H), 7.61 (d, J = 7.5 Hz, 1H), 7.60-7.56 (m, 1H), 7.53-7.48 (m, 1H), 7.43 (dd, J = 9.0, 2.0 Hz, 1H), 7.36-7.35 (m, 1H), 6.14 (dd, J = 7.5, 2.5 Hz, 1H), 5.99 (d, J = 2.5 Hz, 1H), 5.15 (s, 2H), 4.86-4.84 (m, 2H), 3.75-3.71 (m, 2H), 3.54-3.53 (m, 2H), 3.08-3.02 (m, 2H), 2.02-1.99 (m, 2H), 1.86-1.83 (m, 2H) |
| 9 | 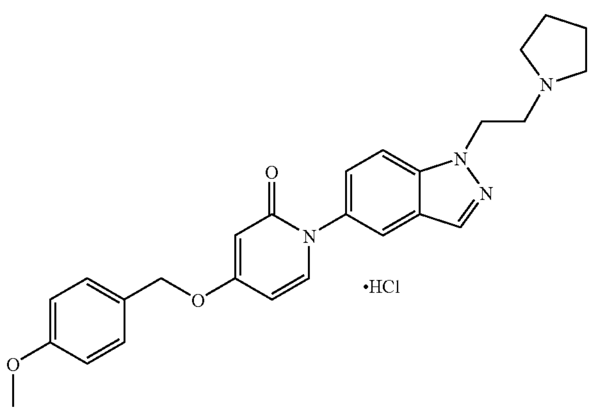 | 445 | $^1$H NMR (500 MHz, DMSO-d$_6$) δ 9.86 (s, 1H), 8.25 (s, 1H), 7.85 (d, J = 9.0 Hz, 1H), 7.79 (s, 1H), 7.58 (d, J = 7.5 Hz, 1H), 7.43-7.39 (m, 3H), 6.99-6.97 (m, 2H), 6.09 (dd, J = 7.5, 2.5 Hz, 1H), 5.99 (d, J = 2.0 Hz, 1H), 5.06 (s, 2H), 4.84-4.83 (m, 2H), 3.78 (s, 3H), 3.74-3.73 (m, 2H), 3.54 (m, 2H), 3.08-3.06 (m, 2H), 2.00 (m, 2H), 1.83 (m, 2H) |
| 10 | 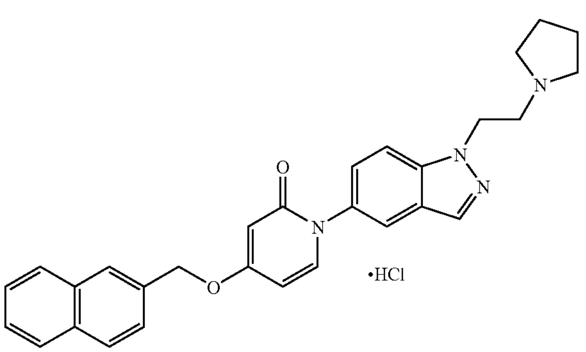 | 465 | $^1$H NMR (500 MHz, DMSO-d$_6$) δ 10.18 (s, 1H), 8.24 (s, 1H), 8.03 (s, 1H), 8.00-7.95 (m, 3H), 7.86 (d, J = 9.0 Hz, 1H), 7.80 (d, J = 1.5 Hz, 1H), 7.63-7.54 (m, 4H), 7.43 (dd, J = 9.0, 2.0 Hz, 1H), 6.09 (dd, J = 7.5, 2.5 Hz, 1H), 6.06 (d, J = 2.5 Hz, 1H), 5.34 (s, 2H), 4.87-4.85 (m, 2H), 3.74-3.70 (m, 2H), 3.54-3.52 (m, 2H), 3.06-3.04 (m, 2H), 2.00-1.99 (m, 2H), 1.85-1.83 (m, 2H) |

TABLE 1-continued

| Ex. No. | Structure | Mass Spec | $^1$H NMR Data |
|---|---|---|---|
| 11 | 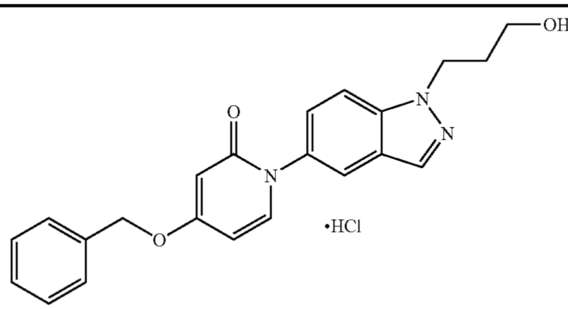 | 376 | $^1$H NMR (500 MHz, DMSO-d$_6$) δ 8.12 (s, 1H), 7.73-7.71 (m, 2H), 7.62 (d, J = 7.5 Hz, 1H), 7.48-7.36 (m, 5H), 7.33 (dd, J = 9.0, 1.5 Hz, 1H), 6.10 (dd, J = 7.5, 2.5 Hz, 1H), 5.99 (d, J = 2.5 Hz, 1H), 5.15 (s, 2H), 4.50 (t, J = 7.0 Hz, 2H), 3.38 (t, J = 6.5 Hz, 2H), 2.01-1.96 (m, 2H) |
| 12 | 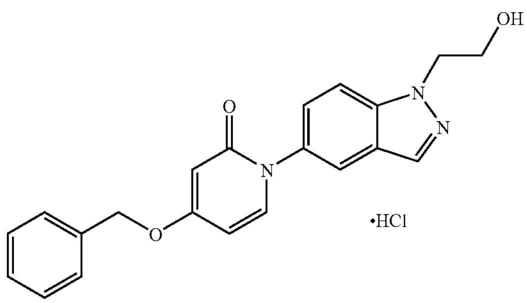 | 362 | $^1$H NMR (500 MHz, DMSO-d$_6$) δ 8.12 (s, 1H), 7.74-7.71 (m, 2H), 7.61 (d, J = 7.5 Hz, 1H), 7.48-7.36 (m, 5H), 7.31 (dd, J = 9.0, 2.5 Hz, 1H), 6.10 (dd, J = 7.5, 2.5 Hz, 1H), 5.99 (d, J = 2.5 Hz, 1H), 5.15 (s, 2H), 4.48 (t, J = 5.5 Hz, 2H), 3.81 (t, J = 5.5 Hz, 2H) |
| 13 | 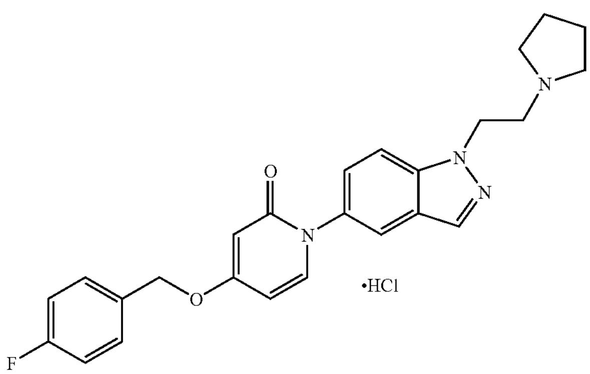 | 433 | $^1$H NMR (500 MHz, DMSO-d$_6$) δ 9.79 (s, 1H), 8.25 (s, 1H), 7 85 (d, J = 8.5 Hz, 1H), 7 80 (d, J = 2.0 Hz, 1H), 7.60 (d, J = 7.5 Hz, 1H), 7.55-7.52 (m, 2H), 7.44-7.42 (m, 1H), 7.28-7.25 (m, 2H), 6.12 (dd, J = 7.5, 2.5 Hz, 1H), 6.00 (d, J = 2.5 Hz, 1H), 5.14 (s, 2H), 4.85-4.84 (m, 2H), 3.74-3 73 (m, 2H), 3.55-3.54 (m, 2H), 3.07 (m, 2H), 2.00-1.99 (m, 2H), 1.84-1.83 (m, 2H) |
| 14 | 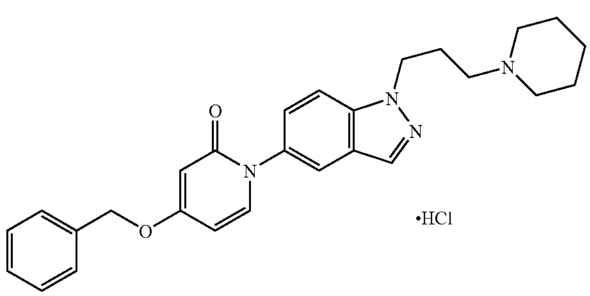 | 443 | $^1$H NMR (500 MHz, DMSO-d$_6$) δ 9.64 (s, 1H), 8.18 (s, 1H), 7.80 (d, J = 8.9 Hz, 1H), 7.76 (s, 1H), 7.60 (d, J = 7.6 Hz, 1H), 7.48-7.35 (m, 6H), 6.12 (dd, J = 7.6, 2.6 Hz, 1H), 5.99 (d, J = 2.6 Hz, 1H), 5.15 (s, 2H), 4.55 (t, J = 6.7 Hz, 2H), 3.45-3.35 (m, 2H), 3.08-3.03 (m, 2H), 2.85-2.80 (m, 2H), 2.30-2.26 (m, 2H), 1.78-1.75 (m, 2H), 1 70-1.64 (m, 3H), 1.40-1.30 (m, 1H) |
| 15 | 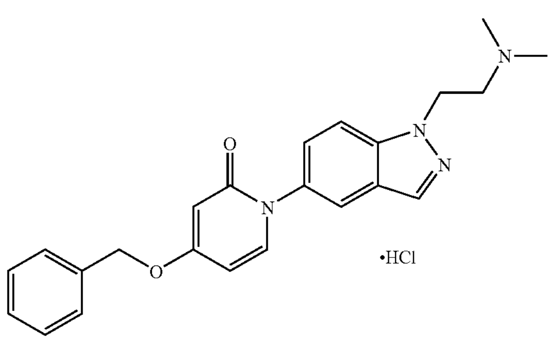 | 389 | $^1$H NMR (500 MHz, DMSO-d$_6$) δ 9.92 (s, 1H), 8.24 (s, 1H), 7 87 (d, J = 9.0 Hz, 1H), 7.79 (d, J = 2.0 Hz, 1H), 7.60 (d, J = 7 5 Hz, 1H), 7.49-7.41 (m, 5H), 7.39-7.35 (m, 1H), 6.13 (dd, J = 7.5, 2.5 Hz, 1H), 5.99 (d, J = 3.0 Hz, 1H), 5.16 (s, 2H), 4.88 (t, J = 6.5 Hz, 2H), 3.63 (m, 2H), 2.20 (d, J = 4.5 Hz, 6H) |

TABLE 1-continued
| Ex. No. | Structure | Mass Spec | ¹H NMR Data |
|---|---|---|---|
| 16 | 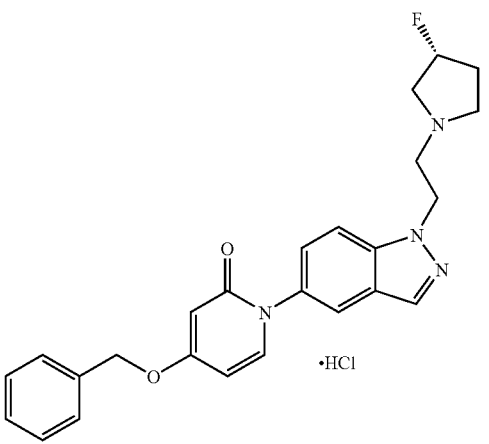 | 433 | ¹H NMR (500 MHz, DMSO-d$_6$) δ 10.58 (br s, 0.5H), 8.24 (s, 1H), 7.84 (d, J = 9.0 Hz, 1H), 7.79 (s, 1H), 7.60 (d, J = 7.5 Hz, 1H), 7.48-7.36 (m, 6H), 6.12 (dd, J = 8.0, 3.0 Hz, 1H), 5.99 (d, J = 2.5 Hz, 1H), 5.53-5.39 (m, 1H), 5.15 (s, 2H), 4.87 (s, 2H), 3.88-3.51 (m, 5H), 3.21-3.16 (m, 1H), 2.15-2.08 (m, 1H), 1.30-1.23 (m, 1H) |
| 17 | 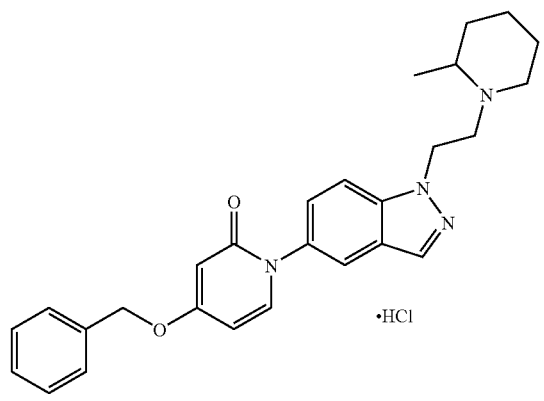 | 443 | ¹H NMR (500 MHz, DMSO-d$_6$) δ 10.08 (s, 1H), 8.24 (d, J = 3.0 Hz, 1H), 7.89 (t, J = 8.8 Hz, 1H), 7.79 (s, 1H), 7.61 (d, J = 7.6 Hz, 1H), 7.49-7.41 (m, 5H), 7.39-7.35 (m, 1H), 6.12 (dd, J = 7.6, 2.7 Hz, 1H), 5.99 (d, J = 2.7 Hz, 1H), 5.16 (s, 2H), 4.94-4.90 (m, 2H), 3.76-3.74 (m, 1H), 3.62-3.52 (m, 2H), 3.23 (m, 1H), 3.06-3.03 (m, 1H), 1.89-1.43 (br m, 6H), 1.31 (d, J = 6.3 Hz, 3H) |
| 18 | 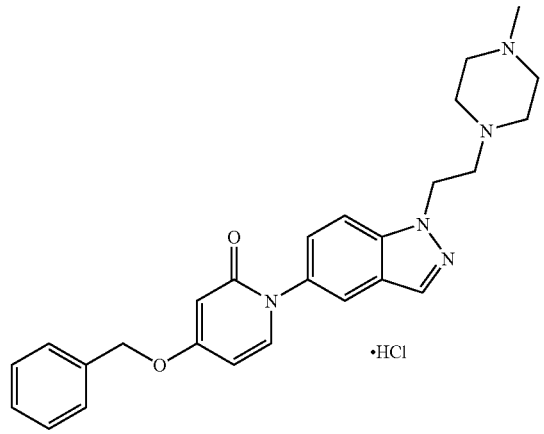 | 444 | ¹H NMR (500 MHz, DMSO-d$_6$) δ 8.17 (s, 1H), 7.83 (d, J = 8.9 Hz, 1H), 7.75 (d, J = 1.2 Hz, 1H), 7.61 (d, J = 7.5 Hz, 1H), 7.49-7.41 (m, 4H), 7.39-7.35 (m, 2H), 6.12 (dd, J = 7.5, 2.5 Hz, 1H), 5.99 (d, J = 2.7 Hz, 1H), 5.15 (s, 2H), 4.71 (s, 2H), 3.64 (br m, 6H), 3.40 (br m, 4H), 2.76 (s, 3H) |

TABLE 1-continued

| Ex. No. | Structure | Mass Spec | ¹H NMR Data |
|---|---|---|---|
| 19 | 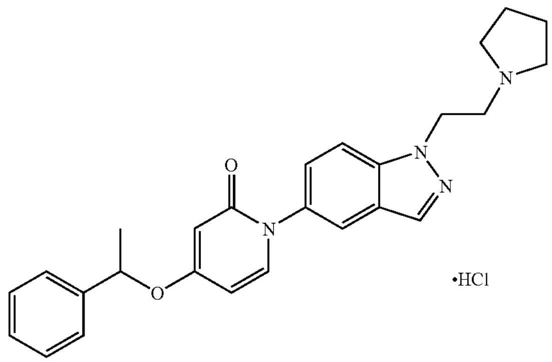 | 429 | ¹H NMR (500 MHz, DMSO-d$_6$) δ 9.82 (s, 1H), 8.15 (s, 1H), 7.75 (d, J = 9.0 Hz, 1H), 7.69 (d, J = 2.0 Hz, 1H), 7.49 (d, J = 7.5 Hz, 1H), 7.38-7.31 (m, 5H), 7.26-7.24 (m, 1H), 6.04 (dd, J = 7.5, 2.5 Hz, 1H), 5.69 (d, J = 3.0 Hz, 1H), 5.51 (q, J = 6.5 Hz, 1H), 4.77-4.75 (m, 2H), 3.66-3.63 (m, 2H), 3.46-3.45 (m, 2H), 3.00-2.99 (m, 2H), 1.93 (m, 2H), 1.78-1.75 (m, 2H), 1.51 (d, J = 6.5 Hz, 3H) |
| 20 | 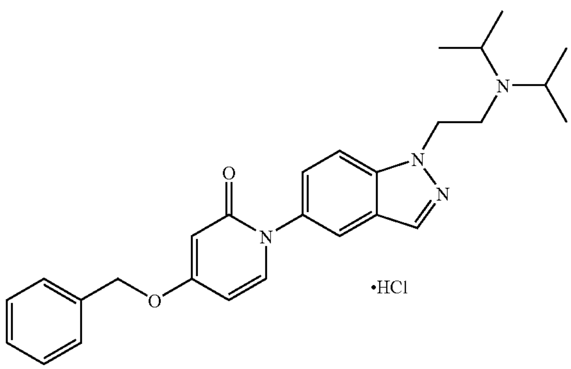 | 445 | ¹H NMR (500 MHz, DMSO-d$_6$) δ 9.65 (s, 1H), 8.25 (s, 1H), 7.85 (d, J = 8.9 Hz, 1H), 7.78 (d, J = 1 7 Hz, 1H), 7.60 (d, J = 7.6 Hz, 1H), 7.40-7.49 (m, 5H), 7.35-7.39 (m, 1H), 6.12 (dd, J = 7.6, 2.7 Hz, 1H), 5.99 (d, J = 2.7 Hz, 1H), 5.16 (s, 2H), 4.90 (t, J = 7.3 Hz, 2H), 3.77 (m, 2H), 3.59 (m, 2H), 1.34 (m, 12H) |
| 21 | 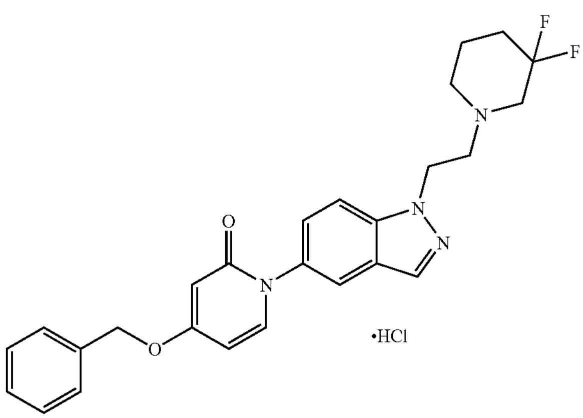 | 465 | ¹H NMR (500 MHz, DMSO-d$_6$) δ 8.22 (s, 1H), 7.85 (d, J = 8.9 Hz, 1H), 7.78 (m, 1H), 7.61 (d, J = 8.0 Hz, 1H), 7.49-7.35 (m, 6H), 6.13-6.10 (m, 1H), 5.99 (d, J = 2.7 Hz, 1H), 5.16 (s, 2H), 4.95-4.85 (m, 2H), 4.15-3.85 (m, 2H), 3.70-3.40 (m, 4H), 2.15-1 75 (m, 4H) |
| 22 | 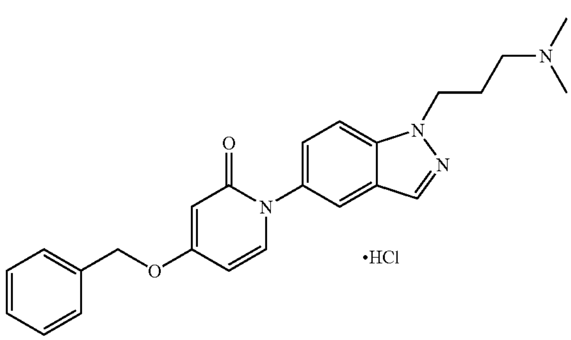 | 403 | ¹H NMR (500 MHz, DMSO-d$_6$) δ 9.93 (s, 1H), 8.17 (d, J = 0.6 Hz, 1H), 7.80 (d, J = 8.9 Hz, 1H), 7.76 (d, J = 1.7 Hz, 1H), 7.60 (d, J = 7.6 Hz, 1H), 7.49-7.35 (m, 6H), 6.12 (dd, J = 7.6, 2.7 Hz, 1H), 5.99 (d, J = 2 7 Hz, 1H), 5.15 (s, 2H), 4.55 (t, J = 6.7 Hz, 2H), 3.11-3.06 (m, 2H), 2.75 (s, 3H), 2.74 (s, 3H), 2.28-2.21 (m, 2H) |

TABLE 1-continued

| Ex. No. | Structure | Mass Spec | ¹H NMR Data |
|---|---|---|---|
| 23 | 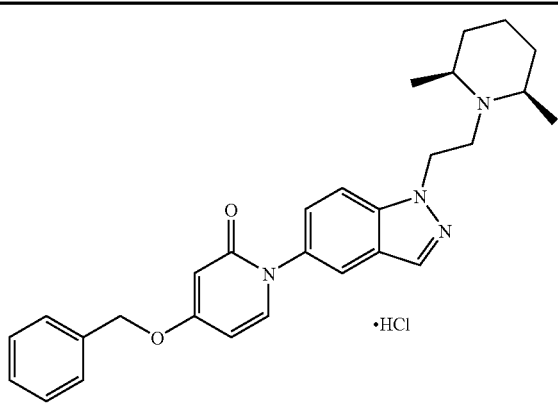 •HCl | 457 | ¹H NMR (500 MHz, DMSO-d₆) δ 9.95 (s, 1H), 8.27 (s, 1H), 7.91 (d, J = 9.0 Hz, 1H), 7.78 (d, J = 1.8 Hz, 1H), 7.60 (d, J = 7.6 Hz, 1H), 7.49-7.36 (m, 6H), 6.12 (dd, J = 7.6, 2.7 Hz, 1H), 5.99 (d, J = 2.7 Hz, 1H), 5.16 (s, 2H), 4.90 (t, J = 6.9 Hz, 2H), 3 71-3.66 (m, 2H), 3.59-3.34 (m, 2H), 1.94-1.85 (m, 2H), 1.75-1.45 (m, 4H), 1.33 (d, J = 6.3 Hz, 6H) |
| 24 | 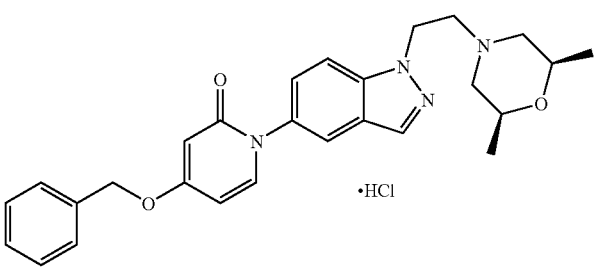 •HCl | 459 | ¹H NMR (500 MHz, DMSO-d₆) δ 11.12 (s, 1H), 8.24 (s, 1H), 7.88 (d, J = 8.9 Hz, 1H), 7.79 (s, 1H), 7.61 (d, J = 7.6 Hz, 1H), 7 49-7.36 (m, 6H), 6.12 (dd, J = 6.6, 1.4 Hz, 1H), 5.99 (d, J = 2.3 Hz, 1H), 5.16 (s, 2H), 4.96 (t, J = 6.9 Hz, 2H), 4.05-3.89 (m, 2H), 3.60-3.55 (m, 4H), 2.76-2.70 (m, 2H), 1.13 (d, J = 6.2 Hz, 6H) |
| 25 | 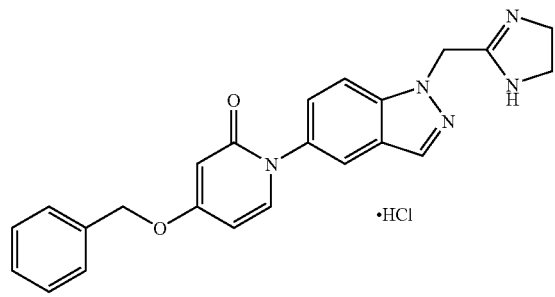 •HCl | 400 | ¹H NMR (500 MHz, DMSO-d₆) δ 10.22 (s, 1H), 8.31 (d, J = 0.7 Hz, 1H), 7.84 (d, J = 8.9 Hz, 1H), 7.82 (d, J = 1.6 Hz,, 1H), 7.59 (d, J = 7.6 Hz, 1H), 7.49-7.36 (m, 6H), 6.12 (dd, J = 7.6, 2.7 Hz, 1H), 5.99 (d, J = 2.7 Hz, 1H), 5.70 (s, 2H), 5.16 (s, 2H), 3.87 (s, 4H) |
| 26 | 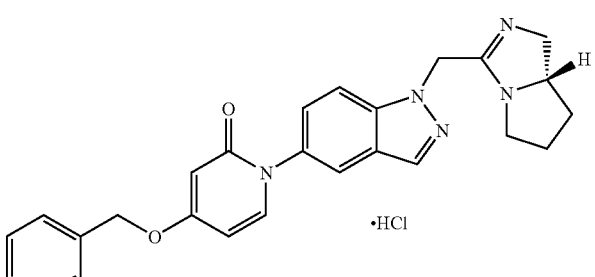 •HCl | 440 | ¹H NMR (500 MHz, DMSO-d₆) δ 10.72 (s, 1H), 8.31 (s, 1H), 7.88 (d, J = 8.9 Hz, 1H), 7.83 (d, J = 1.8 Hz,, 1H), 7.61 (d, J = 7.6 Hz, 1H), 7.49-7.36 (m, 6H), 6.13 (dd, J = 7.6, 1.3 Hz, 1H), 5.99 (d, J = 2.7 Hz, 1H), 5.83 (dd, J = 52.1 Hz, 17.3 Hz, 2H), 5.16 (s, 2H), 4.39-4.35 (m, 1H), 4.01 (t, J = 11.8 Hz, 1H), 3.80-3 70 (m, 2H), 3.15-3.10 (m, 1H), 2.11-2.05 (m, 2H), 1.99-1.91 (m, 1H), 1.65-1.59 (m, 1H) |
| 27 | 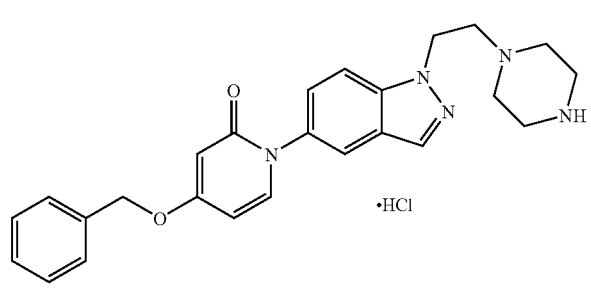 •HCl | 430 | ¹H NMR (500 MHz, DMSO-d₆) δ 8.80 (s, 1H), 8.17 (s, 1H), 7.81 (d, J = 8.8 Hz, 1H), 7 75 (s, 1H), 7.61 (d, J = 7.6 Hz, 1H), 7.49-7.41 (m, 4H), 7.40-7.35 (m, 2H), 6.13-6.10 (m, 1H), 5.99 (d, J = 2.7 Hz, 1H), 5.15 (s, 2H), 4.79-4.51 (m, 2H), 3.51-3 35 (m, 6H), 3.22-2.98 (m, 4H) |

TABLE 1-continued

| Ex. No. | Structure | Mass Spec | ¹H NMR Data |
|---|---|---|---|
| 28 | 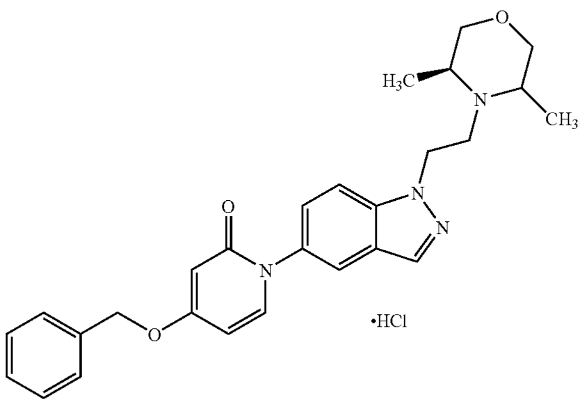 | 459 | ¹H NMR (500 MHz, DMSO-d$_6$) δ 10.85 (s, 1H), 8.28 (s, 1H), 7.94 (d, J = 8.8 Hz, 1H), 7.80 (s, 1H), 7.62 (d, J = 7.6 Hz, 1H), 7.45-7.31 (m, 6H), 6.12 (dd, J = 7.6, 2.6 Hz, 1H), 6.00 (d, J = 2.6 Hz, 1H), 5.16 (s, 2H), 4.95-4.93 (m, 2H), 3.97-3.93 (m, 2H), 3.85-3.75 (m, 2H), 3.61-3.51 (m, 4H), 1.23-1.18 (m, 6H) |
| 29 | 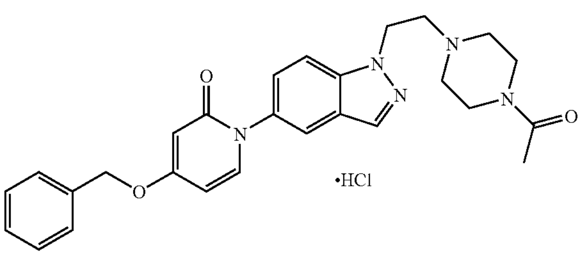 | 472 | ¹H NMR (500 MHz, DMSO-d$_6$) δ 8.13 (s, 1H), 7.76 (d, J = 9 Hz, 1H), 7.72 (s, 1H), 7.51 (d, J = 7.5 Hz, 1H), 7.47-7.32 (m, 6H), 6.10-6.08 (m, 1H), 5.94 (d, J = 2.5 Hz, 1H), 5.15 (s, 2H), 4.80-4.70 (m, 2H), 3.67-3.51 (m, 4H), 3.35-3.27 (m, 4H), 3.05-2.85 (m, 2H), 1.99 (s, 3H) |
| 30 | 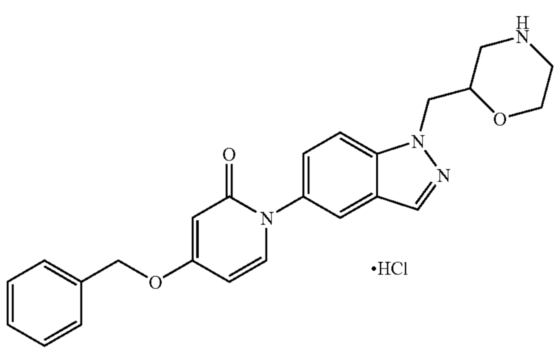 | 417 | ¹H NMR (500 MHz, DMSO-d$_6$) δ 9.15 (s, 1H), 8.18 (s, 1H), 7.75-7.70 (m, 2H), 7.62 (d, J = 7.6 Hz, 1H), 7.49-7.40 (m, 4H), 7.39-7.35 (m, 2H), 6.11 (dd, J = 7.6, 2.7 Hz, 1H), 5.99 (d, J = 2.7 Hz, 1H), 5.15 (s, 2H), 4.64-4.60 (m, 2H), 4.20-4.15 (m, 1H), 3.93-3.88 (dd, J = 12.6, 3.3 Hz, 1H), 3.68-3.60 (m, 1H), 3.36-3.32 (m, 1H), 3.15 (d, J = 12.6 Hz, 1H), 2.96-2.84 (m, 2H) |
| 31 | 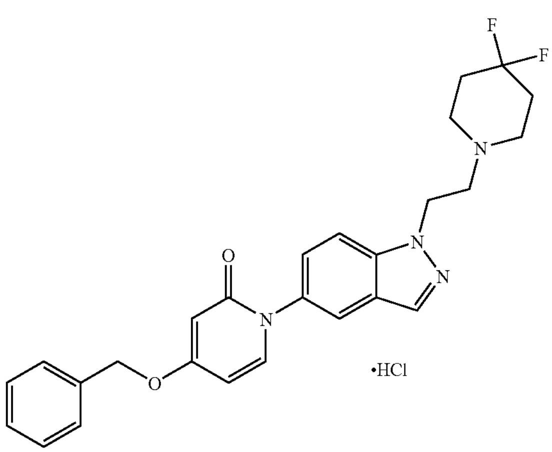 | 465 | ¹H NMR (500 MHz, DMSO-d$_6$) δ 8.23 (s, 1H), 7.86 (d, J = 8.9 Hz, 1H), 7.79 (s, 1H), 7.60 (d, J = 7.6 Hz, 1H), 7.49-7.41 (m, 5H), 7.40-7.36 (m, 1H), 6.12 (dd, J = 7.6, 2.7 Hz, 1H), 5.99 (d, J = 2.7 Hz, 1H), 5.16 (s, 2H), 4.95-4.85 (m, 2H), 3.75-3.65 (m, 4H), 3.29-3.21 (m, 2H), 2.42-2.28 (m, 4H) |

TABLE 1-continued

| Ex. No. | Structure | Mass Spec | $^1$H NMR Data |
|---|---|---|---|
| 32 | 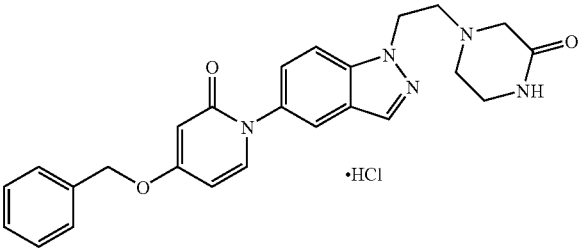 | 444 | $^1$H NMR (500 MHz, DMSO-$d_6$) δ 8.23 (s, 1H), 7.86 (d, J = 8.9 Hz, 1H), 7.78 (s, 1H), 7.61 (d, J = 7.6 Hz, 1H), 7.49-7.35 (m, 6H), 6.12 (dd, J = 7.6, 2.7 Hz, 1H), 5.99 (d, J = 2.7 Hz, 1H), 5.16 (s, 2H), 4.95-4.85 (m, 2H), 3.90-3.55 (m, 4H), 3.41-3 31 (m, 4H), 1 99 (s, 1H) |
| 33 | 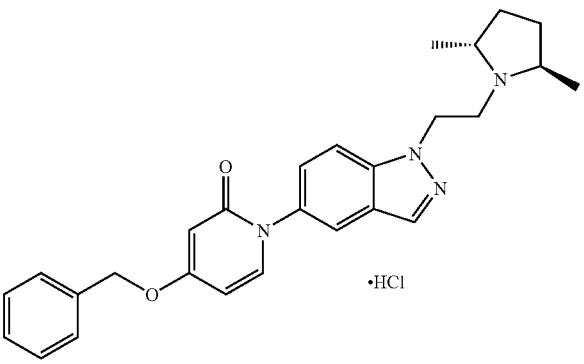 | 443 | $^1$H NMR (500 MHz, DMSO-$d_6$) δ 10.31 (s, 1H), 8.26 (s, 1H), 7.88 (d, J = 8.9 Hz, 1H), 7.79 (d, J = 1.8 Hz, 1H), 7.61 (d, J = 7.6 Hz, 1H), 7.49-7.41 (m, 5H), 7.40-7.35 (m, 1H), 6.12 (dd, J = 7.6, 2.7 Hz, 1H), 5.99 (d, J = 2.7 Hz, 1H), 5.16 (s, 2H), 4.92-4.86 (m, 2H), 3.99-3.95 (m, 1H), 3.71-3.65 (m, 2H), 3.47-3.43 (m, 1H), 2.30-2.24 (m, 1H), 2.16-2.12 (m, 1H), 1.75-1.71 (m, 1H), 1.63-1.58 (m, 1H), 1.40 (d, J = 6.5 Hz, 3H), 1.13 (d, J = 6.6 Hz, 3H) |
| 34 | 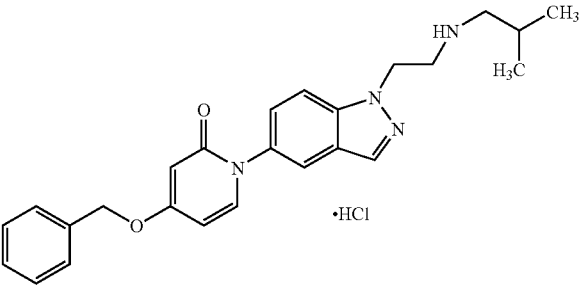 | 417 | $^1$H NMR (500 MHz, DMSO-$d_6$) δ 8.90 (s, 1H), 8.23 (s, 1H), 7.84 (d, J = 8.9 Hz, 1H), 7.78 (d, J = 1.8 Hz, 1H), 7.60 (d, J = 7.6 Hz, 1H), 7.49-7.40 (m, 5H), 7.39-7.35 (m, 1H), 6.12 (dd, J = 7.6, 2.7 Hz, 1H), 5.99 (d, J = 2.9 Hz, 1H), 5.16 (s, 2H), 4.84 (t, J = 6.7 Hz, 2H), 3.45-3.40 (m, 2H), 2.85-2.80 (m, 2H), 2.01-1.94 (m, 1H), 0.95 (d, J = 6.7 Hz, 6H) |
| 35 | 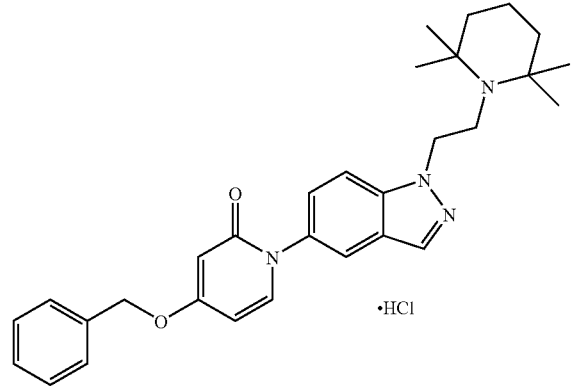 | 485 | $^1$H NMR (500 MHz, DMSO-$d_6$) δ 8.85 (s, 1H), 8.26 (s, 1H), 7.81 (d, J = 9.0 Hz, 1H), 7.78 (s, J = 1.8 Hz, 1H), 7.60 (d, J = 7.6 Hz, 1H), 7.49-7.41 (m, 5H), 7.40-7.35 (m, 1H), 6.12 (dd, J = 7.6, 2 7 Hz, 1H), 5.99 (d, J = 2.7 Hz, 1H), 5.16 (s, 2H), 4.87 (t, J = 8.0 Hz, 2H), 3.62-3.55 (m, 2H), 2.05-1.95 (m, 2H), 1.91-1.83 (m, 1H), 1.78-1 71 (m, 2H), 1.63-1.61 (m, 1H), 1.61-1.56 (m, 6H), 1.37-1.31 (m, 6H) |

TABLE 1-continued

| Ex. No. | Structure | Mass Spec | ¹H NMR Data |
|---|---|---|---|
| 36 | 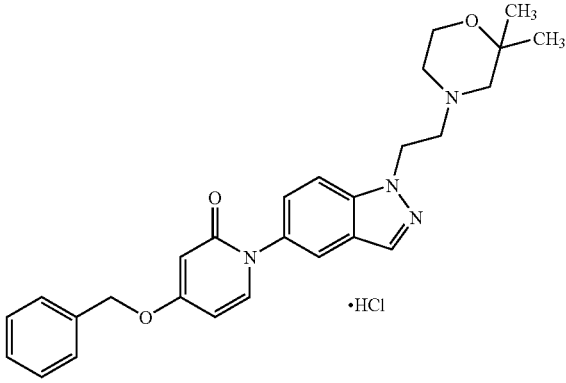 | 459 | ¹H NMR (500 MHz, DMSO-d₆) δ 10.19 (s, 1H), 8.24 (s, 1H), 7.89 (d, J = 8.9 Hz, 1H), 7.79 (d, J = 1.4 Hz, 1H), 7.61 (d, J = 7.6 Hz, 1H), 7.49-7.41 (m, 5H), 7.40-7.35 (m, 1H), 6.12 (dd, J = 7.6, 2.7 Hz, 1H), 5.99 (d, J = 2.7 Hz, 1H), 5.16 (s, 2H), 4.98 (m, 2H), 3.89-3.70 (m, 2H), 3.65-3.52 (m, 3H), 3.45-3.35 (m, 1H), 3.10-2.85 (m, 2H), 1.41 (s, 3H), 1.21 (s, 3H) |
| 37 | 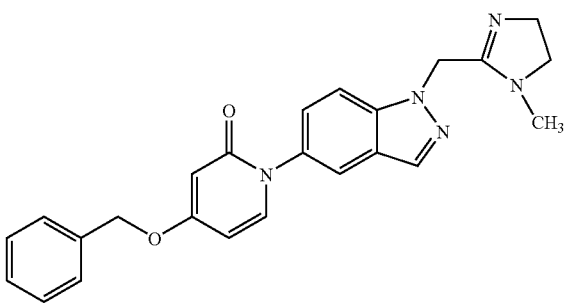 | 414 | ¹H NMR (500 MHz, DMSO-d₆) δ 9.75 (s, 1H), 8.31 (d, J = 0.8 Hz, 1H), 7.86 (d, J = 8.9 Hz, 1H), 7.83 (d, J = 1.5 Hz, 1H), 7.59 (d, J = 7.6 Hz, 1H), 7.49-7.41 (m, 5H), 7.40-7.35 (m, 1H), 6.13 (dd, J = 7.6, 2.9 Hz, 1H), 5.99 (d, J = 2.8 Hz, 1H), 5.82 (s, 2H), 5.16 (s, 2H), 3.95 (t, J = 9.9 Hz, 2H), 3.80-3.75 (m, 2H), 3.15 (s, 3H) |
| 38 | 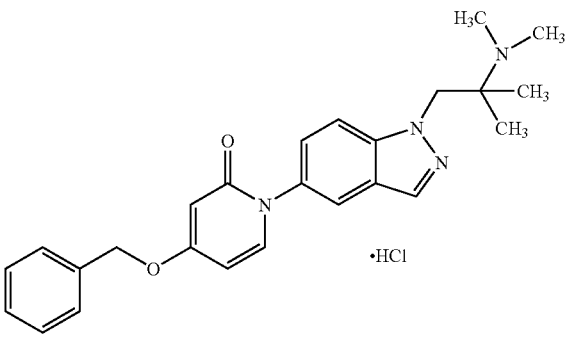 | 417 | ¹H NMR (500 MHz, DMSO-d₆) δ 9.38 (s, 1H), 8.26 (s, 1H), 8.00 (d, J = 9.0 Hz, 1H), 7.82 (s, J = 1.5 Hz, 1H), 7.62 (d, J = 7.5 Hz, 1H), 7.49-7.35 (m, 6H), 6.12 (dd, J = 7.5, 2.5 Hz, 1H), 5.99 (d, J = 3.0 Hz, 1H), 5.16 (s, 2H), 3.91 (d, J = 4.5 Hz, 2H), 2.71 (d, J = 5.0 Hz, 6H), 1.85 (s, 6H) |
| 39 | 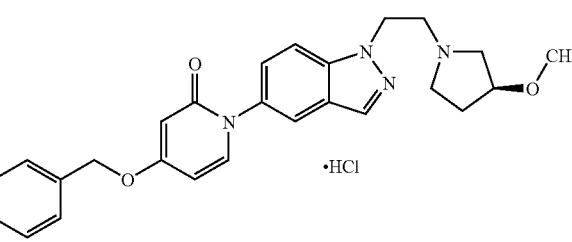 | 445 | ¹H NMR (500 MHz, DMSO-d₆) δ 8.24 (d, J = 4.5 Hz, 1H), 7.88-7.81 (m, 1H), 7.79 (d, J = 1.3 Hz, 1H), 7.60 (d, J = 7.6 Hz, 1H), 7.48-7.35 (m, 6H), 6.13-6.10 (m, 1H), 5.99 (d, J = 2.7 Hz, 1H), 5.16 (s, 2H), 4.89-4.84 (m, 2H), 4.15-4.10 (m, 0.6H), 4.08-4.02 (m, 0.4H), 3.71-3.68 (m, 3H), 3.59-3.51 (m, 1H), 3.23 (s, 3H), 3.20-3.05 (m, 2H), 2.31-2.21 (m, 0.6H), 2.19-2.10 (m, 0.4H), 1.99-1.89 (m, 1H) |
| 40 | 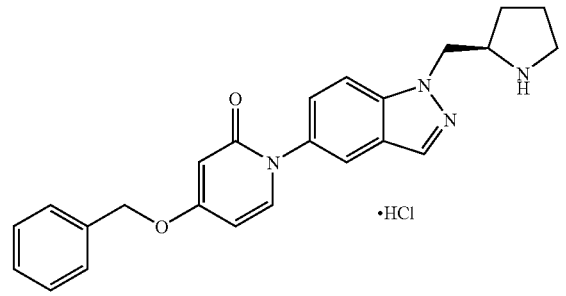 | 401 | ¹H NMR (500 MHz, DMSO-d₆) δ 9.25 (s, 1H), 9.01 (s, 1H), 8.25 (s, 1H), 7.86 (d, J = 8.9 Hz, 1H), 7.79 (d, J = 1.7 Hz, 1H), 7.60 (d, J = 7.6 Hz, 1H), 7.49-7.35 (m, 6H), 6.12 (dd, J = 7.6, 2.6 Hz, 1H), 5.99 (d, J = 2.7 Hz, 1H), 5.16 (s, 2H), 4.85-4.71 (m, 2H), 4.02-3.92 (m, 1H), 3.32-3.22 (m, 1H), 3.20-3.11 (m, 1H), 2.14-2.05 (m, 1H), 2.02-1.92 (m, 1H), 1.91-1.85 (m, 1H), 1.78-1.68 (m, 1H) |

TABLE 1-continued

| Ex. No. | Structure | Mass Spec | ¹H NMR Data |
|---|---|---|---|
| 41 | 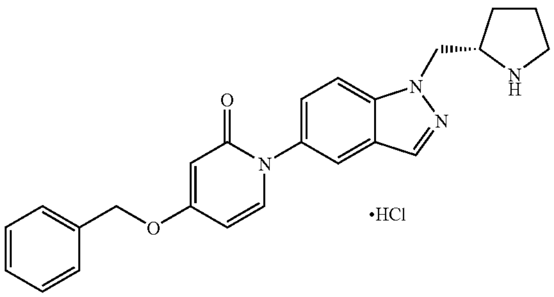 | 401 | ¹H NMR (500 MHz, DMSO-d$_6$) δ 9.15 (s, 1H), 9.01 (s, 1H), 8.26 (s, 1H), 7.86 (d, J = 9.0 Hz, 1H), 7.79 (d, J = 1.5 Hz, 1H), 7.60 (d, J = 8.0 Hz, 1H), 7.49-7.35 (m, 6H), 6.12 (dd, J = 7.5, 2.5 Hz, 1H), 5.99 (d, J = 2.5 Hz, 1H), 5.16 (s, 2H), 4.85-4.71 (m, 2H), 4.02-3.95 (m, 1H), 3.32-3.22 (m, 1H), 3.20-3.11 (m, 1H), 2.14-2.05 (m, 1H), 2.02-1.92 (m, 1H), 1.91-1.85 (m, 1H), 1.78-1.68 (m, 1H) |
| 42 | 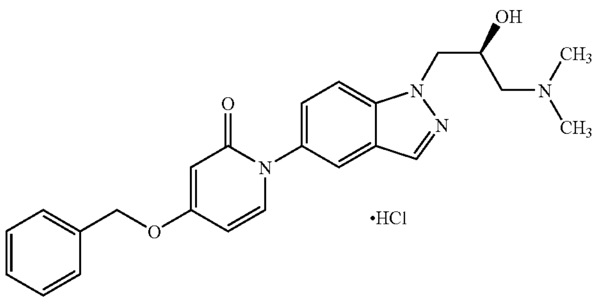 | 419 | ¹H NMR (500 MHz, DMSO-d$_6$) δ 9.49 (s, 1H), 8.18 (s, 1H), 7.78 (d, J = 9.0 Hz, 1H), 7.74 (d, J = 2.0 Hz, 1H), 7.59 (d, J = 7.5 Hz, 1H), 7.49-7.27 (m, 6H), 6.12 (dd, J = 8.0 Hz, 3.0 Hz, 1H), 5.99 (d, J = 3.0 Hz, 1H), 5.96 (s, 1H), 5.16 (s, 2H), 4.56-4.46 (m, 2H), 4.41-4.33 (s, 1H), 3.23-3.17 (m, 1H), 3.12-3.04 (m, 1H), 2.76 (s, 6H) |
| 43 | 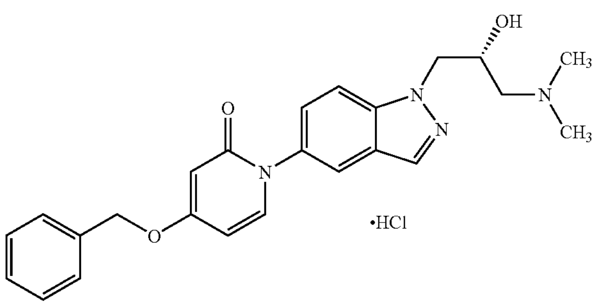 | 419 | ¹H NMR (500 MHz, DMSO-d$_6$) δ 9.46 (s, 1H), 8.17 (s, 1H), 7.78 (d, J = 8.5 Hz, 1H), 7.74 (d, J = 1.5 Hz, 1H), 7.60 (d, J = 7.5 Hz, 1H), 7.49-7.34 (m, 6H), 6.13-6.10 (m, 1H), 5.99 (d, J = 3.0 Hz, 1H), 5.85 (s, 1H), 5.15 (s, 2H), 4.56-4.46 (m, 2H), 4.41-4.33 (s, 1H), 3.20-3.05 (m, 1H), 3.05-2.95 (m, 1H), 2.71 (s, 6H) |
| 44 | 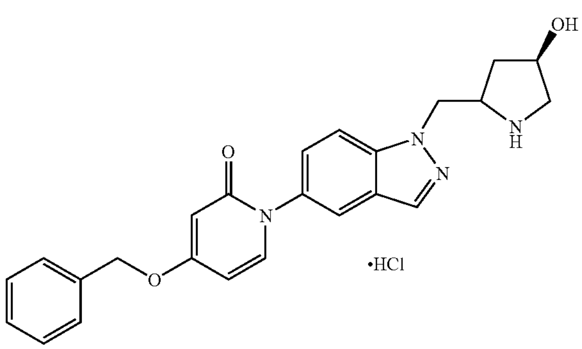 | 417 | ¹H NMR (500 MHz, DMSO-d$_6$) δ 9.38 (s, 1H), 8.91 (s, 1H), 8.27 (s, 1H), 7.84 (d, J = 8.9 Hz, 1H), 7.80 (d, J = 1.4 Hz, 1H), 7.61 (d, J = 7.6 Hz, 1H), 7.49-7.34 (m, 6H), 6.12 (dd, J = 7.6, 2.7 Hz, 1H), 5.99 (d, J = 2.7 Hz, 1H), 5.39 (s, 1H), 5 16 (s, 2H), 4.86 (dd, J = 14.8, 4.7 Hz, 1H), 4.78-4.71 (m, 1H), 4.43 (s, 1H), 4.18 (s, 1H), 3.45-3.38 (m, 1H), 3.08-3.01 (m, 1H), 2.08-2.02 (m, 1H), 1.89-1 81 (m, 1H) |
| 45 | 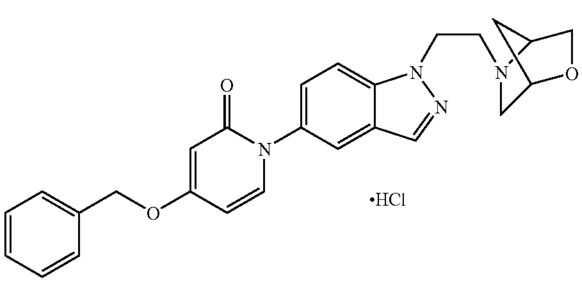 | 443 | ¹H NMR (500 MHz, DMSO-d$_6$) δ 8.02 (s, 1H), 7.66 (d, J = 1.6 Hz, 1H), 7.51 (d, J = 8.9 Hz, 1H), 7.44-7.35 (m, 6H), 7.29 (d, J = 7.4 Hz, 1H), 6.10-6.05 (m, 2H), 5.06 (s, 2H), 4.48 (t, J = 6.9 Hz, 2H), 4.36 (s, 1H), 3.95 (d, J = 7.8 Hz, 1H), 3.59 (dd, J = 7.6, 1.7 Hz, 1H), 3.40 (s, 1H), 3.15-305 (m, 1H), 2.88 (dd, J = 9.9, 1.6 Hz, 1H), 2.53 (d, J = 9.8 Hz, 1H), 1.80-1.74 (m, 2H), 1.72-1.67 (m, 1H) |

TABLE 1-continued

| Ex. No. | Structure | Mass Spec | $^1$H NMR Data |
|---|---|---|---|
| 46 | 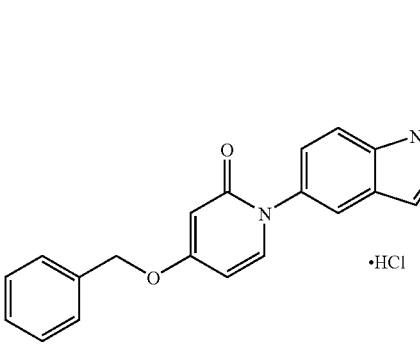 | 428 | $^1$H NMR (500 MHz, DMSO-d$_6$) δ 10.39 (s, 1H), 10.21 (s, 1H), 8.32 (s, 1H), 7.85-7.83 (m, 2H), 7.59 (d, J = 7.5 Hz, 1H), 7.49-7.36 (m, 6H), 6.13 (dd, J = 8.0 Hz, 3.0 Hz, 1H), 5 99 (d, J = 3.0 Hz, 1H), 5.69 (s, 2H), 5.16 (s, 2H), 3.65 (s, 2H), 1.33 (s, 6H) |
| 47 | 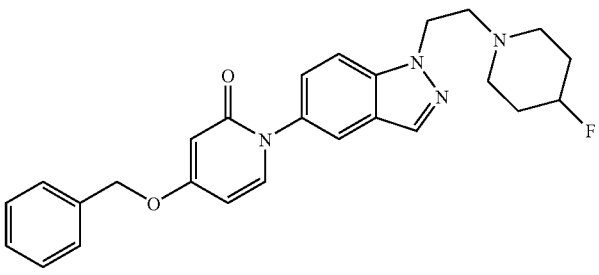 | 447 | $^1$H NMR (500 MHz, DMSO-d$_6$) δ 8.02 (s, 1H), 7.66 (d, J = 1.0 Hz, 1H), 7.48 (d, J = 11.0 Hz, 1H), 7.44-7.35 (m, 6H), 7.29 (d, J = 7.0 Hz, 1H), 6.10-6.05 (m, 2H), 5.06 (s, 2H), 4.73-4.59 (m, 1H), 4.52 (t, J = 7.0 Hz, 2H), 2.88 (t, J = 7.0 Hz, 2H), 2.69-2.60 (m, 2H), 2.49-2.42 (m, 2H), 1.94-1.81 (m, 4H) |
| 48 | 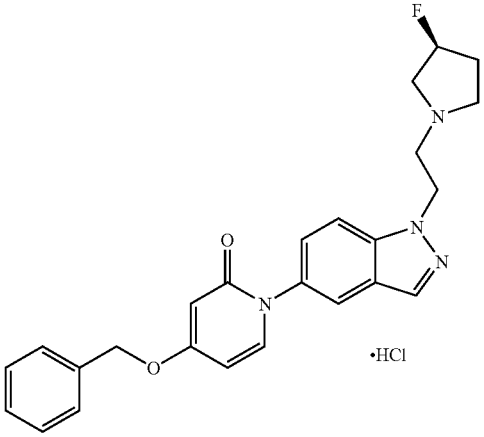 | 433 | $^1$H NMR (500 MHz, DMSO-d$_6$) δ 10.62-10.50 (m, 1H), 8.25 (s, 1H), 7.85 (d, J = 8.0 Hz, 1H), 7.80 (s, 1H), 7.61 (d, J = 7.5 Hz, 1H), 7.48-7.42 (m, 5H), 7.39-7.36 (m, 1H), 6.13 (dd, J = 7.5, 3.0 Hz, 1H), 5.99 (d, J = 2.5 Hz, 1H), 5.54-5.39 (m, 1H), 5.16 (s, 2H), 4.87-4.82 (m, 2H), 3.81-3.53 (m, 4H), 3.55-3.20 (m, 2 H, overlapping with H$_2$O peak), 2.14-2.01 (s, 2H) |
| 49 | 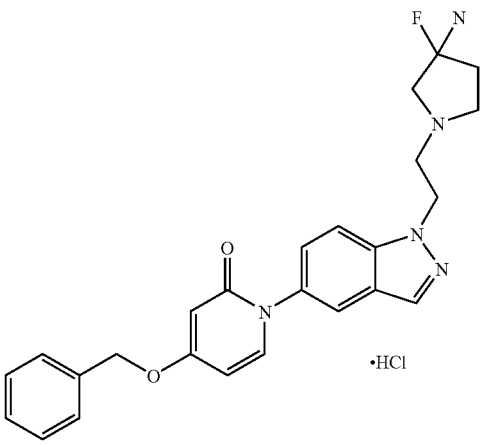 | 451 | $^1$H NMR (500 MHz, DMSO-d$_6$) δ 8.22 (s, 1H), 7.84 (d, J = 9.0 Hz, 1H), 7.77 (s, 1H), 7.61 (d, J = 7.5 Hz, 1H), 7.48-7.36 (m, 6H), 6.12 (dd, J = 7.5, 3.0 Hz, 1H), 5.99 (d, J = 2.5 Hz, 1H), 5.16 (s, 2H), 4.76 (br s, 2H), 3.71 (br s, 8 H, overlapping with H$_2$O peak) |

TABLE 1-continued

| Ex. No. | Structure | Mass Spec | $^1$H NMR Data |
|---|---|---|---|
| 50 | 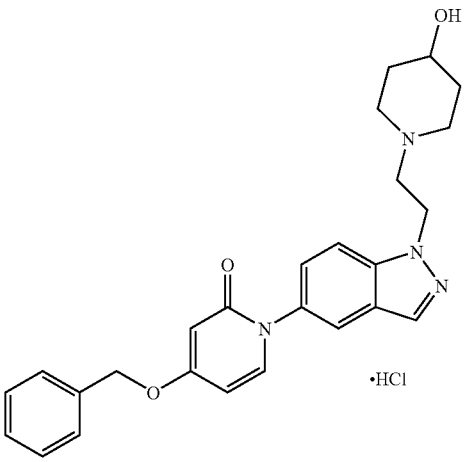 | 445 | $^1$H NMR (500 MHz, DMSO-d$_6$) δ 9.56 (br s, 1H), 8.24 (s, 1H), 7.86 (t, J = 9.5 Hz, 1H), 7.79 (s, 1H), 7.60 (d, J = 7.5 Hz, 1H), 7.48-7.42 (m, 5H), 7.39-7.36 (m, 1H), 6.13 (dd, J = 7.5, 2.5 Hz, 1H), 5.99 (d, J = 2.5 Hz, 1H), 5.16 (s, 2H), 5.08-4.99 (m, 1H), 4.91-4.88 (m, 2H), 3.96-3.93 (m, 1H), 3.72-3.57 (m, 4H), 3.46-3.78 (m, 1H) 3.19-3.15 (m, 1H), 2.09-1.99 (m, 1H), 1.89-1.84 (m, 1H), 1 77-1.70 (m, 1H), 1.59-1.57 (m, 1H) |
| 51 | 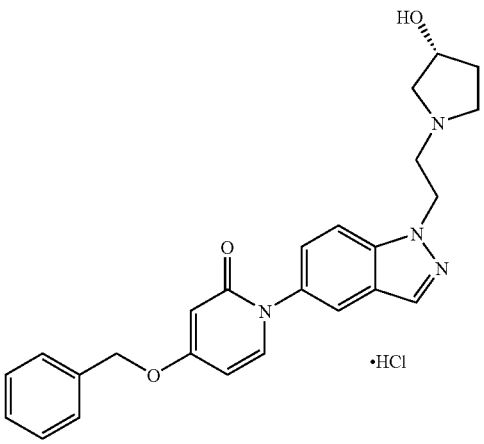 | 431 | $^1$H NMR (500 MHz, DMSO-d$_6$) δ 10.28 (br s, 1H), 8.20 (s, 1H), 7.82 (d, J = 8.0 Hz, 1H), 7.77 (s, 1H), 7.61 (d, J = 7.5 Hz, 1H), 7.48-7.36 (m, 6H), 6.12 (dd, J = 7.5, 2.5 Hz, 1H), 5.99 (d, J = 2.5 Hz, 1H), 5.15 (s, 2H), 4.75 (br s, 2H), 4.32 (br s, 1H), 3.57 (br s, 2H), 3.15-2.99 (m, 2H), 2.11-2.00 (m, 2H) 1 71 (br s, 2H) |
| 52 | 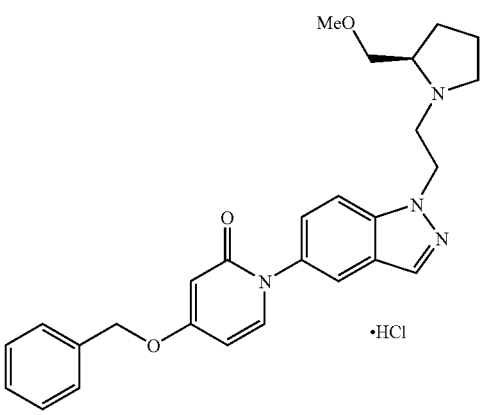 | 459 | $^1$H NMR (500 MHz, DMSO-d$_6$) δ 9.86 (br s, 1H), 8.25 (s, 1H), 7.84 (d, J = 9.0 Hz, 1H), 7.79 (d, J = 1.5 Hz, 1H), 7.61 (d, J = 7 5 Hz, 1H), 7.48-7.42 (m, 5H), 7.39-7.36 (m, 1H), 6.13 (dd, J = 7.5, 2.5 Hz, 1H), 5.99 (d, J = 2.5 Hz, 1H), 5.16 (s, 2H), 4.89-4.81 (m, 2H), 3.94-3.92 (m, 1H), 3.79 (m, 1H), 3.69-3.62 (m, 3H), 3.57-3.54 (m, 1H), 3.32 (s, 3 H, overlapping with H$_2$O peak), 3.15-3.11 (m, 1H), 2.14-2.12 (m, 1H), 2.11-1.99 (m, 1H), 1.89-1.83 (m, 1H), 1.71-1.67 (m, 1H) |

TABLE 1-continued

| Ex. No. | Structure | Mass Spec | ¹H NMR Data |
|---|---|---|---|
| 53 | 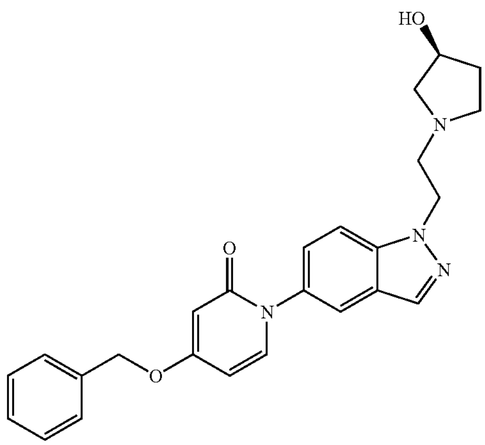 | 431 | ¹H NMR (500 MHz, DMSO-d$_6$) δ 8.12 (s, 1H), 7.75 (d, J = 9.5 Hz, 1H), 7.72 (d, J = 2.0 Hz, 1H), 7.62 (d, J = 7.5 Hz, 1H), 7.48-7.42 (m, 4H), 7.39-7.36 (m, 1H), 7.32 (dd, J = 9.0, 2.0 Hz, 1H), 6.10 (dd, J = 7.5, 2.5 Hz, 1H), 5.99 (d, J = 2.5 Hz, 1H), 5.15 (s, 2H), 4.64 (d, J = 4.5 Hz, 1H), 4.52 (t, J = 6.5 Hz, 2H), 4.13-4.12 (m, 1H), 2.88 (t, J = 6.5 Hz, 2H), 2.76 (dd, J = 9.5, 6.5 Hz, 2H), 2.61-2.53 (m, 1H), 2.32 (dd, J = 9.5, 4.0 Hz, 1H), 1.92-1.88 (m, 1H), 1.50-1.48 (m, 1H) |
| 54 | 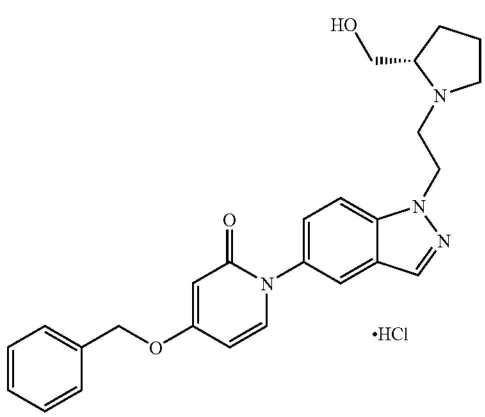 | 445 | ¹H NMR (500 MHz, DMSO-d$_6$) δ 9.62 (br s, 1H), 8.24 (s, 1H), 7.84 (d, J = 8.5 Hz, 1H), 7.79 (d, J = 1.5 Hz, 1H), 7.61 (d, J = 7.5 Hz, 1H), 7.48-7.42 (m, 5H), 7.39-7.36 (m, 1H), 6.13 (dd, J = 7.5, 2.5 Hz, 1H), 5.99 (d, J = 2.5 Hz, 1H), 5.54-5.53 (m, 1H), 5.16 (s, 2H), 4.91-4.82 (m, 2H), 3.94-3.92 (m, 1H), 3.78-3.77 (m, 1H), 3.68-3.62 (m, 3H), 3.57-3.55 (m, 1H), 3.22-3.15 (m, 1H), 2.11-1.98 (m, 2H), 1.87-1.71 (2H) |
| 55 | 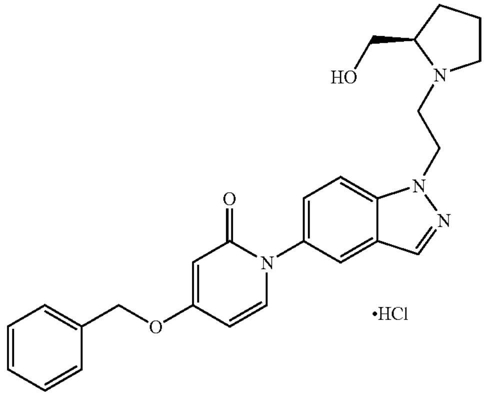 | 445 | ¹H NMR (500 MHz, DMSO-d$_6$) δ 9.70 (br s, 1H), 8.24 (s, 1H), 7.84 (d, J = 9.0 Hz, 1H), 7.79 (d, J = 2.0 Hz, 1H), 7.61 (d, J = 7.5 Hz, 1H), 7.48-7.42 (m, 5H), 7.39-7.36 (m, 1H), 6.12 (dd, J = 8.0, 3.0 Hz, 1H), 5.99 (d, J = 2.5 Hz, 1H), 5.52 (br s, 1H), 5.15 (s, 2H), 4.92-4.83 (m, 2H), 3.94-3.92 (m, 1H), 3.80-3.78 (m, 1H), 3.69-3.64 (m, 3H), 3.57-3.52 (m, 1H), 3.16-3.11 (m, 1H), 2.10-1 97 (m, 2H), 1.87-1 71 (m, 2H) |

TABLE 1-continued

| Ex. No. | Structure | Mass Spec | ¹H NMR Data |
|---|---|---|---|
| 56 | 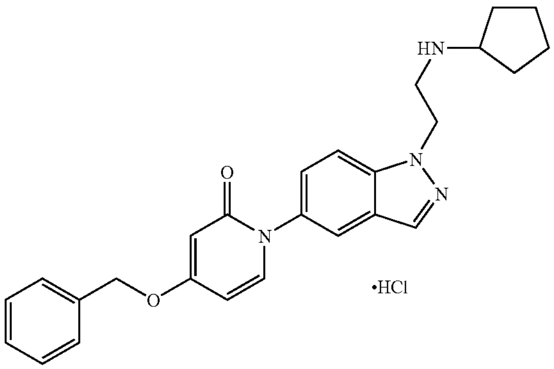 | 447 | ¹H NMR (500 MHz, DMSO-d$_6$) δ 8.95 (br s, 2H), 8.23 (s, 1H), 7.82 (d, J = 8.5 Hz, 1H), 7.79 (d, J = 2.0 Hz, 1H), 7.60 (d, J = 8.0 Hz, 1H), 7.48-7.40 (m, 5H), 7.39-7.36 (m, 1H), 6.12 (dd, J = 7.5, 3.0 Hz, 1H), 5.99 (d, J = 2.5 Hz, 1H), 5.16 (s, 2H), 4.77 (t, J = 6.0 Hz, 2H), 3.55 (br s, 1H), 3.45 (br s, 2H), 1.97-1.93 (m, 2H), 1.71-1.67 (m, 2H), 1.64-158 (m, 2H), 1.56-1.51 (m, 2H) |
| 57 | 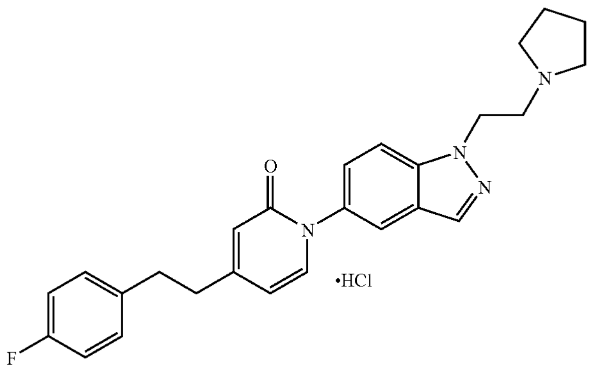 | 431 | ¹H NMR (500 MHz, CD$_3$OD) δ 8.23 (s, 1H), 7.84-7.75 (m, 2H), 7.60-7.54 (dd, J = 6.7, 0.6 Hz, 1H), 7.47-7.41 (dd, J = 8 9, 2.0 Hz, 1H), 7.28-7.20 (m, 2H), 7.04-6.96 (m, 2H), 6.47-6.40 (m, 2H), 4.87 (t, J = 5.7 Hz, 2H), 3.86 (t, J = 5.7 Hz, 2H), 3.74-3.63 (br m, 2H), 3.21-3.10 (br m, 2H), 3.01-2.92 (m, 2H), 2.92-2.83 (m, 2H), 2.23-2.09 (m, 2H), 2.08-1.95 (m, 2H) |
| 58 | 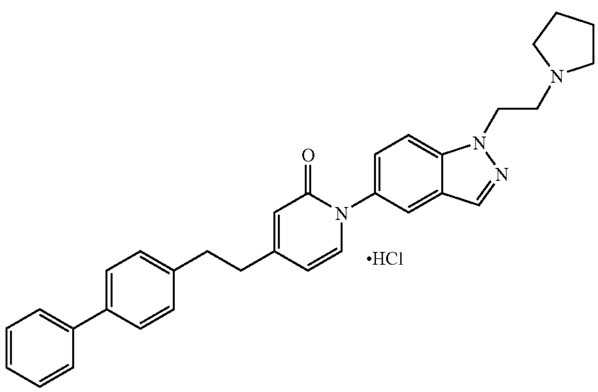 | 489 | ¹H NMR (500 MHz, CD$_3$OD) δ 8.23 (s, 1H), 7.83 (s, 1H), 7.78 (d, J = 8.8 Hz, 1H), 7.61-7.51 (m, 6H), 7.48-7.44 (dd, J = 9.0, 2.0 Hz, 1H), 7.41 (t, J = 7.6 Hz, 2H), 7.35-7.27 (m, 3H), 6.49-6.47 (m, 1H), 4.86 (t, J = 5.7 Hz, 2H), 3.85 (t, J = 5.7 Hz, 2H), 3.74-3.62 (br m, 2H), 3.20-3.11 (br m, 2H), 3.07-3.00 (m, 2H), 2.97-2.91 (br m, 2H), 2.19-2.11 (m, 2H), 2.05-1.96 (br m, 2H) |
| 59 | 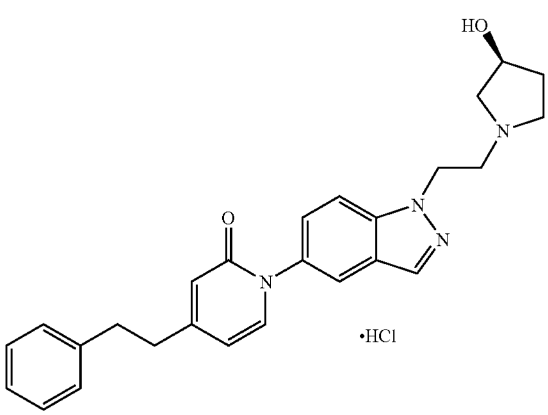 | 429 | ¹H NMR (500 MHz, CDCl$_3$) δ 8.23 (s, 1H), 7.82 (d, J = 1.7 Hz, 1H), 7.77 (d, J = 8.9 Hz, 1H), 7.56 (d, J = 7.5 Hz, 1H), 7.49-7.42 (dd, J = 8.9, 2.0 Hz, 1H), 7.31-7.21 (m, 4H), 7.21-7.15 (m, 1H), 6.47-6.40 (m, 2H), 4.87 (t, J = 5 8, 2H), 4.45 (s, 1H), 4.00-3.78 (br m, 3H), 3.76-3.41 (br m, 2H), 3.24-3.11 (br s, 1H), 3.03-2.95 (m, 2H), 2.95-2.87 (m, 2H), 2.45-1.90 (br m, 2H) |

TABLE 1-continued

| Ex. No. | Structure | Mass Spec | ¹H NMR Data |
|---|---|---|---|
| 60 | 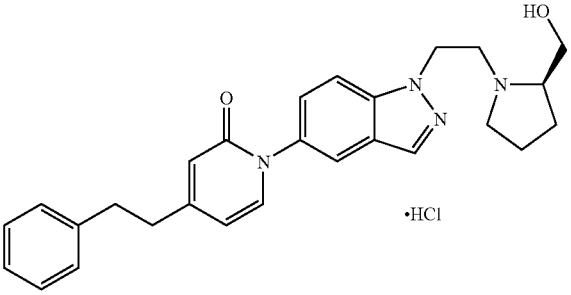 •HCl | 443 | ¹H NMR (500 MHz, CD₃OD) δ 8.18 (s, 1H), 7.77 (d, J = 1 7 Hz, 1H), 7.72 (d, J = 8.9 Hz, 1H), 7.52 (d, J = 7.5 Hz, 1H), 7.41-7.39 (dd, J = 8.9, 1.9 Hz, 1H), 7.25-7.19 (m, 4H), 7.14 (t, J = 7.2 Hz, 1H), 6.40-6.39 (m, 2H), 4.90-4.85 (m, 2H), 4.09-4.03 (m, 1H), 3.87-3.84 (m, 2H), 3.76-3.64 (m, 4H), 2.95-2.92 (m, 2H), 2.87-2.84 (m, 2H), 2.23-2.07 (m, 2H), 2.03-1.84 (m, 2H) |
| 61 | 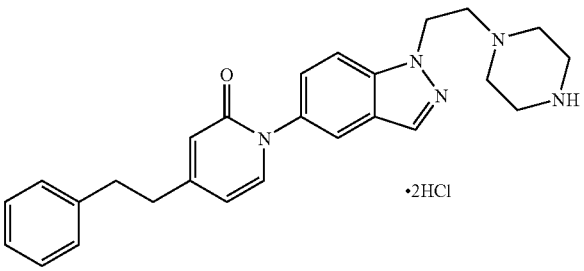 •2HCl | 428 | ¹H NMR (500 MHz, CD₃OD) δ 8.23 (s, 1H), 7.83 (s, 2H), 7.62 (d, J = 6.95 Hz, 1H), 7.46 (d, J = 1.4 Hz, 1H), 7.30-7.17 (m, 5H), 6.51 (dd, J = 7.0, 1.1 Hz, 1H), 6.48 (s, 1H), 4.95 (t, J = 5.85, 2H), 3.57 (m, 2H), 3.61-3.56 (m, 8H), 3.01-2.98 (m, 2H), 2.94-2.91 (m, 2H) |
| 62 | 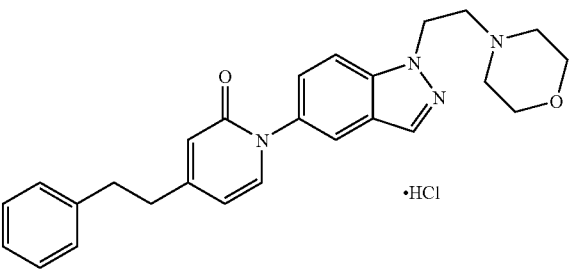 •HCl | 429 | ¹H NMR (500 MHz, CD₃OD) δ 8.23 (s, 1H), 7.82 (d, J = 1.4 Hz, 1H), 7.78 (d, J = 8.9 Hz, 1H), 7.56 (d, J = 7.6 Hz, 1H), 7.47-7.44 (dd, J = 8.9, 1 9 Hz, 1H), 7.30-7.23 (m, 4H), 7.20-7.17 (t, J = 7.2 Hz, 1H), 6.45 (m, 2H), 4.94 (m, 2H), 4.07 (br m, 2H), 3.84-3.78 (m, 4H) 3 63 (m, 2H), 3.34-3.26, (m, 2 H, overlapping with solvent peak), 3.00-2.97 (m, 2H), 2.92-2.89 (m, 2H) |
| 63 | 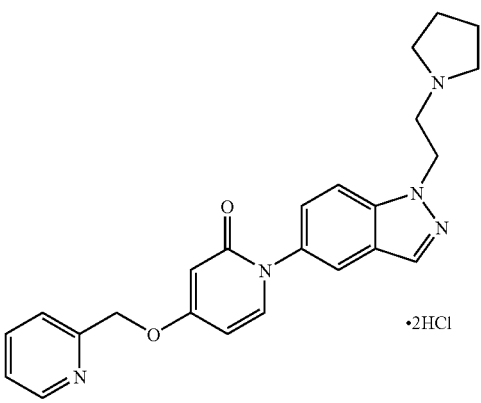 •2HCl | 416 | ¹H NMR (500 MHz, CD₃OD) δ 8.78-8.77 (d, J = 4.9 Hz, 1H), 8.37 (t, J = 7.9 Hz, 1H), 8.23 (s, 1H), 7.96 (d, J = 7.9 Hz, 1H), 7.82-7.79 (m, 3H), 7.66-7.64 (dd, J = 7.4, 1.4 Hz, 1H), 7.47-7.44 (d, J = 9.2 Hz, 1H), 6.41-6.39 (dd, J = 7.5, 2.6 Hz, 1H), 6.17 (d, J = 2.8 Hz, 1H), 5.46 (s, 2H), 4.87 (t, J = 6.0 Hz, 2H), 3.86 (t, J = 6.0 Hz, 2H), 3.70-3.69 (m, 2H), 3.18-3.13 (m, 2H), 2.18-2.15 (m, 2H), 2.03-2.00 (m, 2H) |

TABLE 1-continued

| Ex. No. | Structure | Mass Spec | ¹H NMR Data |
|---|---|---|---|
| 64 | 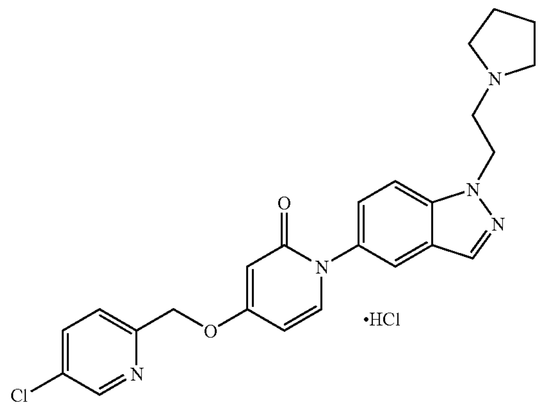 | 450 | ¹H NMR (500 MHz, CD₃OD) δ 8.63 (s, 1H), 8.23 (s, 1H), 8.00-7.98 (dd, J = 8.3, 2.1 Hz, 1H), 7.82 (d, J = 1.9 Hz, 1H), 7.79 (d, J = 8.9 Hz, 1H), 7.66-7.64 (2 overlapping d, J = 8.5, 7.6 Hz, 2H), 7.47-7.44 (dd, J = 8.9, 1.8 Hz, 1H), 6.41-6.39 (dd, J = 7.5, 2.8 Hz, 1H), 6.16 (d, J = 2.6 Hz, 1H), 5.30 (s, 2H), 4.87 (t, J = 5.9 Hz, 2H), 3.86 (t, J = 5.9 Hz, 2H), 3 72 (m, 2H), 3.19-3.13 (m, 2H), 2.18-2.15 (m, 2H), 2.03-1.99 (m, 2H) |
| 65 | 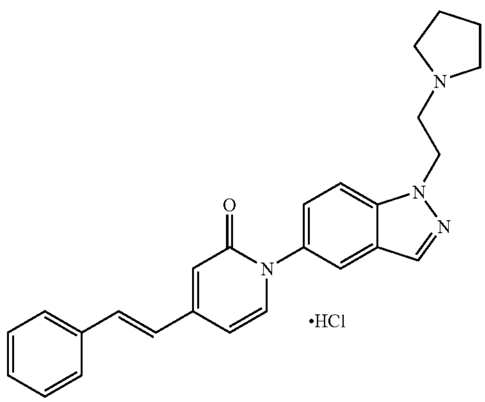 | 411 | ¹H NMR (500 MHz, CD₃OD) δ 8.25 (s, 1H), 7.89 (d, J = 1.4 Hz, 1H), 7.82 (d, J = 8.9 Hz, 1H), 7.69 (d, J = 7.1 Hz, 1H), 7.66 (d, J = 7.4 Hz, 2H), 7.53-7.50 (dd, J = 8.9, 1.7 Hz, 1H), 7.42 (t, J = 7.1 Hz, 2H), 7.49 (d, J = 15.4 Hz, 1H), 7.37-7.33 (m, 1H), 7.17 (d, J = 15.4 Hz, 1H), 6.96-6.94 (m, 1H), 6.75 (s, 1H), 4.89 (t, J = 6.0 Hz, 2H), 3.87 (t, J = 6.0 Hz, 2H), 3.74-3.67 (m, 2H), 3.21-3.12 (m, 2H), 2.22-2.11 (m, 2H), 2.06-1.95 (m, 2H) |
| 66 | 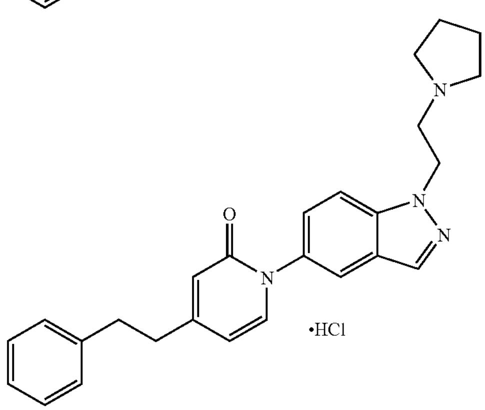 | 413 | ¹H NMR (500 MHz, CD₃OD) δ 8.24 (s, 1H), 7.85 (d, J = 1.9 Hz, 1H), 7.80 (d, J = 8.9 Hz, 1H), 7.65 (d, J = 6.9 Hz, 1H), 7.48-7.46 (dd, J = 8.9, 1 9 Hz, 1H), 7.30-7.24 (m, 4H), 7.19 (m, 1H), 6.56-6.54 (dd, J = 6.9, 1.9 Hz, 1H), 6.52 (s, 1H), 4.88 (t, J = 5.7 Hz, 2H), 3.87-3.85 (m, 2H), 3.73-3.68 (m, 2H), 3.19-3 15 (m, 2H), 3 02-2.98 (m, 2H), 2.95-2.92 (m, 2H), 2.18-2.15 (m, 2H), 2.03-2.00 (m, 2H) |
| 67 | 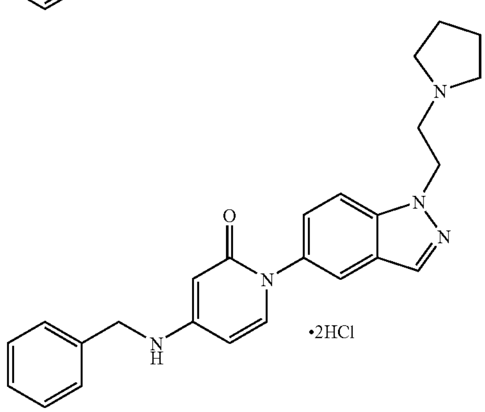 | 414 | ¹H NMR (500 MHz, CD₃OD) δ 8.25 (s, 1H), 7.90 (d, J = 1.8 Hz, 1H), 7.87 (d, J = 8.9 Hz, 1H), 7.75 (s, 1H), 7.51-7.49 (dd, J = 8.9, 1.9 Hz, 1H), 7.40-7.39 (m, 4H), 7.33-7 30 (dd, J = 8.5, 4.3 Hz, 1H), 6.63 (d, J = 7.6 Hz, 1H), 4.90 (t, J = 5.9 Hz, 2H), 4.54 (s, 2H), 3.86 (t, J = 5.9 Hz, 2H), 3 77-3.68 (m, 2H), 3.18-3.13 (m, 2H), 2.17-2.13 (m, 2H), 2.03-2.00 (m, 2H) |

TABLE 1-continued

| Ex. No. | Structure | Mass Spec | $^1$H NMR Data |
|---|---|---|---|
| 68 | 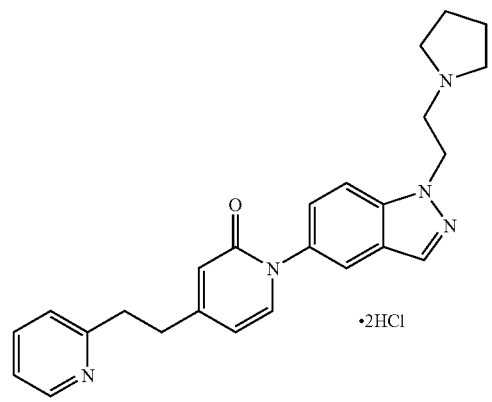 ·2HCl | 414 | $^1$H NMR (500 MHz, CD$_3$OD) δ 8.80-8.79 (d, J = 5.9 Hz, 1H), 8.62-8.58 (t, J = 7.0 Hz, 1H), 8.24 (s, 1H), 8.09 (d, J = 8.1 Hz, 1H), 7.98 (t, J = 7 1 Hz, 1H), 7.83-7.82 (m, 2H), 7.67 (d, J = 6.8 Hz, 1H), 7.47-7.45 (dd, J = 8.9, 1.8 Hz, 1H), 6.52-6.52 (m, 2H), 4.89 (t, J = 5.6 Hz, 2H), 3.86 (t, J = 5.6 Hz, 2H), 3.72-3.68 (m, 2H), 3.48-3.45 (m, 2H), 3.18-3.11 (m, 4H), 2.17-2.13 (m, 2H), 2.04-1.99 (m, 2H) |
| 69 | 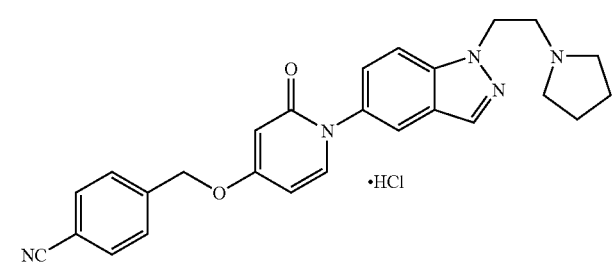 ·HCl | 440 | $^1$H NMR (500 MHz, DMSO-d$_6$) δ 9.83 (s, 1H), 8.25 (s, 1H), 7.92 (d, J = 8.5 Hz, 2H), 7.85 (d, J = 9.0 Hz, 1H), 7.80 (s, 1H), 7.67 (d, J = 8.0 Hz, 2H), 7.63 (d, J = 7.5 Hz, 1H), 7.43 (d, J = 9.0 Hz, 1H), 6.16 (dd, J = 8.0, 2.5 Hz, 1H), 5.98 (d, J = 2.5 Hz, 1H), 5.28 (s, 2H), 4.84 (t, J = 6.5 Hz, 2H), 3 73-3.74 (m, 2H), 3.53-3.54 (m, 2H), 3.05-3.07 (m, 2H), 1.99-2.00 (m, 2H), 1.83-1.85 (m, 2H) |
| 70 | 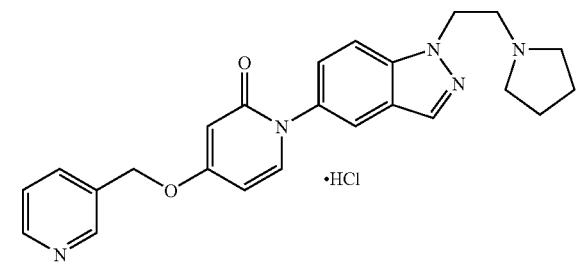 ·HCl | 416 | $^1$H NMR (500 MHz, DMSO-d$_6$) δ 10.24 (s, 1H), 8.81 (s, 1H), 8.70 (d, J = 4.5 Hz, 1H), 8.25 (s, 1H), 8.13 (d, J = 7.5 Hz, 1H), 7.88 (d, J = 9.0 Hz, 1H), 7.80 (d, J = 2.0 Hz, 1H), 7.65-7.68 (m, 1H), 7.64 (d, J = 7.5 Hz, 1H), 7.43 (dd, J = 9.0, 2.0 Hz, 1H), 6.15 (dd, J = 7.5, 2.5 Hz, 1H), 6.05 (d, J = 2.5 Hz, 1H), 5.27 (s, 2H), 4.87 (t, J = 6.5 Hz, 2H), 3 71-3 74 (m, 2H), 3 51-3.54 (m, 2H), 3.02-3.06 (m, 2H), 2.00-2.03 (m, 2H), 1.83-1.85 (m, 2H) |
| 71 | 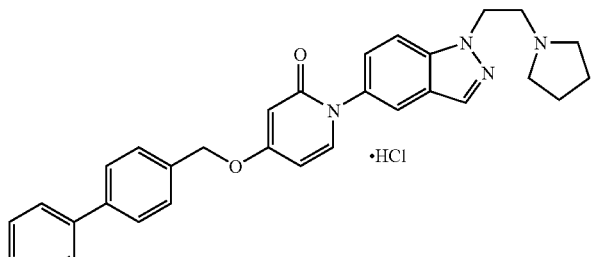 ·HCl | 491 | $^1$H NMR (500 MHz, DMSO-d$_6$) δ 10.23 (s, 1H), 8.25 (s, 1H), 7.87 (d, J = 9.0 Hz, 1H), 7.80 (d, J = 2.0 Hz, 1H), 7.69-7.74 (m, 4H), 7.62 (d, J = 7.5 Hz, 1H), 7.56-7.57 (m, 2H), 7.47-7.50 (m, 2H), 7.43 (dd, J = 9.0, 2.0 Hz, 1H), 7.37-7.40 (m, 1H), 6.15 (dd, J = 7.5, 2.5 Hz, 1H), 6.02 (d, J = 2.5 Hz, 1H), 5.21 (s, 2H), 4.87 (t, J = 6.5 Hz, 2H), 3.70-3.74 (m, 2H), 3.51-3.54 (m, 2H), 3.02-3.06 (m, 2H), 1 99-2.01 (m, 2H), 1.82-1.86 (m, 2H) |
| 72 | 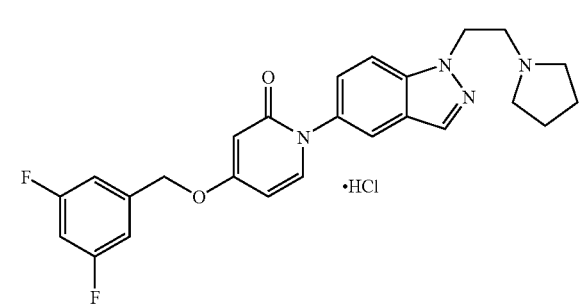 ·HCl | 451 | $^1$H NMR (500 MHz, DMSO-d$_6$) δ 9.99 (s, 1H), 8.25 (s, 1H), 7.86 (d, J = 9.0 Hz, 1H), 7.80 (d, J = 2.0 Hz, 1H), 7.63 (d, J = 7.5 Hz, 1H), 7.43 (dd, J = 9.0, 2.0 Hz, 1H), 7.22-7.28 (m, 3H), 6.17 (dd, J = 7.5, 2.5 Hz, 1H), 5.98 (d, J = 2.5 Hz, 1H), 5.20 (s, 2H), 4.85 (t, J = 6.0 Hz, 2H), 3.71-3.75 (m, 2H), 3.53-3.54 (m, 2H), 3.02-3.08 (m, 2H), 1.99-2.02 (m, 2H), 1.83-1.88 (m, 2H) |

TABLE 1-continued

| Ex. No. | Structure | Mass Spec | ¹H NMR Data |
|---|---|---|---|
| 73 | 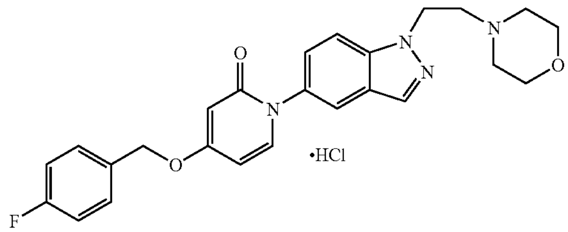 | 449 | ¹H NMR (500 MHz, DMSO-d₆) δ 10.61 (s, 1H), 8.24 (s, 1H), 7.86 (d, J = 9.0 Hz, 1H), 7.79 (s, 1H), 7.61 (d, J = 7.5 Hz, 1H), 7.52-7.55 (m, 2H), 7.43 (d, J = 9.0 Hz, 1H), 7.24-7.29 (m, 2H), 6.12 (dd, J = 7.5, 2.5 Hz, 1H), 6 00 (d, J = 2.5 Hz, 1H), 5.14 (s, 2H), 4.93 (m, 2H), 3.98-4.00 (m, 2H), 3.64-3.74 (m, 4H), 3.52-3.54 (m, 2H), 3.18-3.19 (m, 2H) |
| 74 | 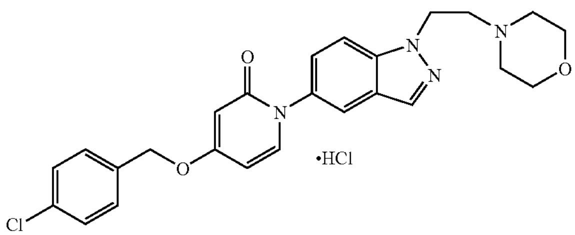 | 465 | ¹H NMR (500 MHz, DMSO-d₆) δ 10.77 (s, 1H), 8.24 (s, 1H), 7.87 (d, J = 8.5 Hz, 1H), 7.79 (d, J = 1.0 Hz, 1H), 7.61 (d, J = 7.5 Hz, 1H), 7.49-7.50 (m, 4H), 7 43 (d, J = 9.0 Hz, 1H), 6.12 (dd, J = 7.5, 2.5 Hz, 1H), 5.98 (d, J = 2.5 Hz, 1H), 5.16 (s, 2H), 4.94 (m, 2H), 3.98-4.00 (m, 2H), 3.67-3.76 (m, 4H), 3.51-3.54 (m, 2H), 3.17-3.19 (m, 2H) |
| 75 | 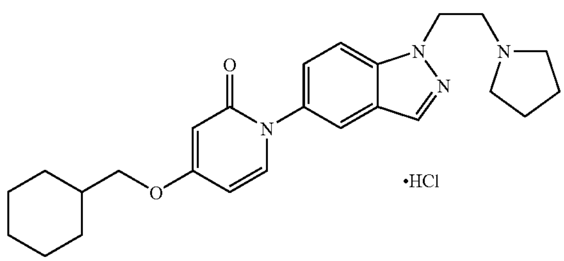 | 421 | ¹H NMR (500 MHz, DMSO-d₆) δ 10.21 (s, 1H), 8.25 (s, 1H), 7 86 (d, J = 9.0 Hz, 1H), 7 78 (d, J = 1 5 Hz, 1H), 7.57 (d, J = 7 5 Hz, 1H), 7.42 (dd, J = 9.0, 2.0 Hz, 1H), 6.05 (dd, J = 8.0, 3.0 Hz, 1H), 5.86 (d, J = 2.5 Hz, 1H), 4.86 (t, J = 6.5 Hz, 2H), 3.83 (d, J = 6.0 Hz, 2H), 3.72 (q, J = 6.0 Hz, 2H), 3.52-3 54 (m, 2H), 3 02-3.06 (m, 2H), 1.99-2.00 (m, 2H), 1.65-1.86 (m, 8H), 1.16-1.30 (m, 3H), 1.00-1.08 (m, 2H) |
| 76 | 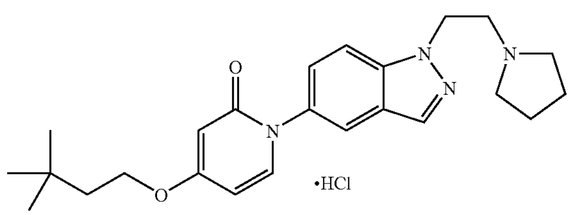 | 409 | ¹H NMR (500 MHz, DMSO-d₆) δ 9.94 (s, 1H), 8.25 (s, 1H), 7.85 (d, J = 9.0 Hz, 1H), 7.79 (d, J = 2.0 Hz, 1H), 7.57 (d, J = 7.5 Hz, 1H), 7.43 (dd, J = 9.0, 1.5 Hz, 1H), 6.03 (dd, J = 7.5, 2.5 Hz, 1H), 5.93 (d, J = 2.5 Hz, 1H), 4.86 (t, J = 5.5 Hz, 2H), 4.07 (t, J = 7.0 Hz, 2H), 3.73-3.74 (m, 2H), 3.53-3.54 (m, 2H), 3.05-3.07 (m, 2H), 1.96-2.01 (m, 2H), 1.83-1.86 (m, 1H), 1.67 (t, J = 7.0 Hz, 2H), 0.9 (s, 9H) |
| 77 | 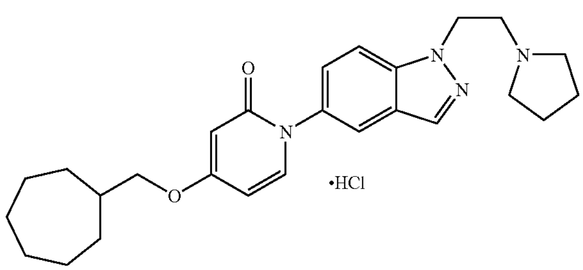 | 435 | ¹H NMR (500 MHz, DMSO-d₆) δ 9.85 (s, 1H), 8.25 (s, 1H), 7.85 (d, J = 9.0 Hz, 1H), 7.79 (d, J = 1.5 Hz, 1H), 7.56 (d, J = 8.0 Hz, 1H), 7.43 (dd, J = 9.0, 2.0 Hz, 1H), 6.05 (dd, J = 7.5, 2.5 Hz, 1H), 5.87 (d, J = 3.0 Hz, 1H), 4.84 (t, J = 6.5 Hz, 2H), 3.81 (d, J = 7.0 Hz, 2H), 3.73 (q, J = 6.0 Hz, 2H), 3.52-3 55 (m, 2H), 3 03-3.08 (m, 2H), 1.77-2.02 (m, 7H), 1.42-1.70 (m, 8H), 1.24-1.31 (m, 2H) |
| 78 | 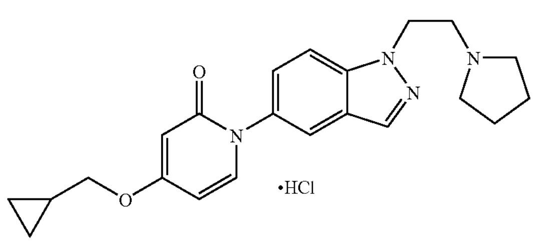 | 379 | ¹H NMR (500 MHz, DMSO-d₆) δ 9.58 (s, 1H), 8.19 (s, 1H), 7.78 (d, J = 9.0 Hz, 1H), 7.72 (s, 1H), 7.50 (d, J = 7.5 Hz, 1H), 7.36 (d, J = 8.5 Hz, 1H), 6.01 (dd, J = 8.0, 3.0 Hz, 1H), 5.77 (d, J = 2.5 Hz, 1H), 4.77 (t, J = 6.5 Hz, 2H), 3.80 (d, J = 7.0 Hz, 2H), 3.66-3.68 (m, 2H), 3.48-3.56 (m, 2H), 3.00-3.07 (m, 2H), 1 77-1.94 (m, 4H), 1 17 (m, 1H), 0.53-0.56 (m, 2H), 0.28-0.29 (m, 2H) |

TABLE 1-continued

| Ex. No. | Structure | Mass Spec | ¹H NMR Data |
|---|---|---|---|
| 79 | (adamantylmethoxy-pyridinone-indazole-ethyl-pyrrolidine) · HCl | 473 | ¹H NMR (500 MHz, CD$_3$OD) δ 8.24 (s, 1H), 7.82 (d, J = 2.0 Hz, 1H), 7.78 (d, J = 9.0 Hz, 1H), 7.58 (d, J = 7.5 Hz, 1H), 7.46 (dd, J = 9.0, 2.0 Hz, 1H), 6.29 (dd, J = 7.5, 3.0 Hz, 1H), 6.04 (d, J = 2.5 Hz, 1H), 4.87 (t, J = 6.5 Hz, 2H), 3.86 (t, J = 5.5 Hz, 2H), 3.69-3.72 (m, 2H), 3.63 (s, 2H), 3.16-3.20 (m, 2H), 2.16-2.19 (m, 2H), 2.00-2.03 (m, 3H), 1.71-1.84 (m, 12H), 1.24-1.31 (m, 2H) |
| 80 | (cyclopentylmethoxy-pyridinone-indazole-ethyl-pyrrolidine) · HCl | 407 | ¹H NMR (500 MHz, CD$_3$OD) δ 8.24 (s, 1H), 7.83 (d, J = 2.0 Hz, 1H), 7.78 (d, J = 9.0 Hz, 1H), 7.60 (d, J = 7.5 Hz, 1H), 7.46 (dd, J = 9.0, 2.0 Hz, 1H), 6.30 (dd, J = 7.5, 2.5 Hz, 1H), 6.07 (d, J = 3.0 Hz, 1H), 4.88 (t, J = 6.0 Hz, 2H), 3.98 (d, J = 7.0 Hz, 2H), 3.86 (t, J = 6.0 Hz, 2H), 3.69-3.73 (m, 2H), 3.15-3.17 (m, 2H), 2.39-2.42 (m, 1H), 2.16-2.19 (m, 2H), 2.00-2.03 (m, 2H), 1.86-1.90 (m, 2H), 1.67-1.72 (m, 4H), 1.38-1.42 (m, 2H) |
| 81 | (benzyloxy-pyridinone-3-methylindazole-ethyl-pyrrolidine) · HCl | 429 | ¹H NMR (500 MHz, DMSO-d$_6$) δ 10.16 (br s, 1H), 7.78-7.77 (m, 2H), 7.60 (d, J = 7.6 Hz, 1H), 7.48-7.38 (m, 6H), 6.12 (dd, J = 7.6, 2.7 Hz, 1H), 5.99 (d, J = 2.7 Hz, 1H), 5.16 (s, 2H), 4.76 (t, J = 6.4 Hz, 2H), 3.70-3.67 (m, 2H), 3.53-3.49 (m, 2H), 3.06-3.03 (m, 2H), 2.52 (s, 3 H, overlapping with solvent peak), 2.01-1.98 (m, 2H), 1.85-1.83 (m, 2H) |
| 82 | (benzyloxy-pyridinone-3-trifluoromethylindazole-ethyl-pyrrolidine) · HCl | 483 | ¹H NMR (500 MHz, DMSO-d$_6$) δ 10.10 (s, 1H), 8.07 (d, J = 9.0 Hz, 1H), 7.85 (s, 1H), 7.66-7.62 (m, 2H), 7.48-7.38 (m, 5H), 6.15 (dd, J = 7.5, 2.5 Hz, 1H), 6.00 (d, J = 2.0 Hz, 1H), 5.17 (s, 2H), 4.99 (t, J = 6.5 Hz, 2H), 3.81-3.77 (m, 2H), 3.55-3.54 (m, 2H), 3.12-3.09 (m, 2H), 2.02-1.99 (m, 2H), 1.86-1.84 (m, 2H) |

As compounds which bind strongly to MCH$_1$, compounds of formula I are expected to be effective in reducing obesity.

The present invention is not limited to the compounds found in the above examples, and many other compounds falling within the scope of the invention may also be prepared using the procedures set forth in the above synthetic schemes. The preparation of additional compounds of formula I using these methods will be apparent to one of ordinary skill in the chemical arts.

The invention has been described in detail with particular reference to some embodiments thereof, but it will be understood by those skilled in the art that variations and modifications can be effected within the spirit and scope of the invention.

The invention claimed is:
1. A compound of formula I:

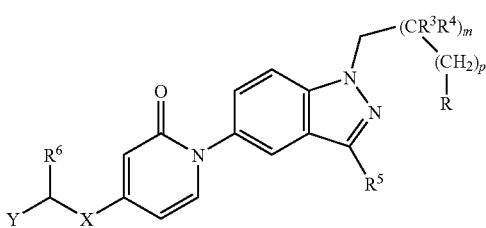

or a pharmaceutically acceptable salt thereof
wherein
$R^5$ is H or lower alkyl which is optionally substituted by up to 3 halo atoms;
m and p are each 0 or 1, provided that m+p is at least 1;
$R^3$ and $R^4$ are each independently selected from H, —OH and lower alkyl;
R is —OH, alkoxy, hydroxyalkoxy, alkoxyalkoxy, or —$NR^1R^2$, wherein (i) $R^1$ and $R^2$ are each independently selected from H and optionally substituted alkyl, or (ii) $R^1$ and $R^2$, together with the N atom to which they are attached, form a 4 to 7-membered optionally substituted non-aromatic ring system which optionally contains 1 or 2 heteroatoms in addition to the N atom shown, or (iii) $NR^1R^2$, taken together with $CR^3R^4$ and, if present, the $CH_2$ between $NR^1R^2$ and $CR^3R^4$, forms a 5 to 10-membered optionally substituted non-aromatic ring system which optionally contains 1 or 2 heteroatoms in addition to the N atom shown;
X is selected from —O—, —NH—, —N-alkyl-, and —$CH_2$—;
$R^6$ is selected from H and lower alkyl;
or X and $CHR^6$ are taken together to form —CH═CH—;
Y is selected from $C_{3-10}$ non-aromatic hydrocarbon and

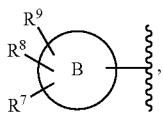

wherein B is an aromatic hydrocarbon or aromatic heterocycle, and $R^7$, $R^8$ and $R^9$ are each independently selected from H, —OH, —O-alkyl, -alkyl, halo, —S(O)-alkyl, —$SO_2$-alkyl, —$CF_3$, —CN and phenyl, wherein the compound is not in the form of a solvate or a pharmaceutically acceptable salt thereof.

2. A compound according to claim 1 wherein R is selected from the group consisting of pyrrolidin-1-yl, piperidin-1-yl, morpholin-4-yl, 4-methyl-piperazin-1-yl, 2-methylpiperidin-1-yl, 3-fluoropyrrolidin-1-yl, dimethylamino, hydroxyl, diisopropylamino, 3,3-difluoropiperidin-1-yl, (2R,6S)-2,6-dimethylpiperidin-1-yl, (2S,6R)-2,6-dimethylmorpholin-4-yl, piperazin-1-yl, 3,5-dimethylmorpholin-4-yl, 4-acetylpiperazin-1-yl, 4,4-difluoropiperidin-1-yl, piperazin-2-one-4-yl, (2R,5R)-2,5-dimethylpyrrolidin-1-yl, isobutylamino, 2,2,6,6-tetramethylpiperidin-1-yl, 2,2-dimethylmorpholin-4-yl, (S)-3-methoxypyrrolidin-1-yl, 2-oxa-5-azabicyclo[2.2.1]heptan-5-yl, 4-fluoropiperidin-1-yl, (S)-3-fluoropyrrolidin-1-yl, 3,3-difluoropyrrolidin-1-yl, 4-hydroxypiperidin-1-yl, (R)-3-hydroxypyrrolidin-1-yl, (R)-2-methoxymethylpyrrolidin-1-yl, (S)-3-hydroxypyrrolidin-1-yl, (R)-2-hydroxymethylpyrrolidin-1-yl, (S)-2-hydroxymethylpyrrolidin-1-yl, and cyclopentylamino.

3. A compound according to claim 1 wherein R is $NR^1R^2$ which, taken together with $CR^3R^4$ and, if present, the $CH_2$ between $NR^1R^2$ and $CR^3R^4$, is a moiety selected from morpholin-2-yl, (R)-pyrrolidin-2-yl, (S)-pyrrolidin-2-yl, 4-(R)-hydroxypyrrolidin-2-yl, 4,5-dihydroimidazol-2-yl, (S)-5,6,7,7a-tetrahydro-1H-pyrrolo[1,2-d]imidazol-2-yl, 1-methyl-4,5-dihydro-1H-imidazol-2-yl, and 4,4-dimethyl-4,5-dihydro-1H-imidazol-2-yl.

4. A compound according to claim 1, wherein m+p is 1.
5. A compound according to claim 1, wherein m+p is 2.
6. A compound according to claim 1, wherein $R^3$ and $R^4$ are both H.
7. A compound according to claim 1, wherein $R^3$ and $R^4$ are both methyl.
8. A compound according to claim 1, wherein one of $R^3$ and $R^4$ is H and the other of $R^3$ and $R^4$ is hydroxyl.
9. A compound according to claim 1, wherein $R^6$ is H.
10. A compound according to claim 1, wherein $R^6$ is lower alkyl.
11. A compound according to claim 10 wherein $R^6$ is methyl.
12. A compound according to claim 1, wherein X is O.
13. A compound according to claim 1, wherein X is NH.
14. A compound according to claim 1, wherein X is N-alkyl.
15. A compound according to claim 1, wherein X is $CH_2$.
16. A compound according to claim 1, wherein X and $R^6$ are taken together to form —CH═CH—.
17. A compound according to claim 1, wherein Y is a $C_{3-10}$ non-aromatic hydrocarbon.
18. A compound according to claim 17 wherein Y is selected from cyclohexane, —$CH_2C(CH_3)_3$, cycloheptane, cyclopropyl, adamant-1-yl, and cyclopentyl.
19. A compound according to claim 1, wherein Y is

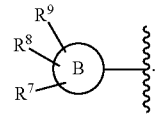

20. A compound according to claim 19 wherein B is selected from phenyl, pyridinyl and naphthyl.
21. A compound according to claim 20 wherein B is selected from pyridin-2-yl, pyridin-3-yl and naphth-2-yl.
22. A compound according to claim 19, wherein $R^7$, $R^8$ and $R^9$ are selected from H, —OH, —O-alkyl, -alkyl, -halo, —$CF_3$, —CN and phenyl.
23. A compound according to claim 19 wherein B, $R^7$, $R^8$ and $R^9$ taken together are selected from phenyl, 4-trifluoromethylphenyl, 4-chlorophenyl, 3-chlorophenyl, 2-chlorophenyl, 3,4-difluorophenyl, 4-methoxyphenyl, naphthyl, 4-fluorophenyl, pyridin-2-yl, 5-chloropyridin-2-yl, 4-cyanophenyl, pyridin-3-yl, biphenyl-4-yl, and 3,5-difluorophenyl.
24. A compound according to claim 1, wherein $R^5$ is H.
25. A compound according to claim 1, wherein $R^5$ is lower alkyl which is optionally substituted by up to three halo atoms.
26. A compound according claim 25 wherein $R^5$ is methyl.
27. A compound according to claim 25 wherein $R^5$ is —$CF_3$.
28. A compound according to claim 1 wherein m is 0, p is 1, R is pyrrolidin-1-yl, $R^6$ is H, and B is phenyl.
29. A compound according to claim 1 wherein the compound is selected from:

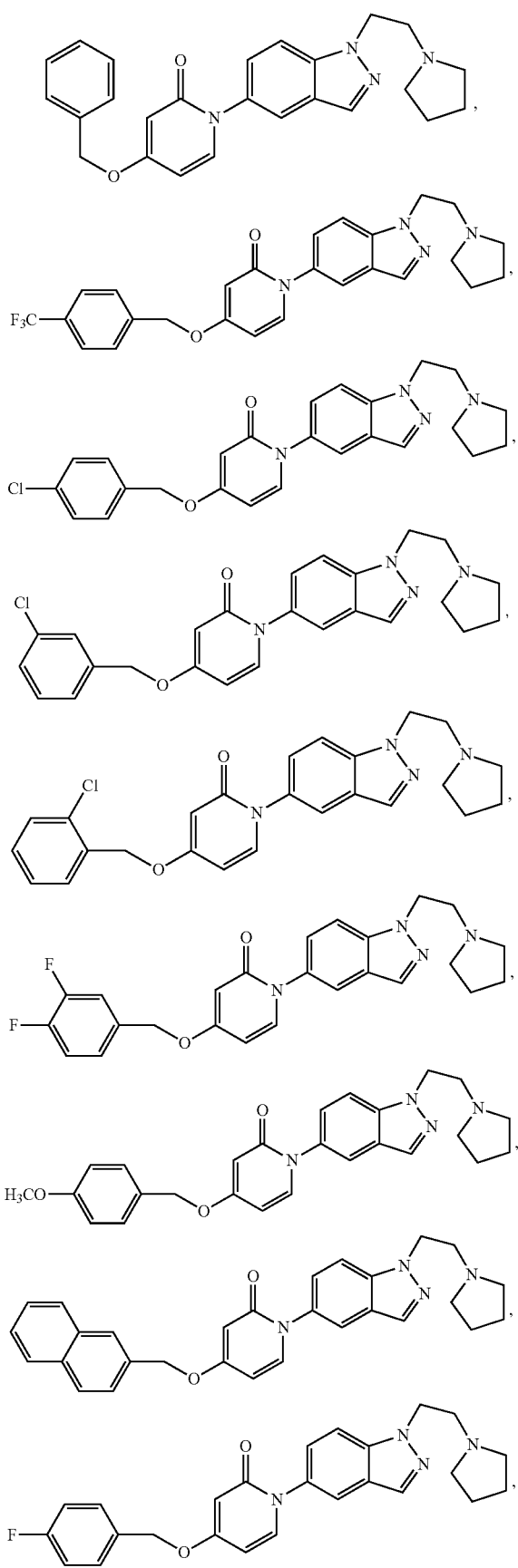
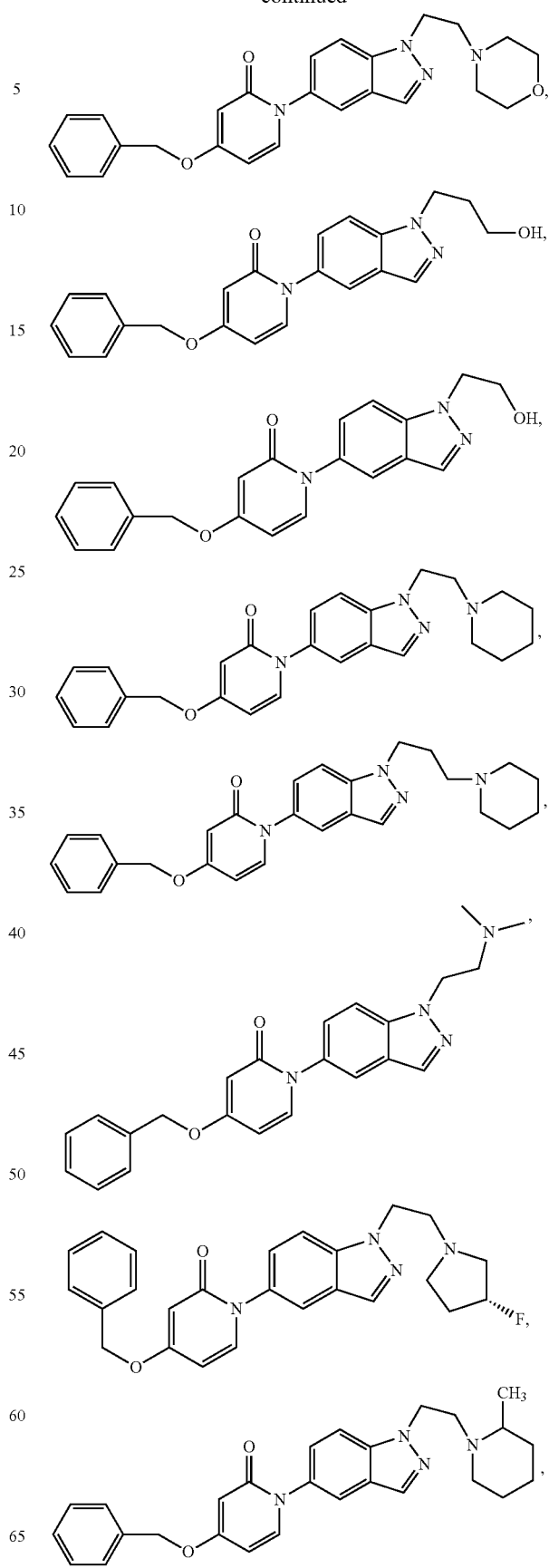

167
-continued
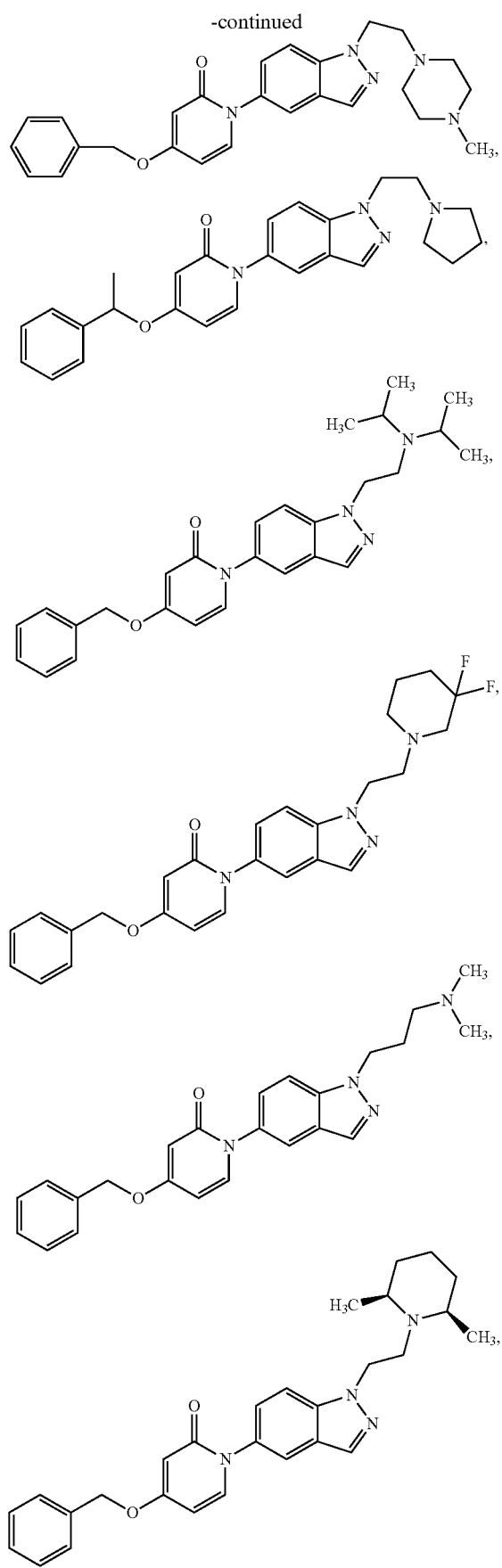
168
-continued
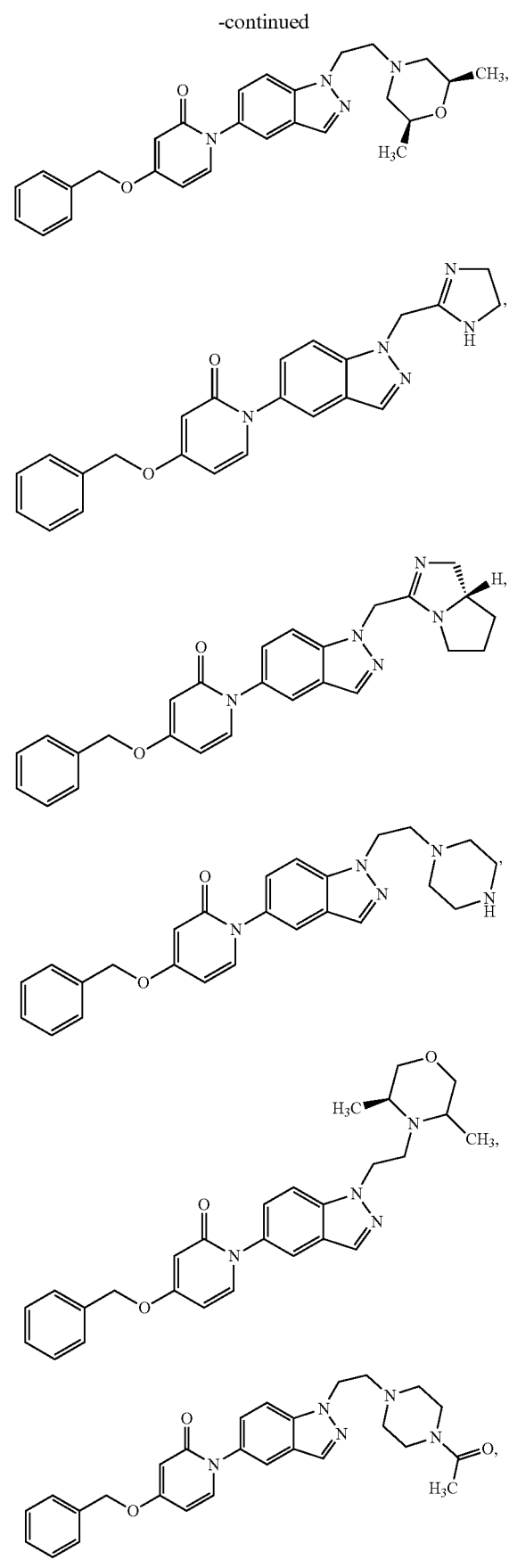

169
-continued
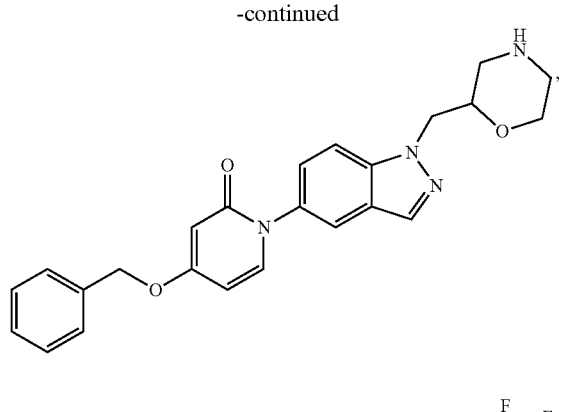
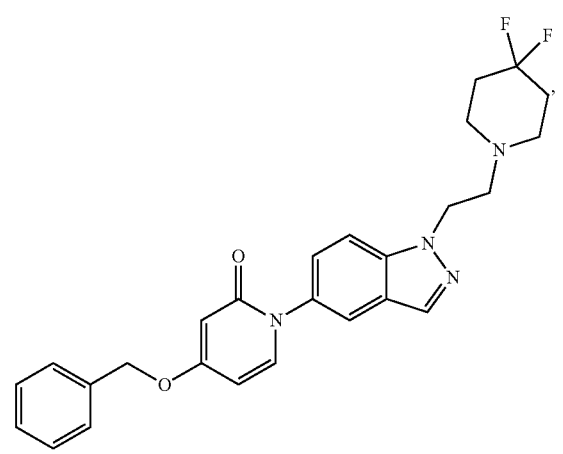
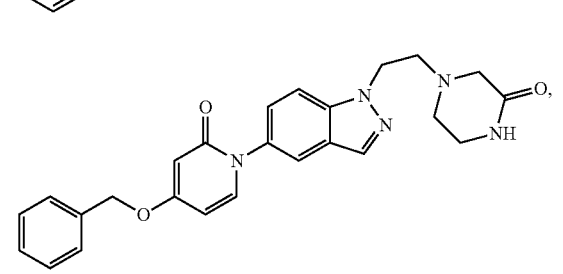
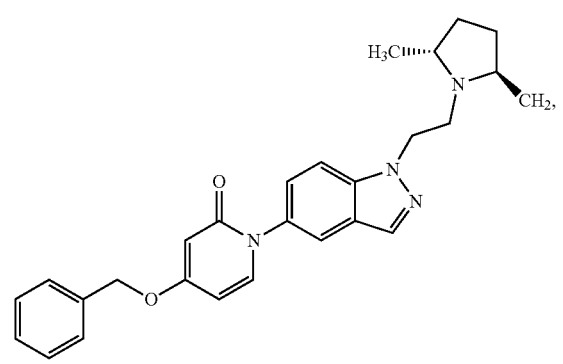
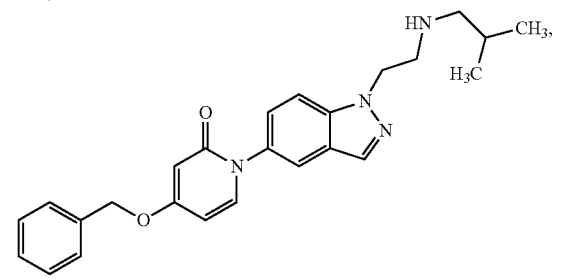
170
-continued
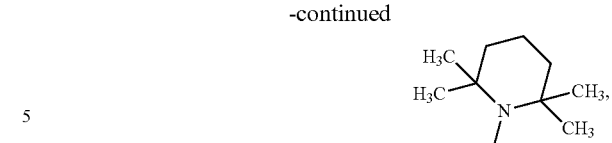
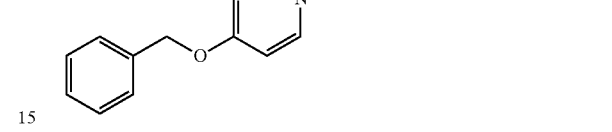
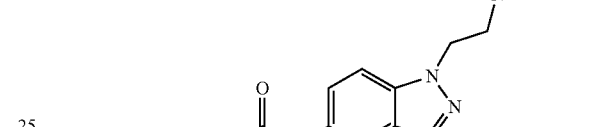
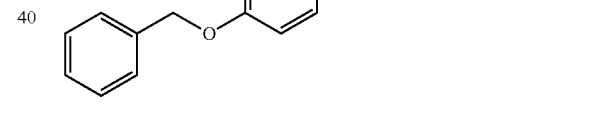
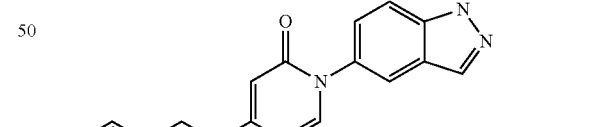

171
-continued
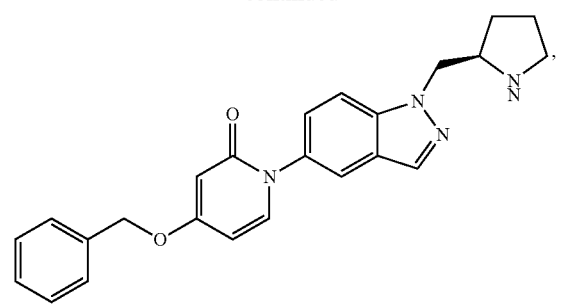
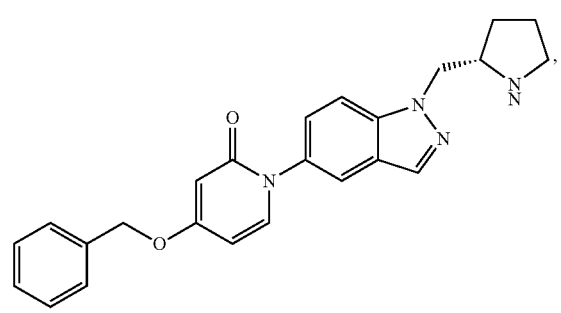
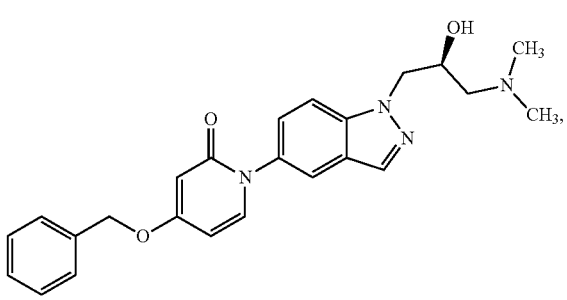
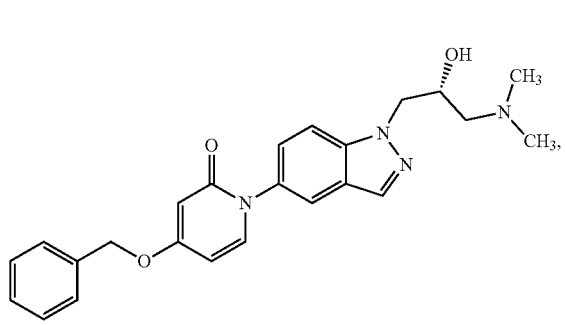
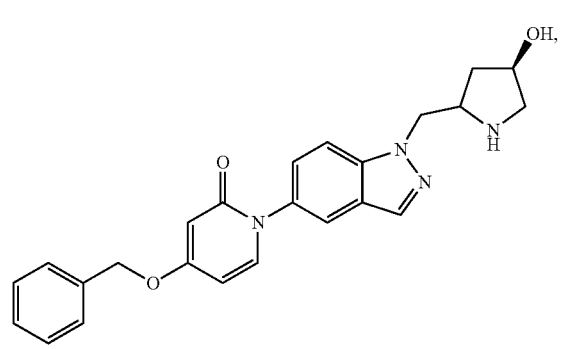
172
-continued
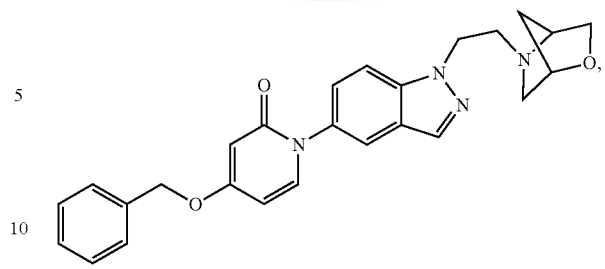
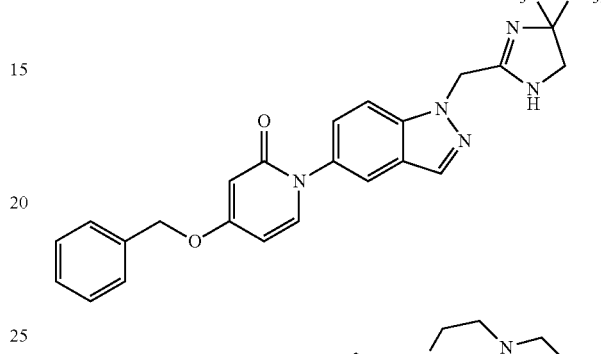
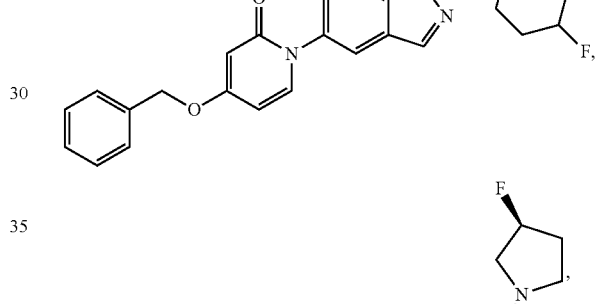
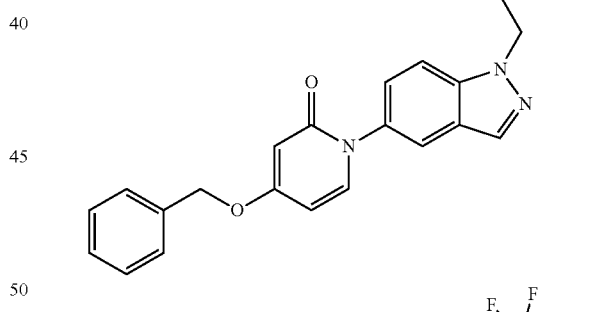
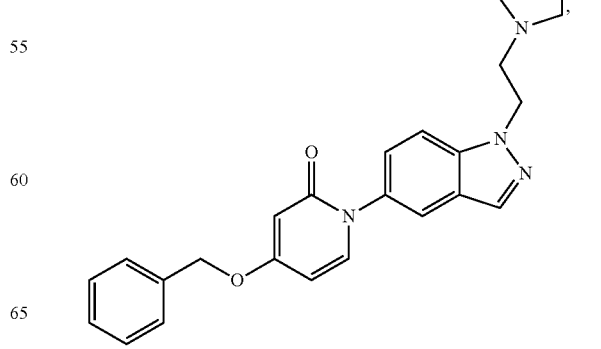

173
-continued
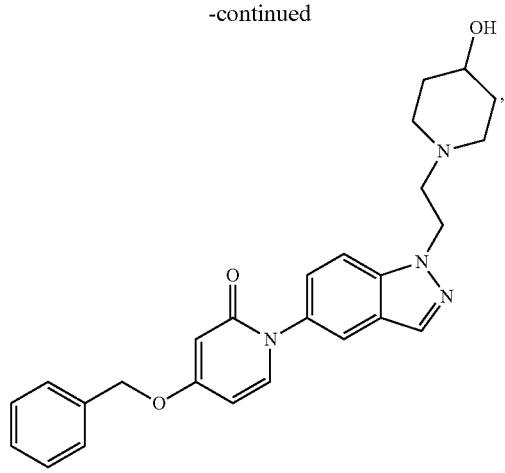
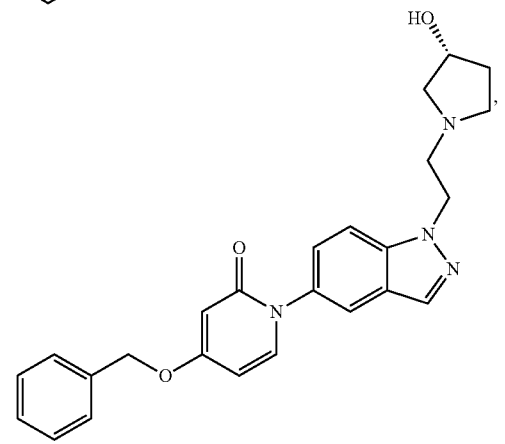
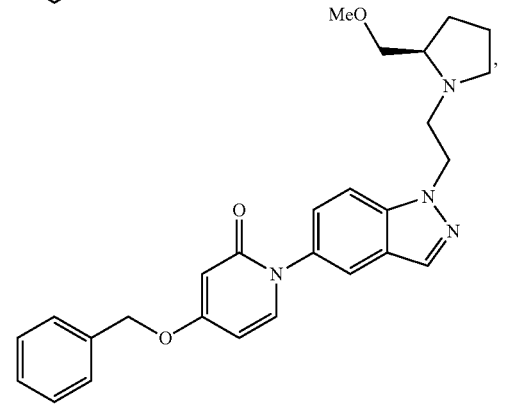
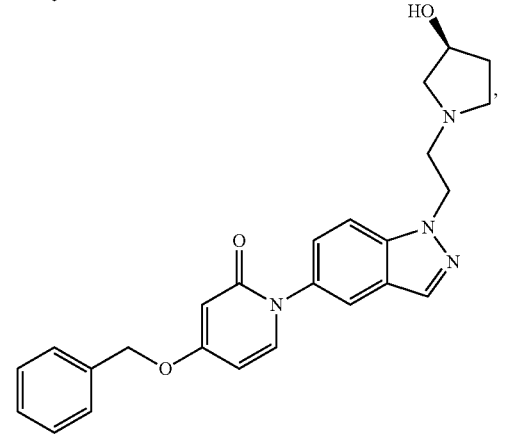
174
-continued
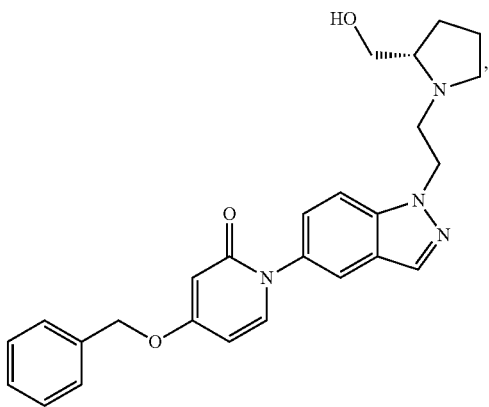
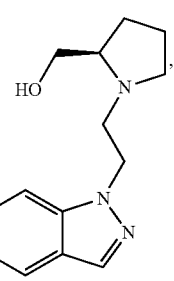
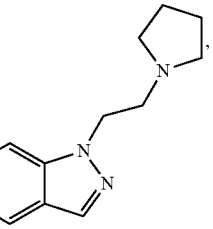

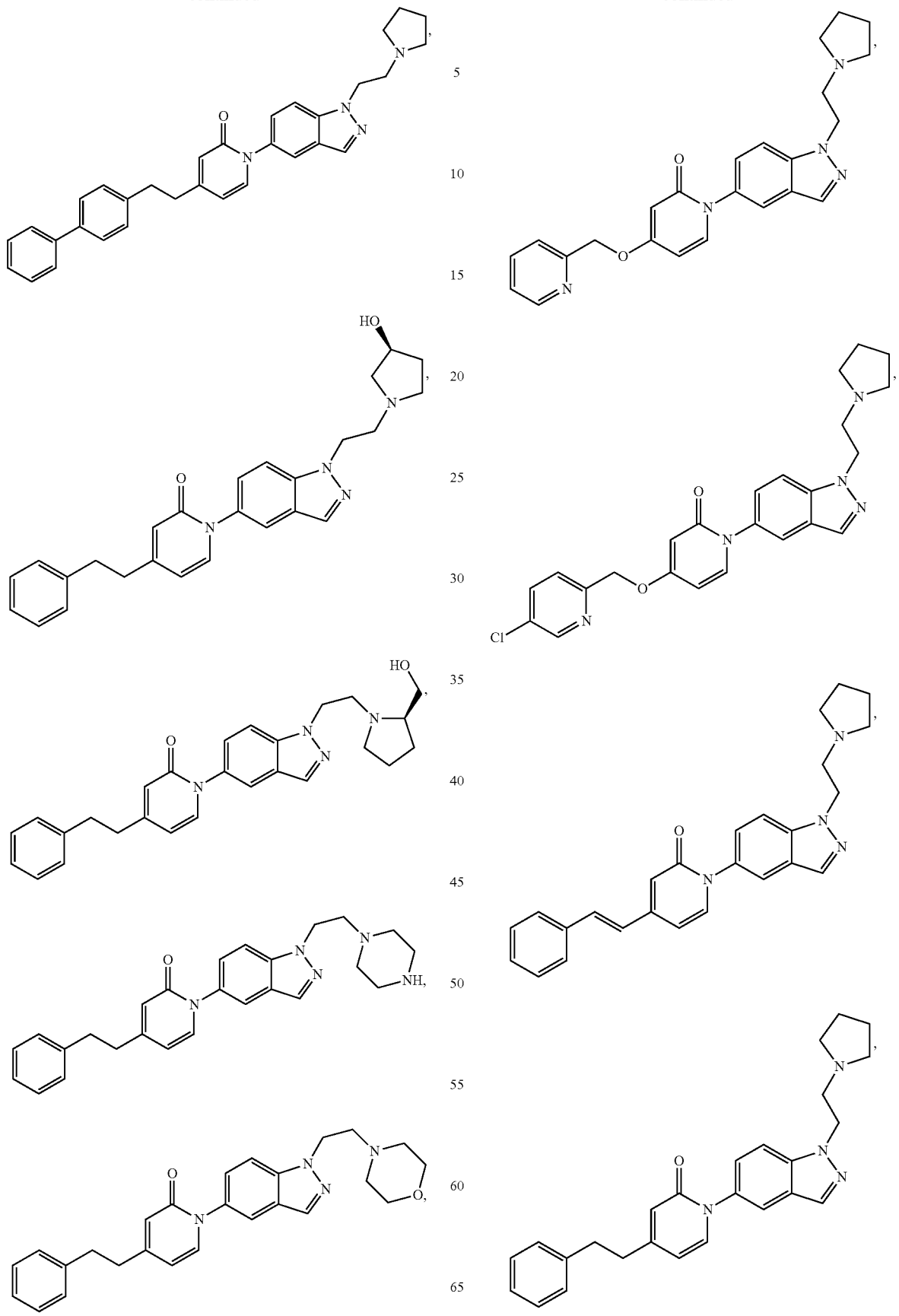

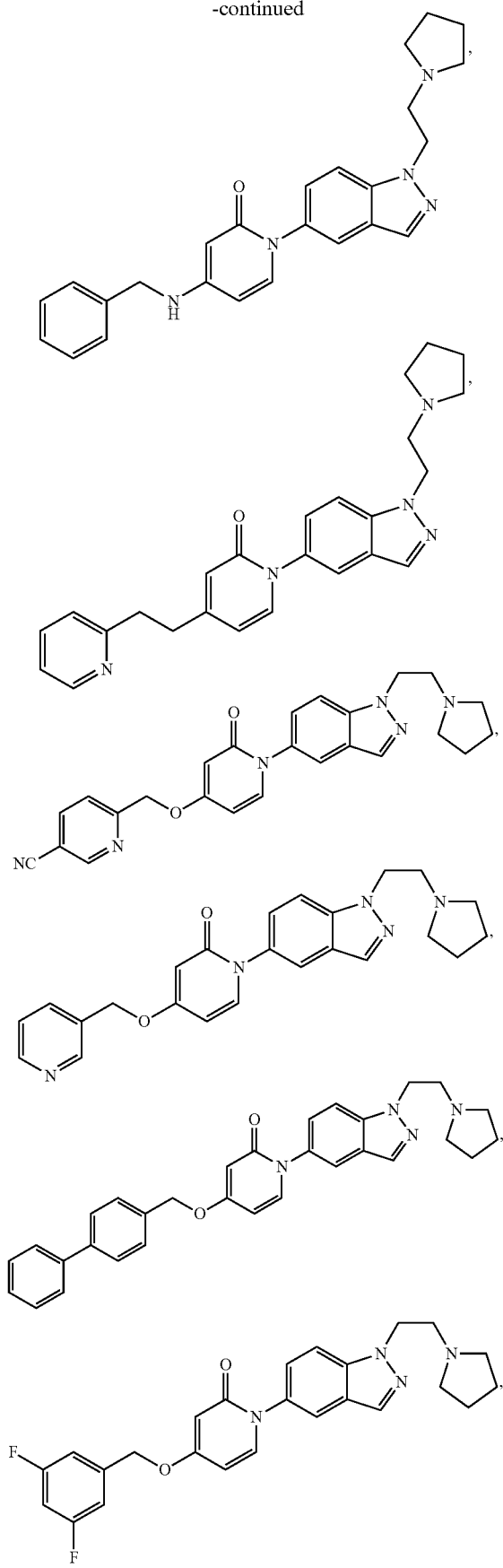
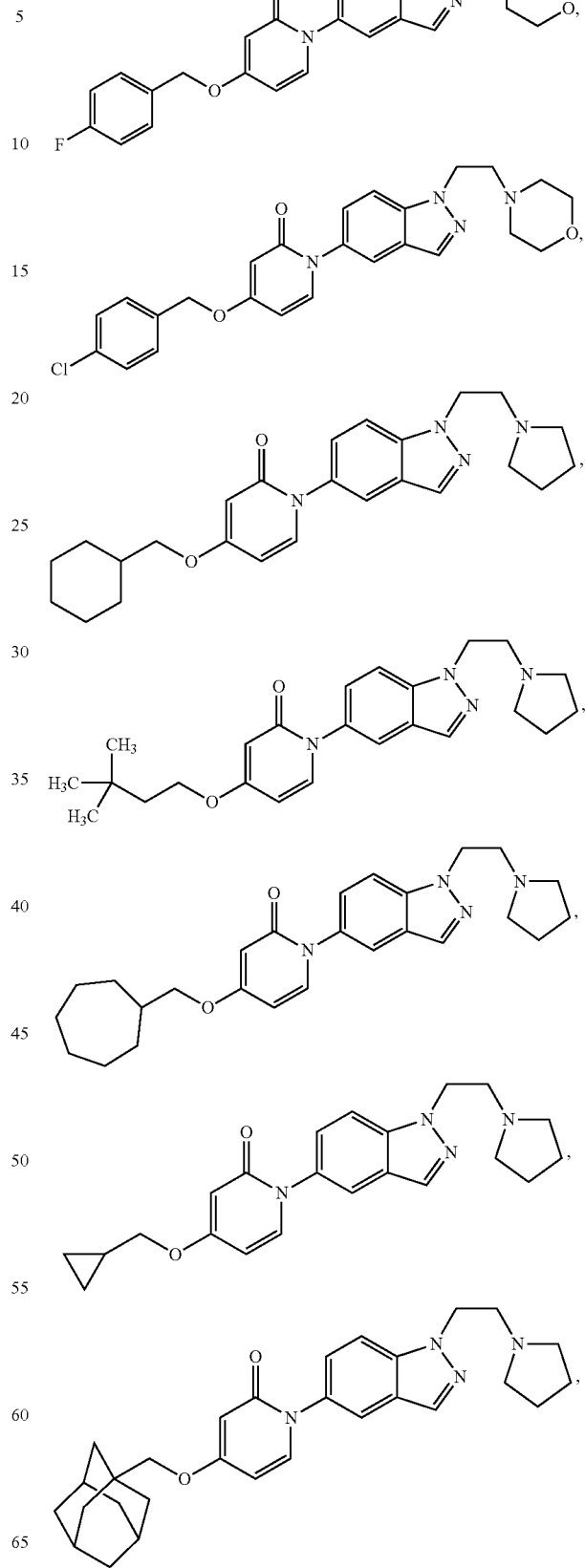

-continued

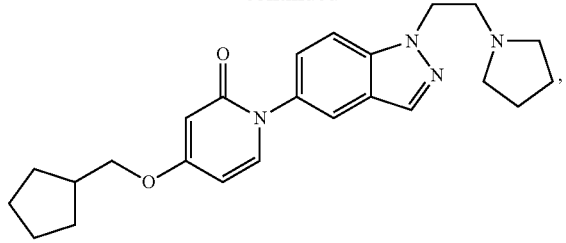

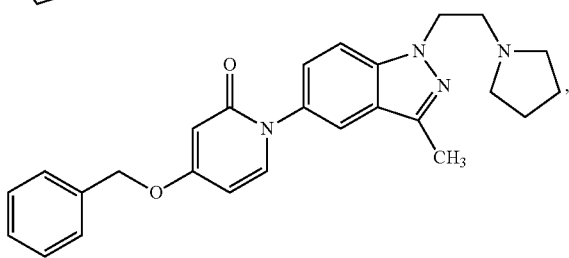

and

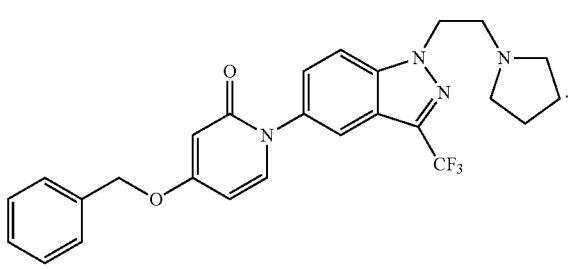

30. A compound according to claim 1, wherein the compound is in a pharmaceutically acceptable salt form.

31. A compound according to claim 30 wherein the salt is an HCl salt.

32. A pharmaceutical composition comprising a compound according to claim 1 and a pharmaceutically acceptable carrier, excipient or diluent therefore.

33. A method of treating obesity, comprising administering to a patient in need of obesity reduction an obesity-reducing effective amount of a compound according to claim 1, wherein treating does not include prevention.

34. A method of treating anxiety, comprising administering to a patient in need of such treatment a therapeutically effective amount of a compound according to claim 1, wherein treating does not include prevention.

35. A method of treating depression, comprising administering to a patient in need of such treatment a therapeutically effective amount of a compound according to claim 1, wherein treating does not include prevention.

36. A method of treating non-alcoholic fatty liver disease, comprising administering to a patient in need of such treatment a therapeutically effective amount of a compound according to claim 1, wherein treating does not include prevention.

* * * * *